(12) United States Patent
Perlroth et al.

(10) Patent No.: US 11,155,610 B2
(45) Date of Patent: Oct. 26, 2021

(54) DUAL PDGF/VEGF ANTAGONISTS

(71) Applicant: KODIAK SCIENCES INC., Palo Alto, CA (US)

(72) Inventors: Daniel Victor Perlroth, Palo Alto, CA (US); Stephen A. Charles, Ravenna, OH (US); James Aggen, Westwood, MA (US); Didier Benoit, San Jose, CA (US); Wayne To, San Mateo, CA (US); Lidia Mosyak, Newton, MA (US); Laura Lin, Weston, MA (US); Justin Cohen, Quincy, MA (US); Tetsuya Ishino, Boston, MA (US); William Somers, Lexington, MA (US)

(73) Assignee: KODIAK SCIENCES INC., Palo Alto, CA (US)

(*) Notice: Subject to any disclaimer, the term of this patent is extended or adjusted under 35 U.S.C. 154(b) by 0 days.

(21) Appl. No.: 15/820,325

(22) Filed: Nov. 21, 2017

(65) Prior Publication Data

US 2018/0244762 A1    Aug. 30, 2018

Related U.S. Application Data

(60) Division of application No. 14/753,824, filed on Jun. 29, 2015, now Pat. No. 9,840,553, which is a continuation of application No. PCT/US2015/038203, filed on Jun. 28, 2015.

(60) Provisional application No. 62/018,579, filed on Jun. 28, 2014.

(51) Int. Cl.
| | |
|---|---|
| *A61K 39/00* | (2006.01) |
| *A61K 39/395* | (2006.01) |
| *A61K 38/17* | (2006.01) |
| *A61K 38/18* | (2006.01) |
| *C07K 16/46* | (2006.01) |
| *C07K 16/22* | (2006.01) |
| *C07K 14/71* | (2006.01) |
| *C07K 16/28* | (2006.01) |

(52) U.S. Cl.
CPC ............ *C07K 16/22* (2013.01); *A61K 38/179* (2013.01); *A61K 38/1858* (2013.01); *A61K 38/1866* (2013.01); *C07K 14/71* (2013.01); *C07K 16/28* (2013.01); *C07K 16/2863* (2013.01); *A61K 2039/505* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/71* (2013.01); *C07K 2317/72* (2013.01); *C07K 2317/76* (2013.01); *C07K 2317/92* (2013.01); *C07K 2318/10* (2013.01); *C07K 2319/036* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,609,707 A | 9/1986 | Nowinski et al. |
| 4,634,664 A | 1/1987 | Oestberg |
| 4,634,666 A | 1/1987 | Engleman et al. |
| 4,777,127 A | 10/1988 | Jukka et al. |
| 4,816,567 A | 3/1989 | Cabilly et al. |
| 4,892,538 A | 1/1990 | Aebischer et al. |
| 5,047,335 A | 9/1991 | Paulson et al. |
| 5,219,740 A | 6/1993 | Dusty et al. |
| 5,225,539 A | 7/1993 | Winter |
| 5,252,713 A | 10/1993 | Morgan, Jr. et al. |
| 5,278,299 A | 1/1994 | Wong et al. |
| 5,283,187 A | 2/1994 | Aebischer et al. |
| 5,325,525 A | 6/1994 | Shan et al. |
| 5,336,603 A | 8/1994 | Capon et al. |
| 5,422,120 A | 6/1995 | Kim et al. |

(Continued)

FOREIGN PATENT DOCUMENTS

| | | |
|---|---|---|
| AU | 2010330727 | 12/2010 |
| AU | 2011239434 | 8/2015 |

(Continued)

OTHER PUBLICATIONS

MacCallum et al. (1996). J. Mol. Biol. 262:732-745.*

(Continued)

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

The invention provides a dual VEGF/PDGF antagonist comprising a VEGF antagonist linked to a PDGF antagonist. The VEGF antagonist is an antibody to a VEGF or VEGFR or is a VEGFR extracellular trap segment (i.e., a segment from the extracellular region of one or more VEGFR receptors that inhibits binding of at least one VEGFR to at least one VEGF). The PDGF antagonist is an antibody to a PDGF or PDGFR or is a PDGFR extracellular trap segment (i.e., segment from the extracellular region of one or more PDGFRs, which inhibits binding of at least one PDGFR and at least one PDGF). The dual antagonist is preferably conjugated to a half-life extending moiety, such as a HEMA-PC polymer. The dual antagonist is particularly useful for treating wet aged related macular degeneration.

22 Claims, 41 Drawing Sheets

Specification includes a Sequence Listing.

(56) References Cited

U.S. PATENT DOCUMENTS

| | | |
|---|---|---|
| 5,510,261 A | 4/1996 | Goochee et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,580,859 A | 12/1996 | Feigner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,663,425 A | 9/1997 | Detroit et al. |
| 5,681,746 A | 10/1997 | Bodner et al. |
| 5,733,743 A | 3/1998 | Johnson et al. |
| 5,741,923 A | 4/1998 | Driver et al. |
| 5,763,548 A | 6/1998 | Matyjaszewski et al. |
| 5,770,429 A | 6/1998 | Lonberg et al. |
| 5,789,487 A | 8/1998 | Matyjaszewski et al. |
| 5,789,650 A | 8/1998 | Lonberg et al. |
| 5,807,937 A | 9/1998 | Matyjaszewski et al. |
| 5,814,318 A | 9/1998 | Lonberg et al. |
| 5,814,482 A | 9/1998 | Dubensky, Jr. et al. |
| 5,834,597 A | 11/1998 | Tso et al. |
| 5,837,242 A | 11/1998 | Holliger et al. |
| 5,858,657 A | 1/1999 | Winter et al. |
| 5,859,205 A | 1/1999 | Adair et al. |
| 5,863,551 A | 1/1999 | Woerly |
| 5,871,907 A | 2/1999 | Winter et al. |
| 5,872,218 A | 2/1999 | Wolf et al. |
| 5,874,299 A | 2/1999 | Lonberg et al. |
| 5,877,218 A | 3/1999 | Herzig et al. |
| 5,877,397 A | 3/1999 | Lonberg et al. |
| 5,882,644 A | 3/1999 | Chang et al. |
| 5,945,491 A | 8/1999 | Matyjaszewski et al. |
| 5,981,786 A | 11/1999 | Kitano et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,162,882 A | 12/2000 | Matyjaszewski et al. |
| 6,270,993 B1 | 8/2001 | Shibuya et al. |
| 6,344,050 B1 | 2/2002 | Chen |
| 6,376,471 B1 | 4/2002 | Lawrence, III et al. |
| 6,383,486 B1 | 5/2002 | Davis-Smyth et al. |
| 6,407,187 B1 | 6/2002 | Matyjaszewski et al. |
| 6,407,213 B1 | 6/2002 | Carter et al. |
| 6,413,942 B1 | 7/2002 | Feigner et al. |
| 6,436,908 B1 | 8/2002 | Koch et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,554,853 B2 | 4/2003 | Chen |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,624,821 B1 | 9/2003 | Shin et al. |
| 6,627,314 B2 | 9/2003 | Matyjaszewski et al. |
| 6,632,926 B1 | 10/2003 | Chen et al. |
| 6,759,491 B2 | 7/2004 | Matyjaszewski et al. |
| 6,790,919 B2 | 9/2004 | Matyjaszewski et al. |
| 6,833,349 B2 | 12/2004 | Xia et al. |
| 6,852,816 B2 | 2/2005 | Lewis et al. |
| 6,870,033 B1 | 3/2005 | Hsei et al. |
| 6,881,557 B2 | 4/2005 | Foote |
| 6,884,879 B1 | 4/2005 | Baca et al. |
| 6,887,962 B2 | 5/2005 | Matyjaszewski et al. |
| 6,979,556 B2 | 12/2005 | Simmons et al. |
| 6,992,176 B2 | 1/2006 | Reiter et al. |
| 7,019,082 B2 | 3/2006 | Matyjaszewski et al. |
| 7,049,373 B2 | 5/2006 | Matyjaszewski et al. |
| 7,052,691 B2 | 5/2006 | Sleeman et al. |
| 7,056,455 B2 | 6/2006 | Matyjaszewski et al. |
| 7,056,509 B2 | 6/2006 | Thorpe et al. |
| 7,060,269 B1 | 6/2006 | Baca et al. |
| 7,060,271 B2 | 6/2006 | Ramakrishnan et al. |
| 7,064,166 B2 | 6/2006 | Matyjaszewski et al. |
| 7,071,159 B2 | 7/2006 | Kendall et al. |
| 7,122,636 B1 | 10/2006 | Hsei et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,297,334 B2 | 1/2007 | Baca et al. |
| 7,214,776 B2 | 5/2007 | Hsei et al. |
| 7,291,721 B2 | 11/2007 | Giles-Komar et al. |
| 7,300,653 B2 | 11/2007 | Wiegand et al. |
| 7,300,990 B2 | 11/2007 | Lewis et al. |
| 7,303,748 B2 | 12/2007 | Wiegand et al. |
| 7,306,799 B2 | 12/2007 | Wiegand et al. |
| 7,345,027 B2 | 3/2008 | Tolentino et al. |
| 7,348,424 B2 | 3/2008 | Miyazawa et al. |
| 7,351,411 B2 | 4/2008 | Holash et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,365,166 B2 | 4/2008 | Baca et al. |
| 7,374,757 B2 | 5/2008 | Papadopoulos et al. |
| 7,375,193 B2 | 5/2008 | Baca et al. |
| 7,378,095 B2 | 5/2008 | Cao et al. |
| 7,507,405 B2 | 3/2009 | Hsei et al. |
| 7,521,541 B2 | 4/2009 | Eigenbrot et al. |
| 7,531,172 B2 | 5/2009 | Stahl et al. |
| 7,560,112 B2 | 7/2009 | Chen et al. |
| 7,569,655 B2 | 8/2009 | Pacetti et al. |
| 7,608,261 B2 | 10/2009 | Furfine et al. |
| 7,612,182 B2 | 11/2009 | Giles-Komar et al. |
| 7,740,844 B2 | 6/2010 | Hong et al. |
| 7,740,850 B2 | 6/2010 | Zhu et al. |
| 7,750,138 B2 | 7/2010 | Fang et al. |
| 7,754,208 B2 | 7/2010 | Ledbetter et al. |
| 7,754,855 B1 | 7/2010 | Cox, III et al. |
| 7,758,859 B2 | 7/2010 | Fuh et al. |
| 7,759,472 B2 | 7/2010 | Shima et al. |
| 7,842,789 B2 | 11/2010 | Hsei et al. |
| 7,855,178 B2 | 12/2010 | Alitalo et al. |
| 7,893,173 B2 | 2/2011 | Matyjaszewski et al. |
| 7,919,099 B2 | 4/2011 | Tahara et al. |
| 7,928,072 B2 | 4/2011 | Scaria et al. |
| 7,955,597 B2 | 6/2011 | Giles-Komar et al. |
| 8,003,097 B2 | 8/2011 | Schroeter et al. |
| 8,007,798 B2 | 8/2011 | Ashkenazi et al. |
| 8,007,799 B2 | 8/2011 | Van Bruggen et al. |
| 8,008,453 B2 | 8/2011 | Gegg et al. |
| 8,034,905 B2 | 10/2011 | Kavlie et al. |
| 8,048,418 B2 | 11/2011 | Noguera-Troise et al. |
| 8,092,797 B2 | 1/2012 | Fuh et al. |
| 8,101,177 B2 | 1/2012 | Fuh et al. |
| 8,110,546 B2 | 2/2012 | Dix et al. |
| 8,124,076 B2 | 2/2012 | Solomon et al. |
| 8,147,830 B2 | 4/2012 | Johnson et al. |
| 8,163,726 B2 | 4/2012 | Wen et al. |
| 8,187,597 B2 | 5/2012 | Shima et al. |
| 8,206,707 B2 | 6/2012 | Shima et al. |
| 8,211,864 B2 | 7/2012 | Ambati et al. |
| 8,216,571 B2 | 7/2012 | Ramachandra et al. |
| 8,216,575 B2 | 7/2012 | Yu |
| 8,231,907 B2 | 7/2012 | Lillard et al. |
| 8,236,312 B2 | 8/2012 | Park et al. |
| RE43,672 E | 9/2012 | Chan et al. |
| 8,268,314 B2 | 9/2012 | Baehner et al. |
| 8,273,353 B2 | 9/2012 | Davis-Smyth et al. |
| 8,309,532 B2 | 11/2012 | Feinstein et al. |
| 8,318,169 B2 | 11/2012 | Trogden et al. |
| 8,324,169 B2 | 12/2012 | Quinn |
| 8,329,866 B2 | 12/2012 | Rosendahl et al. |
| 8,349,325 B2 | 1/2013 | Brophy et al. |
| 8,388,963 B2 | 3/2013 | Vrignaud et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,506,962 B2 | 8/2013 | Trogden et al. |
| 8,512,699 B2 | 8/2013 | Fuh et al. |
| 8,546,345 B2 | 10/2013 | Tolentino et al. |
| 8,557,246 B2 | 10/2013 | Escribano et al. |

(56) References Cited

U.S. PATENT DOCUMENTS

| | | |
|---|---|---|
| 8,571,802 B2 | 10/2013 | Robinson et al. |
| 8,614,235 B2 | 12/2013 | Robinson et al. |
| 8,632,774 B2 | 1/2014 | Misher et al. |
| 8,658,633 B2 | 2/2014 | Poulaki et al. |
| 8,663,639 B2 | 3/2014 | Dor et al. |
| 8,691,226 B2 | 4/2014 | Chiu et al. |
| 8,703,130 B2 | 4/2014 | Baehner et al. |
| 8,703,133 B2 | 4/2014 | Chen et al. |
| 8,765,432 B2 | 7/2014 | Charles |
| 8,785,385 B2 | 7/2014 | Stout et al. |
| 8,790,647 B2 | 7/2014 | Greenwood et al. |
| 8,802,129 B2 | 8/2014 | Whitcup et al. |
| 8,815,236 B2 | 8/2014 | Burke et al. |
| 8,822,645 B2 | 9/2014 | Ghayur et al. |
| 8,834,884 B2 | 9/2014 | Trogden et al. |
| 8,846,021 B2 | 9/2014 | Charles |
| 8,864,869 B2 | 9/2014 | Pakola et al. |
| 8,883,157 B1 | 11/2014 | Clube |
| 8,883,519 B1 | 11/2014 | Perez et al. |
| 8,911,768 B2 | 12/2014 | Whitcup et al. |
| 8,926,972 B2 | 1/2015 | Zhou et al. |
| 8,945,552 B2 | 2/2015 | Baehner et al. |
| 8,962,804 B2 | 2/2015 | Williams |
| 8,986,692 B2 | 3/2015 | Li et al. |
| 9,029,508 B2 | 5/2015 | Ghayur et al. |
| 9,045,551 B2 | 6/2015 | Gu et al. |
| 9,079,953 B2 | 7/2015 | Harding et al. |
| 9,125,940 B2 | 9/2015 | Ma et al. |
| 9,149,427 B2 | 10/2015 | Ling et al. |
| 9,163,093 B2 | 10/2015 | Gu et al. |
| 9,214,906 B2 | 12/2015 | Marsan et al. |
| 9,217,039 B2 | 12/2015 | Pedersen et al. |
| 9,220,631 B2 | 12/2015 | Sigg et al. |
| 9,226,917 B2 | 1/2016 | Strong et al. |
| 9,254,338 B2 | 2/2016 | Yancopoulos |
| 9,334,324 B2 | 5/2016 | Choo et al. |
| 9,353,177 B2 | 5/2016 | Fuh et al. |
| 9,388,239 B2 | 7/2016 | Baldi et al. |
| 9,388,180 B2 | 8/2016 | Clube |
| 9,409,990 B2 | 8/2016 | Zhang |
| 9,416,210 B2 | 8/2016 | Emrick et al. |
| 9,421,256 B2 | 8/2016 | Kavlie et al. |
| 9,428,575 B2 | 8/2016 | Lai et al. |
| 9,567,403 B2 | 2/2017 | Wu et al. |
| 9,575,067 B2 | 2/2017 | Kosmeder et al. |
| 9,650,443 B2 | 5/2017 | Song et al. |
| 9,650,444 B2 | 5/2017 | Wiegand et al. |
| 9,682,144 B2 | 6/2017 | Thorin et al. |
| 9,695,233 B2 | 7/2017 | Duerr et al. |
| 9,708,390 B2 | 7/2017 | Sivakumar et al. |
| 9,708,396 B2 | 7/2017 | Baehner et al. |
| 9,708,397 B2 | 7/2017 | Greenwood et al. |
| 9,815,893 B2 | 11/2017 | Akamatsu |
| 9,840,553 B2 | 12/2017 | Perlroth et al. |
| 9,850,514 B2 | 12/2017 | Laird et al. |
| 9,914,770 B2 | 3/2018 | Shandilya et al. |
| 9,931,330 B2 | 4/2018 | Zarnitsyn et al. |
| 9,937,129 B2 | 4/2018 | Freeman et al. |
| 9,943,573 B2 | 4/2018 | Constable et al. |
| 9,944,720 B2 | 4/2018 | Gu et al. |
| 9,962,333 B2 | 5/2018 | Gailard et al. |
| 10,004,788 B2 | 6/2018 | Constable et al. |
| 10,035,850 B2 | 7/2018 | Gekkieva et al. |
| 10,072,075 B2 | 9/2018 | Koenig et al. |
| 10,106,605 B2 | 10/2018 | Ghosh et al. |
| 10,184,010 B2 | 1/2019 | Lee et al. |
| 10,208,124 B2 | 2/2019 | Le Bouteiller et al. |
| 10,208,355 B2 | 2/2019 | Bais et al. |
| 10,240,207 B2 | 3/2019 | Yu et al. |
| 10,259,862 B2 | 4/2019 | Carter et al. |
| 10,363,290 B2 | 7/2019 | Perlroth et al. |
| 10,421,984 B2 | 9/2019 | Laird et al. |
| 10,456,466 B2 | 10/2019 | Fang et al. |
| 10,456,470 B2 | 10/2019 | Bais et al. |
| 10,519,226 B2 | 12/2019 | Rau et al. |
| 10,526,382 B2 | 1/2020 | Bel Aiba et al. |
| 10,568,951 B2 | 2/2020 | Sigi |
| 10,548,998 B2 | 4/2020 | Bradbury et al. |
| 10,702,608 B2 | 7/2020 | Charles et al. |
| 2002/0032315 A1 | 6/2002 | Baca et al. |
| 2002/0091082 A1 | 7/2002 | Aiello |
| 2003/0113335 A1 | 6/2003 | Li et al. |
| 2003/0118592 A1 | 6/2003 | Ledbetter et al. |
| 2003/0143596 A1 | 7/2003 | Bentley et al. |
| 2003/0171320 A1 | 9/2003 | Guyer |
| 2003/0235536 A1 | 12/2003 | Blumberg et al. |
| 2004/0010376 A1 | 1/2004 | Luo et al. |
| 2004/0063881 A1 | 4/2004 | Lewis et al. |
| 2004/0091490 A1 | 5/2004 | Johnson et al. |
| 2004/0247588 A1 | 12/2004 | Johnson et al. |
| 2004/0253596 A1 | 12/2004 | Pawlak et al. |
| 2004/0266688 A1 | 12/2004 | Nayak |
| 2005/0041080 A1 | 2/2005 | Hall et al. |
| 2005/0074497 A1 | 4/2005 | Schultz |
| 2005/0100550 A1 | 5/2005 | Trikha et al. |
| 2005/0112061 A1 | 5/2005 | Holash et al. |
| 2005/0112088 A1 | 5/2005 | Zhao et al. |
| 2005/0118651 A1 | 6/2005 | Basi et al. |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0180945 A1 | 8/2005 | Chaikof et al. |
| 2005/0214286 A1 | 9/2005 | Epstein et al. |
| 2005/0220880 A1 | 10/2005 | Lewis et al. |
| 2005/0239088 A1 | 10/2005 | Shepard et al. |
| 2005/0276796 A1 | 12/2005 | Tomatsu et al. |
| 2005/0281822 A1 | 12/2005 | Cedarbaum et al. |
| 2005/0281861 A1 | 12/2005 | Hughes et al. |
| 2005/0282233 A1 | 12/2005 | Eriksson et al. |
| 2006/0058234 A1 | 3/2006 | Daly et al. |
| 2006/0067930 A1 | 3/2006 | Adams et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0182783 A1 | 8/2006 | Hughes et al. |
| 2006/0193830 A1 | 8/2006 | Hauswirth et al. |
| 2006/0217285 A1 | 9/2006 | Destarac |
| 2006/0231107 A1 | 10/2006 | Glickman et al. |
| 2006/0234347 A1 | 10/2006 | Harding et al. |
| 2006/0234437 A1 | 10/2006 | Harding et al. |
| 2007/0037183 A1 | 2/2007 | Edwards et al. |
| 2007/0037214 A1 | 2/2007 | Luo et al. |
| 2007/0037760 A1 | 2/2007 | Tolentino et al. |
| 2007/0041967 A1 | 2/2007 | Jung et al. |
| 2007/0059302 A1 | 3/2007 | Baca et al. |
| 2007/0059336 A1 | 3/2007 | Hughes et al. |
| 2007/0071756 A1 | 3/2007 | Peyman |
| 2007/0111279 A1 | 5/2007 | Rosenberg |
| 2007/0134244 A1 | 6/2007 | Slakter et al. |
| 2007/0141104 A1 | 6/2007 | Hauenstein |
| 2007/0167526 A1 | 7/2007 | Zhang et al. |
| 2007/0190058 A1 | 8/2007 | Shams |
| 2007/0196374 A1 | 8/2007 | Baca et al. |
| 2007/0258976 A1 | 11/2007 | Ward et al. |
| 2007/0264236 A1 | 11/2007 | Yang |
| 2008/0008736 A1 | 1/2008 | Glauser |
| 2008/0070855 A1 | 3/2008 | Gills |
| 2008/0096923 A1 | 4/2008 | Girach |
| 2008/0124450 A1 | 5/2008 | Pacetti |
| 2008/0147178 A1 | 6/2008 | Pacetti et al. |
| 2008/0152654 A1 | 6/2008 | Reich et al. |
| 2008/0167600 A1 | 7/2008 | Peyman |
| 2008/0187534 A1 | 8/2008 | Baca et al. |
| 2008/0187966 A1 | 8/2008 | Simmons |
| 2008/0199464 A1 | 8/2008 | Plowman et al. |
| 2008/0226629 A1 | 9/2008 | Baca et al. |
| 2008/0242587 A1 | 10/2008 | Kim et al. |
| 2008/0248030 A1 | 10/2008 | Folkman et al. |
| 2008/0268051 A1 | 10/2008 | Hughes et al. |
| 2008/0292628 A1 | 11/2008 | Hui |
| 2009/0053137 A1 | 2/2009 | Moore |
| 2009/0053217 A1 | 2/2009 | Blank et al. |
| 2009/0053786 A1 | 2/2009 | Kao et al. |
| 2009/0060906 A1 | 3/2009 | Barry et al. |

(56) References Cited

U.S. PATENT DOCUMENTS

| | | |
|---|---|---|
| 2009/0061533 A1 | 3/2009 | Minami |
| 2009/0092664 A1 | 4/2009 | Mumper et al. |
| 2009/0098139 A1 | 4/2009 | Katz et al. |
| 2009/0104259 A1 | 4/2009 | Tolentino et al. |
| 2009/0117103 A1 | 7/2009 | Devalaraja et al. |
| 2009/0220504 A1 | 9/2009 | Chuntharapai et al. |
| 2009/0226441 A1 | 9/2009 | Yan et al. |
| 2009/0249503 A1 | 10/2009 | Rosendahl |
| 2009/0285826 A1 | 11/2009 | Bonnel et al. |
| 2009/0324679 A1 | 12/2009 | Ippoliti et al. |
| 2010/0086551 A1 | 4/2010 | Olwill et al. |
| 2010/0098730 A1 | 4/2010 | Lowman et al. |
| 2010/0059541 A1 | 5/2010 | Downing et al. |
| 2010/0111942 A1 | 5/2010 | Shima et al. |
| 2010/0111963 A1 | 5/2010 | Shams |
| 2010/0129375 A1 | 5/2010 | Junge et al. |
| 2010/0150911 A1 | 6/2010 | Caiado De Castro Neto et al. |
| 2010/0151566 A1 | 6/2010 | Lamdan Ordas et al. |
| 2010/0158850 A1 | 6/2010 | Baker, Jr. et al. |
| 2010/0166700 A1 | 7/2010 | Charles |
| 2010/0233079 A1 | 9/2010 | Jakob et al. |
| 2010/0247515 A1 | 9/2010 | Steward et al. |
| 2010/0254995 A1 | 10/2010 | Steward et al. |
| 2010/0260668 A1 | 10/2010 | Ghayur et al. |
| 2010/0260760 A1 | 10/2010 | Blank et al. |
| 2010/0278896 A1 | 11/2010 | Khaw et al. |
| 2010/0291065 A1 | 11/2010 | Kabanov et al. |
| 2010/0322931 A1 | 12/2010 | Harding et al. |
| 2011/0033378 A1 | 2/2011 | Dimasi et al. |
| 2011/0047103 A1 | 2/2011 | Swamy et al. |
| 2011/0052575 A1 | 3/2011 | Baca et al. |
| 2011/0054031 A1 | 3/2011 | McNamara et al. |
| 2011/0059080 A1 | 3/2011 | Cornfeld et al. |
| 2011/0064738 A1 | 3/2011 | Blank et al. |
| 2011/0076278 A1 | 3/2011 | Khodadoust |
| 2011/0076279 A1 | 3/2011 | Ramachandra et al. |
| 2011/0081342 A1 | 4/2011 | Baca et al. |
| 2011/0104069 A1 | 5/2011 | Xu et al. |
| 2011/0110932 A1 | 5/2011 | Patel |
| 2011/0117189 A1 | 5/2011 | Mazzone et al. |
| 2011/0159608 A1 | 6/2011 | Graham |
| 2011/0165648 A1 | 7/2011 | Campange et al. |
| 2011/0177074 A1 | 7/2011 | Sivakumar et al. |
| 2011/0189174 A1 | 8/2011 | Shafiee et al. |
| 2011/0200593 A1 | 8/2011 | Shima et al. |
| 2011/0262432 A1 | 10/2011 | Plouet et al. |
| 2011/0263827 A1 | 10/2011 | Ghayur et al. |
| 2012/0003641 A1 | 1/2012 | Graham et al. |
| 2012/0006716 A1 | 1/2012 | Frey et al. |
| 2012/0009185 A1 | 1/2012 | Shams |
| 2012/0067176 A1 | 1/2012 | Frey et al. |
| 2012/0070428 A1 | 3/2012 | Chan et al. |
| 2012/0076787 A1 | 3/2012 | Adamson et al. |
| 2012/0100136 A1 | 4/2012 | Patel et al. |
| 2012/0100166 A1 | 4/2012 | Roschke et al. |
| 2012/0128626 A1 | 5/2012 | Smith |
| 2012/0134993 A1 | 5/2012 | Pan et al. |
| 2012/0135070 A1 | 5/2012 | Kros et al. |
| 2012/0156202 A1 | 6/2012 | Shantha et al. |
| 2012/0164079 A1 | 6/2012 | Sharma |
| 2012/0014957 A1 | 7/2012 | Ghayur et al. |
| 2012/0213705 A1 | 8/2012 | Dimasi et al. |
| 2012/0244147 A1 | 9/2012 | Theuer et al. |
| 2012/0258108 A1 | 10/2012 | Ghayur et al. |
| 2012/0263722 A1 | 10/2012 | Ghayur et al. |
| 2012/0276083 A1 | 11/2012 | Junge et al. |
| 2012/0282211 A1 | 11/2012 | Washburn et al. |
| 2012/0301478 A1 | 11/2012 | Ohura et al. |
| 2012/0322738 A1 | 12/2012 | Behrens et al. |
| 2013/0004486 A1 | 1/2013 | Chan et al. |
| 2013/0004511 A1 | 1/2013 | Thorin et al. |
| 2013/0034517 A1 | 2/2013 | Charles et al. |
| 2013/0040889 A1 | 2/2013 | Bolt et al. |
| 2013/0045522 A1 | 2/2013 | Charles et al. |
| 2013/0058927 A1 | 3/2013 | Baca et al. |
| 2013/0071394 A1 | 3/2013 | Troyer et al. |
| 2013/0129733 A1 | 5/2013 | Ye et al. |
| 2013/0129749 A1 | 5/2013 | Ye et al. |
| 2013/0129830 A1 | 5/2013 | Chen et al. |
| 2013/0142796 A1 | 6/2013 | Ray et al. |
| 2013/0195806 A1 | 8/2013 | Gay et al. |
| 2013/0202613 A1 | 8/2013 | Pakola et al. |
| 2013/0259881 A1 | 10/2013 | Fandl et al. |
| 2013/0323242 A1 | 12/2013 | Everett et al. |
| 2013/0323302 A1 | 12/2013 | Constable et al. |
| 2013/0330341 A1 | 12/2013 | Chiron et al. |
| 2013/0337534 A1 | 12/2013 | Charles |
| 2013/0344129 A1 | 12/2013 | Washburn et al. |
| 2014/0010823 A1 | 1/2014 | Robinson et al. |
| 2014/0024776 A1 | 1/2014 | Charles et al. |
| 2014/0051642 A1 | 2/2014 | Castan |
| 2014/0170140 A1 | 2/2014 | Bennett et al. |
| 2014/0065137 A1 | 3/2014 | Huang et al. |
| 2014/0065142 A1 | 3/2014 | Roschke et al. |
| 2014/0079694 A1 | 3/2014 | Robinson et al. |
| 2014/0081003 A1 | 3/2014 | Laird et al. |
| 2014/0086934 A1 | 3/2014 | Shams |
| 2014/0093499 A1 | 4/2014 | Gschwing et al. |
| 2014/0128575 A1 | 5/2014 | Kao et al. |
| 2014/0134169 A1 | 5/2014 | Kuhnert et al. |
| 2014/0154246 A1 | 6/2014 | Robinson et al. |
| 2014/0154255 A1 | 6/2014 | Akamatsu |
| 2014/0161817 A1 | 6/2014 | Siedler et al. |
| 2014/0186350 A1 | 7/2014 | Ghosh et al. |
| 2014/0193486 A1 | 7/2014 | Liu et al. |
| 2014/0213769 A1 | 7/2014 | Hong et al. |
| 2014/0242082 A1 | 8/2014 | Shima et al. |
| 2014/0287025 A1 | 9/2014 | Liu et al. |
| 2014/0294810 A1 | 10/2014 | Lowman et al. |
| 2014/0302009 A1 | 10/2014 | Ogura et al. |
| 2014/0339122 A1 | 11/2014 | Weeks et al. |
| 2014/0341893 A1 | 11/2014 | Andres et al. |
| 2014/0341977 A1 | 11/2014 | Constable et al. |
| 2015/0004128 A1 | 1/2015 | Charles et al. |
| 2015/0017095 A1 | 1/2015 | Ghayur et al. |
| 2015/0023951 A1 | 1/2015 | Baca et al. |
| 2015/0030598 A1 | 1/2015 | Croasdale et al. |
| 2015/0037422 A1 | 2/2015 | Kaplan et al. |
| 2015/0044214 A1 | 2/2015 | Imhof-Jung et al. |
| 2015/0050714 A1 | 2/2015 | Charles |
| 2015/0056195 A1 | 2/2015 | Bertolotto-Ballotti |
| 2015/0065781 A1 | 3/2015 | Bais et al. |
| 2015/0071861 A1 | 3/2015 | Kondo et al. |
| 2015/0071924 A1 | 3/2015 | Swamy et al. |
| 2015/0071941 A1 | 3/2015 | Sodhi et al. |
| 2015/0073381 A1 | 3/2015 | Kauper et al. |
| 2015/0079084 A1 | 3/2015 | Her et al. |
| 2015/0079089 A1 | 3/2015 | Wadehra et al. |
| 2015/0093375 A1 | 4/2015 | Junge et al. |
| 2015/0093390 A1 | 4/2015 | Bansal |
| 2015/0098988 A1 | 4/2015 | Bollag et al. |
| 2015/0104452 A1 | 4/2015 | Ghayur et al. |
| 2015/0105734 A1 | 4/2015 | Bryant et al. |
| 2015/0110788 A1 | 4/2015 | Kim et al. |
| 2015/0147317 A1 | 5/2015 | Robblee et al. |
| 2015/0148585 A1 | 5/2015 | Das et al. |
| 2015/0158952 A1 | 6/2015 | Mao et al. |
| 2015/0175689 A1 | 6/2015 | Fuh et al. |
| 2015/0182623 A1 | 7/2015 | Everett et al. |
| 2015/0191535 A1 | 7/2015 | Baehner et al. |
| 2015/0202289 A1 | 7/2015 | Shima et al. |
| 2015/0203591 A1 | 7/2015 | Liang et al. |
| 2015/0210771 A1 | 7/2015 | Crystal et al. |
| 2015/0216795 A1 | 8/2015 | Assadourian et al. |
| 2015/0232548 A1 | 8/2015 | Klien et al. |
| 2015/0017163 A1 | 9/2015 | Matthew et al. |
| 2015/0246124 A1 | 9/2015 | Fyfe et al. |
| 2015/0250874 A1 | 9/2015 | Yan et al. |
| 2015/0266962 A1 | 9/2015 | Pfizer |
| 2015/0376271 A1 | 9/2015 | Yan et al. |
| 2015/0297675 A1 | 10/2015 | Osborne |
| 2015/0307551 A1 | 10/2015 | Pfizer |
| 2015/0315283 A1 | 11/2015 | Ghayur et al. |
| 2015/0368329 A1 | 12/2015 | Hastings et al. |

(56) References Cited

U.S. PATENT DOCUMENTS

| | | |
|---|---|---|
| 2015/0376272 A1 | 12/2015 | Chung et al. |
| 2016/0008485 A1 | 1/2016 | Marquette et al. |
| 2016/0015770 A1 | 1/2016 | Zacks et al. |
| 2016/0046730 A1 | 2/2016 | Ghayur et al. |
| 2016/0068613 A1 | 3/2016 | Regula et al. |
| 2016/0129080 A1 | 5/2016 | Osborne |
| 2016/0130321 A1 | 5/2016 | Burian |
| 2016/0130336 A1 | 5/2016 | Lai et al. |
| 2016/0137717 A1 | 5/2016 | Burian |
| 2016/0144025 A1 | 5/2016 | Vitti et al. |
| 2016/0158320 A1 | 6/2016 | Schultz et al. |
| 2016/0159893 A1 | 6/2016 | Burian |
| 2016/0159894 A1 | 6/2016 | Hartmann et al. |
| 2016/0168240 A1 | 6/2016 | Burian et al. |
| 2016/0184445 A1 | 6/2016 | Perlroth et al. |
| 2016/0194370 A1 | 7/2016 | Quian et al. |
| 2016/0194389 A1 | 7/2016 | Regula et al. |
| 2016/0199501 A1 | 7/2016 | Charles et al. |
| 2016/0243225 A1 | 8/2016 | Ioffe et al. |
| 2016/0243227 A1 | 8/2016 | Fyfe et al. |
| 2016/0257738 A1 | 9/2016 | Baca et al. |
| 2016/0279241 A1 | 9/2016 | Dupont et al. |
| 2016/0024483 A1 | 10/2016 | Sanjaya |
| 2016/0287715 A1 | 10/2016 | Charles et al. |
| 2016/0289317 A1 | 10/2016 | Bollag et al. |
| 2016/0296550 A1 | 10/2016 | Patel et al. |
| 2016/0297854 A1 | 10/2016 | Ghosh et al. |
| 2016/0340420 A1 | 11/2016 | Zhang et al. |
| 2016/0038589 A1 | 12/2016 | Bernhard et al. |
| 2016/0346400 A1 | 12/2016 | Emrick et al. |
| 2016/0347843 A1 | 12/2016 | Broering et al. |
| 2016/0369005 A1 | 12/2016 | Lippincott et al. |
| 2017/0002056 A1 | 1/2017 | Ke et al. |
| 2017/0002060 A1 | 1/2017 | Bolen et al. |
| 2017/0007581 A1 | 1/2017 | Robinson et al. |
| 2017/0007710 A1 | 1/2017 | Charles et al. |
| 2017/0015755 A1 | 1/2017 | Walsh et al. |
| 2017/0029494 A1 | 2/2017 | Ashman et al. |
| 2017/0035883 A1 | 2/2017 | Gragoudas et al. |
| 2017/0056469 A1 | 3/2017 | Lezzi |
| 2017/0079955 A1 | 3/2017 | Boyd |
| 2017/0100478 A1 | 4/2017 | Fyfe et al. |
| 2017/0114127 A1 | 4/2017 | Trout et al. |
| 2017/0129962 A1 | 5/2017 | Regula |
| 2017/0143826 A1 | 5/2017 | Dupont et al. |
| 2017/0143841 A1 | 5/2017 | Charles et al. |
| 2017/0143848 A1 | 5/2017 | Calias et al. |
| 2017/0159114 A1 | 6/2017 | Graham et al. |
| 2017/0190766 A1 | 7/2017 | Perlroth et al. |
| 2017/0210796 A1 | 7/2017 | Siedler et al. |
| 2017/0224815 A1 | 8/2017 | Tirgan |
| 2017/0232199 A1 | 8/2017 | Fiedler |
| 2017/0233444 A1 | 8/2017 | Stout et al. |
| 2017/0240626 A1 | 8/2017 | Baehner et al. |
| 2017/0240629 A1 | 8/2017 | Bedoucha et al. |
| 2017/0253651 A1 | 9/2017 | Chen et al. |
| 2017/0290876 A1 | 10/2017 | Ghosh et al. |
| 2017/0275353 A1 | 11/2017 | Sheng et al. |
| 2017/0313780 A1 | 11/2017 | Kao et al. |
| 2017/0327569 A1 | 11/2017 | Lu et al. |
| 2017/0349669 A1 | 12/2017 | Imhof-Jung et al. |
| 2017/0362317 A1 | 12/2017 | Lee et al. |
| 2017/0369564 A1 | 12/2017 | Baca et al. |
| 2017/0369566 A1 | 12/2017 | Baehner et al. |
| 2018/0000779 A1 | 1/2018 | Sakamoto et al. |
| 2018/0000933 A1 | 1/2018 | Ingram et al. |
| 2018/0042765 A1 | 2/2018 | Noronha et al. |
| 2018/0057602 A1 | 3/2018 | Theuer et al. |
| 2018/0092897 A1 | 4/2018 | Zarnitsyn et al. |
| 2018/0133288 A1 | 5/2018 | Kim et al. |
| 2018/0134780 A1 | 5/2018 | Klein et al. |
| 2018/0334499 A1 | 5/2018 | Olwill et al. |
| 2018/0155431 A1 | 6/2018 | Herting et al. |
| 2018/0161407 A1 | 6/2018 | Borodic |
| 2018/0186866 A1 | 7/2018 | Falkenstein et al. |
| 2018/0207292 A1 | 7/2018 | Burian et al. |
| 2018/0208642 A1 | 7/2018 | Lim et al. |
| 2018/0221339 A1 | 8/2018 | Boyd et al. |
| 2018/0221483 A1 | 8/2018 | Gaillard et al. |
| 2018/0230540 A1 | 8/2018 | Gosh et al. |
| 2018/0236066 A1 | 8/2018 | Maecher et al. |
| 2018/0237484 A1 | 8/2018 | Kwon et al. |
| 2018/0251545 A1 | 9/2018 | Cao et al. |
| 2018/0276336 A1 | 9/2018 | Perlee et al. |
| 2018/0298092 A1 | 10/2018 | Gekkieva et al. |
| 2018/0326126 A1 | 11/2018 | Fiedler |
| 2018/0334496 A1 | 11/2018 | Perlroth et al. |
| 2018/0344847 A1 | 12/2018 | Dupont et al. |
| 2018/0355030 A1 | 12/2018 | Greene et al. |
| 2018/0369380 A1 | 12/2018 | Gragoudas et al. |
| 2018/0371072 A1 | 12/2018 | Theuer et al. |
| 2019/0000919 A1 | 1/2019 | Brockmeyer et al. |
| 2019/0011455 A1 | 1/2019 | Lebert et al. |
| 2019/0016817 A1 | 1/2019 | Taddei et al. |
| 2019/0031750 A1 | 1/2019 | Koenig et al. |
| 2019/0031783 A1 | 1/2019 | Gu et al. |
| 2019/0062444 A1 | 2/2019 | Walsh et al. |
| 2019/0085056 A1 | 3/2019 | Lebert et al. |
| 2019/0091331 A1 | 3/2019 | Yang et al. |
| 2019/0100581 A1 | 4/2019 | Koenig et al. |
| 2019/0100582 A1 | 4/2019 | Blumenkran et al. |
| 2019/0127454 A1 | 5/2019 | Yang et al. |
| 2019/0127455 A1 | 5/2019 | Simpson et al. |
| 2019/0142975 A1 | 5/2019 | Keravala et al. |
| 2019/0153119 A1 | 5/2019 | Migone et al. |
| 2019/0153471 A1 | 5/2019 | Paul et al. |
| 2019/0161549 A1 | 5/2019 | Choong |
| 2019/0185555 A1 | 6/2019 | Swamy et al. |
| 2019/0194713 A1 | 6/2019 | Mandell et al. |
| 2019/0202904 A1 | 7/2019 | Fellouse et al. |
| 2019/0211091 A1 | 7/2019 | Simpson et al. |
| 2019/0216945 A1 | 7/2019 | Yang et al. |
| 2019/0218263 A1 | 7/2019 | Trese et al. |
| 2019/0224046 A1 | 7/2019 | Heitzmann et al. |
| 2019/0231986 A1 | 8/2019 | Devaraneni |
| 2019/0233517 A1 | 8/2019 | Wu |
| 2019/0255074 A1 | 8/2019 | Song et al. |
| 2019/0255155 A1 | 8/2019 | Perlroth et al. |
| 2019/0256556 A1 | 8/2019 | Giese et al. |
| 2019/0262476 A1 | 8/2019 | Lorenz et al. |
| 2019/0231799 A1 | 9/2019 | Peters et al. |
| 2019/0270806 A1 | 9/2019 | Jacobson et al. |
| 2019/0292239 A1 | 9/2019 | Carter et al. |
| 2019/0300607 A1 | 10/2019 | Isumi |
| 2019/0307691 A1 | 10/2019 | Gaillard et al. |
| 2019/0321467 A1 | 10/2019 | Santos et al. |
| 2019/0322732 A1 | 10/2019 | Murakami et al. |
| 2019/0330335 A1 | 10/2019 | Schwabe et al. |
| 2019/0336482 A1 | 11/2019 | Boyd |
| 2019/0343918 A1 | 11/2019 | Graham et al. |
| 2019/0358335 A1 | 11/2019 | Russell et al. |
| 2019/0360027 A1 | 11/2019 | Perlee et al. |
| 2019/0381008 A1 | 12/2019 | Zeitz et al. |
| 2019/0381194 A1 | 12/2019 | Tretiakova et al. |
| 2019/0388522 A1 | 12/2019 | Burian et al. |
| 2020/0002411 A1 | 1/2020 | Famili et al. |
| 2020/0002426 A1 | 1/2020 | Sheng et al. |
| 2020/0048341 A1 | 2/2020 | Ghosh et al. |
| 2020/0055923 A1 | 2/2020 | Torella et al. |
| 2020/0055933 A1 | 2/2020 | Hailman et al. |
| 2020/0055958 A1 | 2/2020 | Chen et al. |
| 2020/0057058 A1 | 2/2020 | Olsen et al. |
| 2020/0086139 A1 | 3/2020 | Das et al. |
| 2020/0087389 A1 | 3/2020 | Theuer et al. |
| 2020/0095309 A1 | 3/2020 | Peters |
| 2020/0095310 A1 | 3/2020 | Regula et al. |
| 2020/0171179 A1 | 6/2020 | Charles et al. |
| 2020/0261590 A1 | 8/2020 | Charles et al. |
| 2020/0262905 A1 | 8/2020 | Perlroth et al. |

FOREIGN PATENT DOCUMENTS

| | | |
|---|---|---|
| AU | 2015207898 | 8/2015 |
| AU | 2017201930 | 4/2017 |

(56) References Cited

FOREIGN PATENT DOCUMENTS

| | | |
|---|---|---|
| BR | 11 2012 014556 | 3/2017 |
| BR | 11 2012 0261185 | 8/2017 |
| CA | 2783615 | 6/2011 |
| CA | 2795667 | 10/2011 |
| CL | 02881/2012 | 7/2013 |
| CN | 101389690 | 3/2009 |
| CN | 102250246 A | 11/2011 |
| CN | 102311502 | 11/2012 |
| CN | 102811713 | 12/2012 |
| CN | 103134874 | 6/2013 |
| CN | 103193819 | 7/2013 |
| CN | 103421039 | 12/2013 |
| CN | 103492489 | 1/2014 |
| CN | 103898101 | 7/2014 |
| CN | 106075466 | 11/2016 |
| CN | 106432557 | 2/2017 |
| CN | 106905431 A | 6/2017 |
| CN | 107208076 | 9/2017 |
| CN | 107428824 | 12/2017 |
| CN | 108712911 A | 10/2018 |
| CO | 12119310 | 12/2012 |
| CO | 12203725 | 2/2013 |
| EP | 0345242 | 12/1989 |
| EP | 0282610 | 5/1995 |
| EP | 0577648 | 6/2001 |
| EP | 0968291 | 1/2004 |
| EP | 1179541 | 6/2004 |
| EP | 0929323 | 12/2004 |
| EP | 1325932 | 4/2005 |
| EP | 0971959 | 12/2005 |
| EP | 0973804 | 12/2006 |
| EP | 1465933 | 8/2007 |
| EP | 1135498 | 1/2008 |
| EP | 1592719 | 3/2008 |
| EP | 1988910 | 11/2008 |
| EP | 1605847 | 9/2009 |
| EP | 1732621 | 12/2009 |
| EP | 1968594 | 9/2010 |
| EP | 2260873 | 12/2010 |
| EP | 1802373 | 7/2011 |
| EP | 2301580 | 1/2012 |
| EP | 1660057 | 5/2012 |
| EP | 2029746 | 7/2012 |
| EP | 1802334 | 8/2012 |
| EP | 2329821 | 8/2012 |
| EP | 2512462 | 10/2012 |
| EP | 2203180 | 11/2012 |
| EP | 2199306 | 6/2013 |
| EP | 2155783 B1 | 7/2013 |
| EP | 2446890 | 9/2013 |
| EP | 2344537 | 1/2014 |
| EP | 2274008 | 2/2014 |
| EP | 2042597 | 5/2014 |
| EP | 2524693 | 5/2014 |
| EP | 2540843 | 7/2014 |
| EP | 1991275 | 11/2014 |
| EP | 2443150 | 1/2015 |
| EP | 1802325 | 2/2015 |
| EP | 1989231 | 5/2015 |
| EP | 2217261 | 10/2015 |
| EP | 2596807 | 12/2015 |
| EP | 2200700 | 1/2016 |
| EP | 2307055 | 1/2016 |
| EP | 2259795 | 4/2016 |
| EP | 2516465 | 5/2016 |
| EP | 1763365 B1 | 8/2016 |
| EP | 2411411 | 8/2016 |
| EP | 2575881 | 9/2016 |
| EP | 2473526 | 8/2017 |
| EP | 2491134 | 8/2017 |
| EP | 3222142 | 9/2017 |
| EP | 2327415 | 10/2017 |
| EP | 2785744 | 10/2017 |
| EP | 2188302 | 11/2017 |
| EP | 2467156 | 11/2017 |
| EP | 2894167 | 11/2017 |
| EP | 2925778 | 11/2017 |
| EP | 2784092 | 12/2017 |
| EP | 3254678 | 12/2017 |
| EP | 2792687 | 5/2018 |
| EP | 2319925 | 7/2018 |
| EP | 2662388 | 8/2018 |
| EP | 2872534 | 8/2018 |
| EP | 3122878 | 10/2018 |
| EP | 3401331 | 11/2018 |
| EP | 1861096 | 12/2018 |
| EP | 2726612 | 3/2019 |
| EP | 3038647 | 3/2019 |
| EP | 3020731 | 6/2019 |
| EP | 2924052 | 7/2019 |
| EP | 2846836 | 8/2019 |
| EP | 3327026 | 8/2019 |
| EP | 2951307 | 12/2019 |
| EP | 3450553 | 12/2019 |
| EP | 3600441 | 2/2020 |
| EP | 3038646 | 3/2020 |
| EP | 3104880 | 3/2020 |
| EP | 3216803 | 3/2020 |
| GB | 2200651 | 8/1988 |
| JP | H04-502850 | 5/1992 |
| JP | H10 139832 | 5/1998 |
| JP | H11 217588 | 8/1999 |
| JP | 2003-064132 | 3/2003 |
| JP | 2005-239989 | 9/2005 |
| JP | 2005-255969 | 9/2005 |
| JP | 2006-503549 | 2/2006 |
| JP | 2007-263935 | 10/2007 |
| JP | 2007-531513 | 11/2007 |
| JP | 2008-133434 | 6/2008 |
| JP | 2008-524247 | 7/2008 |
| JP | 2008-536496 | 9/2008 |
| JP | 2009-042617 | 2/2009 |
| JP | 2009-532330 | 9/2009 |
| JP | 2009-533519 | 9/2009 |
| JP | 2009-542862 | 12/2009 |
| JP | 2009-543895 | 12/2009 |
| JP | 2010-117189 | 5/2010 |
| JP | 2010-279389 | 12/2010 |
| JP | 2011-50073 | 1/2011 |
| JP | 2011501945 A | 1/2011 |
| JP | 2011-518546 | 5/2011 |
| JP | 2012-025820 | 2/2012 |
| JP | 2012-521768 | 9/2012 |
| JP | 2013-515099 | 5/2013 |
| JP | 2013-519699 | 5/2013 |
| JP | 2013-534931 | 9/2013 |
| JP | 2014-043456 | 3/2014 |
| JP | 2014043405 | 3/2014 |
| JP | 5528710 | 6/2014 |
| JP | 2015502397 A | 1/2015 |
| JP | 5760007 | 6/2015 |
| JP | 5745009 | 7/2015 |
| JP | 2016-14015 | 1/2016 |
| JP | 5846044 | 1/2016 |
| JP | 2016-040371 | 3/2016 |
| JP | 5990629 | 8/2016 |
| JP | 2016-530302 | 9/2016 |
| JP | 2017-31410 | 2/2017 |
| JP | 2018-87330 | 6/2018 |
| JP | 6416832 | 10/2018 |
| KR | 10-0808116 | 3/2008 |
| KR | 20120123340 | 11/2012 |
| KR | 2013-0097636 | 9/2013 |
| KR | 10-1852044 | 4/2018 |
| MX | 2012006970 | 10/2012 |
| MX | 2012011876 | 11/2012 |
| MX | 346423 | 3/2017 |
| MX | 2016017290 | 8/2017 |
| WO | WO 1987/04462 | 7/1987 |
| WO | WO 1990/07936 | 7/1990 |
| WO | WO 1990/11092 | 10/1990 |
| WO | WO 1991/02805 | 3/1991 |
| WO | WO 91/10741 | 7/1991 |
| WO | WO 1991/14445 | 10/1991 |

(56) References Cited

FOREIGN PATENT DOCUMENTS

| | | |
|---|---|---|
| WO | WO 91/17271 | 11/1991 |
| WO | WO 92/01047 | 1/1992 |
| WO | WO 1993/03769 | 3/1993 |
| WO | WO 1993/10218 | 5/1993 |
| WO | WO 93/12227 | 6/1993 |
| WO | WO 1993/11230 | 6/1993 |
| WO | WO 1993/19191 | 9/1993 |
| WO | WO 93/25673 | 12/1993 |
| WO | WO 1993/25234 | 12/1993 |
| WO | WO 1993/25698 | 12/1993 |
| WO | WO 1994/03622 | 2/1994 |
| WO | WO 1994/016748 | 8/1994 |
| WO | WO 1994/23697 | 10/1994 |
| WO | WO 1994/12649 | 11/1994 |
| WO | WO 1994/28938 | 12/1994 |
| WO | WO 1995/00655 | 1/1995 |
| WO | WO 1995/07994 | 3/1995 |
| WO | WO 1995/13796 | 5/1995 |
| WO | WO 1995/11984 | 7/1995 |
| WO | WO 1995/30763 | 11/1995 |
| WO | WO 1996/17072 | 6/1996 |
| WO | WO 97/14702 | 4/1997 |
| WO | WO 97/14703 | 4/1997 |
| WO | WO 1997/37029 | 10/1997 |
| WO | WO 1997/42338 | 11/1997 |
| WO | WO 98/45331 | 10/1998 |
| WO | WO 99/42133 A1 | 8/1999 |
| WO | WO 1999/064065 | 12/1999 |
| WO | WO 2000/09560 | 5/2000 |
| WO | WO 2000/034337 | 6/2000 |
| WO | WO 2000/059968 | 10/2000 |
| WO | WO200100854 A2 | 1/2001 |
| WO | WO 0141827 | 6/2001 |
| WO | WO 2002/028929 | 4/2002 |
| WO | WO2003020906 A2 | 3/2003 |
| WO | WO 2003/062290 | 7/2003 |
| WO | WO 2003/074026 | 9/2003 |
| WO | WO 2003/074090 | 9/2003 |
| WO | WO 2004/003144 A2 | 1/2004 |
| WO | WO 2004/020405 | 3/2004 |
| WO | WO 2004/063237 | 7/2004 |
| WO | WO 2004/065417 | 8/2004 |
| WO | WO 2004/091494 | 10/2004 |
| WO | WO 2004/113394 | 12/2004 |
| WO | WO 2005/028539 | 3/2005 |
| WO | WO 2005/058367 | 6/2005 |
| WO | WO 2005/120166 A2 | 12/2005 |
| WO | WO 2006/063055 | 6/2006 |
| WO | WO 2006/118547 | 11/2006 |
| WO | WO 2007/005253 | 1/2007 |
| WO | WO 2007/011873 | 1/2007 |
| WO | WO 2007/075534 | 7/2007 |
| WO | WO 2007/100902 | 9/2007 |
| WO | WO 2007/1112675 | 10/2007 |
| WO | WO 2008/020827 | 2/2008 |
| WO | WO 2008/025856 | 3/2008 |
| WO | WO 2008/055206 A2 | 5/2008 |
| WO | WO 2008/098930 | 8/2008 |
| WO | WO 2008/112257 | 9/2008 |
| WO | WO 2008/112289 | 9/2008 |
| WO | WO 2008/119565 A2 | 10/2008 |
| WO | WO 2008/119567 A2 | 10/2008 |
| WO | WO 2008/144248 | 11/2008 |
| WO | WO 2008/155134 | 12/2008 |
| WO | WO 2009/052249 | 4/2009 |
| WO | WO 2005/047334 | 5/2009 |
| WO | WO 2009/052439 | 6/2009 |
| WO | WO 2009/092011 | 7/2009 |
| WO | WO 2009/105669 | 8/2009 |
| WO | WO 2009/134711 A1 | 11/2009 |
| WO | WO 2009/138473 | 11/2009 |
| WO | WO09149205 A2 | 12/2009 |
| WO | WO 2010/040508 | 4/2010 |
| WO | WO 2010/068862 | 6/2010 |
| WO | WO 2010/068864 | 6/2010 |
| WO | WO 2010/085542 | 7/2010 |
| WO | WO 2010/111625 | 9/2010 |
| WO | WO2010136492 A2 | 12/2010 |
| WO | WO 01/18080 | 3/2011 |
| WO | WO 2011/057014 A1 | 5/2011 |
| WO | WO 2011/075185 | 6/2011 |
| WO | WO 2011/075736 | 6/2011 |
| WO | WO 2011/101284 | 6/2011 |
| WO | WO 2011/116387 | 9/2011 |
| WO | WO 2011/119656 | 9/2011 |
| WO | WO 2011/130694 | 10/2011 |
| WO | WO 2011/153243 | 12/2011 |
| WO | WO 2012/145746 A1 | 10/2012 |
| WO | WO2012146610 A1 | 11/2012 |
| WO | WO 2013/051937 | 4/2013 |
| WO | WO 2013/059137 | 4/2013 |
| WO | WO2013071016 A2 | 5/2013 |
| WO | WO 2013/093809 | 6/2013 |
| WO | WO2013082563 | 6/2013 |
| WO | WO 2013/173129 | 11/2013 |
| WO | WO2014006113 A1 | 1/2014 |
| WO | WO2014033184 A1 | 3/2014 |
| WO | WO 2014/060401 | 4/2014 |
| WO | WO 2014/068443 A1 | 5/2014 |
| WO | WO 2014/072888 A1 | 5/2014 |
| WO | WO2014101287 A1 | 7/2014 |
| WO | WO 2014/160507 | 10/2014 |
| WO | WO 2014/177460 | 11/2014 |
| WO | WO2015004616 A1 | 1/2015 |
| WO | WO 2015/035342 | 3/2015 |
| WO | WO2015058048 A1 | 4/2015 |
| WO | WO2015058369 A1 | 4/2015 |
| WO | WO2015059220 A1 | 4/2015 |
| WO | WO 2015/109898 | 7/2015 |
| WO | WO2015109898 A1 | 7/2015 |
| WO | WO2015110067 A1 | 7/2015 |
| WO | WO 2015/135583 | 9/2015 |
| WO | WO 2015/168468 A1 | 11/2015 |
| WO | WO2015168321 A2 | 11/2015 |
| WO | WO 2015/200905 | 12/2015 |
| WO | WO2015198240 A2 | 12/2015 |
| WO | WO2015198243 A2 | 12/2015 |
| WO | WO2016008975 A1 | 1/2016 |
| WO | WO2016044041 A1 | 3/2016 |
| WO | WO2016045626 A1 | 3/2016 |
| WO | WO 2016/061562 | 4/2016 |
| WO | WO 2016/073157 | 5/2016 |
| WO | WO2016073894 A1 | 5/2016 |
| WO | WO2016085750 A1 | 6/2016 |
| WO | WO2016145189 A1 | 9/2016 |
| WO | WO 2016/160923 A1 | 10/2016 |
| WO | WO 2016/170039 | 10/2016 |
| WO | WO 2017/046140 | 3/2017 |
| WO | WO 2017/075173 A2 | 5/2017 |
| WO | WO 2017/117464 | 7/2017 |
| WO | WO 2017/120600 | 7/2017 |
| WO | WO 2017/120601 | 7/2017 |
| WO | WO 2017/129064 A1 | 8/2017 |
| WO | WO 2017/204298 | 11/2017 |
| WO | WO 2017/205559 | 11/2017 |
| WO | WO 2018/114728 | 6/2018 |
| WO | WO 2018/122053 | 7/2018 |
| WO | WO 2018/139991 | 8/2018 |
| WO | WO 2018/175319 | 9/2018 |
| WO | WO 2018/175752 | 9/2018 |
| WO | WO 2018/182527 | 10/2018 |
| WO | WO 2018/185110 | 10/2018 |
| WO | WO 2018/191548 | 10/2018 |
| WO | WO 2018/217995 | 11/2018 |
| WO | WO 2018/218215 | 11/2018 |
| WO | WO 2019/020777 | 1/2019 |
| WO | WO 2019/038552 | 2/2019 |
| WO | WO 2019/040397 | 2/2019 |
| WO | WO 2019/043649 | 3/2019 |
| WO | WO 2019/057946 | 3/2019 |
| WO | WO 2019/067540 | 4/2019 |
| WO | WO 2019/091384 | 5/2019 |
| WO | WO 2019/099786 | 5/2019 |
| WO | WO 2019/104279 | 5/2019 |

(56) References Cited

FOREIGN PATENT DOCUMENTS

| WO | WO 2019/113225 | 6/2019 |
|---|---|---|
| WO | WO 2019/134686 | 7/2019 |
| WO | WO 2019/147944 | 8/2019 |
| WO | WO 2019/154349 | 8/2019 |
| WO | WO 2019/154776 | 8/2019 |
| WO | WO 2019/164219 | 8/2019 |
| WO | WO 2019/020418 | 9/2019 |
| WO | WO 2019/169341 | 9/2019 |
| WO | WO 2019/173482 | 9/2019 |
| WO | WO 2019/175727 | 9/2019 |
| WO | WO 2019/178438 | 9/2019 |
| WO | WO 2019/184909 | 10/2019 |
| WO | WO 2019/195313 | 10/2019 |
| WO | WO 2019/200181 | 10/2019 |
| WO | WO 2019/201866 | 10/2019 |
| WO | WO 2019/204380 | 10/2019 |
| WO | WO 2019/229116 | 12/2019 |
| WO | WO 2020/006486 | 1/2020 |
| WO | WO 2020/043184 | 3/2020 |

OTHER PUBLICATIONS

De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Office Action dated Jun. 4, 2019 in Japanese Patent Application No. JP 2016-575823.
Advisory Action dated Apr. 18, 2019 in U.S. Appl. No. 15/394,500.
Office Action dated May 14, 2019 U.S. Appl. No. 15/099,234.
Office Action dated Apr. 23, 2019 in Korean Patent Application No. KR 10-2017-7013268.
U.S. Appl. No. 09/253,689, filed Feb. 20, 1999, Fung et al.
Alconcel, S.N.S. et al., "FDA-approved poly(ethylene glycol)-protein conjugate drugs," www.rsc.org/polymers, Polymer Chemistry, vol. 2, Issue 7, pp. 1442, 2011.
Alley, S. et al., "Contribution of linker stability to the activities of anticancer immunoconjugates," Bioconjugate Chem., vol. 19, No. 3, pp. 759-765, 2008.
Altamirano, C.V. et al., "Association of tetramers of human butyrylcholinesterase is mediated by conserved aromatic residues of the carboxy terminus," Chemico-Biological Interactions, vols. 119-120, pp. 53-60, May 14, 1999.
Anderson, W.F., "Human gene therapy," Science, vol. 256, No. 5058, pp. 808-813, May 8, 1992.
Baldwin, A. et al., "Reversible maleimide-thiol adducts yield glutathione-sensitive poly(ethylene glycol)-heparin hydrogels," Polymer Chemistry, vol. 4, Issue 1, pp. 133-143, Jan. 7, 2013.
Baldwin, A. et al. "Tunable degradation of maleimide-thiol adducts in reducing environments," Bioconjug Chem, vol. 22, No. 10, pp. 1946-1953, Oct. 19, 2011.
Blong, M. Renee et al., "Tetramerization domain of human butyrylcholinesterase is at the C-terminus," Biochemical Journal, vol. 327, No. 3, pp. 747-757, Nov. 1, 1997.
Bontempo, et al., "Cysteine-Reactive Polymers Synthesized by Atom Transfer Radical Polymerization for Conjugation to Proteins," J. Am. Chem. Soc. (2004), 126, pp. 15372-15373.
Cannard, K., "The acute treatment of nerve agent exposure," Journal of the Neurological Sciences, vol. 249, Issue 1, pp. 86-94.
Capon, D. et al., "Designing CD4 immunoadhesins for AIDS therapy," Nature, vol. 337, pp. 525-531, 1989.
Cascio, C. et al., "Use of serum cholinesterases in severe organophosphorus poisoning," Minerva Anestesiologica, vol. 54, in 6 pages, 1988.
Casset, F. et al. A Peptide Mimetic of an Anti0CD4 Monoclonal Antibody by Rational Design, Biochemical and Biophysical Research Communications, vol. 307, pp. 198-205, (2003).
Chen, et al., "Lubrication at Physiological Pressures by Polyzwitterionic Brushes," Science, (2009), 323, pp. 1698-1701.
Chen, et al. "Polymeric Phosphorylcholine-Camptothecin Conjugates Prepared by Controlled Free Radical Polymerizationand Click Chemistry," Bioconjugate Chem., (2009), 20:12, pp. 2331-2341.
Chen, Y et al. Selection and Analysisi an Optimized Anti-VEGF Antibody: Crystal Structure of an Affinity-Matured Complex with Antigen, J. Mol. Biol vol. 293, pp. 865-881, (1999).
Chothia, C. et al., "Conformations of immunoglobulin hypervariable regions," Nature, vol. 342, pp. 877-883, Dec. 1989.
Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Daneshian, M. et al., "In vitro pyrogen test for toxic or immunomodulatory drugs," Journal of Immunological Methods, vol. 313, Issues 1-2, pp. 169-175, Jun. 30, 2006.
Ding, J.L. et al., "A new era of pyrogen testing," Trends in Biotechnology, vol. 19, Issue 8, pp. 277-281, Aug. 1, 2001.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Du et al. "pH-Sensitive Vesicles based on a Biocompatible Zwitterionic Diblock Copolymer" J. Am. Chem. Soc., Dec. 1, 2005, 127, 17982-17983.
Ellman, G. et al., "A new and rapid colorimetric determination of acetylcholinesterase activity," Biochemical Pharmacology, vol. 7, Issue 2, pp. 88-95, Jul. 1961.
Engelgau, M et al. Evolving Diabetes Burden in the United States. Ann of Int Med. 140 (11): 945-951, 2004.
"Facts About Diabetic Eye Disease", National Eye Institute, https://nei.nih.gov/health/diabetic/retinopathy, publication reviewed Sep. 2015, accessed Mar. 27, 2018, in 7 pages. The reference is a webpage, aApplicants note that the webpage was printed on Mar. 27, 2018, and has a copyright date of 2015 ; however, the webpage may have been available, in some form, prior to this date.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Foster, Graham R., "Pegylated interferons for the treatment of chronic Hepatitis C," Drugs, vol. 70, Issue 2, pp. 147-165, Jan. 2010.
Gillies, et al., "Dendrimers and Dedritic Polymers in Drug Delivery," Drug Delivery today, Jan. 2005, vol. 10, No. 1, pp. 35-43.
Goodson, R.J. et al., "Site-directed pegylation of recombinant interleukin-2 at its glycosylation site," Nature Biotechnology, vol. 8, pp. 343-346, 1990.
Goel, N. et al., "Certolizumab pegol," mAbs, vol. 2, No. 2, pp. 137-147, Mar. /Apr. 2010.
Gordon, M. et al., "Determinatino of the normality of cholinesterase solutions," Analytical Biochemistry, vol. 85, Issue 2, pp. 519-527, Apr. 1978.
Gorun, V. et al., "Modified Ellman procedure for assay of cholinesterases in crude enzymatic preparations," Analytical Biochemistry, vol. 86, Issue 1, pp. 324-326, May 1978.
Greene T.W. et al., "Protective Groups in Organic Synthesis," 3rd Edition, John Wiley and Sons, Inc., New York, 1999.
Gualberto, Antonio, "Brentuximab Vedotin (SGN-35), an antibody-drug conjugate for the treatment of CD30-positive malignancies," Expert Opinion on Investigational Drugs, vol. 21, Issue 2, pp. 205-216, 2012.

(56) References Cited

OTHER PUBLICATIONS

Haddleton, et al., "Phenolic Ester-Based Initiators for Transition Metal Mediated Living Polymerization," Macromolecules, (1999), 32, pp. 8732-8739.

Haupt, H. et al., "Isolierung and physikalisch-chemische Charakterisierung der Cholinesterase aus Humanserum," Blut, vol. 14, Issue 2, pp. 65-75, Nov. 1966.

Heise et al., "Starlike Polymeric Architectures by Atom Transfer Radical Polymerization: Templates for the Production of Low Dielectric Constant Thin Films," Macromolecules, Jan. 17, 2000, 33:2346-2354.

Heise, et al., "Investigation of the Initiation Behavior of a Dendritic 12-Arm Initiator in Atom Transfer Radical Polymerization," Macromolecules, (2001), 34:11, pp. 3798-3801.

Heredia, et al., In Situ Preparation of Protein-'Smart' Polymer Conjugates with Retention of Bioactivity, J. Am. Chem. Soc., (2005), 127, pp. 16955-16960.

Hoffmann, S. et al., "International validation of novel pyrogen tests based on human monocytoid cells," Journal of Immunological Methods, vol. 298, Issues 1-2, pp. 161-173, Mar. 2005.

Holash, J et al. VEGF-Trap: A VEGF Blocker with Potent Antitumor Effects, PNAS, vol. 9, No. 17, pp. 11393-11398, (2002).

Holliger, P. et al., "'Diabodies': small bivalent and bispecific antibody fragments," Proc. Natl. Acad. Sci. USA, vol. 90, No. 14, pp. 6444-6448, Jul. 15, 1993.

Hong, et al., "Preparation of Segmented Copolymers in the Presence of an Immobilized/Soluble Hybrid ATRP Catalyst System," Macromolecules, (2003), 36:1, pp. 27-35.

Huang, Y.J. et al., "Recombinant human butyrylcholinesterase from milk of transgenic animals to protect against organophosphate poisoning," PNAS, vol. 104, No. 34, pp. 13603-13608, Aug. 21, 2007.

Huang, Y-S. et al., "Engineering a pharmacologically superior form of granulocyte-colony-stimulating factor by fusion with gelatinlike-protein polymer," European Journal of Pharmaceutics and Biopharmaceutics, vol. 74, Issue 3, pp. 435-441, Mar. 2010.

Huston, James S., "Protein engineering of single-chain Fv analogs and fusion proteins," Methods of Enzymology, vol. 203, pp. 46-96, 1991.

Beranger, et al., IMGT Scientifitc Chart, http://www.imgt.org/IMGTScientificChart/Numbering/Hu_IGHGnber.html, created May 5, 2001.

IUPAC Gold Book, Random Copolymerization, available at https://goldbook.iupac.org/html/R/R05126.html, Feb. 24, 2014 The reference is a webpage, aApplicants note that the webpage was printed on Nov. 21, 2017, and has a copyright date of 2014 ; however, the webpage may have been available, in some form, prior to this date.

Iwasaki, et al., "Platelet compatible blood filtration fabrics using a phosphorylcholine polymer having high surface mobility ," Biomaterials, (2003), 24 pp. 3599-3604.

Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.

Jaffe, G. et al., "Intraocular drug delivery," CRC Press, Mar. 2006.

Jakubowski, et al., "Activators Regenerated by Electron Transfer for Atom Transfer Radical Polymerization of Styrene," Macromolecules, (2006), 39:1, pp. 39-45.

Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.

Janssen, Alzheimer Immunotherapy Research & Development, LLC, AAB-001 in Patients With Mild to Moderate Alzheimer's Diesear, Clinical Trials, gov, NIH, 2005, [retrieved on Jun. 19, 2012]. Retreived from the Internet: <http://clinicaltrials.gov/ct2/show/NCT00112073?term=aab-001&rank=3>.

Jeon, et al., "Synthesis of High Molecular Weight 3-Arm Star PMMA by ARGET ATRP," Macromolecular, 17:4 pp. 240-244, (2009).

Jones, A., Analysis of Polypeptides and Proteins, Adv. Drug Delivery Rev. 10:, pp. 29-90, (1993).

Kabat, E.A. et al., "Sequences of proteins of immunological interest," in 10 pages, 1991 (includes title page and table of contents only).

Kallis, G.B. et al., "Differential reactivity of the functional sulfhydryl groups of cysteine-32 and cysteine-35 present in the reduced form of thioredoxin from *Escherichia coli*.," The Journal of Biological Chemistry, vol. 255, No. 21, pp. 10261-10266, Nov. 10, 1980.

Kempen, J, et al. The Prevalence of Diabetic Retinopathy Among Adults in the United States, Arch Opthalmol., vol. 122, pp. 532-563, (2004).

Kizhakkedathu, et al., "Synthesis of Well-Defined Environmentally Responsive Polymer Brushes by Aqueous ATRP," Macromolecules, (2004), 37:3, pp. 734-743.

Kwiatdowski, et al., "High Molecular Weight Polymethacrylates by AGET ATRP under High Pressure," Macromolecules, (2008), 41:4, pp. 1067-1069.

Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.

Lee, Ernes C., "Clinical manifestations of sarin nerve gas exposure," J. Am. Med. Assoc., vol. 290, No. 5, pp. 659-662, Aug. 6, 2003.

Lee, Vincent H.L., "Peptide and Protein Drug Delivery," CRC Press, 1990.

Lena, et al., "Investigation of metal ligand affinities of atom transfer radical polymerization catalysts with a quadrupole ion trap," Dalton Transactions, (2009), 41, pp. 8884-8889.

Lewis, et al., "Crosslinkable coatings from phosphorylcholinebased polymers," Biomaterials, (2001), 22, pp. 99-111.

Lewis, et al., "Poly(2-methacryloyloxyethyl phosphorylcholine) for Protein Conjugation," Bioconjugate Chem., (2008), 19:11, pp. 2144-2155.

Lin, Weifeng et al., "A novel zwitterionic copolymer with a short poly(methyl acrylic acid) block for improving both conjugation and separation efficiency of a protein without losing its bioactivity". Journal of Materialos Chemistry B. May 21, 2013, vol. 1, No. 19, pp. 2482-2488. See abstract; and p. 2487.

Lindley, H., "A study of the kinetics of the reaction between thiol compounds and chloroacetamide," Biochem J., vol. 74, pp. 577-584, Mar. 1960.

Liu, et al., "Syntheses and Micellar Properties of Well-Defined Amphiphilic $AB_2$ and $A_2B$ Y-Shaped Miltoarm Star Copolymers of ε-Caprolactone and 2-(Dimethylamino) ethyl Methacdrylate," *Journal of Polymer Science: Part A: Polymer Chemistry*, DOI 10.1002/pola, published online in Wiley InterSciences (www.intersience.wiley.com), Sep. 22, 2006; accepted Nov. 23, 2006.

Lockridge, O. et al., "Complete amino acid sequence of human serum cholinesterase," The Journal of Biological Chemistry, vol. 262, pp. 549-557, Jan. 15, 1987.

Lockridge, O. et al., "Large scale purification of butyrylcholinesterase from human plasma suitable for injection into monkeys; A potential new therapeutic for protection against cocaine and nerve agent toxicity," The Journal of Medical, Chemical, Biological, and Radiological Defense, 3:nimhs5095, doi: 10.1901/jaba.2005.3-nihms5095, 2005.

Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.

Luxon, B. et al, "Pegylated interferons for the treatment of chronic hepatitis C infection," Clinical Therapeutics, vol. 24, Issue 9, pp. 1363-1383, Sep. 2002.

Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.

Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.

(56) References Cited

OTHER PUBLICATIONS

Maccallum, R. et al., Antibody-Antigen Interactions: Contact Analysis and Binding Site Toopgraphy, J/. Mol Biol., vol. 262, pp. 732-745, (1996).

Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.

Matyjaszewski, et al., "Diminishing catalyst concentration in atom transfer radical polymerization with reducing agents," PNAS, (Oct. 17, 2006), 103:42, pp. 15309-15314.

Mayadunne, R. et al. Living Free Radical Polymerization with Reversible Addition-Fragmentation Chain Transfer (RAFT Polymerization): Approaches to Star Polymers, Macromolecules, vol. 36, pp. 1505-1513, (2003).

Mcpherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.

McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).

Meng, X. et al. New Generation Recombinant hBuChe-FC Fusion with In-Vivo Performance Equivilanet to Gold Standard Plasma-Derive hbuChe-A First-in-Class Broad Spectrum Bioscanvenger that is Sustainable, Scalable, and Highly Cost-Effective on a Troop-Equivalent-Dose (TED) Basis.

Millard, C.B. et al., "Design and expression of organophosphorus acid anhydride hydrolase activity in human butyrylcholinesterase," Biochemistry, vol. 34, No. 49, pp. 15925-15933, 1995.

Min, et al., "Use of Ascorbic Acid as Reducing Agent for Synthesis of Well-Defined Polymers by ARGET ATRP," Macromolecules, (2007), 40:6, pp. 1789-1791.

Miyamoto, et al., "Effect of water-soluble Phospholipid polymers conjugated with papain on the enzymatic stability," Biomaterials, (2004), 25, pp. 71-76.

Ng, et al., "Successful Cu-Mediated Atom Transfer Radical Polymerization in the Absence of Conventional Chelating Nitrogen Ligans," Macromolecules, (2010), 43:2, pp. 592-594.

Ogikubo, Y. et al., "Evaluation of the bacterial endotoxin test for quantification of endotoxin contamination of porcine vaccines," Biologicals, vol. 32, Issue 2, pp. 88-93, Jun. 2004.

Oh, et al., "Preparation of Poly(oligo(ethylene glycol) monomethyl ether methacrylate) by Homogeneous Aqueous AGET ATRP," Macromolecules, (2006), 39:9, pp. 3161-3167.

Palma, et al., "A new bispphosphonate-containing [99]mTc(I) tricarbonyl complex potentially useful as bone-seeking agent: synthesis and biological evaluation," J Biol Inorg Chem, 12:667-679, (2007).

Pasut, et al., "Protein peptide and non-peptide drug PEGylation for therapeutic application," Expert Opin. Ther. Patents, 14(6) 859-894 (2004).

Pennock, S. et al Vascular Endothelial Growth Factor A Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).

Piedmonte, D. et al., "Formulation of Neulasta® (pegfilgrastim)," Advanced Drug Delivery Reviews, vol. 60, Issue 3, pp. 50-58, Jan. 3, 2008.

Pietrasik, et al., "Synthesis of High Molecular Weight Poly(styrene-co-acrylonitrile) Copolymers with Controlled Architecture," Macromolecules, (2006), 39:19, pp. 6384-6390.

Poljak, R. "Production and structure of diabodies," Structure, vol. 2, Issue 12, pp. 1121-1123, Dec. 1994.

Pratt, et al. End-Functionalized Phosphorycholine Methacrylate and Their Use in Protein Conjugation, Biomacromlecules, vol. 9, pp. 2891-2897, (2008).

Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.

*Regeneron Pharmaceuticals Inc.* vs. *Bayer Pharma AG* Approved Judgment dated Feb. 21, 2013.

Roberts et al., "Chemistry for Peptide and Protein PEGylation," Advanced Drug Delivery Reviews 2002 54:459-476.

Robinson, K. et al. Controlled Polymerization of 2-Hydroxyethyl Methacrylate by ATRP at Ambient Temperature, Macromolecules, vol. 34, pp. 3155-3158, (2001).

Rudikoff, S. et al, Single Amino Acid Substituon Altering Antigen-Bidning Specificity, Proc Natl. Acad. Sci. USA, vol. 79, pp. 1979-1983, (1982).

Ruiz, et al., "Synthesis structure and surface dynamics of phosphorylcholine functional biomimicking polymers," Biomaterials, (1998), 19, pp. 987-998.

Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.

Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.

Samanta, et al. "End-Functionalized Phosphorylcholine Methacrylates and their Use in Protein Conjugation," Biomacromolecules, (2008), 9:(10), pp. 2891-2897.

Sayers, et al., "The Reduced Viscosity of PolyPEG® Compared with Linear PEG," WEP designer polymers, www.wep-ltd.co.uk, in 1 page, Feb. 11, 2009.

Schellenberger, V. et al., "A recombinant polypeptide extends the in vivo half-life of peptides and proteins in a tunable manner," Nature Biotechnology, vol. 27, pp. 1186-1190, 2009.

Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.

Seo et al., "Conformational Recovery and Preservation of Protein Nature from Heat-Induced Debaturation by Water-Soluble Phospholipid Plymer Conjugation," Biomaterials, vol. 30, 2009, pp. 4859-4867.

Shen, B.Q. et al., "Conjugation site modulates the in vivo stability and therapeutic activity of antibody-drug conjugates," Nature Biotechnology, vol. 30, pp. 184-189, 2012.

Shim et al., "Structures of a platelet-derived growth factor/propeptide complex and a platelet-derived growth factor/receptor complex," PNAS, vol. 107, No. 25, pp. 11307-11312, 2010.

Stenzel, Martina H., "Bioconjugation using thiols: Old chemistry rediscovered to connect polymers with nature's building blocks," ACS Macro letters, vol. 2, No. 1, pp. 14-18, 2013.

Stuttfeld et al., "Structure and function of VEGF receptors," Life, vol. 61, No. 9, pp. 915-922, 2009.

Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.

Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.

Tao, Lei et al., "Branched polymer-protein conjugates made from mid-chain-functional P (HPMA)", Biomacromolecules, 2009, vol. 10, No. 10, pp. 2487-2851. See abstract; pp. 2847 and 2850; and scheme 2.

Tonkinson, J. et al., "New Drugs: Antisense Oligodeoxynucleotides as Clinical Therapeutic Agents," Cancer Investigation, vol. 14, No. 1, pp. 54-65, 1996.

Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).

UniProtKB-G3R0B5, reterived on Mar. 19, 2016.

(56) References Cited

OTHER PUBLICATIONS

Vafa, O. et al. An Engineered FC Variant of an IG Elimaties All Immune Effecotr Functions via Structral Pertubations, Methods, vol. 65, pp. 114-126, (2014).
Venditto, et al., "Cancer Therapies Utilizing the Camtothecins: A Review of the Vivo Literature," Molecular Pharmaceutics, vol. 7, No. 2, pp. 307-349 (2010).
Veronese, Francesco M., "Peptide and protein PEGylation: a review of problems and solutions," Biomaterials, vol. 22, Issue 5, pp. 405-417, Mar. 1, 2001.
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wang, X. et al., "Disulfide scrambling in IgG2 monoclonal antibodies: Insights from molecular dynamics simulations," Pharmaceutical Research, vol. 28, Issue 12, pp. 3128-3144, Dec. 2011.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Warwick Effect Polymers, PowerPoint presentation, "Polymers for the Healthcare and Specialty Materials Industries," Jan. 2009, pp. 1-29.
Wolfe, A. et al., "Use of cholinesterases as pretreatment drugs for the protection of rhesus monkeys against soman toxicity," Toxicology and Applied Pharmacology, vol. 117, Issue 2, pp. 189-193, Dec. 1992.
Wu, G.Y. et al., "Receptor-mediated in vitro gene transformation by a soluble DNA carrier system," Journal of Biological Chemistry, vol. 262, pp. 4429-4432, Apr. 5, 1987.
Wu, H et al., Humanization of a Murine Monoclonal Antibody by Simultaneous Optimization of Frameork and CDR Resiudes, J. Mol. Biol., vol. 294, pp. 151-162, (1999).
Xiaoying, S. et al. Synthesis and Chacterization of a Multiarm Star Polymer, Journal of Polymer Science, vol. 42, pp. 2356-2364, (2004).
Yaseen, et al., "The Structure of Zwitterionic Phosphoacholine Surfactant Monolayers," Langmuir, (2006), 22:13, pp. 5825-5832.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yu, L et al. Internaction Between Bevacizumab and Murie VEGF-A: A Reassessment, Investigative Opthalmology & Visual Science, vol. 49, No. 2, pp. 522-527, (2008).
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zhang, X et al. Synthesis of Functional Polystyrenes by Atom Transfer Radical Polymerization Using Protected and Unprotected Carboxylic Acid Initiatiotrs, Macromoleucles, vol. 32, pp. 7349-7353, (1999).
Zhang, X et al., Prevalence of Diabetic Retinopathy in the United States, 2005-2008, JAMA. vol. 304, No. 6, pp. 649-656, (2010).
Advisory Action dated Jun. 12, 2014 in U.S. Appl. No. 13/959,563.
Advisory Action dated Nov. 29, 2018 in U.S. Appl. No. 14/916,180.
Advisory Action dated Dec. 11, 2018 in U.S. Appl. No. 14/916,180.
Extended European Search Report received in European Patent Application No. 17165316.5 dated Aug. 2, 2017.
Extended European Search Report received in European Patent Application No. 17181272.0 dated Feb. 23, 2018 in.
Extended European Search Report dated Mar. 21, 2016 in EP Application No. 11769715.1, dated Jul. 18, 2016 s.
Extended Search Report received in European Patent Application No. 14841835.3 dated Mar. 14, 2017.
Extended Search Report received in European Patent Application No. 15851363.0 dated Jan. 30,2 2018.
First Examination Report in NZ Application No. 6009449, dated Mar. 14, 2013.
First Examination Report in NZ Application No. 603048, dated Jun. 13, 2013 in 2 pages.
International Preliminary Report on Patentability dated Feb. 11, 2014 in PCT Application No. PCT/US2011/32768.
International Preliminary Report on Patentability dated Apr. 18, 2017 in International Application No. PCT/US2015/056112.
International Preliminary Report on Patentability dated Jul. 3, 2018 for International Patent Application No. PCT/US2016/069336 filed Dec. 29, 2016.
International Search Report and Written Opinion dated Feb. 27, 2013 in Internatnional Application No. PCT/US2012/060301.
International Search Report and Written Opinion for PCT/US2018/027378 dated Sep. 27, 2018.
International Search Report and Written Opinion dated Mar. 30, 2017 for International Patent Application No. PCT/US2016/069336 filed Dec. 29, 2016.
International Search Report in PCT Application No. PCT/US2007/005372, dated Aug. 8, 2008.
International Search Report and Written Opinion dated Sep. 9, 2010 in PCT Application No. PCT/US2010/034252.
International Search Report and Written Opinion dated May 9, 2011 in PCT Application No. PCT/US2010/61358.
International Search Report and Written Opinion dated Dec. 16, 2011 in PCT Application Np. PCT/US2011/327681.
International Search Report in PCT Application No. PCT/US2014/054622, dated Feb. 27, 2015.
International Search Report and Written Opion dated Apr. 1, 2016 in in International Application No. PCT/US2015/056112.
Notice of Allowance dated Jul. 31, 2014 in U.S. Appl. No. 13/959,563.
Notice of Allowance dated Sep. 26, 2018 in Canadian Patent Application No. 2,783,615.
Notice of Allowance dated Jan. 28, 2014 in U.S. Appl. No. 13/515,913.
Notice of Allowance dated Aug. 9, 2017 in U.S. Appl. No. 14/753,824.
Notice of Allowance dated Sep. 11, 2018 in U.S. Appl. No. 14/932,913.
Notice of Allowance dated Jan. 30, 2019 in U.S. Appl. No. 14/932,913.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Notice of Rejection received in Japanese Patent Application No. 2016-159104 dated Jun. 27, 2017.
Notice of Rejection received in Japanese Patent Application No. 2016-159104 dated Feb. 26, 2018.
Notice to File a Response received in Korean Patent Application No. 10-2012-7018788 dated Sep. 13, 2017.
Office Action dated Jun. 21, 2018 in U.S. Appl. No. 15/394,500.
Office Action dated Jan. 7, 2019 in U.S. Appl. No. 15/394,500.
Office Action in U.S. Appl. No. 13/959,563, dated Oct. 10, 2013.
Office Action in U.S. Appl. No. 13/959,563, dated Feb. 20, 2014.
Office Action in U.S. Appl. No. 14/456,875, dated Jun. 9, 2015.
Office Action in U.S. Appl. No. 14/456,875, dated Oct. 5, 2016 in 10 pages.
Office Action in U.S. Appl. No. 14/456,875, dated Apr. 20, 2017.
Office Action dated Feb. 7, 2012 in U.S. Appl. No. 12/281,071.
Office Action in CA Application No. 2783615, dated Sep. 16, 2016.
Office Action dated Dec. 14, 2015 in U.S. Appl. No. 14/265,174.
Office Action in JP Patent Application No. 2008-557399, dated May 25, 2013.
Office Action in CA Application No. 2783615, dated Jan. 9, 2018.
Office Action Received in Chinese Patent Application No. 201080062252.7 dated Apr. 20, 2017.
Office Action Received in Chinese Patent Application No. 201610439969.8 dated Jul. 24, 2018.
Office Action in EP Application No. 10838353.0, dated Oct. 4, 2016.
Office Action in European Patent Application No. 17181272.0 dated Oct. 31, 2018.

(56) References Cited

OTHER PUBLICATIONS

Office Action in European Patent Application No. 17181272.0 dated Mar. 22, 2019.
Office Action in JP Application No. 2012-544945, dated Jul. 9, 2014.
Office Action dated Feb. 8, 2018 in Indian Patent Application No. 6116/CHENP/2012.
Office Action in KR Application No. 10-2012-7018788, dated Mar. 10, 2017.
Office Action dated Dec. 31, 2013 in U.S. Appl. No. 13/516,173.
Office Action dated Jul. 2, 2014 in U.S. Appl. No. 13/516,173.
Office Action dated Dec. 16, 2014 in U.S. Appl. No. 13/516,173.
Office Action dated May 30, 2017 U.S. Appl. No. 15/099,234.
Office Action dated Oct. 19, 2018 U.S. Appl. No. 15/099,234.
Office Action dated Apr. 12, 2018 in Australian Patent Application Np. 2017201930.
Office Action dated Mar. 27, 2019 in Australian Patent Application Np. 2017201930.
Office Action dated Jun. 2, 2016 U.S. Appl. No. 13/901,483.
Office Action dated Feb. 9, 2018 in U.S. Appl. No. 15/368,376.
Office Action dated Sep. 10, 2018 in U.S. Appl. No. 15/368,376.
Office Action dated Mar. 11, 2019 in U.S. Appl. No. 15/368,376.
Office Action dated Apr. 6, 2017 Canadian Patent Application No. 2,795,667.
Office Action dated Dec. 29, 2017 Canadian Patent Application No. 2,795,667.
Office Action in CN Application No. 201180028682.1, dated Aug. 21, 2014.
Office Action in CN Application No. 201180028682.1, dated Jan. 26, 2015.
Office Action in CN Application No. 20118002868.1, dated Aug. 11, 2015.
Office Action received in Chinese Patent Application No. 201610446624.5 dated Mar. 12, 2018 in 12 pages.
Office Action received in Chinese Patent Application No. 201610446624.5 dated Nov. 26, 2018.
Office Action received in European Patent Application No. 11769715.1 dated Nov. 9, 2017.
Office Action Dated Jun. 27, 2018 in Indian Patent Application No. 9476/CHENP/2012 in 5 pages.
Office Action in JP Application No. 2013-505799, dated Feb. 19, 2015.
Office Action in JP Application No. 2015-165282, dated Aug. 15, 2016.
Office Action in JP Application No. 2015-165282, dated Aug. 1, 2017.
Office Action in JP Application No. 2015-165282, dated Sep. 27, 2018.
Office Action dated Nov. 27, 2018 in Japanese Patent Application No. JP 2017-231724.
Office Action in KR Application No. 10-2012-7029878, dated Mar. 8, 2017.
Office Action dated Mar. 9, 2018 in KR Application No. 10-2017-703456.
Office Action dated Aug. 28, 2018 in KR Application No. 10-2017-703456.
Office Action dated Oct. 26, 2018 in KR Application No. 10-2017-703456.
Office Action received in Mexican Patent Application No. MX/a/2012/011876 dated Jul. 13, 2017.
Office Action dated Jan. 16, 2018 in MX Application No. MX/a/2012/011876.
Office Action dated Jun. 6, 2018 in Mexican patent Application No. MX/a/2012/011876.
Office Action dated Dec. 17, 2018 in Mexican patent Application No. MX/a/2012/011876.
Office Action dated Jan. 23, 2019 in European Patent Application No. EP 14841835.3.
Office Action dated Jul. 13, 2018 in Japanese Patent Application No. 2016-540916.
Office Action dated Jan. 24, 2018 in U.S. Appl. No. 14/916,180.
Office Action dated Aug. 10, 2018 in U.S. Appl. No. 14/916,180.
Office Action dated Mar. 8, 2019 in U.S. Appl. No. 14/916,180.
Office Action dated Feb. 27, 2017 in U.S. Appl. No. 14/753,824.
Office Action dated May 8, 2017 in U.S. Appl. No. 14/932,913.
Office Action dated Dec. 15, 2017 in U.S. Appl. No. 14/932,913.
Office Action dated May 4, 2018 in U.S. Appl. No. 14/932,913.
Office Action dated Feb. 21, 2019 in European Patent Application No. 15851363.0.
Office Action dated May 8, 2018 in Japanese Patent Application No. 2017-520515.
Office Action dated Dec. 18, 2018 in Japanese Patent Application No. 2017-520515.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016.
Patent Examination Report in AU Application No. 2015207898, dated May 27, 2017.
PCT Invitation to Pay Additional Fees dated Feb. 3, 2016 in International Application No. PCT/US2015/056112.
Restriction Requirement dated Mar. 7, 2018 in U.S. Appl. No. 15/394,500.
Restriction Requirement dated Jun. 20, 2011 in U.S. Appl. No. 12/28107.
Restriction Requirement dated Jul. 15, 2015 in U.S. Appl. No. 14/265,174.
Restriction Requirement dated Aug. 14, 2013 in U.S. Appl. No. 13/515,913.
Restriction Requirement dated Sep. 3, 2013 in U.S. Appl. No. 13/516,173.
Restriction Requirement dated Feb. 9, 2017 U.S. Appl. No. 15/099,234.
Restriction Requirement dated Nov. 3, 2015 U.S. Appl. No. 13/901,483.
Restriction Requirement dated Aug. 21, 2017 in U.S. Appl. No. 15/368,376.
Restriction Requirement dated Jan. 30, 2017 in U.S. Appl. No. 14/916,180.
Restriction Requirement dated Aug. 16, 2017 in U.S. Appl. No. 14/916,180.
Restriction Requirement dated Jan. 13, 2017 in U.S. Appl. No. 14/932,913.
Supplemental European Search Report received in European Patent Application No. EP 07752096.3 dated Feb. 19, 2013.
Supplemental European Search Report dated Feb. 2, 2015 in European Patent Application No. EP 10838353.0 dated Feb. 3, 2015.
File History of U.S. Appl. No. 15/952,092, filed Apr. 12, 2018.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 12/281,071, filed Aug. 28, 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 14/916,180, filed Mar. 2, 2016.
File History of U.S. Appl. No. 14/753,824, filed Jun. 29, 2015.
File History of U.S. Appl. No. 14/932,913, filed Nov. 4, 2015.
File History of U.S. Appl. No. 16/290,128, filed Mar. 1, 2019.
Ambati et al., "Mechanisms of age-related macular degeneration," Neuron, vol. 75, No. 1, pp. 26-39, 2012.
Andrae et al., "Role of platelet-derived growth factors in physiology and medicine," Genes & Development, vol. 22, pp. 1276-1312, 2008.
Armulik, A. et al., "Endothelial/Pericyte Interactions," Circulation Research, vol. 97, Issue 6, pp. 512-523, Sep. 16, 2005.
Baluk, P. et al., "Cellular abnormalities of blood vessels as targets in cancer," Current Opinion in Genetics & Development, vol. 15, Issue 1, pp. 102-111, Feb. 2005.

(56) References Cited

OTHER PUBLICATIONS

Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.

Berthold, W. et al. "Protein Purification: Aspects of Processes for Pharmaceutical Products," Biologicals, vol. 22, Issue 2, pp. 135-150, Jun. 1994.

Bowen-Pope et al., "History of Discovery: Platelet-derived Growth Factor," Arterioscler Thromb Vasc Biol., vol. 31, No. 11, pp. 2397-2401, Nov. 2011.

Brown, D. et al., "Ranibizumab versus Verteporfin for Neovascular Age-Related Macular Degeneration," The New England Journal of Medicine, vol. 355, No. 14, pp. 1432-1444, Oct. 5, 2006.

Carmeliet, P., "Angiogenesis in healt and disease," Nature Medicine, vol. 9, pp. 653-660, (2003).

Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.

Carmeliet, "Mechanisms of angiogenesis and arteriogenesis," Nature Medicine, vol. 6, No. 3, pp. 389-395, 2000.

Chen et al., "Factors affecting endotoxin removal from recombinant therapeutic proteins by anion exchange chromatography," Protein Expression and Purification, vol. 64, pp. 76-81, 2009.

Chothia, C. et al., "Canonical structures for the hypervariable regions of immunoglobulins," Journal of Molecular Biology, vol. 196, Issue 4, pp. 901-917, Aug. 20, 1989.

Christy, N.E. et al., "Antibiotic prophylaxis of postoperative endophthalmitis," Annals of Ophthalmology, vol. 11, No. 8, pp. 1261-1265, Aug. 1, 1979.

Cohen, S.Y. et al., "Causes of unsuccessful ranibizumab treatment in exudative age-related macular degeneration in clinical settings," Retina, vol. 32, Issue 8, pp. 1480-1485, Sep. 2012.

De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.

Declaration of Harvey N. Masonson, M.D., under 37 C.F.R., for U.S. Appl. No. 12/465,051, filed May 13, 2009, including Exhibits A, B, and C, signed Jul. 6, 2011, in 50 pages.

Dillon et al., "Structural and functional characterization of disulfide isoforms of the human IgG2 subclass," The Journal of Biological Chemistry, vol. 283, No. 23, pp. 16206-16215, 2008.

Edelman et al., "The covalent structure of an entire yG immunoglobulin molecule," Proceedings of the National Academy of Sciences, vol. 63, pp. 78-85, May 1, 1969.

Ferrara, N. et al., "Discovery and development of bevacizumab, an anti-VEGF antibody for treating cancer," Nature Reviews Drug Discovery, vol. 3, pp. 391-400, May 2004.

Ferrara, N. et al., "The Biology of Vascular Endothelial Growth Factor," Endocrine Reviews, vol. 18, No. 1, pp. 4-25, (1997).

Ferrara, et al. Development of Ranibizumab, An Anti-Vascular Endothelial Growth, as Therapy for Neovascular Age-Related Macular Degeneration, Retina, The Journal of Retinal and Vitreous Diseas, vol. 26, Issue No. 8, pp. 859-870, (2006).

Ferrara, et al , "The Biology of VEGF and its Receptors", Nature Medicine, vol. 9 No. 6, pp. 669-676, (2003).

Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.

Folkman, J., "Angiogenesis: an organizing principle for drug discover?" Nature Reviews, Drug Discovery, vol. 6, pp. 273-286, Apr. 2007.

Fontaine et al., "Long-Term Stabilization of Maleimide-Thiol Conjugates," Bioconjugate Chem., vol. 26, pp. 145-152, 2015.

Friedman, D.S. et al., "Prevalence of age-related macular degeneration in the United States," Arch. Ophthalmol., vol. 122, No. 4, pp. 564-572, Apr. 2004.

Greene et al., "Protective Groups in Organic Synthesis," 3rd Edition, John Wiley and Sons, Inc., New York, (1999). In 52 pages which includes only the Title Page and Table of Contents.

Haishima, Y et al. Estimation of uncertainty in kinetic-colorimetric assay of bacterial endotoxins, J Pharm Biomed Analysis, 32: 1, pp. 495-503, (2003).

Hirayama, C. et al., "Chromatographic removal of endotoxin from protein solutions by polymer particles," Journal of Chromatography B, vol. 781, Issues 1-2, pp. 419-432, Dec. 5, 2002.

Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.

Ishikawa, K. et al., "Molecular mechanisms of subretinal fibrosis in age-related macular degeneration," Experimental Eye Research, vol. 142, pp. 19-25, Jan. 2016.

Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.

Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.

Kostelny, S.A. et al., "Formation of a bispecific antibody by the use of leucine zippers," J. Immunol., vol. 148, No. 5, pp. 1547-1553, Mar. 1, 1992.

Kuhnert, F. et al. "Soluble receptor-mediated selective inhibition of VEGFR and PDGFR_ signaling during physiologic and tumor angiogenesis", PNAS, vol. 105, No. 29, pp. 10185-10190, (2008).

Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.

Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.

Lafaut et al., "Clinicopathological correlation in exudative age related macular degeneration: histological differentiation between classic and occult choroidal neovascularisation," Br J Ophthalmol, vol. 84, pp. 239-243, 2000.

Lucentis ramibizumab (reb) Name of the Medicine, Active ingredient Ranibizumab, Product Information Sheet, in 30 pages, based on CDS dated Aug. 30, 2013.

Mabry, R. et al., "A dual-targeting PDGFRβ/VEGF-A molecule assembled from stable antibody fragments demonstrates anti-angiogenic activity in vitro and in vivo", Landes Bioscience, vol. 2, Issue 2, pp. 20-34 (2010).

Magalhaes et al., "Methods of Endotoxin Removal from Biological Preparations: a Review," J. Pharm Pharmaceut Sci., vol. 10, No. 3, pp. 388-404, 2007.

Marticorena, J. et al., "Sterile endophthalmitis after intravitreal injections," Mediators of Inflammation, vol. 2012, 6 pages, (2012).

Masson, P. et al., "Expression and Refolding of Functional Human butyrylcholinesterase from *E. coli*", Multidisciplinary Approaches to Cholinesterase Functions, New York, pp. 49-52, 1992.

Mones, Jordi, Inhibiting VEGF and PDGF to Treat AMD, http://www.reviewofophthalmology.com/content/d/retinal_insider/c/29979/#stash.fJePfjQ4.dpuf, Spain, Sep. 9, 2011.

Morris, G.E., "Epitope mapping protocols in methods in molecular biology," vol. 66, 1996.

Neuberger, M., "Generating high-avidity human Mabs in mice," Nature Biotechnology, vol. 14, pp. 826, 1996.

Ong, K. et al., "A rapid highly-sensitive endotoxin detection system," Biosensors and Bioelectronics, vol. 21, Issue 12, pp. 2270-2274, Jun. 15, 2006.

(56) References Cited

OTHER PUBLICATIONS

Ostberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Paul, W., Fundamental Immunology, 2nd ed. Raven Press, N.Y., (1989). table of contents.
Petsch, D. et al., "Endotoxin removal from protein solutions," Journal of Biotechnology, vol. 76, Issues 2-3, pp. 97-119, Jan. 21, 2000.
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Rycroft, B.W., "Penicillin and the control of deep intra-ocular infection," British J. Ophthalmol, vol. 29, No. 2, pp. 57-87, Feb. 1945.
Songsivilai, S. et al., "Bispecific antibody: a tool for diagnosis and treatment of disease," Clin Exp. Immunol., vol. 79, No. 3, pp. 315-321, Mar. 1990.
Uutela et al., "PDGF-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
International Preliminary Report on Patentability (IPRP) dated Jun. 24, 2014, in International Application No. PCT/IB2012/057491, 10 pages.
International Preliminary Report on Patentability (IPRP) dated Jul. 5, 2016, in International Application No. PCT/US2015/038203.
International Search Report and Written Opinion for PCT/US2015/038203, dated Dec. 8, 2015.
International Search Report dated Jun. 4, 2013, in International Application No. PCT/IB2012/057491.
Office Action dated Aug. 16, 2017 in U.S. Appl. No. 14/932,913.
Office Action dated Jan. 20, 2020 in Japanese Patent Application No. JP 2016-575823.
Bock, F. et al. Safety Profile of Topical VEGF Neutralization at the Cornea, Investigative Opthalmology & Visual Science, vol. 50, No. 5, pp. 2095-2012, (2009).
Chames, Patrick et al., "Therapeutic antibodies: successes, limitations and hopes for the future," British Journal of Pharmacology, Wiley-Blackwell, UK; Biosciences Information Service, vol. 157, No. 2, May 1, 2009, pp. 220-233.
Jorg T. Regula, et al., "Targeting key angiogenic pathways with a bispecific CrossMab, optimized for neovascular eye diseases," EMBO Molecular Medicine (online), vol. 8, No. 11, Oct. 14, 2016, pp. 1265-1288.
Pan, C. et al. Comparison of Long-Acting Bevacizumab Formulations in the Treatment of Choroidal Neovascularization in a Rat Model, Journal of Ocular Pharmacology and Therapeutics., vol. 27, No. 3, pp. 219-224, (2011).
Partial Supplementary European Search Report dated Jul. 22, 2019 in European Patent Application No. 16882707.9.
Written Opinion, Singapore Patent Application No. 11201805420S, dated Dec. 22, 2019.
Search Report, Singapore Patent Application No. 11201805420S, dated Dec. 22. 2019.
Extended European Search Report, EP16882707.9. dated Nov. 19. 2019.
Final Office Action, U.S. Appl. No. 15/394,500, dated Dec. 30, 2019.
Office Action, U.S. Appl. No. 15/394,500, dated Aug. 7, 2019.
Final Office Action, U.S. Appl. No. 15/394,500 dated Jan. 7, 2019.
Office Action received in Chinese Patent Application No. 201580046779.3 dated Apr. 3, 2020.
U.S. Appl. No. 16/795,450, filed Feb. 19, 2020, Perlroth et al.
Office Action dated Feb. 18, 2020 in Japanese Application No. 2017-520515 with English Translation.
Supplementary Partial European Search Report dated Dec. 21, 2017 in European Patent Application No. 15812238.2.
Extended European Search Report dated Mar. 29, 2018 in European Patent Application No. 15812238.2.
Office Action dated Mar. 18, 2020 in Australian Application No. 2015279560.
Office Action, U.S. Appl. No. 16/290,128, dated May 22, 2020.
Office Action, U.S. Appl. No. 15/952,092, dated Jun. 30, 2020.
Office Action, U.S. Appl. No. 15/394,500, dated Jun. 23, 2020.
Office Action Dated Aug. 7, 2019 in U.S. Appl. No. 15/394,500.
Office Action, Russian Patent Application No. 2018126519, dated Apr. 28, 2020.
Office Action received in Chinese Patent Application No. 2015800564492 dated Apr. 22, 2020.
OA Japanese Patent Application No. 2017-520515, dated Feb. 17, 2020.
Office Action dated Nov. 14, 2019 in Korean Patent Application 10-2017-7013268.
Office Action dated Feb. 17, 2020 in Korean Patent Application 10-2017-7013268.
Office Action dated Oct. 18, 2019, European Patent Application No. 15851363.0.
Restriction Requirement Dated Mar. 3, 2020 in U.S. Appl. No. 15/952,092.
Edwards et al., "The Remarkable Flexibility of the Human Antibody Repertoire; Isolation of Over One Thousand Different Antibodies to a Single Protein, BLyS", J. Mol. Biol., vol. 334, pp. 103-118, 2003.
Katschke et al., "Inhibiting Alternative Pathway Complement Activation by Targeting the Factor D Exosite", The Journal of Biological Chemistry, vol. 287, No. 16, pp. 12886-12892, Apr. 13, 2012.
Lloyd et al., "Modelling the human immune response: performance of a 1011 human antibody repertoire against a broad panel of therapeutically relevant antigens", Protein Engineering Design & Selection, vol. 22, No. 3, pp. 159-168, 2009.
Roitt, I.M., "Immunology-Second Edition", Gower Medical Publishing, 1989.
Office Action dated Jul. 15, 2020 in Mexican Application No. MX/a/2016/017290 with English Translation.
Office Action dated Aug. 3, 2020 in U.S. Appl. No. 16/402,602.
Office Action dated Jul. 9, 2020 in European Application No. 15 812 238.2.
Office Action dated Sep. 30, 2020 in Canadian Application No. 3,059,938.
Office Action dated Sep. 2, 2020 in Japanese Application No. 2017-520515 with English Translation.

(56) References Cited

OTHER PUBLICATIONS

Pakula, et al., "Genetic Analysis of Protein Stability and Function," Annual Reviews of Genetics, vol. 23, pp. 289-310, Dec. 1989.
Office Action dated Sep. 8, 2020 in Russian Patent Application No. 2018126519.
Perederni, et al., "Endocrine Ophthalmopathy," Eye Diseases 5. Complete reference, Feb. 6, 2008, pp. 154-158, 162.
Office Action dated Sep. 28, 2020 in European Patent Application No. EP16882707.9.
Notice of Acceptance for Patent Application, Australian Application No. 2015279560, dated Sep. 2, 2020, in 3 pages.
Decision of Refusal in JP Application No. 2016-575823 dated Oct. 27, 2020.
U.S. Appl. No. 17/066,856, filed Oct. 9, 2020, Ehrlich et al.
Allen et al., "Combined antiangiogenic and anti-PD-L1 therapy stimulates tumor immunity through HEV formation", Science Translational Medicine, 9(385): dated Apr. 12, 2017.
Binder S, Stanzel BV, Krebs 1, Glittenberg C. 2007. Transplantation of the RPE in AMD. Prog Retn Eye Res. 26:516-554.
Boyd et al., "The effect of the removal of sialic acid, galactose and total carbohydrate on the functional activity of Campath-1 H", Molecular Immunology, vol. 32: dated Dec. 1995, pp. 1311-1318.
Capel et al., "Heterogeneity of human IgG Fc receptors", Immunomethods, 4(1): dated Feb. 1994 pp. 25-34.
Chiou et al., Gene Therapeutics: Methods And Applications Of Direct Gene Transfer, J.A. Wolff, ed., 1994.
Connelly, "In Vivo Gene Delivery and Expression of Physiological Levels of Functional Human Factor VIII in Mice" Human Gene Therapy, 1995, 1:185.
Curiel, "High-Efficiency Gene Transfer Mediated by Adenovirus Coupled to DNA-Polylysine Complexes" Hum. Gene Ther., 1992, 3 (2):pp. 147-154.
Dayhoff, M.O. (ed.) Atlas of Protein Sequence and Structure, National Biomedical Research Foundation, Washington DC vol. 5, Suppl. 3, pp. 345-358. 1978.
De Haas et al., "Fc gamma receptors of phagocytes", Journal of Laboratory and Clinical Medicine, 126(4): dated Oct. 1995, pp. 330-341.
Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Findeis et al., "Targeted delivery of DNA for gene therapy via receptors" Trends Biotechnol., 1993, 11: pp. 202-205.
Guyer et al., "Immunoglobulin Binding by Mouse Intestinal Epithelial Cell Receptors", The Journal of Immunology, 117(2): dated Aug. 1, 1976, pp. 587-893.
Hein J., 1990, Unified Approach to Alignment and Phylogenies pp. 626-645 Methods in Enzymology vol. 183, Academic Press, Inc., San Diego, CA.
Higgins, D.G. and Sharp, P.M., "Fast and sensitive multiple sequence alignments on a microcomputer" CABIOS 5: dated 1989, pp. 151-153.
Hinton et al., "Engineered human IgG antibodies with longer serum half-lives in primates", Journal of Biological Chemistry, 279(8): dated Feb. 20, 2004 in 5 pages.
Hsu et al., "Differential N-Glycan Patterns of Secreted and Intracellular IgG Produced in Trichoplusia ni Cells" Journey of Biol. Chem. Vol. 272: dated 1997, pp. 9062-9070.
Hwang et al., "Hepatic uptake and degradation of unilamellar sphingomyelin/cholesterol liposomes: a kinetic study", Proceedings of the National Academy of Sciences of the United States of America, 77(7): dated Jul. 1980, pp. 4030-4034.
Iwahashi et al.," CDR substitutions of a humanized monoclonal antibody (CC49): contributions of individual CDRs to antigen binding and immunogenicity," Mol. Immunol. 36: Issue 15-16, 1079-1091, 1999.
Jefferis et al., "Glycosylation of Antibody Molecules: Structural and Functional Significance", Antibody Engineering, vol. 65: dated 1997, pp. 111-128.

Johnson et al., "Kabat Database and its applications: 30 years after the first variability plot", Nucleic Acids Research, 28(1): Jan. 1, 2000, pp. 214-218.
Kaplitt, "Long-term gene expression and phenotypic correction using adeno-associated virus vectors in the mammalian brain" Nature Genetics, 1994, 8:148.
Kimura, "Retroviral Delivery of DNA into the Livers of Transgenic Mice Bearing Premalignant and Malignant Hepatocellular Carcinomas" Human Gene Therapy, 1994, 5(7): pp. 845-852.
Kim et al., "Identifying amino acid residues that influence plasma clearance of murine IgG 1 fragments by site-directed mutagenesis", European Journal of Immunology, 24(3): dated Mar. 1994.
Klein R, Klein BE, Jensen SC, Meuer SM. 1997. The five-year incidence and progression of age-related maculopathy: The Beaver Dam Eye Study. Ophthal. 104:7-21.
Kohler et al., "Continuous cultures of fused cells secreting antibody of predefined specificity", Nature, vol. 256: dated 1975, pp. 495-497.
Kunik et al., "Paratome: an online tool for systematic identification of antigen-binding regions in antibodies based on sequence or structure", Nucleic Acids Research, vol. 40: Jun. 6, 2012, W521-524.
Lazar et al., "Engineered antibody Fc variants with enhanced effector function", Proc Natl Acad Sci U S A, 103(11): dated Mar. 14, 2006 in 6 pages.
Lefranc et al., "IMGT unique numbering for immunoglobulin and T cell receptor variable domains and Ig superfamily V-like domains", Developmental and Comparative Immunology, vol. 27: dated 2003, pp. 55-77.
Makabe et al., "Thermodynamic Consequences of Mutations in Vernier Zone Residues of a Humanized Anti-human Epidermal Growth Factor Receptor Murine Antibody, 528", Journal of Biological Chemistry, vol. 283: dated Jan. 11, 2008, pp. 1156-1166.
Martin et al., "Modeling antibody hypervariable loops: A combined algorithm", Proc. Natl. Acad. Sci. USA, vol. 86: dated Dec. 1989, pp. 9268-9272.
McCafferty et al., "Phage antibodies: filamentous phage displaying antibody variable domains", Nature, vol. 348: dated 1990, pp. 552-554.
Myers, E.W. and Muller W., "Optimal alignments in linear space" CABIOS 4: dated 1988, pp. 11-17.
Philip, "Efficient and sustained gene expression in primary T lymphocytes and primary and cultured tumor cells mediated by adeno-associated virus plasmid DNA complexed to cationic liposomes." Mol. Cell Biol., 1994, 14(4): pp. 2411-2418.
RAVETCH et al., "FC Receptors," 1991, Ann. Rev. Immunol., vol. 9:457-92.
Robinson, D.F, "Comparison of Labeled Trees with Valency Three," Journal of Combinatorial Theory 11: pp. 105-119 (1997).
Samudrala et al., "Ab initio protein structure prediction using a combined hierarchical approach", Proteins, Structure, and Genetics Suppl, 37(S3): dated 1999, pp. 194-198.
Saitou, N., Nei, M., "The neighbor-joining method: a new method for reconstructing phylogenetic trees." Mol. Biol. Evol. Vol. 4: dated 1987, pp. 406-425.
Tsukamoto et al., "Combined Blockade of IL6 and PD-1/PD-L1 Signaling Abrogates Mutual Regulation of Their Immunosuppressive Effects in the Tumor Microenvironment", Cancer Research, 78(17): dated Sep. 2018 in 12 pages.
Umana et al., "Engineered glycoforms of an antineuroblastoma IgG1 with optimized antibody-dependent cellular cytotoxic activity." 1999, Nature Biotech. 17:176-180.
Wilbur, W.J. and Lipman, D.J., "Rapid similarity searches of nucleic acid and protein data banks" 1983, Proc. Natl. Acad. Sci. USA 80: pp. 726-730.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Woffendin, "Nonviral and viral delivery of a human immunodeficiency virus protective gene into primary human T cells" Proc. Natl. Acad. Sci., 1994, 91: pp. 11581-11585.

(56) References Cited

OTHER PUBLICATIONS

Wright et al., "Effect of glycosylation on antibody function: implications for genetic engineering", Trends Biotechnol, 15(1): dated Jan. 1997, pp. 26-32.
Wu et al., "Receptor-mediated Gene Delivery and Expression in Vivo" J. Biol. Chem., 1988, 263.
Wu et al., "Receptor-mediated Gene Delivery in Vivo" J. Biol. Chem., 1991, 266.
Wu et al., "Incorporation of Adenovirus into a Ligand-based DNA Carrier System Results in Retention of Original Receptor Specificity and Enhances Targeted Gene Expression" J. Biol. Chem., 1994, 269 (15): pp. 11542-11546.
Wu, "Targeting Genes: Delivery and Persistent Expression of a Foreign Gene Driven by Mammalian Regulatory Elements in Vivo" J. Biol. Chern., 1989, 264(29):16985-19687.
Wyss et al.," Current Opinion in Biotechnology," vol. 7 (4): pp. 409-146, 1996.
Zenke et al., "Receptor-mediated endocytosis of transferrin-polycation conjugates: an efficient way to introduce DNA into hematopoietic cells." Proc. Natl. Acad. Sci. USA, 1990, 87(10):3655-3659.
Office Action dated Apr. 13, 2020 in U.S. Appl. No. 16/402,602.
Office Action in U.S. Appl. No. 16/402,602, dated Nov. 20, 2020.
Office Communication received in U.S. Appl. No. 16/290,128 dated Nov. 12, 2020.
File History of U.S. Appl. No. 16/424,265, filed Aug. 11, 2014.
File History of U.S. Appl. No. 15/368,376, filed Dec. 2, 2016.
File History of U.S. Appl. No. 13/641,342, filed Dec. 2, 2016.
File History of U.S. Appl. No. 16/7818,69, filed Mar. 2, 2016.
File History of U.S. Appl. No. 16/795,450, filed Jun. 29, 2015.
File History of U.S. Appl. No. 16/402,602, filed Nov. 4, 2015.
Office Action received in Chinese Patent Application No. 201580564492 dated Oct. 27, 2020.
Notice of Allowance dated Oct. 26, 2020 in Korean Application No. 10-2017-7013268.
Bakri et al., "Pharmacokinetics of Intravitreal Ranibizumab [Lucentis]," Dec. 2007, Ophthalmology vol. 114, Issue 12, pp. 2179-2182.
Daniel et al., 2014, "Risk of Scar in the Comparison of Age-related Macular Degeneration in clinical settings," Retina 32: 1480-1485.
Drolet et al., "Pharmacokinetics and Safety of an Anti-Vascular Endothelial Growth Factor Aptamer (NX1838) Following Injection into the Vitreous Humor of Rhesus Monkeys," 2000, Pharm Res. 17:1503-1510.
Dvorak, et al., "Vascular Permeability Factor/Vascular Endothelial Growth Factor and the Significance of Microvascular Hyperpermeability in Angiogenesis," 1999, Curr Top Microbiol Immunol, 237: 97-132.
Gaudreault et al., "Pharmacokinetics and retinal distribution of ranibizumab, a humanized antibody fragment directed against VEGF-A following intravitreal administration in rabbits," Nov. 2007 Retina vol. 27, Issue 9, pp. 1260-1266.
Halekoh et al., "The R Package geepack for Generalized Estimating Equations," Jan. 2006, Journal of Statistical Software vol. 15, Issue 2, pp. 1-11.
Kong, et al., "Platelet-Derived Growth Factor-D Overexpression Contributes to Epithelial-Mesenchymal Transition of PC3 Prostate Cancer Cells," Jun. 2008, Stem Cells vol. 26, Issue 6 pp. 1425-1435.
Lloyd et al., "Food and Drug Administration approval process for ophthalmic drugs in the U.S.," May 2008, Current Opinion Opthalmology, vol. 19 Issue 3 pp. 190-194.
Nork et al., "Prevention of Experimental Choroidal Neovascularization and Resolution of Active Lesions byVEGFtrapin Nonhuman Primates," 2011, Arch Opthalmol, 129(8):1042-1052.
Ray et al., "Platelet-derived Growth Factor D, Tissue-specific Expression in the Eye, and a Key Role in Control of Lens Epithelial Cell Proliferation," Mar. 2005, J Biol Chem., vol. 280, No. 9 pp. 8494-8502.
Sinapis et al., "Pharmacokinetics of intravitreal bevacizumab (Avastin®) in rabbits," 2011, Clinical Ophthalmology 5:697-704.
Strohl, William R, "Optimization of Fc-mediated effector functions of monoclonal antibodies," Dec. 2009, Curr Opin. In Biotech vol. 20 Issue 6, pp. 685-691.
Struble et al., "Pharmacokinetics and ocular tissue penetration of VEGF Trap after intravitreal injections in rabbits," Sep. 2008, vol. 86, Issue s243.
Office Action with English Translation received in Chinese Application No. 201580046779.3 dated Feb. 28, 2021.
Causes and Risk Factors, Diabetic Retinopathy, United State National Libnrary of Medecine, Sep. 15, 2009, Archived web page at http://www.nei.nih qovhsalth'diabsticiretnopathy.asp,. dated Sep. 23, 2009 Joralemon et al., PEGylated Polymers For Medicine From Conjugation To Self-Assembled Systems, Chemical Communications, vol. 46, No. 9, pp. 1377, 2010.
Claims filed Nov. 4, 2020 in U.S. Appl. No. 17/066,856.
Brown, David, "Novel Anti-VEGF Antibody Biopolymer Conjugate KSI-301 with Potential for Extended Durability in Retinal Vascular Diseases," powerpoint presented at the Retina Society Annual Meeting on Sep. 15, 2019 in 19 pgs.
Decision to Grant with English Translation in dated Jan. 21, 2021 in Russian Application No. 2018126519/10.
Examiners Comments with English Translation Received in Singaporean Patent Application No. 11201805420S dated Feb. 10, 2021.
Examination Report Dated Jan. 22, 2021 in Singapore Application No. 11201805420S.
Final Office Action Received in U.S. Appl. No. 15/952,092 dated Nov. 27, 2020.
International Search Report with written Opinion dated Feb. 8, 2021 in PCT Application No. US2020/055074.
Joralemon et al., PEGylated Polymers For Medicine From Conjugation To Self-Assembled Systems, Chemical Communications, vol. 46, No. 9, pp. 1377, 2010.
Kernt et al. "Improvement of Diabetic Retinopathy with Intravitreal Ranibizumab," Diabetes Research and clinical Practice, Feb. 5, 2013 (05.02.2013), vol. 100, No. 1, pp. 11-13. entire document.
Notice of Allowance Received in U.S. Appl. No. 15/394,500 dated Mar. 11, 2021.
Notice of Allowance Received in U.S. Appl. No. 16/402,602.
Notice of Allowance with English Translation Received in Russian Application No. 2018126519 dated Feb. 5, 2021.
Extended European Search Report dated Jan. 21, 2021 in EP Application No. 18784891.6 in 15 pages.
Office Action Received in U.S. Appl. No. 15/394,500 dated Nov. 30, 2020.
Office Action with English Translation dated Jan. 26, 2021 in Japanese Application No. 2018-534732 in 9 pages.
Office Action with English translation dated Feb. 26, 2021 in Chinese Patent Application No. 201580046779.3 in 29 pages.
Paul, "Fv Structure and Diversity in Three Dimensions," Fundamental Immunology, 1993, 3rd Edition, pp. 292-295.
RecName: Full=Complement factor D; EC=3.4.21.46; AltName: Full=Adipsin; AltName: Full=C3 convertase activator; AltName: Full=Properdin factor D; Flags: Precursor, UNIPROT, Jul. 21, 1986 (Jul. 21, 1986), XP002614847, [retrieved on Jul. 21, 1986].
Restriction Requirement dated Feb. 2, 2021 in U.S. Appl. No. 17/066,856 in 6 pages.
Williams et al., "The Immunoglobulin Superfamily-Domains for Cell Surface Recognition," 1988, Ann. Rev. Immunol 6:381-405.
Pre-Appeal Report with machine translation, in Japanese Patent Application No. JP 2016-575823, dated May 11, 2021.
Office Action with English translation in Chinese Patent Application No. 201580046779.3, dated Jun. 2, 2021.
Office Action dated Mar. 26, 2021 in Canadian Application No. 2,953,698 in 4 pages.
Restriction Requirement dated Mar. 24, 2021 in U.S. Appl. No. 16/795,450 in 5 pages.
Final Office Action dated Mar. 22, 2021 in U.S. Appl. No. 16/290,128 in 78 pages.
Office Action dated Jun. 25, 2021 in U.S. Appl. No. 16/795,450 in 117 pages.
Office Action with English Translation for Mexican Application No. MX/a/2018/008068 dated Aug. 20, 2021.

(56) References Cited

OTHER PUBLICATIONS

Office Action with English Translation for Japanese Application No. 2018-534732 dated Aug. 10, 2021.
Notice of Allowance in U.S. Appl. No. 17/066,856 dated Sep. 9, 2021.

* cited by examiner

```
   1 MRLPGAMPAL ALKGELLLLS LLLLLEPQIS QGLVVTPPGP ELVLNVSSTF VLTCSGSAPV
  61 VWERMSQEPP QEMAKAQDGT FSSVLTLTNL TGLDTGEYFC THNDSRGLET DERKRLYIFV
 121 PDPTVGFLPN DAEELFIFLT EITEITIPCR VTDPQLVVTL HEKKGDVALP VPYDHQRGFS
 181 GIFEDRSYIC KTTIGDREVD SDAYYVYRLQ VSSINVSVNA VQTVVRQGEN ITLMCIVIGN
 241 EVVNFEWTYP RKESGRLVEP VTDFLLDMPY HIRSILHIPS AELEDSGTYT CNVTESVNDH
 301 QDEKAINITV VESGYVRLLG EVGTLQFAEL HRSRTLQVVF EAYPPPTVLW FKDNRTLGDS
 361 SAGEIALSTR NVSETRYVSE LTLVRVKVAE AGHYTMRAFH EDAEVQLSFQ LQINVPVRVL
 421 ELSESHPDSG EQTVRCRGRG MPQPNIIWSA CRDLKRCPRE LPPTLLGNSS EEESQLETNV
 481 TYWEEEQEFE VVSTLRLQHV DRPLSVRCTL RNAVGQDTQE VIVVPHSLPF KVVVISAILA
 541 LVVLTIISLI ILIMLWQKKP RYEIRWKVIE SVSSDGHEYI YVDPMQLPYD STWELPRDQL
 601 VLGRTLGSGA FGQVVEATAH GLSHSQATMK VAVKMLKSTA RSSEKQALMS ELKIMSHLGP
 661 HLNVVNLLGA CTKGGPIYII TEYCRYGDLV DYLHRNKHTF LQHHSDKRRP PSAELYSNAL
 721 PVGLPLPSHV SLTGESDGGY MDMSKDESVD YVPMLDMKGD VKYADIESSN YMAPYDNYVP
 781 SAPERTCRAT LINESPVLSY MDLVGFSYQV ANGMEFLASK NCVHRDLAAR NVLICEGKLV
 841 KICDFGLARD IMRDSNYISK GSTFLPLKWM APESIFNSLY TTLSDVWSFG ILLWEIFTLG
 901 GTPYPELPMN EQFYNAIKRG YRMAQPAHAS DEIYEIMQKC WEEKFEIRPP FSQLVLLLER
 961 LLGEGYKKKY QQVDEEFLRS DHPAILRSQA RLPGFHGLRS PLDTSSVLYT AVQPNEGDND
1021 YIIPLPDPKP EVADEGPLEG SPSLASSTLN EVNTSSTISC DSPLEPQDEP EPEPQLELQV
1081 EPEPELEQLP DSGCPAPRAE AEDSFL   (SEQ. ID No.: 33)
```

FIG. 1

```
   1 MVSYNDIGYL LCALLLSCLLL TGSSSGSKLK DPELSLKGTQ HIMQAGQILH LQCRGEAAHK WSLPEMVSKE SERLSITKSA
  81 CGRNGKQFCS TLTLNTAQAN HTGFYSCKYL AVPTSKKKET ESAIYIFISD TGRPFVEMYS EIPEIIHMTE GRELVIPCRV
 161 TSPNITVTLK KFPLDTLIPD GKRIIWDSRK GFIISNATYK EIGLLTCEAT VNGHLYKTNY LTHRQTNTII DVQISTPRPV
 241 KLLRGHTLVL NCTATTPLNT RVQMTWSYPD EKNKRASVRR RIDQSNSHAN IFYSVLTIDK MQNKDKGLYT CRVRSGPSFK
 321 SVNTSVHIYD KAFITVKHRK QQVLETVAGK RSYRLSMKVK AFPSPEVVWL KDGLPATEKS ARYLTRGYSL IKDVTEEDA
 401 GNYTILLSIK QSNVFKNLTA TLIVNVKPQI YEKAVSSFPD PALYPLGSRQ ILLTCTAYGIP QPTIKWFWHP CNHNESEARC
 481 DFCSNNEESF ILDADSNMGN RIESITQRMA IEEGKNKMAS TLVVADSRIS GIYICIASNK VGTVGRNISF YITDVPNGPH
 561 VNLEKMPTEG EDLKLSCTVN KFLYRDVTWI LLRTVNNRTM HYSISKQKMA ITKEHSITLN LTIMNVSLQD SGTYACRARN
 641 VVTGKEILQK KEITIRDQEA PYLLRNLSDH TVAISSSTTL DCHANGVPEP QITWFKNNHK IQQEPGIILG PGSSTLPIER
 721 VTEEDRGVYH CKATNQKGSV ESSAYLTVQG ESSAYLTVQG TSDKSNLELI TLTCTCVAAT LFWLLLTLFI RKMKRSSSEI KTDYLSIIMD
 801 PDEVPLDEQC ERLPYDASKW EPARERLKLG KSLGRGAFGK VVQASAFGIK KSPTCRTVAV KMLKEGATAS EYKALMTELK
 881 ILTHIGHHLN VVNLLGACTK QGGPLMVIVE YCKYGNLSNY LKSKRDLFFL NKDAALHMEP KKEKMEPGLE QGKKPRLDSV
 961 TSSESFASSG FQEDKSLSDV EEEDSDGFY KEPITMEDLI SYSPQVARGM EPLSSRKCIH RDLAARNILL SENNVVKICD
1041 FGLARDIYKN PDYVRKGDTR LPLKWMAPES IFDKIYSTKS DVWSYGVLLW EIPSLGGSPY PGVQMDEDFC SRLRBGMRMR
1121 APEYSTPEIY QIMLDCWHRD PKERPRFAEL VEKLGDLLQA NVQQDGKDYI PINAILTGNS GFTYSTPAFS EDFFKESISA
1201 PKFNSGSSDD VRYVNAFKFM SLERIKTFEE LLPNATSMPD DYQGDSSTLL ASPMLKRFTW TDSKPKASLK IDLRVTSKSK
1281 ESGLSDVSRP SFCHSSCCHV SEGKRRFTYD HAELERKIAC CSPPPDYNSV VLYSTPPI   (SEQ. ID NO:34)
```

FIG. 2

```
   1 MQSKVLLAVA LWLCVETRAA SVGLPSVSLD LPRLSQKDI LNIKANTTLQ ITCRGQRDLD WLMPNNQSGS EQRVEVTECS
  81 DGLFCKTLTI PKVIGNDTGA YKCFYRETDL ASVIYVYQD YRSPFIASVS DQHGVVYITE NKNKTVIPC LGSTSNLNVS
 161 LCARYPEKRF VPDGNRISWD SKKGFTIPSY MISTAGNVFC EAKINDESYQ SIMYIVVVG YRIYDVLSP SHGIKLSVGE
 241 KLVLNCTART ELNVGIDFNW EYPSSKHQHK KLVNRDLKTQ SGSEMKKFLS TLTIDGVTRS DQGLYTCAAS SGLMTKKNST
 321 FVRVHEKPFV APGSGMESLV EATVGERVRI PAKYLGYPPP EIKWYKNGIP LESNHTIKAG HVLTIMEVSE RDTGNYTVIL
 401 TNPISKEKQS HVVSLVYVYP PQIGEKSLIS PVDSYQYGTI QTLTCTVIAI PPPHHIHWYN QLEEECANEP SQAVSVTNPY
 481 PCEEWRSVED FQGGNKIEVN KNQFALIEGK NKTVSTLVIQ AANVSALYKC EAVNKVGRGE RVISFHVTRG PEITLQPDMQ
 561 PTEQESVSLW CTADRSTFEN LTWYKLGPQP LPIBVGELPT PVCKNLDTLW KLNATMFSNS TNDILIMELK NASLQDQGDY
 641 VCLAQDRKTK KRHCVVRQLT VLERVAPTIT GNLENQTSI GESIEVSCTA SGNPPPQIMW FKDNETLVED SGIVLKDGNR
 721 NLITRRVRKE DEGLYTCQAC SVLGCAKVEA FFIEGAQEK TNLETIILVG TAVIAMFFWL LLVILRTVK RANGGELKTG
 801 YLSIVMDPDE LPLDEHCERL PYDASKWEFP RDRLKLGKPL GRGAFGQVIE ADAFGIDKTA TCRTVAVKML KEGATHSEHR
 881 ALMSELKILI HIGHHLNVVN LLGACTKPGG PLMVIVEPCK FGNLSTYLRS KRNEFVPYKT KGARFRQGKD YVGAIPVDLK
 961 RRLDSITSSQ SSASSGFVEE KSLSDVEEEE APEDLYKDFL TLEHLICYSF QVAKGMEFLA SRKCIHRDLA ARNILLSEKN
1041 VVKICDFGLA RDIYKDPDYV RKGDARLPLK WMAPETIFDR VYTIQSDVWS FGVLLWEIFS LGASPYPGVK IDEEFCRRLK
1121 EGTRMRAPDY TTPEMYQTML DCWHGEPSQR PTFSELVEHL GNLLQANAQQ DGKDYIVLPI SETLSMEEDS GLSLPTSPVS
1201 CMEEEEWCDP KFHYDNTAGI SQYLQNSKRK SRPVSVKTFE DIPLEEPEVK VIPDDNQTDS GMVLASEELK TLEDRTKLSP
1281 SFGGMVPSKS RESVASEGSN QTSGYQSGYH SDDTDTTVYS SEEAELLKLI EIGVQTGSTA QILQPDSGTT LSSPPV (SEQ. ID No.: 35)
```

FIG. 3

```
  1 MQRGAALCLR LWLCLGLLDG LVSGYSMTPP TLNITEESHV IDTGDSLSIS CRGQHPLEWA WPGAQEAPAT GDKDSEDTGV
 81 VRDCEGTDAR PYCKVLLLHE VHANDTGSYV CYYKYIKARI EGTAASSYV FVRDFEQPFI NKPDTLLVNR KDAMWVPCLV
161 SIPGLNVTLR SQSSVLWPDG QEVVWDDRRG MLVSTPLLHD ALYLQCETTW GDQDFLSNPF LVHITGNELY DIQLLPRKSL
241 ELLVGEKLVL NCTVWAEFNS GVTFDWDYPG KQAERGKWVP ERRSQQTHTE LSSILTIHNV SQHDLGSYVC KANMGIQRFR
321 ESTEVIVHEN PFISVEWLKG PTLEATAGDE LVKLPVKLAA YPPEFQWYK PHALVLKEVT DGKALSGRHS RASTGYTLA
401 LWNSAAGLRR NISLELVVNV PPQHEKRAS SPSIYSRHSR QALCTAYGV PLPLSIQWHW RPWTPCKMFA QRSLRRRQQQ
481 DLMPQCRDWR AVFTQDAVNP IESLDTWTEF VEGKNKTVSK LVIQNANVSA MIKCVVSNKV GQDERLIYFY VTTIPDGFTI
561 ESKPSEELIE GQPVLLSCQA DSYKYEHLRW YRINLSTLHD AHGNPLLLDC KNVHLFATPL AASLEEVAPG ARHATLSLSI
641 PRVAPEHEGH YVCEVQDRRS HDKHCHKKYL SVQALEAPRL TQMLTDLLVN VSDSLEMQCL VAGAHAPSIV WYKDERLLEE
721 KSGVDLADSN QKLSIQRVRE EDAGRYLCSV CNAKGCVNSS ASVAVEGSED KGSMEIVILV GTGVLAVFFW VLLLIFCNM
801 RRPAHADIKT GYLSIIMDPG EVPLEEQCEY LSYDASQWEF PRERLHLGRV LGYGAFGKVV EASAFGIHKG SSCDTVAVRM
881 LKEGATASEH RALMSELKIL IHIGNHLNVV NLLGACTKPQ GPLMVTVEYC KYGNLSNFLR AKRDAFSPCA EKSPEQRGRF
961 RAMVELARLD RRRPGSSDRV LFARPSKTEG GARRASPDQE AEDLWLSPLT MEDLVCYSFQ VARGMEFLAS RKCTHRDLAA
1041 RNILLSESDV VKICDFGLAR DIYKDPDYVR KGSARLPLKW MAPESTFDKV YTTQSDVWSF GVLLWEIFSL GASPYPGVQI
1121 NEEFCQRLRD GTRMRAPELA TPAIRRIMLN CWSGDPKARP AFSELVEILG DLLQGRGLQE EEEVCMAPRS SQSSEEGSFS
1201 QVSTMALHIA QADAERDSPPS LQRHSLAARY YNWVSFPGCL ARGAETRGSS RMKTEEFPM TPTTYKGSVD NQTDSGMVLA
1281 SEEFEQIESR ERQESGFSCK GPGQNVAVTR AHPDSQGRRR RPERGARGGQ VPYNSEYGEL SEPSEEDHCS PSARVTFFTD
1361 NSY (SEQ ID No.: 36)
```

A. LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

B. HEAVY CHAIN

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK (SEQ. ID No.: 2)
```

FIG. 6

A. Light Chain Sequence

```
  1 DIQLTQSPSS LSASVGDRVT ITCSASQDIS NYLNWYQQKP GKAPKVLIYF TSSLHSGVPS RFSGSGSGTD FTLTITSSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 12)
```

B. Heavy Chain Sequence

```
  1 EVQLVESGGG LVQPGGSLRL SCAASGYDFT HYGMNWVRQA PGKGLEWVGW INTYTGEPTY AADFKRRFTF SLDTSKSTAY
 81 LQMNSLRAED TAVYYCAKYP YYGTSHWYF DWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH T (SEQ. ID No.: 13)
```

PDGFR-GS10-ANTI-VEGF-A LIGHT CHAIN:

```
  1 LVTTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVTLHEK RKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSTLHIPSAE LEDSGTYTCN VTESVNDHQD EKAINITVVE SGGGGSGGGG SDIQMTQSP SSLSASVGDR VTITCSASQD
321 ISNYLNWYQQ KPGKAPKVLI YFTSSLHSGV PSRFSGSGSG TDFTLTISSL QPEDFATYYC QQYSTVPWTF GQGTKVEIKR
401 TVAAPSVFIF PPSDEQLKSG TASVVCLLNN FYPREAKVQW KVDNALQSGN SQESVTEQDS KDSTYSLSST LTLSKADYEK
481 HKVYACEVTH QGLSSPVTKS FNRGEC (SEQ. ID No.: 19)
```

FIG. 7A

ANTI-VEGF-A HEAVY CHAIN (WILD TYPE Fc):

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK (SEQ. ID No.: 2)
```

FIG. 7B

PDGFR-GG-ANTI-VEGF-A LIGHT CHAIN:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDEQD EKAINITVVE SGGGDIQMPQ SPSSLSASVG DRVTITCSAS QDISNYLNWY
321 QQKPGKAPKV LIYFTSSLHS GVPSRFSGSG SGTDFTLTIS SLQPEDFATY YCQQYSTVPW TFGQGTKVEI KRTVAAPSVF
401 IFPPSDEQLK SGTASVVCLL NNFYPREAKV QWKVDNALQS GNSQESVTEQ DSKDSTYSLS STLTLSKADY EKHKVYACEV
481 THQGLSSPVT KSFNRGEC    (SEQ. ID No.: 3)
```

FIG. 8A

ANTI-VEGF-A HEAVY CHAIN (WILD TYPE Fc):

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGK   (SEQ. ID No.: 2)
```

FIG. 8B

PDGFR-GS10-ANTI-VEGF-A HEAVY CHAIN (WILD TYPE Fc):

```
  1 LVTTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVTLHE  KKGDVALPVP YDHQRGFSGI FEDRSYICKT
161 TIGDREVDSD ATY

PDGFR-GG-ANTI-VEGF-A HEAVY CHAIN (WILD TYPE Fc):

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGEVQLVE SGGGLVQPGG SLRLSCAASG YTFTNYGMNW
321 VRQAPGKGLE WVGWINTYTG EPTYAADFKR RFTFSLDTSK STAYLQMNSL RAEDTAVYYC AKYPHYGSS HWYFDVWGQG
401 TLVTVSSAST KGPSVFPLAP SSKSTSGGTA ALGCLVKDYF PEPVTVSWNS GALTSGVHTF PAVLQSSGLY SLSSVVTVPS
481 SSLGTQTYIC NVNHKPSNTK VDKKVEPKSC DKTHTCPPCP APELLGGPSV FLFPPKPKDT LMISRTPEVT CVVVDVSHED
561 PEVKFNWYVD GVEVHNAKTK PREEQYNSTY RVVSVLTVLH QDWLNGKEYK CKVSNKALPA PIEKTISKAK GQPREPQVYT
641 LPPSREEMTK NQVSLTCLVK GFYPSDIAVE WESNGQPENN YKTTPPVLDS DSFFLYSKL TVDKSRWQQG NVFSCSVMHE
721 ALHNHYTQKS LSLSPGK (SEQ. ID No.: 6)
```

FIG. 10A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 10B

ANTI-VEGF-A HEAVY CHAIN (WILD TYPE Fc)-GS21-PDGFR-β TRAP:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TCPPCPAPEL
241 LGGPSVFLFP PKPKDTLMIS RTPEVTCVVV DVSHEDPEVK FNWYVDGVEV HNAKTKPREE QYNSTYRVVS VLTVLHQDWL
321 NGKEYKCKVS NKALPAPIEK TISKAKGQPR EPQVYTLPPS REEMTKNQVS LTCLVKGFYP SDIAVEWESN GQPENNYKTT
401 PPVLDSDGSF FLYSKLTVDK SRWQQGNVFS CSVMHEALHN HYTQKSLSLS PGGGGSGGG GSGGGGSGGG GSGLVTPPG
481 PELVLNVSST TPSVLTLIN LHEKKGDVAL PVPYDHQRGE SGIFEDRSYI CKTTIGDREV
561 VPDPTVGFLP NDAEELFIFL TEITEITIPC RVTDPQLVVT LHEKKGDVAL PVPYDHQRGE SGIFEDRSYI CKTTIGDREV
641 DSDATYVYRL QVSSINVSVN AVQTVVRQGE NITLMCIVIG NEVVNFEWTY PRKESGRLVE PVTDFLLDMP YHIRSIHHIP
721 SAELEDSGTY TCNVTESVND HQDEKAINIT VVESG  (SEQ. ID No.: 7)
```

FIG. 11A

ANTI-VEGF LIGHT CHAIN:

```
  1 DIQMTQSPSS LSASVGDRVT ITCSASQDIS NYLNWYQQKP GKAPKVLIYF TSSLESGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC  (SEQ. ID No.: 5)
```

FIG. 11B

PDGFR-β-GS10-ANTI-VEGF-A HEAVY CHAIN (Q347C):

```
  1 LVVTPPGPEL VLNVSSTFVL TCSGSAPVVW ERMSQEPPQE MAKAQDSTFS SVLTLTNLTG LDTGEYFCTH NDSRGLETDE
 81 RKRLYIFVPD PTVGPLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVROGENIT LMCIVIGNEV VNFKWTYPRK BSGRLVEPVT DFLLDMPYHI
241 RSILHIPSAE LEDSGTYTCN VTESVNDHQD EKAINITVVE SGYGGSGSGG GSEVQLVESG GGLVQPGGSL RLSCAASGYD
321 PTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THTCPPCPAP ERAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPCVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS LSPGK     (SEQ. ID No.: 8)
```

FIG. 12A

ANTI-VEGF LIGHT CHAIN:

```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC     (SEQ. ID No.: 12)
```

FIG. 12B

PDGFR-GS10-ANTI-VEGF-A HEAVY CHAIN (L443C):

```
  1  LVVTPPGPEL VLNVSSTFVL TCSGSAPVVW ERMSQEPPQE MAKAQDGTFS SVLTLTNLTG LDTGEYFCTH NDSRGLETDE
 81  RKRLYIFVPD PTVGFLPNDA EELIFLTEI TEITIPCRVT DPQLVVTLHE KKGDVALPVP YDHQRGFSGI FEDRSYICKT
161  TIGDREVDSD AYYVRLQVS SINVSVNAVQ TVVRQGENIT LMCTVIGNEV VNFEWTYPRK ESGRLVEPVT DFLLDMPYHI
241  RSILHIPSAE LEDSGTYTCN VTESVNDHQD EKAINITVVE SGGGGSGGGG GSEVQLVESG GGLVQPGGSL RLSCAASGYD
321  FTHYGMNWVR QAPGKGLEWV GWINTYTGEP TYAADFKRRF TFSLDTSKST AYLQMNSLRA EDTAVYYCAK YPYYYGTSHW
401  YFDVWGQGTL VTVSSASTKG PSVFPLAPSS KSTSGGTAAL GCLVKDYFPE PVTVSWNSGA LTSGVHTFPA VLQSSGLYSL
481  SSVVTVPSS LGTQTYICNV NHKPSNTKVD KKVEPKSCDK THTCPPCPAP EAAGAPSVFL FPPKPKDTLM ISRTPEVTCV
561  VVDVSHEDPE VKFNWYVDGV EVHNAKTKPR EEQYNSTYRV VSVLTVLHQD WLNGKEYKCK VSNKALPAPI EKTISKAKGQ
641  PREPQVYTLP PSREEMTKNQ VSLTCLVKGF YPSDIAVEWE SNGQPENNYK TTPPVLDSDG SFFLYSKLTV DKSRWQQGNV
721  FSCSVMHEAL HNHYTQKSLS CSPGK    (SEQ ID No.: 9)
```

FIG. 13A

ANTI-VEGF LIGHT CHAIN:

```
  1  DIQLTQSPSS LSASVGDRVT ITCSASQDIS NYLNWYQQKP GKAPKVLIYF TSSLHSGVPS RFSGSGSGTD FTLTISSLQP
 81  EDFATYYCQQ YSTVPWTFGQ GTKVEIKRTV AAPSVFIFPP SDEQLKSGTA SVVCLLNNFY PREAKVQWKV DNALQSGNSQ
161  ESVTEQDSKD STYSLSSTLT LSKADYEKHK VYACEVTHQG LSSPVTKSFN RGEC    (SEQ ID No.: 12)
```

FIG. 13B

PDGFR-GS10-ANTI-VEGF-A LIGHT CHAIN:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD ATYVRLQVS SINVSNAVQ TVVRQGENIT LMCIVGNEV VNFEWTYPRK ESGRLVEPVT DFLLDMPYHI
241 RSILHIPSAE LEDSGTYTCN VTESVNDHQD EKAINITVVE SGGGGSGGGG GSDIQMTQSP SSLSASVGDR VTITCSASQD
321 ISNYLNWYQQ KPGKAPKVLI YFTSSLHSGV PSRFSGSGSG TDFTLTISSL QPEDFATYYC QQYSTVPWTF GQGTKVEIKR
401 TVAAPSVFIF PPSDEQLKSG TASVVCLLNN FYPREAKVQW KVDNALQSGN SQESVTEQDS KDSTYSLSST LTLSKADYEK
481 HKVYACEVTH QGLSSPVTKS FNRGEC     (SEQ. ID No.: 1)
```

FIG. 14A

ANTI-VEGF-A FAB:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKR VEPKSCDKTH T   (SEQ. ID No.: 21)
```

FIG. 14B

PDGFR-GG-ANTI-VEGF-A LIGHT CHAIN:

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLNVILHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGDIQMTQ SPSSLSASVG DRVTITCSAS QDISNYLNWY
321 QQKPGKAPKV LIYFTSSLHS GVPSRFSGSG SGTDFTLTIS SLQPEDFATY YCQQYSTVPW TFGQGTKVEI KRTVAAPSVF
401 IFPPSDEQLK SGTASVVCLL NNFYPREAKV QWKVDNALQS GNSQESVTEQ DSKDSTYSLS STLTLSKADY EKHKVYACEV
481 THQGLSSPVT KSFNRGEC (SEQ ID No.: 3)
```

FIG. 15A

ANTI-VEGF-A FAB:

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH T (SEQ ID No.: 21)
```

FIG. 15B

PDGFR-GS10-ANTI-VEGF-A FAB:

```
  1 LVVTPRGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYT
321 FTNYGMNWVR QAPGKGLEWV GWINTYTGEP TYAADFKRRF TFSLDTSKST AYLQMNSLRA EDTAVYYCAK YPHYYGSSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THT (SEQ. ID No.: 22)
```

FIG. 16A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 16B

PDGFR-GG-ANTI-VEGF-A FAB:

```
  1 LIVTPPGEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITTPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGEVQLVE SGGGLVQPGG SLRLSCAASG YTFTNYGMNW
321 VRQAPGKGLE WVGWINTYTG EPTYAADFKR RFTFSLDTSK STAYLQMNSL RAEDTAVYYC AKYPHYYGSS HWYFDVWGQG
401 TLVTVSSAST KGPSVFPLAP SSKSTSGGTA ALGCLVKDYF PEPVTVSWNS GALTSGVHTF PAVLQSSGLY SLSSVVTVPS
481 SSLGTQTYIC NVNHKPSNTK VDKKVEPKSC DKTHT (SEQ. ID No.: 23)
```

FIG. 17A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 17B

ANTI-VEGF-A FAB-GS21-PDGFR-β TRAP:

```
  1 EVQLVESGGG LVQPGGSLRL SCAASGYTFT NYGMNWVRQA PGKGLEWVGW INVTYTGEPTY AADFKRRFTF SLDTSKSTAY
 81 LQMNSLRAED TAVYYCAKYP HYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGGSGGG
241 GSGGGGSGGG GSGLVTPPG PELVLNVSST FVLTCSGSAP VVWERMSQEP PQEMAKAQDG TFSSVLTLTN LTGLDTGEYF
321 CTHNDSRGLE TDERKRLYIF VPDPTVGFLP NDAEELFIFL TEITEITIPC RVTDPQLVVT LHEKKGDVAL PVPYDHQRGP
401 SGIFEDRSYI CKTTIGDREV DSDAYYVYRL QVSSINVSVN AVQTVVRQGE NITLMCIVIG NEVVNFEWTY PRKESGRLVE
481 PVTDFLLDMP YHTRSTLHIP SAELEDSGTY TCNVTESVND HQDEKAINIT VVESG   (SEQ. ID No.: 24)
```

FIG. 18A

ANTI-VEGF LIGHT CHAIN:

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 18B

PDGFR-β-GS10-ANTI-VEGF-A FAB:

```
  1 LVVTPRGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVMAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THL (SEQ ID No.: 25)
```

FIG. 19A

ANTI-VEGF LIGHT CHAIN:

```
  1 DIQLTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ ID No.: 12)
```

FIG. 19B

PDGFR-β-ANTI-VEGF-A HEAVY CHAIN:

```
  1 LVTTPPGPE LVLNVSSTFV LTCSGSAPVV WERMSQEPPQ EMAKAQDGTF SSVLTLTNLT GLDTGEYFCT HNDSRGLETD
 80 ERKRLYIFVP DPTVGFLPND AEELFIFLTE ITEITTPCRV TDPQLVVTLH EKKGDVALPV PYDHQRGFSG IFEDRSYICK
160 TTIGDREVDS DAYYVYRLQV SSINVSVNAV QTVVRQGENI TLMCIVIGNE VVNFEWTYPR KESGRLVEPV TDFLLDMPYH
240 IRSILHIPSA ELEDSGTYTC NVTESVNDHQ DEKAINITVV ESGEVQLVES GGGLVQPGGS LRLSCAASGY TFTNYGMNWV
320 RQAPGKGLEW VGWINTYTGE PTYAADFKRR PTFSLDTSKS TAYLQMNSLR AEDTAVYYCA KYPHYGSSH WYPDVWGQGT
400 LVTVSSASTK GPSVFPLAPS SKSTSGGTAA LGCLVKDYFP EPVTVSWNSG ALTSGVHTFP AVLQSSGLYS LSSVVTVPSS
480 SLGTQTYICN VNHKPSNTKV DKKVEPKSCD KTHTCPPCPA PELLGGPSVF LFPPKPKDTL MISRTPEVTC VVVDVSHEDP
560 EVKFNWYVDG VEVHNAKTKP REEQYNSTYR VVSVLTVLHQ DWLNGKEYKC KVSNKALPAP IEKTISKAKG QPREPQVYTL
640 PPSREEMTKN QVSLTCLVKG FYPSDIAVEW ESNGQPENNY KTTPPVLDSD GSFFLYSKLT VDKSRWQQGN VFSCSVMHEA
720 LHNHYTQKSL SLSPGK (SEQ. ID No.: 26)
```

FIG. 20A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 20B

PDGFR-β-ANTI-VEGF-A HEAVY CHAIN:

```
  1 VGFLPNDAEE LFIFLTEITE ITTPCRVTDP QLVVTLHEKK GDVALPVPYD HQRGFSGIFE DRSYICKTTI GDREVDSDAY
 81 YVVRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH TCPPCPAPEL LGGPSVFLFP PKPKDTLMIS RTPEVTCVVV DVSHEDPEVK FNWYVDGVEV
481 HNAKTKPREE QYNSTYRVVS VLTVLHQDWL NGKEYKCKVS NKALPAPIEK TISKAKGQPR EPQVYTLPPS REEMTKNQVS
561 LTCLVKGFYP SDIAVEWESN GQPENNYKTT PPVLDSDGSF FLYSKLTVDK SRWQQGNVFS CSVMHEALHN HYTQKSLSLS
641 PGK (SEQ. ID No.: 27)
```

FIG. 21A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 21B

PDGFR-β-ANTI-VEGF-A FAB:

```
  1 VGFLPNDAEE LFIFLTEITE ITTPCRVTDP QLVVTLHEKK GDVALPVPYD HQRGESGIFE DRSYICKTTI GDREVDSDAY
 81 YVVRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH T (SEQ ID No.: 28)
```

FIG. 22A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ ID No.: 5)
```

FIG. 22B

PDGFR-β-ANTI-VEGF-A FAB:

```
  1 VGFLPNDAEE LRTELRITIE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG GGSGGGGSG GGGSGGGGSE GGGSGGGGSL VQLVESGGGL VQPGGSLRLS
241 CAASGFTFTN YGMNWVRQAP GKGLEWVGWI NTYTGEPTYA ADFKRRFTFS LDTSKSTAYL QMNSLRAEDT AVYYCAKYPH
321 YYGSSHWYFD VWGQGTLVTV SSASTKGPSV FPLAPSSKST SGGTAALGCL VKDYFPEPVT VSWNSGALTS GVHTFPAVLQ
401 SSGLYSLSSV VTVPSSSLGT QTYICNVNHK PSNTKVDKKV EPKSCDKTHT (SEQ. ID No.: 29)
```

FIG. 23A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC (SEQ. ID No.: 5)
```

FIG. 23B

PDGFR-β-6XGS-ANTI-VEGF-A FAB:

```
  1 VGFLPNDAEE LPLELTITE ITTPCRVTDP QLVVTLHEKK GDVALPVPYD HQRGFSGIFE DRSYICKTTI GDREVDSDAY
 81 YVVRLQVSSI NVSVNAVQTV VRQGENTTLM CIVIGNEVVN FEWTYPRKES GRLVEPVTDP LLDMPYHIRS ILHIPSAELE
161 DSGTYTCNVT ESVNDHQDEK AINITVVESG GGSGGGGSG GGSGGGGSSE VQLVESGGGL VQPGGSLRLS
241 CAASGYTFTN YGMNWVRQAP GKGLEWVGWI NTYTGEPTYA ADFKRRFTFS LDTSKSTAYL QMNSLRAEDT AVYYCAKYPH
321 YYGSSHWYFD VWGQGTLVTV SSASTKGPSV FPLAPSSKST SGGTAALGCL VKDYFPEPVT VSWNSGALTS GVHTFPAVLQ
401 SSGLYSLSSV VTVPSSSLGT QTYICNVNHK PSNTKVDKKV EPKSCDKTHT    (SEQ. ID No.: 29)
```

FIG. 24A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTYPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC      (SEQ. ID No.: 5)
```

FIG. 24B

ANTI-VEGF-A FAB-6XGS-PDGFR-β

```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGSGGGGS
241 GGGGSGGGGS GGGGSGGGGS VGFLPNDAEE LFIFLTEITE ITIPCRVTDP QLVTLHEKK GDVALPVYD HQRGFSGIFE
321 DRSYICKTTI GDREVDSDAY YVYRLQVSSI NVSVNAVQTV VRQGENITLM CIVIGNEVVN FEWTYPRKES GRLVEPVTDF
401 LLDMPYHIRS ILHIPSAELE DSGTYTCNVT ESVNDHQDEK AINITVVESG  (SEQ. ID No.: 30)
```

FIG. 25A

ANTI-VEGF-A LIGHT CHAIN

```
  1 DIQMTQSPSS LSASVGDRVT ITCSASQDIS NYLNWYQQKP GKAPKVLIYF TSSLHSGVPS RFSGSGSGTD FTLTISSLQP
 81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC  (SEQ. ID No.: 5)
```

FIG. 25B

COMPOUND L

COMPOUND K

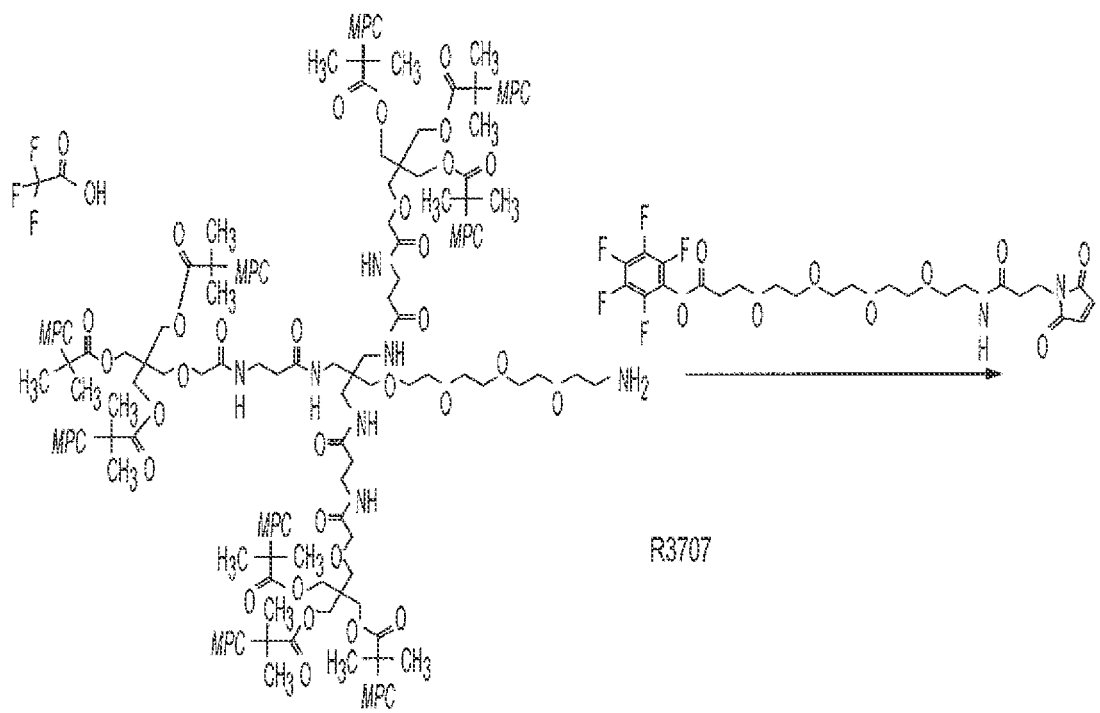
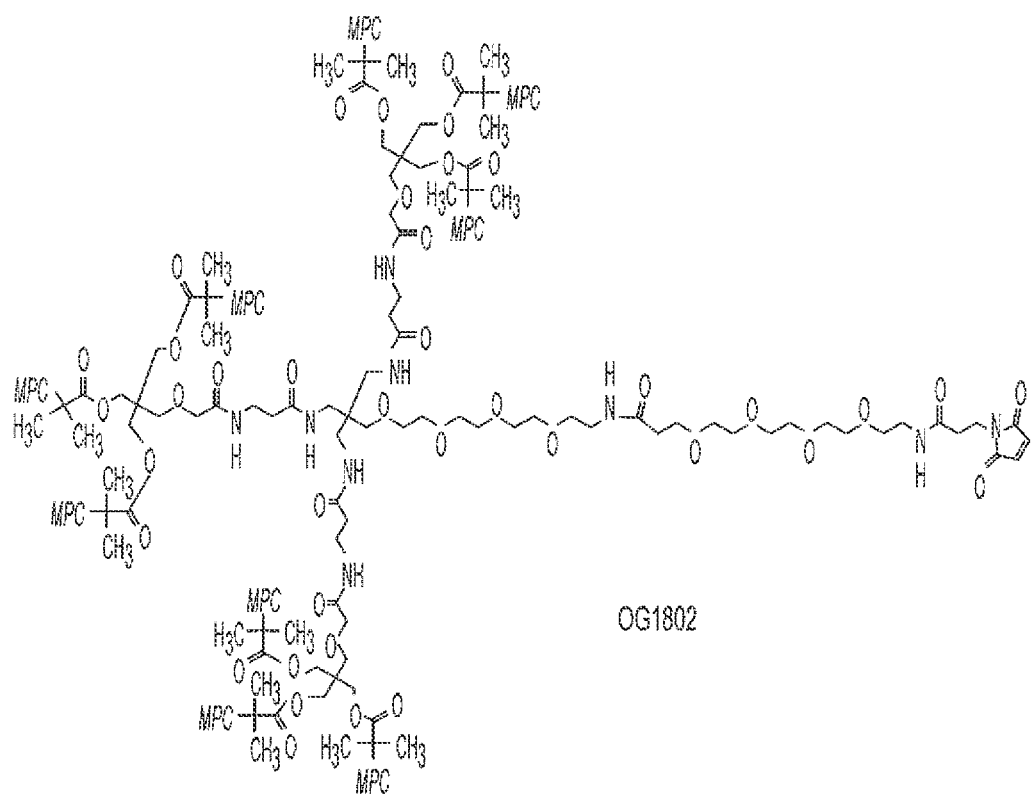
FIG. 29

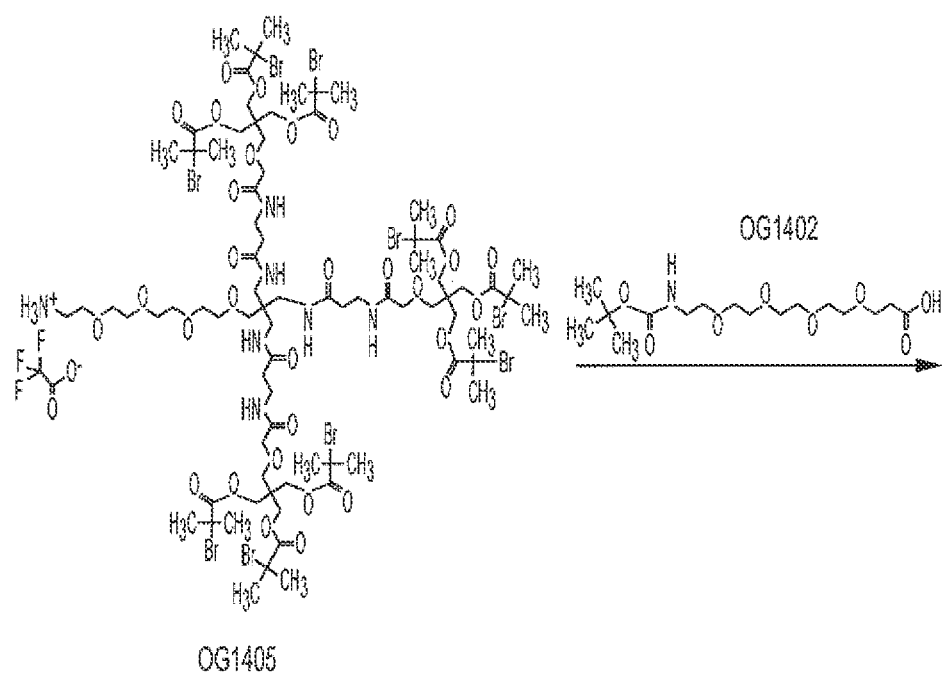
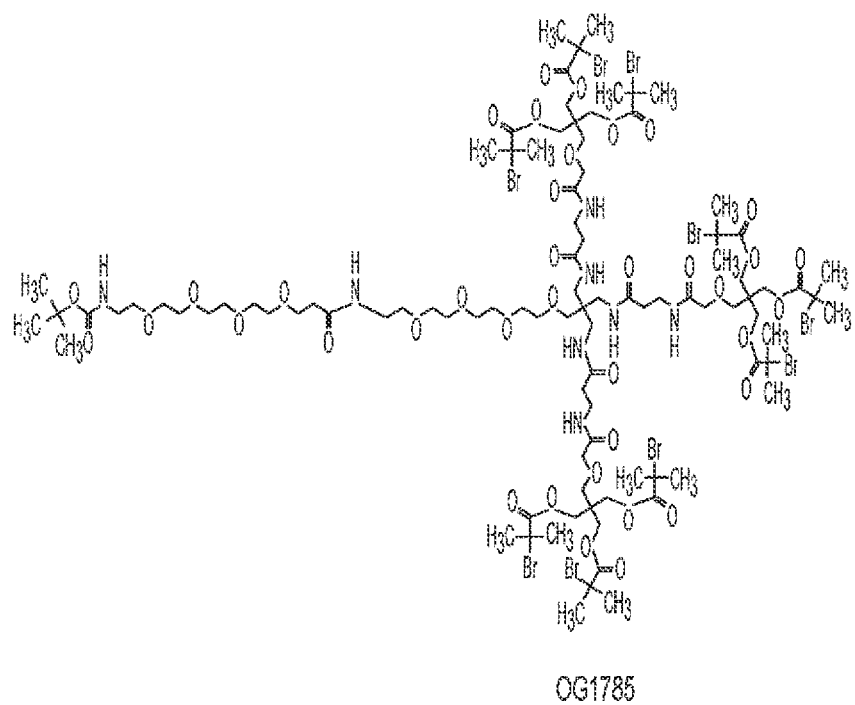
FIG. 34

DUAL PDGF/VEGF ANTAGONISTS

CROSS-REFERENCE TO RELATED APPLICATION

The present application is being filed with a Sequence Listing in electronic format. The Sequences are provided in an ASCII txt file designated SeqListKDIAK009D1.txt of 224,708 bytes, created Mar. 7, 2018, and which was replaced with the Sequence Listing provided as a file entitled KDIAK-009D1 Substitute Sequence Listing.txt, created May 16, 2018, which is 224, 692 bytes in size. The information in the electronic format of the Sequence Listing is incorporated herein by reference in its entirety.

BACKGROUND

Angiogenesis (the formation of blood vessels) occurs throughout an organism's development. Indeed, the first organ in an embryo is a blood vessel. Angiogenesis is also crucial for wound healing, restoring blood flow to damaged tissue. However, improper or dysregulated angiogenesis contributes to or causes many diseases including cancer, psoriasis, arthritis and blindness. Carmeliet P. 2003. Angiogenesis in health and disease. Nature Med 9(6):653-660.

Age related macular degeneration (AMD) is a leading cause of vision loss and blindness in the elderly. About ten million Americans are afflicted with AMD. The prevalence of AMD in the population increases steadily with age: at 40 years of age only about 2% of the population is affected by AMD but by the age of 80 it is about 25%. Friedman, D. S. et al. 2004. Arch. Ophthalmol. 122:564-572. There are generally two types of AMD: dry and wet.

Dry AMD is the most common form of the disease. In dry AMD, there is a depletion of the layer of the retinal pigment epithelial cells in the macula. Dry AMD is chronic and generally causes some loss of vision. In severe cases of dry AMD, patients can develop near total blindness. Wet AMD develops in some 10-15% of patients with dry AMD. Wet AMD is characterized by angiogenesis, specifically choroidal neovascularization (CNV). CNV is characterized by the presence of new immature blood vessels which grow towards the outer retina from the choroid. These immature blood vessels leak fluid below and in the retina, causing vision loss and blindness. Wet AMD blindness is typically acute.

Angiogenesis also plays a crucial role in cancer and tumor formation and maintenance. The recruitment of new blood vessels is an essential component of the metastatic Factors identified as mediators of angiogenesis include: basic and acidic fibroblast growth factor, transforming growth factors α and β, platelet-derived growth factor (PDGF), angiogenin, platelet-derived endothelial cell growth factor, IL8, and vascular endothelial growth factor (VEGF). The role of VEGF in angiogenesis has been extensively reported on.

It has been shown that VEGF signaling presents a crucial rate limiting step in physiological angiogenesis. VEGF also plays a central role in pathological angiogenesis (e.g., tumor growth). Ferrara N and Davis-Smyth T. 1997. The biology of vascular endothelial growth factor. Endocr. Rev. 18: 4-25. VEGF is also known to induce vascular leakage. Bates D O and Curry F E. 1997. Vascular endothelial growth factor increases microvascular permeability via a Ca (2+)-dependent pathway. Am J Physiol. 273: H687-H694; Roberts W G and Palade G E. 1995. Increased microvascular permeability and endothelial fenestration induced by vascular endothelial growth factor. J Cell Sci. 108:2369-2379.

Anti-VEGF therapeutics have been successfully used to treat wet AMD and cancer. Genentech's anti-VEGF monoclonal antibody bevacizumab (Avastin®) received FDA approval in 2004 for the treatment of cancer. Anti-VEGF agents have been approved for the treatment of wet AMD. In 2004, the FDA approved Eyetech/Pfizer Macugen®. Genentech's Lucentis® was approved in 2006 for wet AMD. Bevacizumab is also used off label for the treatment of wet AMD. In 2011, Regeneron's Eylea® was approved for treatment of wet AMD.

Despite the success of anti-VEGF therapeutics, none of them causes regression in the pathological neovascular (NV) tissue. Hence, NV tissue remains despite continued anti-VEGF treatment and can prevent significant vision gain for treated patients. The NV tissue consists of endothelial cells, pericytes and inflammatory cells (i.e., occasional macrophages). The presence of pericytes on capillaries not only leads to NV support and stabilization but promotes endothelial cell survival through chemical signaling and physical interactions including pericyte production of VEGF. This endothelial survival signaling by integrated pericytes is critical and may explain the resistance of the NV tissue to VEGF withdrawal, i.e., lack of NV regression to monotherapy anti-VEGF treatment. In addition, over time the pathological NV tissue can lead to fibrosis and scarring.

Subretinal scarring develops in nearly half of treated eyes within two years of anti-VEGF therapy. Daniel E, Toth C A, Grunwald J E. 2014. Risk of scar in the comparison of age-related macular degeneration in clinical settings. Retina 32:1480-1485. Subretinal fibrosis formation can cause permanent dysfunction of the macular system; it causes destruction of photoreceptors, retinal pigment epithelium and choroidal vessels. Ishikawa K, Ram K, Hinton D R. 2015. Molecular mechanisms of subretinal fibrosis in age-related macular degeneration. Eye Res. xxx:1-7. While anti-VEGF therapy generally stabilizes or improves visual acuity, scar formation has been identified as one of the causes of loss of visual acuity after treatment. Cohen S Y, Oubraham H, Uzzan J, et al. 2012. Causes of unsuccessful ranibizumab treatment in exudative age-related macular degeneration in clinical settings. Retina 32:1480-1485.

PDGF has been reported to play a role in pericyte recruitment, maturation and resistance to anti-VEGF mediated regression. Corneal and choroidal neovascularization animal models have been reported to have demonstrated that administration of agents that block the PDGF-B/PDGFR-β interaction leads to pericyte stripping from the pathological neovasculature. Jo N, Mailhos C, Ju M, et al. 2006. Inhibition of Platelet-Derived Growth Factor B Signaling Enhances the Efficacy of Anti-Vascular Endothelial Growth Factor Therapy in Multiple Models of Ocular Neovascularization. American J Path. 168(6):2036-2053.

To target both pathways, clinical trials are currently underway in which patients receive two medications: Lucentis® (an anti-VEGF Fab) and Fovista™ a PEGYlated aptamer directed against PDGF by Ophthotech. Fovista is directed against only a single PDGF ligand: PDGF-BB. However, there are many other PDGF ligands: PDGF-AA, PDGF-CC and PDGF-DD. PDGF-DD, for example, has been shown to play a crucial role in ocular angiogenesis. Kumar A, Hou X, Chunsik L, et al. 2010. Platelet-derived Growth Factor-DD Targeting Arrests Pathological Angiogenesis by Modulating Glycogen Synthase Kinase-3β Phosphorylation. J Biol Chem 285(20):15500-15510. Yet Fovista does not interact with PDGF-DD. There is a need in the art for broader based anti-PDGF therapies.

In addition, aptamer based therapeutics in general have poor pharmacokinetic properties in that aptamers are subject to renal filtration and to serum digestion. While these problems can be somewhat overcome with PEGylation, PEGylation tends to reduce binding to target. Aptamers typically bind with much lower affinity to targets than their antibody counterparts. PEGylation will tend to reduce binding even further. There is, thus, a need in the art for non-aptamer based anti-PDGF therapeutics.

Current clinical plans for Fovista double the number of injections patients must receive for treatment relative to the currently approved anti-VEGF therapies. Fovista is formulated separately from the anti-VEGF agent so patients must be given two injections instead of one. Moreover the injections cannot be at the same time because of build-up in intraocular pressure caused by a single injection.

From the view point of both patients and treating physicians, intravitreal injections are not trivial. Many patients experience pain and discomfort from the injection and patient compliance is a serious issue. Common side effects of intravitreal injections include conjunctival hemorrhage, eye pain, vitreous floaters, increased intraocular pressure, and intraocular inflammation. Intravitreal injections are associated with relatively rare serious adverse events, including endophthalmitis, retinal detachment and traumatic cataracts.

There is thus a need in the art for therapies that do not increase the number of intravitreal injections that patients must endure. In addition, current anti-VEGF therapies often require once a month injections. There is also a need for therapies which are needed less frequently than once a month.

SUMMARY OF THE CLAIMED INVENTION

The invention provides a dual VEGF/PDGF antagonist comprising a VEGF antagonist linked to a PDGF antagonist, wherein the VEGF antagonist (a) is an antibody to a VEGF or VEGFR or (b) is a VEGFR extracellular trap segment and the PDGF antagonist (a) is an antibody to a PDGF or PDGFR or (b) is a PDGFR extracellular trap segment, provided that the VEGF and PDGF antagonists are not both antibodies. Optionally, the VEGF antagonist is an antibody comprising a heavy chain and a light chain and the PDGF antagonist is the PDGFR extracellular trap segment, and the heavy chain of the antibody is fused via a linker to the C-terminus of the PDGFR extracellular trap segment, and the light chain is complexed with the heavy chain. Optionally, the antibody is a Fab fragment. Optionally, the antibody is an intact antibody. Optionally, the PDGF antagonist is an extracellular trap segment of a PDGFR-α or PDGFR-β receptor and the VEGF antagonist is an antibody to a VEGF. Optionally, the PDGFR extracellular trap segment comprises one or more of domains D1-D5 of PDGFR-β. Optionally, the PDGFR extracellular trap segment comprises domains D1-D3 of PDGFR-β. Optionally, the PDGFR extracellular trap segment comprises amino acids 33 to 314 of SEQ ID NO. 11. Optionally, the VEGF antagonist comprises an anti-VEGF antibody. Optionally, the anti-VEGF antibody is an anti-VEGFA antibody. Optionally, the PDGFR extracellular trap segment is located C-terminal of the heavy or light chain. Optionally, the PDGFR extracellular trap segment is located N-terminal of the heavy or light chain.

Optionally, the dual VEGF/PDGF antagonist of further comprising a linker which is located between the PDGFR trap and the anti-VEGF antibody heavy chain. Optionally the linker is GGGGSGGGGS, GG, or GGGGSGGGGSGGGGSGGGGSG.

Optionally, the anti-VEGF antibody heavy chain comprises $CDR_H1$: GYDFTHYGMN, $CDR_H2$: WINTYTGEPTYAADFKR, and $CDR_H3$: YPYYYGTSHWYFDV. Optionally, the anti-VEGF light chain comprises $CDR_L1$: SASQDISNYLN, $CDR_L2$: FTSSLHS and $CDR_L3$: QQYSTVPWT.

Optionally, the anti-VEGF heavy chain isotype is IgG1 comprising a $CH_1$, hinge, $CH_2$ and $CH_3$ domains and the light chain isotype is kappa. Optionally the IgG1 constant domain has the sequence set forth in SEQ ID NO. 17 and the light chain constant region has the sequence set forth in SEQ ID NO. 18.

Optionally, the IgG1 constant domain has one or more mutations to reduce effector function. Optionally the mutations are to one or more of the following amino acid positions (EU numbering): E233, L234, L235, G236, G237, A327, A330, and P331. Optionally, the mutations are selected from the group consisting of: E233P, L234V, L234A, L235A, G237A, A327G, A330S and P331S. Optionally, mutations are L234A, L235A and G237A.

Optionally, the dual VEGF/PDGF antagonist comprises a heavy chain further comprising a cysteine residue added by recombinant DNA technology. Optionally, the cysteine residue is selected from the group consisting of (EU numbering) Q347C and L443C.

Optionally, the dual VEGF/PDGF antagonist has a heavy chain comprising the amino acid sequence off SEQ ID NO. 9 and the light chain has an amino acid sequence of SEQ ID NO. 10.

Optionally, the dual VEGF/PDGF antagonist comprises a PDGFR trap extracellular segment comprising one or more of domains D1-D5 of PDGFR-β. Optionally, the PDGFR trap extracellular segment comprises domains D1-D3 of PDGFR-β. Optionally, the PDGFR trap extracellular segment comprises amino acids 33 to 314 of SEQ ID NO. 11.

Optionally, the dual VEGF/PDGF antagonist comprises a VEGF antagonist, which is an anti-VEGF antibody. Optionally, the antibody is an anti-VEGF-A Fab fragment. Optionally, the PDGFR extracellular trap segment is located C-terminal of the Fab heavy or light chain. Optionally, the PDGFR extracellular trap segment is located N-terminal of the Fab heavy or light chain.

Optionally, the dual VEGF/PDGF comprises a heavy chain comprising an anti-VEGF-A Fab fragment heavy chain and a light chain comprising an anti-VEGF-A light chain. Optionally, the dual antagonist further comprises a linker which is located between the PDGFR trap and the anti-VEGF Fab fragment heavy chain. Optionally, the linker is selected from group consisting of GGGGSGGGGS, GG, and GGGGSGGGGSGGGGSGGGGSG. Optionally, the anti-VEGF Fab fragment heavy chain comprises $CDR_H1$: GYDFTHYGMN, $CDR_H2$: WINTYTGEPTYAADFKR, and $CDR_H3$: YPYYYGTSHWYFDV. Optionally, the anti-VEGF light chain comprises $CDR_L1$: SASQDISNYLN, $CDR_L2$: FTSSLHS and $CDR_L3$: QQYSTVPWT. Optionally, the anti-VEGF heavy chain isotype is IgG1 comprising a $CH_1$ domain and the light chain isotype is kappa.

Any of the dual VEGF/PDGF antagonists can further comprise a half-life extending moiety. Optionally, the half-life extending moiety comprises a polymer, which is PEG or a zwitterionic polymer. Optionally, the zwitterionic polymer comprises a monomer comprising phosphorylcholine. Optionally, the monomer comprises 2-(acryloyloxyethyl)-2'-(trimethylammoniummethyl) phosphate. Optionally, the monomer comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer has 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da. Optionally, the dual VEGF/PDGF antagonist is covalently bonded to the polymer. Optionally, the polymer is covalently bonded to at least one of an amino group, a hydroxyl group, a sulfhydryl group and a carboxyl group. Optionally, the sulfhydryl group is from a naturally occurring cysteine residue. Optionally, the sulfhydryl group is from a cysteine residue added by recombinant DNA technology. Optionally, the polymer is covalently bonded to the cysteine residue at position 731 of SEQ ID NO. 9.

Optionally, the VEGF antagonist comprises a VEGFR extracellular trap segment comprising one or more extracellular segments of VEGFR-1, VEGFR-2 and VEGFR-3 and the PDGF antagonist is an anti-PDGF antibody. Optionally, the extracellular segment of VEGFR comprises one or more of domains D1-D7. Optionally, the extracellular segment comprises D2 from VEGFR-1 and D3 from VEGFR-2. Optionally, the D2 is N-terminal to the D3 and further comprises a linker between the domains. Optionally, the PDGF antagonist is an intact antibody. Optionally, the PDGF antagonist is a Fab fragment. Optionally, the anti-PDGFR antibody is humanized 2A1E2, HuM4Ts.22, humanized 1B3, humanized 2C5, anti-PDGF-BB, anti-PDGF-DD, anti-PDGF-BB or anti-PDGF-AB. Optionally, the heavy chain is IgG1 and the light chain is kappa. Optionally, the heavy chain sequence has a cysteine added via recombinant DNA technology the cysteine selected from the groups consisting of Q347C or a L443C. Optionally, the dual VEGF/PDGF antagonist further comprises a half-life extending moiety conjugated to the cysteine. Optionally, the dual VEGF/PDGF antagonist protein has a half-life extending moiety comprising a zwitterionic polymer, the polymer comprising one or more monomer units and wherein at least one monomer unit comprises a zwitterionic group, such as phosphorylcholine. Optionally, the monomer comprises 2-(acryloyloxyethyl)-2'-(trimethylammoniumethyl) phosphate. Optionally, the monomer comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer has 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da.

In some dual VEGF/PDGF antagonists the PDGF antagonist comprises a PDGF extracellular trap segment comprising one or more extracellular segments of a PDGFR selected from the group consisting of PDGFR-α and PDGFR-β and the VEGF antagonist is a VEGF extracellular trap segment comprising one or more extracellular segments of a VEGFR selected from the group consisting of VEGFR-1, VEGFR-2 and VEGFR-3. Optionally, the extracellular trap segment of VEGFR comprises one or more of domains D1-D7. Optionally, the extracellular trap segment comprises D2 from VEGFR-1 and D3 from VEGFR-2. Optionally, the D2 is N-terminal to the D3 and further comprises a linker between the domains. Optionally, the PDGFR trap comprises one or more of domains D1-D5 of PDGFR-β. Optionally, the PDGFR trap comprises domains D1-D3 of PDGFR-β. Optionally, the PDGFR trap comprises amino acids 33 to 314 of SEQ ID NO. 11. Optionally, the dual VEGF/PDGF antagonist further comprises a linker sequence between the VEGF antagonist and the PDGF antagonist. Optionally, the dual VEGF/PDGF antagonist further comprises a half-life extending moiety. Optionally, the half-life extending moiety comprises a polymer selected from the group consisting of PEG and a zwitterionic polymer. Optionally, the half-life extending moiety comprises a zwitterionic polymer. Optionally, the zwitterionic polymer comprises a monomer comprising phosphorylcholine. Optionally, the monomer comprises 2-(acryloyloxyethyl)-2'-(trimethylammoniumethyl) phosphate. Optionally, the monomer comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer portion of the conjugate has a peak molecular weight of between 300,000 and 1,750,000 Da. Optionally, the polymer portion of the conjugate has a peak molecular weight between 500,000 and 1,000,000 Da. Optionally, the polymer portion of the conjugate has a peak molecular weight between 600,000 to 800,000 Da. Optionally, the polymer has 9 arms. Optionally, the dual VEGF/PDGF antagonist is covalently bonded to the polymer. Optionally, the polymer is covalently bonded to at least one of an amino group, a hydroxyl group, a sulfhydryl group and a carboxyl group. Optionally, the sulfhydryl group is from a naturally occurring cysteine residue. Optionally, the sulfhydryl group is from a cysteine residue added by recombinant DNA technology.

Any dual VEGF/PDGF antagonist as described above can be used in treatment or prophylaxis of disease, particularly a neovascular disorder, optionally an ocular neovascular disorder, such as wet age related macular degeneration.

BRIEF DESCRIPTION OF THE DRAWINGS

FIG. 1: Protein Sequence of human PDGFR-β
FIG. 2: Protein Sequence of VEGFR-1
FIG. 3: Protein Sequence of VEGFR-2
FIG. 4: Protein Sequence of VEGFR-3
FIG. 5: bevacizumab sequence (DrugBank DB00112)
FIG. 6: ranibizumab (published by Novartis).
FIGS. 7A, B: Protein Sequence of A. PDGFRβ-GS10-anti-VEGF-A light chain and B. anti-VEGF-A heavy chain.
FIGS. 8A, B: A. Protein Sequence of PDGFRβ-GG-anti-VEGF-A light chain and B. anti-VEGF-A heavy chain.
FIGS. 9A, B. Protein Sequence of A. PDGFRβ-GS10-anti-VEGF-A heavy chain (wild type Fc) and B. anti-VEGF-A light chain.
FIGS. 10A, B. Protein Sequence of A. PDGFRβ-GG-anti-VEGF-A heavy chain (wild type Fc) and B. anti-VEGF-A light chain.
FIGS. 11A, B. Protein Sequence of A. anti-VEGF-A heavy chain (wild type Fc)-GS21-PDGFRβ and B. anti-VEGF-A light chain.
FIGS. 12A, B. Protein Sequence of A. PDGFRβ-GS21-anti-VEGF-A heavy chain (Q347C) and B. anti-VEGF-A light chain (TAF347).

FIGS. 13A, B. Protein Sequence of A. PDGFR-β-GS21-anti-VEGF-A heavy chain (L443C) and B. anti-VEGF-A light chain (TAF443).

FIGS. 14A, B. Protein Sequence of A. PDGFRβ-GS10-anti-VEGF-A light chain and B. anti-VEGF-A Fab.

FIGS. 15A, B. Protein Sequence of A. PDGFRβ-GG-anti-VEGF-A light chain and B. anti-VEGF-A Fab.

FIGS. 16A, B. Protein Sequence of A. PDGFRβ-GS10-anti-VEGF-A Fab and B. anti-VEGF-A light chain.

FIGS. 17A, B. Protein Sequence of A. PDGFRβ-GG-anti-VEGF-A Fab and B. anti-VEGF-A light chain.

FIGS. 18A, B. Protein Sequence of A. anti-VEGF-A Fab-GS21-PDGFRβ and B. anti-VEGF-A light chain.

FIGS. 19A, B. Protein Sequence of A. PDGFRβ-GS10-anti-VEGF-A Fab with certain mutations and B. anti-VEGF-A light chain.

FIGS. 20A, B. Protein Sequence of A. PDGFRβ-anti-VEGF-A heavy chain and B. anti-VEGF-A light chain (1a).

FIGS. 21A, B. Protein Sequence of A. PDGFR-β (D2-D3)-anti-VEGF-A heavy chain and B. anti-VEGF-A light chain (1b).

FIGS. 22A, B. Protein Sequence of A. PDGFR-β (D1-D3)-anti-VEGF-A Fab and B. anti-VEGF-A light chain (2b).

FIGS. 23A, B. Protein Sequence of A. PDGFR-β (D2-D3)-6×GS-anti-VEGF-A Fab and B. anti-VEGF-A light chain (2b').

FIGS. 24A, B. Protein sequence of A. PDGFR-β-6×GS-anti-VEGF-A Fab and B. anti-VEGF-A light chain.

FIGS. 25A, B: Protein Sequence of A. anti-VEGF-A Fab-6×GS-PDGFR-β (D2-D3) and B. anti-VEGF-A light chain (3).

FIG. 29 shows the synthesis of OG1802 from R3707.

FIG. 34 shows the synthesis of OG1785 from OG1405.

BRIEF DESCRIPTION OF SEQ ID NOS

Figure 26:
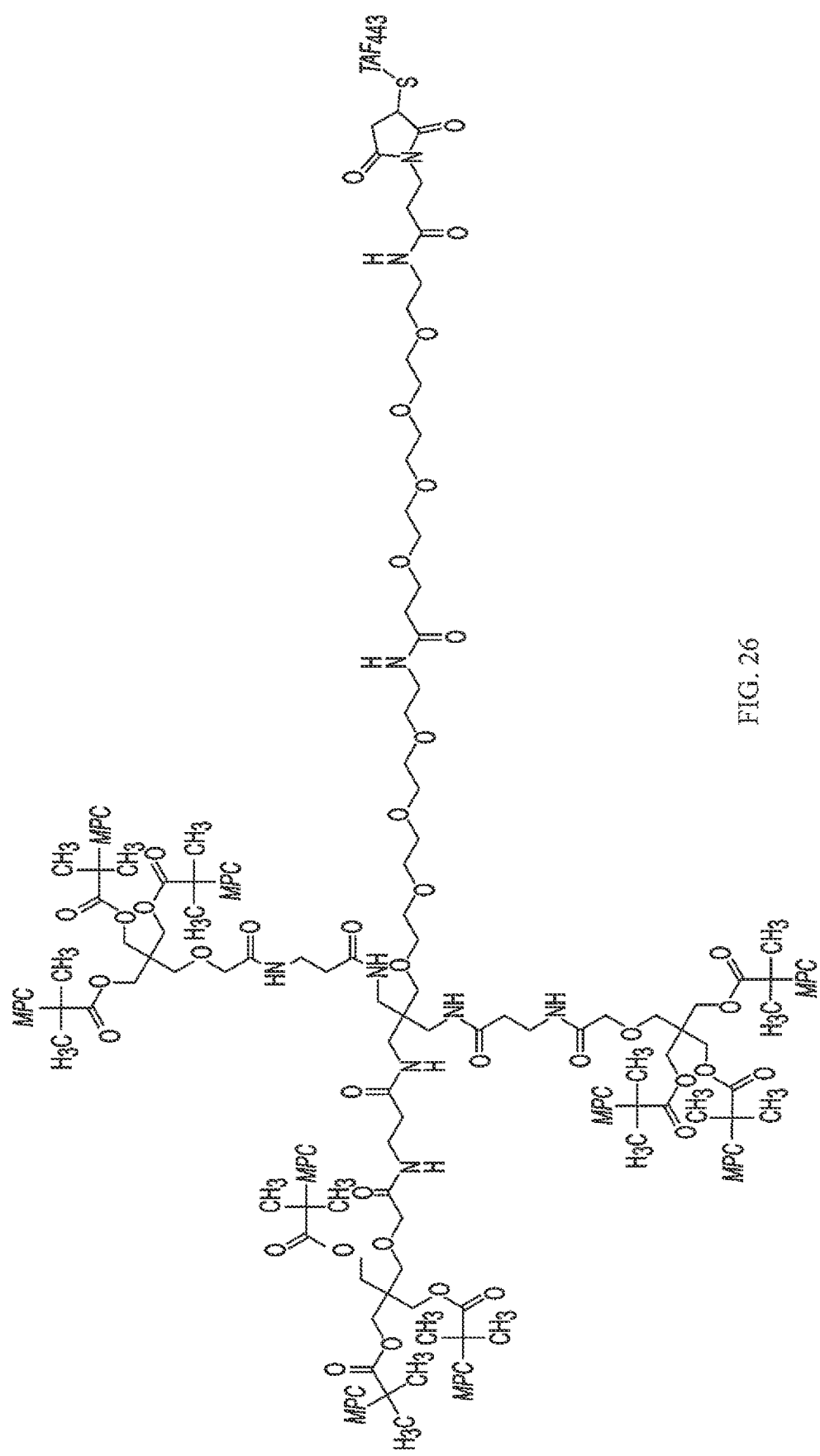
FIG. 26 shows the chemical structure of OG1448.

SEQ ID NO. 1 is the protein sequence of PDGFRb-GS10-LightChain anti-VEGF-A (Bevacizumab).

SEQ ID NO. 2 is the anti-VEGF-A Bevacizumab heavy chain.

SEQ ID NO. 3 is protein sequence of PDGFRb-GG-Light Chain anti-VEGF-A (Bevacizumab).

SEQ ID NO. 4 is PDGFRβ-GS10-Heavy Chain-anti-VEGF-A (Bevacizumab).

SEQ ID NO. 5 is the anti-VEGF-A Bevacizumab light chain.

SEQ ID NO. 6 is PDGFRβ-GG-Heavy Chain-anti-VEGF-A (Bevacizumab).

SEQ ID NO. 7 is anti-VEGF-A Heavy Chain (Bevacizumab)-GS21-PDGFRβ.

SEQ ID NO.8 is the amino acid sequence of the heavy chain trap extracellular segment of TAF347: PDGFR-β trap-anti-VEGF-A heavy chain (Q 347C).

SEQ ID NO. 9 is the amino acid sequence of the heavy chain trap extracellular segment of TAF443: PDGFR-β trap-anti-VEGF-A heavy chain (L-443C) and SEQ ID NO:10 is the amino acid sequence of the light chain of anti-VEGF-A.

SEQ ID NO. 11 is human PDGFR-β.

SEQ ID NO. 12 is the ranibizumab light chain.

SEQ ID NO. 13 is the ranibizumab heavy chain.

SEQ ID NO. 14 is human VEGFR-1.

SEQ ID NO. 15 is human VEGFR-2.

SEQ ID NO. 16 is human VEGFR-3.

SEQ ID NO. 17 is a human IgG1 constant region.

SEQ ID NO. 18 is a human kappa light constant region.

SEQ ID NO. 19 is FIG. 7. PDGFR-GS10-anti-VEGF-A light chain.

SEQ ID NO. 20 is FIG. 8. PDGFR-GG-anti-VEGF-A light chain.

SEQ ID NO. 21 is a Bevacizumab Fab.

SEQ ID NO. 22 is a PDGFR-β-GS10-anti-VEGF-A Fab.

SEQ ID NO. 23 is a PDGFR-β-GG-anti-VEGF-A Fab.

SEQ ID NO. 24 is an anti-VEGF-A Fab-GS21-PDGFR-β.

SEQ ID NO. 25 is a PDGFR-β-GS10-anti-VEGF-A Fab with certain mutations.

SEQ ID NO. 26 is a protein sequence of PDGFRβ-anti-VEGF-A heavy chain (1a).

SEQ ID NO. 27 is a protein sequence of PDGFR-β (D2-D3)-anti-VEGF-A heavy chain (1b).

SEQ ID NO. 28 is a protein sequence of PDGFR-β (D2-D3)-anti-VEGF-A Fab (2b).

SEQ ID NO. 29 is a protein sequence of PDGFR-β (D2-D3)-6×GS-anti-VEGF-A Fab.

SEQ ID NO. 30 is a protein sequence of anti-VEGF-A Fab-6×GS-PDGFR-β (D2-D3).

SEQ ID NO. 31 is a nucleic acid encoding a heavy chain anti-VEGF-PDGFR fusion.

SEQ ID NO. 32 is a nucleic acid encoding a light chain anti-VEGF.

GGGGS (SEQ ID NO. 37), GGGS (SEQ ID NO. 38), GGGES (SEQ ID NO. 39), GGGGSGGGGS (SEQ ID NO. 40) and GGGGSGGGGSGGGGSGGGGSG) (SEQ ID NO. 41).

Ranibizumab CDRs are: $CDR_H1$: GYDFTHYGMN, $CDR_H2$: WINTYTGEPTYAADFKR, and $CDR_H3$: YPYYYGTSHWYEDV (SEQ ID NOS. 42-44), $CDR_L1$: SASQDISNYLN, $CDR_L2$: FTSSLHS and $CDR_L3$: QQYSTVPWT (SEQ ID NOS. 45-47). Bevacizumab $CDR_H1$ is GYTFTNYGMN (SEQ ID NO. 48) and $CDR_H3$ is YPHYYGSSHWYFDV (SEQ ID NO:49).

DEFINITIONS

A "neovascular disorder" is a disorder or disease state characterized by altered, dysregulated or unregulated angiogenesis. Examples of neovascular disorders include neoplastic transformation (e.g. cancer) and ocular neovascular disorders including diabetic retinopathy and age-related macular degeneration.

An "ocular neovascular" disorder is a disorder characterized by altered, dysregulated or unregulated angiogenesis in the eye of a patient. Such disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

A "polypeptide linker" is a polypeptide comprising two or more amino acid residues joined by peptide bonds that are used to link two polypeptides (e.g., a VH and VL domain or a VH domain and an extracellular trap segment). Examples of such linker polypeptides are well known in the art (see, e.g., Holliger P, Prospero T, Winter (i. 1993. PNAS USA. 90:6444-6448; Poljak R J. 1994. Production and Structure of Diabodies. Structure 2:1121-1123). Exemplary linkers include G, GG, GGGGS, GGGS, and GGGES, and oligomers of such linkers (e.g., GGGGSGGGGS and GGGGSGGGGSGGGGSGGGGSG).

Dual antagonists or other biologics described herein are typically provided in isolated form. This means that an antagonist is typically at least 50% w/w pure of interfering proteins and other contaminants arising from its production or purification but does not exclude the possibility that the antagonist is combined with an excess of pharmaceutical acceptable excipient intended to facilitate its use. Sometimes antagonists are at least 60, 70, 80, 90, 95 or 99% w/w pure of interfering proteins and contaminants from production or purification. Often an antagonist is the predominant macromolecular species remaining after its purification.

The term antibody includes intact antibodies and binding fragments thereof. A binding fragment refers to a molecule other than an intact antibody that comprises a portion of an intact antibody that binds the antigen to which the intact antibody binds. Examples of binding fragments include Fv, Fab', Fab'-SH, F(ab')2; diabodies; linear antibodies; single-chain antibody molecules (e.g. scFv); and multispecific antibodies formed from antibody fragments. scFv antibodies are described in Houston J S. 1991. Methods in Enzymol. 203:46-96. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

Specific binding of an antibody, extracellular trap segment or dual antagonist to its target antigen(s) means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcR binding.

Light chains are classified as either kappa or lambda. Heavy chains are classified as gamma, mu, alpha, delta, or epsilon, and define the antibody's isotype as IgG, IgA, IgD and IgE, respectively. Within light and heavy chains, the variable and constant regions are joined by a "J" segment of about 12 or more amino acids, with the heavy chain also including a "D" segment of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai S, Lachmann P C. 1990. Bispecific antibody: a tool for diagnosis and treatment of disease. Clin Exp Immunol. 79:315-321; Kostelny S A, Cole M S, Tso J Y. 1992. Formation of bispecific antibody by the use of leucine zippers. J Immunol. 148: 1547-1553). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. For convenience, the variable heavy CDRs can be referred to as $CDR_H1$, $CDR_H2$ and $CDR_H3$; the variable light chain CDRs can be referred to as $CDR_L1$, $CDR_L2$ and $CDR_L3$. The assignment of amino acids to each domain is in accordance with the definitions of Kabat E A, et al. 1987 and 1991. Sequences of Proteins of Immunological Interest (National Institutes of Health, Bethesda, Md.) or Chothia C, Lesk A M. 1987. Canonical Structures for the Hypervariable Regions of Immunoglobulins. Mol Biol 196:901-917; Chothia C, et al. 1989. Conformations of Immunoglobulin Hypervariable Regions. Nature 342:877-883. Kabat also provides a widely used numbering convention (Kabat numbering) in which corresponding residues between different heavy chain variable regions or between different light chain variable regions are assigned the same number. Although Kabat numbering can be used for antibody constant regions, EU numbering is more commonly used, as is the case in this application. Although specific sequences are provided for exemplary dual antagonists, it will be appreciated that after expression of protein chains one to several amino acids at the amino or carboxy terminus of the light and/or heavy chain, particularly a heavy chain C-terminal lysine residue, may be missing or derivatized in a proportion or all of the molecules.

The term "epitope" refers to a site on an antigen to which an antibody or extracellular trap segment binds. An epitope on a protein can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody (or Fab fragment) bound to its antigen to identify contact residues.

Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50: 1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, PASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., De Pascalis R, Iwahashi M, Tamura M, et al. 2002. Grafting "Abbreviated" Complementary-Determining Regions Containing Specificity-Determining Residues Essential for Ligand Contact to Engineer a Less Immunogenic Humanized Monoclonal Antibody. J Immunol. 169:3076-3084: Vajdos F F, Adams C W, Breece T N, Presta L G, de Vos A M, Sidhu, S S. 2002. Comprehensive functional maps of the antigen-binding site of an anti-ErbB2 antibody obtained with shotgun scanning mutagenesis. J Mol Biol. 320: 415-428; Iwahashi M, Milenic D E, Padlan E A, et al. 1999. CDR substitutions of a humanized monoclonal antibody (CC49): Contributions of individual CDRs to antigen binding and immunogenicity. Mol Immunol. 36:1079-1091; Tamura M, Milenic D E, Iwahashi M, et al. 2000. Structural correlates of an anticarcinoma antibody: Identification of specificity-determining regions (SDRs) and development of a minimally immunogenic antibody variant by retention of SDRs only. J Immunol. 164:1432-1441).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan E A. 1991. A possible procedure for reducing the immunogenicity of antibody variable domains while preserving their ligand-binding properties. Mol Immunol, 28:489-98) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Östberg L, Pursch E. 1983. Human×(mouse×human) hybridomas stably producing human antibodies. Hybridoma 2:361-367; Östberg, U.S. Pat. No. 4,634,664; and Engleman et al., U.S. Pat. No. 4,634,666, use of transgenic mice including human immunoglobulin genes (see, e.g., Lonherg et al., W093/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1.990 and phage display methods (see, e.g. Dower et al., WO 91/17271 and McCafferty et al. WO 92/01047, U.S. Pat. Nos. 5,877,218, 5,871,907, 5,858,657, 5,837,242, 5,733,743 and 5,565,332.

"Polymer" refers to a series of monomer groups linked together. A polymer is composed of multiple units of a single monomer (a homopolymer) or different monomers (a heteropolymer). High MW polymers are prepared from monomers that include, but are not limited to, acrylates, methacrylates, acrylamides, methacrylamides, styrenes, vinylpyridine, vinyl-pyrrolidone and vinyl esters such as vinyl acetate. Additional monomers are useful in the high MW polymers of the present invention. When two different monomers are used, the two monomers are called "comonomers," meaning that the different monomers are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using the monomers or comonomers of the present invention. The polymerization can be a conventional free radical polymerization or preferably a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger is typically a halogen, but can also be an organic moiety, such as a nitrile. In some embodiments of the present invention, the initiator contains one of more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

"Phosphorylcholine," also denoted as "PC," refers to the following:

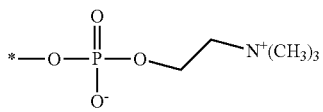

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate (HEA-PC shown below in Example 51) as monomer.

Poly(methacryloyloxyethyl phosphorylcholine) containing polymer refers to a polymer containing 2-(methacryloyloxy)ethyl-2-(trimethylammonium)ethyl phosphate (HEMA-PC) as monomer.

"Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In a preferred embodiment of the present invention, the molecular weight is measured by SEC-MALS (size exclusion chromatography—multi angle light scattering). The polymeric reagents of the invention are typically polydisperse (i.e., number average molecular weight and weight average molecular weight of the polymers are not equal), preferably possessing low polydispersity values of, for example, less than about 1.5, as judged, for example, by the PDI value derived from the SEC-MALS measurement. In other embodiments, the polydispersities (PDI) are more preferably in the range of about 1.4 to about 1.2, still more preferably less than about 1.15, and still more preferably less than about 1.10, yet still more preferably less than about 1.05, and most preferably less than about 1.03.

The phrase "a" or "an" entity refers to one or more of that entity; for example, a compound refers to one or more compounds or at least one compound. As such, the terms "a" (or "an"), "one or more", and "at least one" can be used interchangeably herein.

"About" means variation one might see in measurements taken among different instruments, samples, and sample preparations.

"Protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," $3^{rd}$ Edition, John Wiley and Sons, Inc., New York, 1999.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched)) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=N H, —NH—C(NH$_2$)=NR', —S(O)R', —S(O)$_2$R'—S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. The term "alkyl" is include groups such as haloalkyl (e.g., —CF$_3$ and —CH$_2$CF$_3$) and acyl (e.g., —C(O)CH$_3$, —C(O)CF$_3$, —CH (O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means a cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" in the context of this invention is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms, Cycloalkyl groups include fused, bridged and Spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3 dithiane, 1,4-dithiane, 4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be Mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl Or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl, Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$— or —S(O)$_2$NR'—. The substituent R' in —NR'— and —S(O)$_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, (uranyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkylamines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

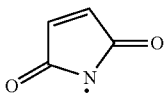

which upon reaction with a sulfhydryl (e.g., a thio alkyl) forms an —S-maleimido group having the structure

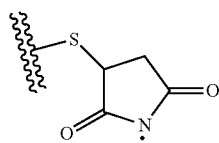

where "•" indicates the point of attachment for the maleimido group and "⸾" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L, asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as N-alpha-methyl amino acids (e.g. sarcosine), 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. Preferably, the halide is a bromine.

"Pharmaceutically acceptable excipient" refers to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Dual antagonists are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a pre-clinical or clinical trial in a population of treated patients relative to a control population of untreated patients.

The "biological half-life" of a substance is a pharmacokinetic parameter which specifies the time required for one half of the substance to be removed from a tissue or an organism following introduction of the substance.

"HEMA-PC" is 2-(methacryloyloxyethyl)-2'-(trimethylammoniumethyl) phosphate.

"TAF" means a PDGFRβ-GS10-anti-VEGF-A heavy chain/anti-VEGF-A light chain wherein amino acids 1-282 of the heavy chain correspond to amino acids 33 to 314 of human PDGFR-β (UniProtKB/Swiss-Prot: P09619.1), fused as a single open reading frame via a glycine-serine linker (GGGGSGGGGS) linked to the N terminus of a bevacizumab heavy chain sequence having the following mutations in the variable region: T28D, N31H, H97Y, S100aT (Ferrara N, Damico L, Shams N, et al. 2006. Development of Ranibizumab, an anti-vascular endothelial growth factor antigen binding fragment, as therapy for neovascular age-related macular degeneration. Retina 26(8):859-870); and the following in the Fc region: L234A, L235A, and G237A (EU numbering) (Strobl W R. 2009. Optimization of Fe-mediated effector functions of monoclonal antibodies. Curr Opin in Biotech. 20: 685-691). The light chain is the bevacizumab light chain having an M4L mutation. TAF normally exists as a dimer having two heavy chains and two light chains. TAF may or may not have carbohydrate or other post-translational modifications after being expressed from cells. TAF is also sometimes called TAFwt or TAFWT, which indicates that the molecule in question does not have either the Q347C or L443C mutations in the heavy chain (Fe region) as do TAF347 or TAF443, defined infra.

"TAF347" is the same as TAF except that it has the Q347C mutation.

"TAF443" is the same as TAF except that it has the L443C mutation. TAF443 is sometimes referred to herein as OG1321.

Figure 35:
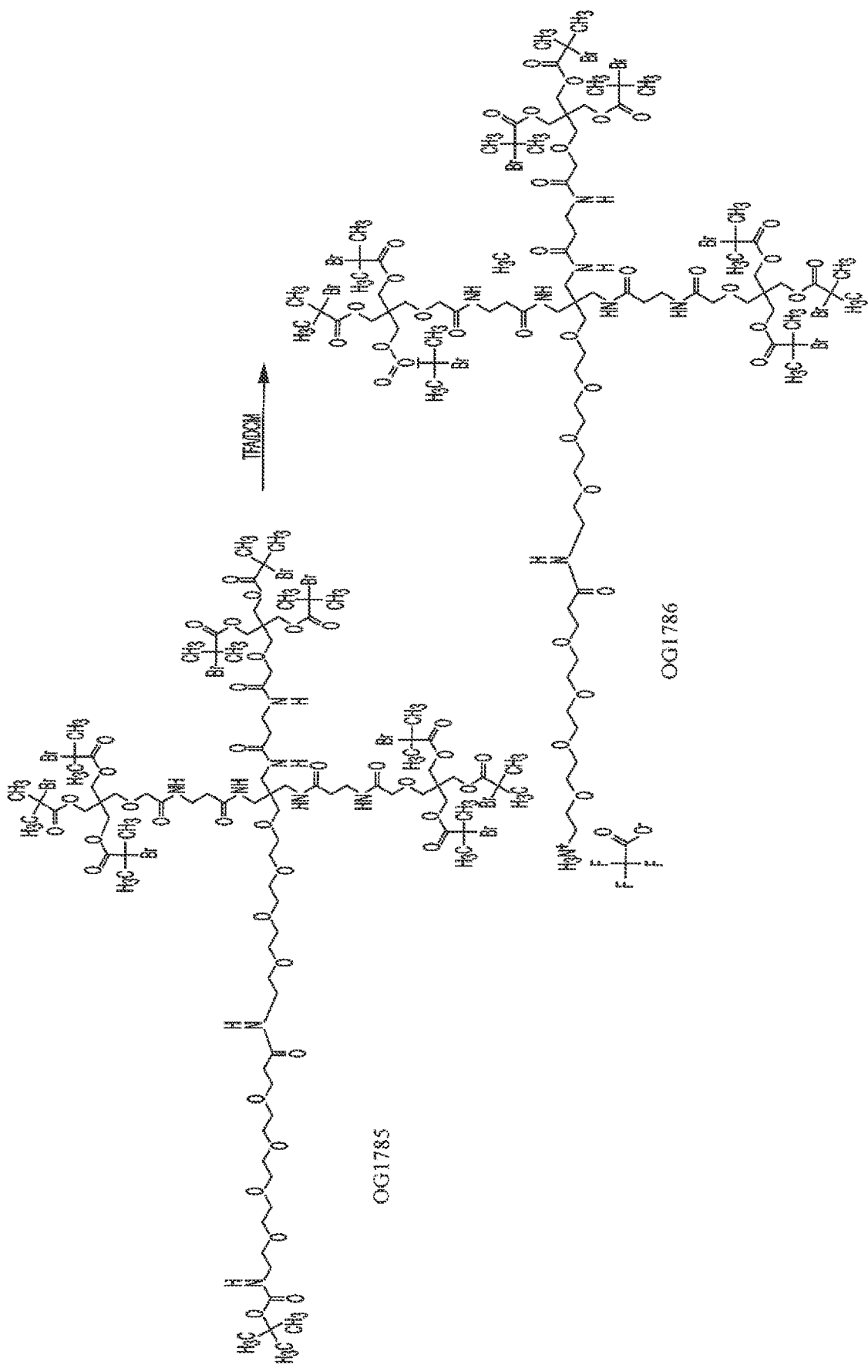
FIG. 35 shows the synthesis of OG1786 from OG1785.

"OG1786" is a 9-arm initiator used for polymer synthesis with the structure shown in FIG. 35, which depicts that salt form of OG1786 with trifluoroacetic acid. OG1786 may be used in accordance with the present invention as other salts or as the free base.

"OG1801" is an approximately (+/−15%) 750 kDa polymer (either by Mn or Mp) made using OG1.786 as an inflator for ATRP synthesis using the monomer HEMA-PC.

Figure 36:
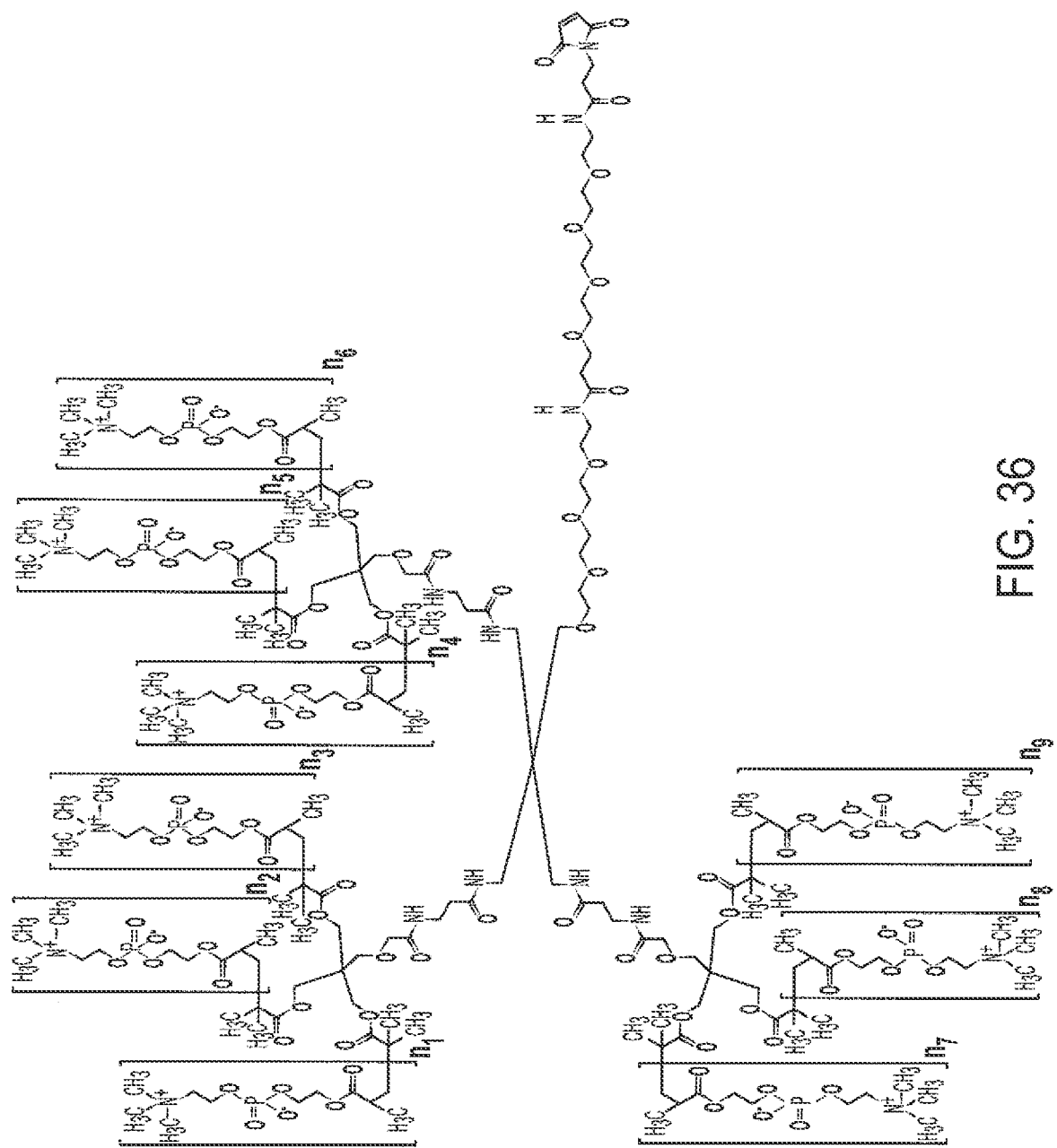
FIG. 36 shows OG1802.
Figure 37:
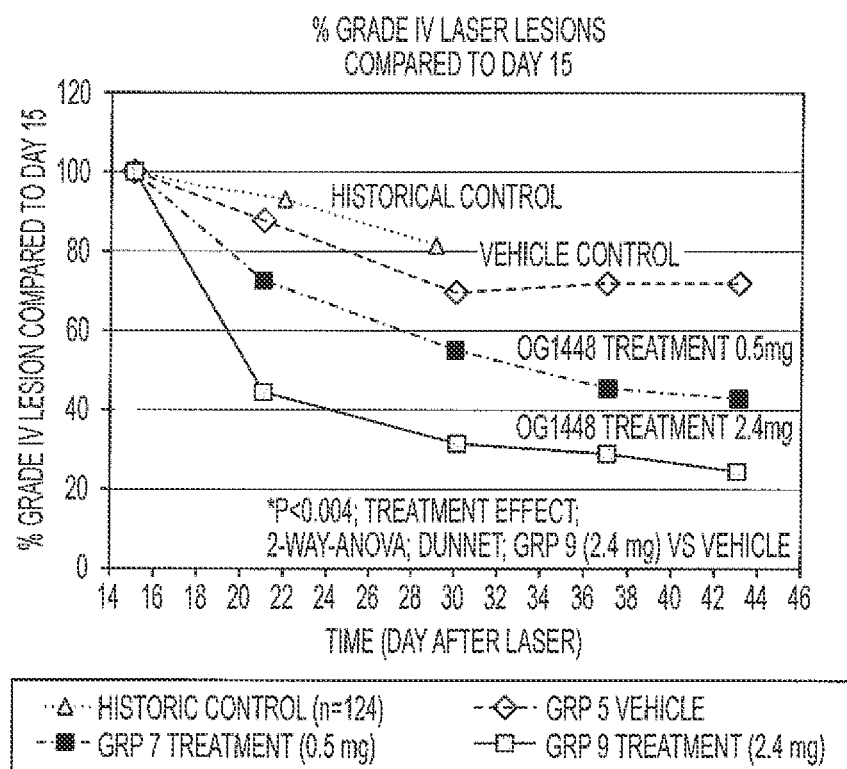
FIG. 37 shows a graph of percent Grade IV laser lesions.

"OG1802" is OG1801 with a maleimide functionality added and is shown in FIG. 36 wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% daltons.

"OG1448" is TAF443 conjugated to the OG1802 biopolymer.

DETAILED DESCRIPTION

I. General

The present invention provides a dual VEGF/PDGF antagonist comprising a VEGF antagonist linked to a PDGF antagonist. The VEGF antagonist is an antibody to a VEGF or VEGFR or is a VEGFR extracellular trap segment (i.e., a segment from the extracellular region of one or more VEGFR receptors that inhibits binding of at least one VEGFR to at least one VEGF). The PDGF antagonist is an antibody to a PDGF or PDGFR or is a PDGFR extracellular trap segment (i.e., segment from the extracellular region of one or more PDGFRs, which inhibits binding of at least one PDGFR and at least one PDGF). At least one of the antagonists is not an antibody, or put another way, at least one of the antagonists is an extracellular trap segment. Preferably, the dual antagonist includes an antibody antagonist and one extracellular trap segment antagonist. In such a dual antagonist the extracellular trap segment is preferably fused, optionally via a linker to the N-terminus of the antibody heavy chain. The antibody light chain is complexed with the antibody heavy chain in similar manner to that in a natural antibody. Such dual antagonists are preferably provided in the form of conjugates with a half-life extending moiety conjugated to the dual antagonist. Preferably, a cysteine residue is used for conjugation which has been introduced into the antagonist. More preferably, the cysteine residue is at positions 347 or 443 of an IgG1 heavy chain. It is preferred that the half-life extending moiety is a zwitterionic polymer. Most preferably the zwitterionic polymer is a phosphorylcholine containing polymer.

Angiogenesis is the process by which new blood vessels are created and plays a crucial role in development (going from embryo to adult) and in wound healing (restoring blood flow to damaged or injured tissue). However, when angiogenesis is dysregulated, it contributes to the pathologies of many disorders, including cancer, psoriasis, arthritis and blindness. Carmeliet P. 2003. Angiogenesis in health and disease. Nature Med 9(6):653-660.

Abnormal angiogenesis is associated with wet age related macular degeneration (a leading cause of blindness in the elderly) and with cancer. Angiogenesis is characterized by an increase in proliferating endothelial and stromal cells and vasculature with altered morphology. See, generally, Folkman J. 2007. Angiogenesis: an organizing principle for drug discovery?. Nat Rev Drug 6:273-286 and Baluk P, Hashizume H, McDonald D M. 2005. Cellular abnormalities of blood vessels as targets in cancer. Curr Opin Genet Dev. 15:102-111.

As mentioned above, neovascularization (NV) is a normal process occurring both in development and in wound healing but can become pathological when angiogenesis is dysregulated and occurs in tissues associated with tumors (cancer), avascular cornea or the subretinal space (wet AMD). The proliferation, invastion and migration of NV vessels is controlled by a complex interplay between growth factors, vascular endothelial cells, extracellular matrix molecules, chemokines and cell signaling molecules.

NV tissue is composed of endothelial cells (EC), pericytes and inflammatory cells (e.g. macrophages). Pericytes are derived via differentiation from mast cells. The process of neovascularization first involves the formation of angiogenic sprouts composed of EC from existing capillaries into the avascular space. VEGF signaling is understood to be the master switch for this NV process. In this regard, VEGF has been localized in the tip cell fiopodia which leads the angiogenic sprout.

Following sprout formation, the newly formed vessels are coated by pericytes, leading to maturation of the NV. Pericyte coating of NV leads to stabilization and support of NV both physically and through signaling, including pericyte production of VEGF. Armulik A, Abramsson A, Betsholtz C. 2005. Endothelial/Pericyte Interactions. Circ Res. 97:512-523.

Approved wet AMD therapies are all directed at the suppression of VEGF signaling. These therapies include pegaptanib (Macugen®), approved in 2004, Genentech's bevacizumab (Avastin®), approved in 2004 for cancer, used off label for AMD, Genentech's ranibizumab (Lucentis®), approved in 2006, and Regeneron's aflibercept (Eylea®) approved in 2011. Pegaptanib is an aptamer based therapeutic, but with a limited market compared with protein based therapeutics likely due to the limited gains in visual acuity for patients. Bevacizumab is an anti-VEGFA IgG1 antibody approved for cancer treatment, but is widely used off label for treatment of AMD. Ranibizumab is a Fab which was affinity matured from bevacizumab and is approved for AMD. However, the market for Ranibizumab is substantially undercut by use of the much cheaper bevacizumab. Finally, aflibercept is a VEGF trap, employing a soluble receptor fragment decoy.

Anti-VEGF monotherapy has not lead to disease-modifying regression of pathological NV. Brown D M, Kaiser P K, Michels M, et al. 2006. ANCHOR Study Group. Ranibizumab versus verteporfin for neovascular age-related macular degeneration. N Engl J Med 355(14):1432-1444; Rosenfeld P J, Brown D M, Meier J S, et al. 2006. MARINA study group. Ranibizumab for neovascular age-related macular degeneration. N Engl J Med 355(14):1419-1431; Regillo C D, Brown D M, Abraham P, et al. 2008. Randomized, double-masked, sham0controlled trial of ranibizumab for neovacular age-related macular degeneration: PIER study year 1. Am J Ophthalmol. 145:239-248. Instead the majority of the efficacy or therapeutic benefit of anti-VEGF therapies is due to their anti-permeability property. Zebrowski B K, Yano S, Liu W, et al. 1999. Vascular endothelial growth factor levels and induction of permeability in malignant pleural effusions. Clin Cancer Res 5:3364-3368.

Because conventional anti-VEGF therapies do not cause regression of pathological NV, visual acuity gains for many patients have been quite limited. Moreover, neovasculature can also lead to subretinal fibrosis which is a cause of blindness in wet AMD patients.

Subretinal scarring develops in nearly half of treated eyes within two years of anti-VEGF therapy. Daniel E, Toth C A, Grunwald J E. 2014. Risk of scar in the comparison of age-related macular degeneration in clinical settings. Retina 32:1480-1485. Subretinal fibrosis formation can cause permanent dysfunction of the macular system; it causes destruction of photoreceptors, retinal pigment epithelium and choroidal vessels. Ishikawa K, Ram K, Hinton D R. 2015. Molecular mechanisms of subretinal fibrosis in age-related macular degeneration. Eye Res. Mar. 13, 2015 Epub 1-7. Although anti-VEGF therapy generally stabilizes or improves visual acuity, scar formation has been identified as one of the causes of loss of visual acuity after treatment. Cohen S Y, Oubraham H, Uzzan J, et al. 2012. Causes of unsuccessful ranibizumab treatment in exudative age-related macular degeneration in clinical settings. Retina 32:1480-1485.

Proangiogenic factors are generally upregulated in pathological angiogenesis, including two members of the vascular endothelial growth factor (VEGF) family: VEGF-A and placental growth factor (PGF). VEGF-A and PGF activate quiescent endothelial cells, promote cell proliferation and vascular permeability. VEGF-A has been identified as a major factor in vascular leak in wet AMD. Dvorak HF, Nagy J A, Feng D, Brown L F, Dvorak A M. 1999. Vascular permeability factor/vascular endothelial growth factor and the significance of microvascular hyperpermeability in angiogenesis. Curr Top Microbiol Immunol. 237:97-132.

Platelet derived growth factor "PDGF" signaling plays an important role in NV maturation and in particular to the coating of NV by pericytes. The coating of NV endothelial cells by pericytes begins with EC expression of the paracrine platelet-derived growth factor B, which forms the homodimer PDGF-BB. PDGF-BB is highly retained in the tip cells of the angiogenic sprouts by heparin sulfate proteoglycan. This PDGF-BB is then recognized by the pericyte bound receptor PDGFR-β, which initiates the proliferation and migration of pericytes along the growing neovascularization.

PDGF-DD had also been discovered to play a central role in pathological angiogenesis. Kumar A, Hou X, Chunsik L, et al. 2010. Platelet-derived Growth Factor-DD Targeting Arrests Pathological Angiogenesis by Modulating Glycogen Synthase Kinase-3β Phosphorylation. J Biol Chem 285(20): 15500-15510. PDGF-DD overexpression induces blood vessel maturation during angiogenesis. Kong D, Wang Z, Sarkar F H, et al. 2008. Platelet-Derived Growth Factor-D Overexpression Contributes to Epithelial-Mesenchymal Transition of PC3 Prostate Cancer Cells. Stem Cells 26:1425-1435. PDGF-DD is highly expressed in the eye. Ray S, Gao C, Wyatt K, et al. 2005. Platelet-derived Growth Factor D, Tissue-specific Expression in the Eye, and a Key Role in Control of Lens Epithelial Cell Proliferation. J Biol. Chem. 280:8494-8502. Kumar et al. (2010) found that PDGF-DD expression was upregulated during pathological angiogenesis and that inhibition of PDGF-DD signaling decreased choroidal and retinal neovascularization.

The term "PDGF" as used herein means any member of the class of growth factors that (i) bind to a PDGF receptor such as PDGFR-β, or PDGFR-α; (ii) activates a tyrosine kinase activity associated with the PDGF receptor; and (iii) thereby affects angiogenesis or an angiogenic process. The term "PDGF" generally refers to those members of the class of growth factors that induce DNA synthesis and mitogenesis through the binding and activation of a platelet-derived growth factor cell surface receptor (i.e., PDGFR) on a responsive cell type. PDGFs effect specific biological effects including, for example: directed cell migration (chemotaxis) and cell activation; phospholipase activation; increased phosphatidylinositol turnover and prostaglandin metabolism; stimulation of both collagen and collagenase synthesis by responsive cells; alteration of cellular metabolic activities, including matrix synthesis, cytokine production, and lipoprotein uptake; induction, indirectly, of a proliferative response in cells lacking PDGF receptors; fibrosis and potent vasoconstrictor activity. The term "PDGF" is meant to include both a "PDGF" polypeptide and its corresponding "PDGF" encoding gene or nucleic acid.

The PDGF family consists of disulfide bonded homoffdimers of PDGF-A (Swiss Protein P04085), -B (P01127), -C (Q9NRA1) and -D (Q9GZP0) and the hetero dimer PDGF-AB. The various PDGF isoforms exert their effect by binding to α and β-tyrosine kinase receptors (PDGFR-α (P16234) and PDGFR-β (P09619) respectively). See generally U.S. Pat. No. 5,872,218 which is incorporated herein by reference for all purposes. The a and β receptors are structurally similar: both have extracellular domains with five immunoglobulin (Ig) like domains and intracellular domains with a kinase function. PDGF binding occurs mainly through domains 2 and 3 of the receptors and causes dimerization of the receptors. Ig like domain 4 is involved in receptor dimerization. Receptor dimerization is a key component of PDGF signaling: receptor dimerization leads to receptor auto-phosphorylation. Auto-phosphorylation in turns causes a conformational change in the receptor and activates the receptor kinase. PDGF-A, -B, -C and -D bind to the two different receptors with different affinities and effects. PDGF-AA, -AB, -BB and -CC induce αα receptor homodimers, PDGF-BB and -DD induced ββ homodimers and PDGF-AB, -BB, -CC and -DD produce αβ receptor heterodimers.

In terms of function, PDGFR-α and PDGFR-β appear to have substantially different roles. PDGFR-α signaling is involved in gastrulation and in development of the cranial and cardiac neural crest, gonads, lung, intestine, skin, CNS and skeleton. PDGFR-β signaling is involved in blood vessel formation and early hematopoiesis. Andrae J, Radiosa G, Betsholtz C. 2008. Role of platelet-derived growth factors in physiology and medicine. Genes Develop 22:1276-1312. In terms of interaction of the various PDGF ligands with the receptors, PDGF-AA and PDGF-CC exclusively bind to and interact with PDGFR-α. PDGF-BB and PDGF-AB bind with α and β receptors. PDGF-DD exclusively interacts with PDGFR-β. Raica M, Cimpean A M. 2010. Platelet-Derived Growth Factor (PDGF)/PDGF Receptors (PDGFR) Axis as Target for Antitumor and Antiangiogenic Therapy. Pharmaceut. 3:572-599.

Unless otherwise apparent from the context reference to a PDGF means any of PDGF-A, -B, -C and in any of the natural isoforms or natural variants or induced variants having at least 90, 95, 98 or 99% sequence identity to a natural form. Preferably, such PDGFs are human PDGFs. Likewise reference to a PDGFR means PDGFR-A (P16234) or PDGFR-B including any natural isoform or natural variant, or an induced variant having at least 90, 95, 98 or 99% or 100% sequence identity to a natural sequences.

The amino acid sequence of human PDGFR-β (UniProtKB/Swiss-Prot: P09619.1) is set forth in FIG. 1, which shows a full-length human PDGFR-β (including the leader sequence), a 1106 amino acid protein. Amino acids 1-32 are part of the leader peptide which is cleaved off in the mature protein. PDGFR-β has five extracellular domains D1-D5. Williams A F, Barclay A N. 1988. The immunoglobulin superfamily—domains for cell surface recognition. Annu Rev Immunol. 6:381-405. The full-length extracellular region runs from about amino acid 33 to 532, the transmembrane domain from about residue 533 to 553 and the cytoplasmic domain from about residue 554 to 1106. The extracellular region includes five immunoglobulin-like domains, D1-D5. The D1 domain is typically considered to be from about amino acid 33 (Leu) to about 123 (Pro). In accordance with the present invention, D1 may also be from 33 to 122 (Val). D2 is typically considered to be from about 124 (Thr) to about 213 (Ser). In accordance with the present invention, D2 may be 129 (Pro) to 210 (Gln). D3 is typically considered to be from about amino acid 214 (Ile) to 314 (Gly). In accordance with the present invention, D3 may be from 21.4 (Ile) to 309 (Thr). 1)4 is typically considered to be from about amino acid 315 (Tyr) to 416 (Pro). D5 is typically considered to be from about amino acid 417 (Val) to 531 (Lys).

The exact boundaries of the D1-D5 domains can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid. The essential characteristic of each domain is its ability to bind to its cognate ligands.

A "PDGF antagonist" or a molecule that "antagonizes PDGF" is an agent that reduces, or inhibits, either partially or fully, at least one activity of a PDGF including its ability to specifically bind to a PDGFR, and consequent cellular responses, such as proliferation. PDGF antagonists include antibodies that specifically hind to a PDGF or PDGFR and extracellular trap segments from a PDGFR.

One or more portions of a PDGFR-β extracellular receptor sequence can be used as an antagonist for PDGF-PDGFR-β signaling. The term extracellular trap segment refers to a full length extracellular region or any portion thereof, or combination of portions from different PDGF receptors that can antagonize PDGF-PDGFR-beta signaling. Such portions are typically used free of the transmembrane and intracellular sequence of the PDGFR and are consequently referred to as being soluble. The portions antagonize by acting as a trap or decoy for a cognate PDGF. PDGF binds to the soluble PDGFR-β segment trap and is unable to bind to the corresponding membrane bound receptor. Preferably, such traps include one of more of PDGFR-β domains D1-D5. Preferably, the trap contains at least one of D2 and D3. More preferably, the trap contains D1, D2 and D3. More preferably the trap is a contiguous segment corresponding to amino acids 33 to 314 of FIG. 8 which contains D1-D3. PDGFR-alpha likewise includes domains D1 through D5 and extracellular trap segments incorporating corresponding domains of PDGFR-alpha can likewise be used instead of PDGFR-beta.

Antibodies can also be used as antagonists of PDGFR-β, including antibodies which bind to the receptor (e.g., 2A1E2 [U.S. Pat. No. 7,060,271]; HuM4Ts.22 [U.S. Pat. No. 5,882, 644]; or 1B3 or 2C5 [U.S. Pat. No. 7,740,850]), and anti-PDGF antibodies such as anti-PDGF BB, anti-PDGF-DD, anti-PDGF-BB and anti-PDGF-AB.

"VEGF" or "vascular endothelial growth factor" is a human vascular endothelial growth factor that affects angiogenesis or an angiogenic process. In particular, the term VEGF means any member of the class of growth factors that (i) bind to a VEGF receptor such as VEGFR-1 (Flt-1), VEGFR-2 (KDR/Flk-1), or VEGFR-3 (FLT-4); (ii) activates a tyrosine kinase activity associated with the VEGF receptor; and (iii) thereby affects angiogenesis or an angiogenic process.

The VEGF family of factors is made up of five related glycoproteins: VEGF-A (also known as VPE), -B, -C, -D and PGF (placental growth factor). Of these, VEGF-A is the most well studied and is the target of anti-angiogenic therapy. Ferrara et al, (2003) Nat. Med. 9:669-676. VEGF-A exists as a number of different isotypes which are generated both by alternative splicing and proteolysis: $VEGF-A_{206}$, $VEGF-A_{189}$, $VEGF-A_{165}$, and $VEGF-A_{121}$. The isoforms differ in their ability to bind heparin and non-signaling binding proteins called neuropilins. The isoforms are all biologically active as dimers.

The various effects of VEGF are mediated by the binding of a VEGF, e.g., VEGF-A (P15692), -B (P49766), -C (P49767) and -D (Q43915), to receptor tyrosine kinases (RTKs). The VEGF family receptors belong to class V RTKs and each carry seven Ig-like domains in the extracellular domain (ECD). In humans, VEGF binds to three types of RTKs: VEGFR-1 (Flt-1) (P17948), VEGFR-2 (KDR, Elk-1) (P935968) and VEGFR-3 (Flt-4) (P35916). A sequence of VEGFR-1 is shown in FIG. 2. Unless otherwise apparent from the context reference to a VEGF means any of VEGF-A, -B, -C, -D, and PGF, in any of the natural isoforms or natural variants or induced variants having at least 90, 95, 98 or 99% or 100% sequence identity to a natural form. Preferably, such VEGFs are human VEGFs. Likewise reference to a VEGFR means any of VEGR-1, R-2 or R-3, including any natural isoform or natural variant, or an induced variant having at least 90, 95, 98 or 99% or 100% sequence identity to a natural sequences.

The extracellular region runs from about amino acid 27-758, the transmembrane domain from about amino acid 759 to 780 and the intracellular region from about 781-1338. The extracellular region includes seven immunoglobulin-like domains, D1-D7. Domain 1 of VEGFR-1 is from 32 (P) to 128 (I), Domain 2 from 134 (P) to 125 (Q), Domain 3 from 232 (V) to 331 (K), Domain 4 from 333 (F) to 428 (P), Domain 5 is from 431 (Y) to 553 (T), Domain 6 from 558 (G) to 656 (R) and Domain 7 from 662 (Y) to 751 (T). See generally U.S. Pat. No. 8,273,353, incorporated herein by reference for all purposes. The exact boundaries of the domains D1-D7 of VEGFR-1 can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid.

The protein sequence of VEGFR-2 is shown below in FIG. 3.

The extracellular region runs from about residues 20-764, the transmembrane domain from about residues 765-785 and the intracellular domain from about residues 786 to 1356. The extracellular region includes seven immunoglobulin-like domains, D1-D7. Domain 1 of VEGFR-2 is from 32 (P) to 118 (V), Domain 2 is from 124 (P) to 220 (G), Domain 3 is from 226 (V) to 327 (K), Domain 4 is from 329 (F) to 421 (P), Domain 5 is from 424 (G) to 548 (T), Domain 6 is from 553 (I) to 662 (L), and Domain 7 is from 668 (T) to 757 (A). See generally U.S. Pat. No. 8,273,353, incorporated herein by reference for all purposes. The exact boundaries of the domains D1-D7 of VEGFR-2 can vary depending on how the analysis is done. Preferably, the boundaries vary by 9 amino acids or less. Typically they vary by 7 amino acids of less, more typically by 5 amino acids or less. Usually, boundary variance be by 3 amino acids or less. Most typically the boundaries 1 vary by only an amino acid.

The protein sequence of VEGFR-3 is shown below in FIG. 4. The extracellular region runs from about residues 25-775, the transmembrane domain from about residues 776-796 and the intracellular domain from about residues 797-1363. The extracellular domain includes seven immunoglobulin-like domains D1-D7. Domain 1 of VEGFR-3 is from 30 (P) to 132 (V), Domain 2 is from 138 (P) to 226 (G), Domain 3 is from 232 (I) to 330 (N), Domain 4 is from 332 (F) to 422 (P), Domain 5 is from 425 (H) to 552 (T), Domain 6 is from 557 (G) to 673 (Q), and Domain 7 is from 679 (R) to 768 (5). See generally U.S. Pat. No. 8,273,353, incorporated herein by reference for all purposes. The exact boundaries of the domains D1-D7 of VEGFR-3 can vary depending on how the analysis is done. Preferably, the boundaries vary by 9 amino acids or less. Typically they vary by 7 amino acids of less, more typically by 5 amino acids or less. Usually, boundary variance is 3 amino acids or less. Most typically the boundaries vary by only an amino acid.

VEGFR-2 is expressed predominately on vascular endothelial cells. VEGFR-1 is also expressed on the vascular endothelium, but in addition is also expressed by a number of other cell types: neutrophils, monocytes, macrophages, mural cells and endothelial progenitor cells. VEGFR-1 has a higher affinity for VEGF-A than does VEGFR-2. However, when VEGFR-1 is bound to VEGF-A in endothelial cells, VEGFR-1 exhibits only very weak tyrosine phosphorylation. Hence, it is believed that the effects of VEGF-A (including its various isoforms) on the vascular endothelium are mediated by the binding of VEGF-A to VEGFR-2.

PGF and VEGF-B bind only to VEGFR-1. PGF and VEGF-B have been implicated in pathogenic vascular remodeling. Carmeliet P, Moons L, Lutten A, et al. 2001. Synergism between vascular endothelial growth factor and placental growth factor contributes to angiogenesis and plasma extravasation in pathological conditions. Nat Med. 7(5); 575-583. VEGF-C and -D bind with high affinity to VEGFR-3, which is primarily found on lymphatic endothelial cells in the adult. VEGF-C and -D are thought to play a role in regard to Lymphangiogenesis.

A "VEGF antagonist" or a molecule that "antagonizes VEGF" is an agent that reduces, or inhibits, either partially or fully, an activity of a VEGF including its ability to specifically bind to its receptor a VEGFR and consequent cellular responses, such as angiogenesis and cellular proliferation. VEGF antagonists include antibodies specifically binding to a VEGF or a VEGFR or a VEGFR extracellular trap segment.

The term extracellular trap segment refers to a full length extracellular region or any portion thereof, or combination of portions from different VEGFR receptors that can antagonize signaling between at least one VEGF and VEGFR. Preferably, the extracellular trap segment includes at least one domain from one of VEGFR-1, -2 or -3 defined above, and more preferably at least two contiguous domains, such as D2 and D3. Optionally, an extracellular domain includes at least one domain as defined above from at least two different VEGFRs. A preferred extracellular domain comprises or consists essentially of D2 of VEGFR-1 and D3 of VEGFR-2.

VEGF antagonist therapies have been approved for the treatment of certain cancers and wet AMD. Bevacizumab (AVASTIN®, Genentech/Roche) is a humanized mouse monoclonal antibody that binds to and neutralizes human VEGF, in particular to all isoforms of VEGF-A and to bioactive proteolytic fragments of VEGF-A. See, e.g., Ferrara N, Hillan K J, Gerber H P, Novotny W. 2004. Discovery and development of bevacizumab, an anti-VEGF antibody for treating cancer. Nat Rev Drug Discov. 3(5):391-400. Bevacizumab has been approved for the treatment of certain cancers. The protein sequence of the heavy and light chains of bevacizumab (DrugBank DB00112) is shown below in FIG. 5 with CDRs underlined (see also SEQ ID NOs. 2 and 5).

Bevacizumab variable light chain CDRs are $CDR_L1$: SASQDISNYLN, $CDR_L2$: FTSSLHS and $CDR_L3$: QQYSTVPWT. Bevacizumab variable heavy chain CDRs are $CDR_H1$: GYTFTNYGMN, $CDR_H2$: WINTYTGEPTYAADFKR, and $CDR_H3$: YPHYYGSSHWYFDV. CDRs are defined by Kabat except CDRH1 is the composite Kabat/Chothia definition.

Another anti-VEGF molecule, derived from the same mouse monoclonal antibody as bevacizumab has been approved as a treatment for wet AMD: ranibizumab (LUCENTIS®, Genentech/Roche). Ranibizumab is an antibody fragment or Fab. Ranibizumab was produced by affinity maturation of the variable heavy and light chains of bevacizumab. The sequence of the heavy and light chains of ranibizumab is shown below (as published by Novartis) in FIG. 6 (see also SEQ ID NOs. 12 and 13):

Ranibizumab variable light chain CDRs are $CDR_L1$: SASQDISNYLN, $CDR_L2$: FTSSLHS and $CDR_L3$: QQYSTVPWT. Ranibizumab variable heavy chain CDRs are $CDR_H1$: GYDFTHYGMN, $CDR_H2$: WINTYTGEPTYAADFKR, and $CDR_H3$: YPYYYGTSHWYFDV.

Antibodies competing with bevacizumab for binding to VEGF-A or binding to the same epitope on VEGF-A as bevacizumab can also be used.

Another anti-VEGF therapy is a VEGF Trap. For example, aflibercept (Eylea®, Regeneron), consists of the second Ig like domain of VEGFR-1 and the third Ig like domain of VEGFR-2 expressed as an in line fusion with the constant region (Fc) of human IgG1. Papadopoulos N, et al. 2012. Binding and neutralization of vascular endothelial growth factor (VEGF) and related ligands by VEGF Trap, ranibizumab and bevacizumab. Angiogenesis 15:171-185. In theory, aflibercept binds not only VEGF-A, but also VEGF-B and PGF thereby antagonizing their interaction with VEGFR-1.

In accordance with the present invention, a dual. VEGF/PDGF antagonist is provided comprising a VEGF antagonist linked to a PDGF antagonist. The linkage preferably includes a fusion of protein chains to form a hybrid chain formed from components of both antagonists. Alternatively, the components can be joined by chemical cross linking. As an example, of linkage by fusion, if the dual antagonist is formed from an antibody and an extracellular trap segment, then a heavy or light chain of the antibody can be fused to the extracellular trap segment. Preferably, the extracellular trap segment is fused directly or indirectly via a linker to the N-terminus of the antibody heavy or light chain. Whichever chain is not fused to the extracellular trap segment can associate with the chain that is in similar fashion to heavy light chain association in a natural antibody. For example, an exemplary format has an extracellular trap segment fused to the N-terminus of an antibody heavy chain via a linker and the antibody light chain complexed with the antibody heavy chain. The antibody in such a dual antagonist can be an intact antibody or any of the binding fragments described above, such as a Fab fragment. Preferably, in such dual antagonists, the VEGF antagonist is an antibody to VEGF-A, such as bevacizumab or ranibizumab, and the PDGF antagonist is an extracellular trap segment from PDGR-1.

In an alternative format, the VEGF antagonist and PDGF antagonist are both extracellular trap segments. The two segments can be fused in either orientation with respect to one another, directly or via a linker. That is the VEGFR extracellular trap region can be joined to the N-terminus or the C-terminus of the PDGFR extracellular trap region. The C-terminus of such a fusion protein can be linked to an Fc region of an antibody forming an Fc fusion proteins.

In preferred embodiments, the PDGFR is PDGFR-β and the extracellular trap segment comprises one or more of domains D1-D5 of PDGFR-β. More preferably, the extracellular trap segment comprises domains D1-D3 of PDGFR-13. Still more preferably, the extracellular trap segment comprises or consists of amino acids 33 to 314 of SEQ ID NO. 11. In preferred embodiments, the VEGF antagonist is an anti-VEGF antibody, preferably an anti-VEGF-A antibody.

In dual antagonists having antibody and extracellular trap components fused to one another, the respective components, typically the antibody heavy chain and the extracellular trap segment are separated by a linker sequence. The linker is preferably GGGGSGGGGS, GG, or GGGGSGGGGSGGGGSGGGGSG or an oligomers of any of these. More preferably, the linker is GGGGSGGGGS.

In accordance with an aspect of the present invention, the anti-VEGF-A antibody heavy chain has at least the following CDR sequences: $CDR_H$ GYDFTHYGMN, $CDR_H2$: WINTYTGEPTYAADFKR, and $CDR_H3$: YPYYYGTSH-WYFDV. Preferably, the anti-VEGF-A light chain has at least the following CDRs: SASQDISNYLN, $CDR_L2$: FTSSLHS and $CDR_L3$: QQYSTVPWT. In the case of the anti-VEGF-A antibody heavy chain, it is preferred that its isotype is IgG1 and has a $CH_1$, hinge, $CH_2$, and $CH_3$ domains. It is also preferred that the light chain isotype is kappa. The constant region of the preferred IgG1 sequence is set forth in SEQ ID NO. 17. The sequence of the light chain constant region is preferably set forth in SEQ ID NO. 18.

The IgG1 domain of the anti-VEGF-A antibody preferably has one or more mutations to reduce or lower effector function. Preferred amino acids to use for effector function reducing mutations include (EU numbering) E233P, L234V, L235, G236, G237, delG236, D270A, K322A, A327G, P329A, A330, A330S, P331S, and P331A, in which the second mentioned amino acid is the mutation. Preferably, the mutations include one or more of the following: E233P, L234V, L234A, L235A, G237A, A327G, A330S and P331S (EU numbering). More preferably, the anti-VEGF-A heavy chain has the following mutations: L234A, L235A and G237A. The number of such mutations relative to a natural human IgG1 sequence is no more than 10, and preferably no more than 5, 4, 3, 2 or 1.

Alternatively, the IgG domain can be IgG2, IgG3 or IgG4, preferably, human IgG2, IgG3 or IgG4, or a composite in which a constant regions is formed from more than one of these isotypes (e.g., CH1 region from IgG2 or IgG4, hinge, CH2 and CH3 regions from IgG1). Such domains can contain mutations to reduce effector function at one or more of the EU position mentioned for IgG1. Human IgG2 and IgG4 have reduced effector functions relative to human IgG1 and IgG3.

The anti-VEGF-A heavy chain can also contain a cysteine residue added as a mutation by recombinant DNA technology which can be used to conjugate a half-life extending moiety. Preferably, the mutation is (EU numbering) Q347C and/or L443C, More preferably, the mutation is L443C. Preferably, the stoichiometry of dual antagonist to polymer is 1:1; in other words, a conjugate consists essentially of molecules each comprising one molecule of dual antagonist conjugated to one molecule of polymer.

A preferred dual antagonist including an antibody to VEGF-A and a PDGFR extracellular trap segment comprises a fusion protein of the antibody heavy chain and the PDGFR extracellular trap segment having the amino acid sequence of SEQ ID NO. 9 and the antibody light chain having the amino acid sequence of SEQ ID NO. 10, or variants thereof including sequences differing each of from SEQ ID NO: 9 and 10 by no more than 110, 9, 8, 7, 6, 5, 4, 3, 2 or 1 amino acids.

In another aspect of the present invention, a dual VEGF/PDGF antagonist is presented having a PDGF antagonist constituting one or more segments of a PDGFR as described above and a VEGF antagonist constituting an anti-VEGF Fab fragment. For this aspect of the present invention, the PDGFR extracellular trap comprises one or more of domains D1-D5 of PDGFR-β. More preferably, the PDGFR trap constitutes domains D1-D3 of PDGFR-β. More preferably, the PDGFR trap is amino acids 33 to 314 of SEQ ID NO. 11.

The PDGFR trap is preferably located C-terminal of the Fab heavy or light chain. The PDGFR trap is also preferentially located N-terminal of the Fab heavy or light chain. Preferably, the dual antagonist includes an anti-VEGF-A Fab fragment heavy chain fused via a linker to a PDGFR extracellular trap segment and an anti-VEGF-A light chain.

In another aspect of the invention, a dual VEGF/PDGF antagonist is presented wherein the extracellular trap segment binds to one or more of PDGF-AA, PDGF-BB, PDGF-AB, PDGF-CC and PDGF-DD. Preferably, the extracellular trap binds PDGF-AB, PDGF-BB and PDGF-DD. Still more preferably, the extracellular trap inhibits PDGF-AB, PDGF-BB and PDGF-DD from binding to any one of PDGFR-αα, PDGFR-αβ, and PDGFR-ββ receptors.

A linker is preferably located between the PDGFR trap and the anti-VEGF Fab fragment heavy chain. Preferably, the linker is selected from group consisting of GGGGSGGGGS, GG, and GGGGSGGGGSGGGGSGGGGSG, and oligomers of any of these. More preferably, the linker is GGGGSGGGGS.

The anti-VEGF Fab fragment heavy chain preferably has at least the following CDRs: $CDR_H1$: GYDFTHYGMN, $CDR_H2$: WINTYTGEPTYAADFKR, and $CDR_H3$: YPYYYGTSHWYFDV. The anti-VEGF-A light chain preferably has at least the following CDRs: $CDR_L1$; SASQDIS-NYLN, $CDR_L2$: FTSSLHS and $CDR_L3$: QQYSTVPWT.

A preferred anti-VEGF Fab fragment heavy chain isotype is IgG1 and comprises a $CH_1$ domain and the light chain isotype is kappa.

The dual VEGF/PDGF antagonist can have a half-life extending moiety attached. Preferably the half-life extending moiety is a zwitterionic polymer but PEG or other half-life extenders discussed below can alternatively be used. More preferably, the zwitterionic polymer is formed of monomers having a phosphorylcholine group. Preferably the monomer is 2-(acryloyloxyethyl)-2'-(trimethylammoniumethyl) phosphate. More preferably, the monomer is 2-(methacryloyloxyethyl)-2'-(trimethylammoniumethyl) phosphate (HEMA-PC).

A polymer conjugated to a dual antagonist preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. Preferably, the polymer peak molecular weight is between 300,000 and 1,750,000 Da. More preferably, the polymer has a peak molecular weight between 500,000 and 1,000,000 Da. Still more preferably, the polymer has a peak molecular weight between 600,000 to 800,000 Da.

The polymer can be covalently bonded to the dual antagonist via conjugation. Preferably, the polymer is conjugated to the dual VEGF/PDGF antagonist via a group such as an amino group, a hydroxyl group, a sulfhydryl group or a carboxyl group. The sulfhydryl group can be from a naturally occurring cysteine residue. The sulfhydryl group can also be from a cysteine residue added by recombinant DNA technology.

In a preferred aspect of the present invention, the polymer is conjugated to the cysteine residue at position 731 of SEQ ID NO. 9, or aligned position of any variants of SEQ ID NO: 9 disclosed herein.

In another aspect of the present invention, a dual VEGF/PDGF antagonist having a VEGFR trap containing one or more extracellular segments of a VEGFR, such as VEGFR-1, VEGFR-2 or VEGFR-3, fused to an anti-PDGF antibody or Fab fragment heavy or light chain and an anti-PDGF antibody or Fab fragment heavy or light chain not included in fusion.

In accordance with an aspect of the present invention, the extracellular segment of VEGFR is preferably one or more of domains D1-D7. More preferably, the extracellular segment comprises D2 from VEGFR-1 and D3 from VEGFR-2. Still more preferably, the D2 is N-terminal to the D3 and further comprises a linker between the domains.

In preferred embodiments of this aspect of the present invention, the PDGF antagonist is an antibody. More preferably, the antibody is selected from the group consisting of humanized 2A1E2, HuM4Ts.22, humanized 1B3, humanized 2C5, anti-PDGF-BB, anti-PDGF-DD, anti-PDGF-BB and anti-PDGF-AB. The PDGF antagonist is also preferably a Fab fragment.

In accordance with this aspect of the present invention, the antibody heavy chain is preferably IgG1, more preferably human IgG1 and the light chain is preferably kappa, human kappa. The heavy chain can have a cysteine added via recombinant DNA technology. Preferably, the cysteine is selected from the group consisting of Q347C and L443C. Preferably, there is a half-life extending moiety conjugated to the cysteine.

Preferably, the half-life extending moiety is a zwitterionic polymer having one or more monomer units and wherein at least one monomer unit has a zwitterionic group. Preferably, the zwitterionic group is phosphorylcholine. The monomer is preferably 2-(acryloyloxyethyl)-2'-(trimethylammoniumethyl) phosphate. More preferably, the monomer is 2-(methacryloyloxyethyl)-2'-(trimethylammoniumethyl) phosphate (HEMA-PC).

In accordance with this aspect of the present invention, the polymer preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. In accordance with an aspect of the present invention, the polymer peak molecular weight of between 300,000 and 1,750,000 Da. More preferably, the polymer has a peak molecular weight between 500,000 and 1,000,000 Da. Still more preferably, the polymer has a peak molecular weight between 600,000 to 800,000 Da.

In accordance with an aspect of the present invention, the polymer is covalently bound to the polymer via conjugation. Preferably, the polymer is conjugated to the dual VEGF/PDGF antagonist via a group selected from the group consisting of an amino group, a hydroxyl group, a sulfhydryl group and a carboxyl group. Preferably, the sulfhydryl group is from a naturally occurring cysteine residue. In other preferred embodiments, the sulfhydryl group is from a cysteine residue added by recombinant DNA technology.

In preferred aspects of the present invention, the PDGF trap-VEGF trap is conjugated to a half-life extending moiety as discussed with other dual antagonists.

Preferably, the half-life extending moiety is a zwitterionic polymer having one or more monomer units and wherein at least one monomer unit has a zwitterionic group. Preferably, the zwitterionic group is phosphorylcholine. The monomer is preferably 2-(acryloyloxyethyl)-2'-(trimethylammoniumethyl) phosphate. More preferably, the monomer is 2-(methacryloyloxyethyl)-2'-(trimethylammoniumethyl) phosphate (HEMA-PC).

In accordance with this aspect of the present invention, the polymer preferably has at least 2 and more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. In accordance with an aspect of the present invention, the polymer peak molecular weight of between 300,000 and 1,750,000 Da, More preferably, the polymer has a peak molecular weight between 500,000 and 1,000,000 Da. Still more preferably, the polymer has a peak molecular weight between 600,000 to 800,000 Da.

In accordance with an aspect of the present invention, the polymer is covalently bound to the polymer via conjugation. Preferably, the polymer is conjugated to the dual VEGF/PDGF antagonist via a group such as an amino group, a hydroxyl group, a sulfhydryl group or a carboxyl group. In some conjugates, the sulfhydryl group is from a naturally occurring cysteine residue. In some conjugates, the sulfhydryl group is from a cysteine residue added by recombinant DNA technology.

Dual PDGF/VEGF antagonists can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing dual antagonists, e.g. constitutively or on induction, and (v) isolating the dual antagonist, e.g. from the culture medium or by harvesting the transformed cells, in order to (vi) obtain purified dual antagonist.

Dual antagonists can be produced by expression in a suitable prokaryotic or eukaryotic host system characterized by producing a pharmacologically acceptable dual antagonist molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the dual antagonist and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1 or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

The half-life of dual antagonists can be extended by attachment of a "half-life extending moieties" or "half-life extending groups," which terms are herein used interchangeably to refer to one or more chemical groups attached to one or more amino acid site chain functionalities such as —SH, —OH, —COOH, —CONH2, —NH2, or one or more N- and/or O-glycan structures and that can increase in vivo circulatory half-life of proteins/peptides when conjugated to these proteins/peptides. Examples of half-life extending moieties include polymers described herein, particularly those of zwitterionic monomers, such as HEMA-phosphorylcholine, PEG, biocompatible fatty acids and derivatives thereof. Hydroxy Alkyl Starch (HAS) e.g. Hydroxy Ethyl Starch (HES), Poly Ethylene Glycol (PEG), Poly (Glyx-Sery) (HAP), Hyaluronic acid (HA), Heparosan polymers (HEP), Fleximers, Dextran, Poly-sialic acids (PSA), Fc domains, Transferrin, 25 Albumin, Elastin like (ELP) peptides, XTEN polymers, PAS polymers, PA polymers, Albumin binding peptides, CTP peptides, FcRn binding peptides and any combination thereof.

In one embodiment a half-life extending moiety can be conjugated to a dual antagonist via free amino groups of the protein using N-hydroxysuccinimide (NHS) esters. Reagents targeting conjugation to amine groups can randomly react to ε-amine group of lysines, α-amine group of N-terminal amino acids, and δ-amine group of histidines.

However, dual antagonists of the present have many amine groups available for polymer conjugation. Conjugation of polymers to free amino groups, thus, might negatively impact the ability of the dual antagonist proteins to bind to VEGF and/or PDGF.

In another embodiment, a half-life extending moiety is coupled to one or more free SH groups using any appropriate thiol-reactive chemistry including, without limitation, maleimide chemistry, or the coupling of polymer hydrazides or polymer amines to carbohydrate moieties of the dual antagonist after prior oxidation. The use of maleimide coupling is a particularly preferred embodiment of the present invention. Coupling preferably occurs at cysteines naturally present or introduced via genetic engineering.

Polymers are preferably covalently attached to cysteine residues introduced into dual antagonist by site directed mutagenesis. It is particularly preferred to employ cysteine residues in the Fc portion of the dual antagonist. For preferred sites to introduce cysteine residues into an Fc region see WO 2013/093809, U.S. Pat. No. 7,521,541, WO 2008/020827, U.S. Pat. Nos. 8,008,453, 8,455,622 and US2012/0213705, incorporated herein by reference for all purposes. Particularly preferred cysteine mutations are Q347C and 11,443C referring to the human IgG heavy chain by EU numbering.

The invention provides conjugates of dual antagonist and high MW polymers serving as half-life extenders. A preferred conjugate comprises a dual antagonist is coupled to a zwitterionic polymer wherein the polymer is formed from one or more monomer units and wherein at least one monomer unit has a zwitterionic group. Preferably, the zwitterionic group is phosphorylcholine.

Preferably, one of the monomer units is 2-(acryloyloxyethyl)-2'-(trimethylammoniumethyl) phosphate or 2-(methacryloyloxyethyl)-2'-(trimethylammoniumethyl) phosphate (HEMA-PC). In other preferred embodiments, polymer is synthesized from a single monomer which is preferably 2-(acryloyloxyethyl)-2'-(trimethylammoniumethyl) phosphate or 2-(methacryloyloxyethyl)-2'-(trimethylammoniumethyl) phosphate.

Some dual antagonist conjugates have 2 or more preferably 3 or more polymer arms wherein the monomer is HEMA-PC. Preferably, the conjugates have 2, 3, 4, 5, 6, 7, 8, 9, 10, 11, or 12 polymer arms wherein the monomer is HEM A-PC. More preferably, the conjugates have 3, 6 or 9 arms. Most preferably, the conjugate has 9 arms.

Polymer-dual antagonist conjugates preferably have a polymer portion with a molecular weight of between 100,000 and 1,500,000 Da. More preferably the conjugate has a polymer portion with a molecular weight between 500,000 and 1,000,000 Da. Still more preferably the conjugate has a polymer portion with a molecular weight between 600,000 to 800,000 Da. Most preferably the conjugate has a polymer portion with a molecular weight between 600,000 and 850,000 Da and has 9 arms. When a molecular weight is given for a dual VEGF/PDGF antagonist conjugated to a polymer, the molecular weight will be the addition of the molecular weight of the protein, including any carbohydrate moieties associated therewith, and the molecular weight of the polymer.

In accordance with an aspect of the present invention, a dual VEGF/PDGF antagonist having a HEMA-PC polymer which has a molecular weight measured by Mw of between about 100 kDa and 1500 kDa. More preferably, the molecular weight of the polymer as measured by Mw is between about 500 kDa and 1000 kDa. Still more preferably, the molecular weight of the polymer as measured by Mw is between about 600 kDa to about 900 kDa. Most preferably, the polymer molecular weight as measured by Mw is 750 kDa plus or minus 15%.

In this aspect of the present invention, the polymer is preferably made from an initiator suitable for ATRP having one or more polymer initiation sites. Preferably, the polymer initiation site has a 2-bromoisobutyrate site. Preferably, the initiator has 3 or more polymer initiation sites. More preferably, the initiator has 3, 4, 5, 6, 7, 8, 9, 10, 11 or 12 polymer initiation sites. More preferably, the initiator has 3, 6 or 9 polymer initiation sites. Still more preferably, the initiator has 9 polymer initiation sites. Most preferably, the initiator is OG1786.

The invention provides methods for synthesizing a zwitterionic polymer-dual antagonist conjugate, the conjugate having one or more functional agents and one or more polymer arms wherein each of the polymer arms has one or more monomer units wherein at least one of the units has a zwitterion. The method can have the steps of a. providing an initiator having one or more sites for monomer polymerization and a first linker having an amine group wherein the initiator is a trifluoro acetic acid salt;
b. providing one or more monomers suitable for polymerization wherein at least one of the monomers is zwitterionic;
c. reacting the monomers with the initiator to form one or more polymer arms each corresponding to the sites for monomer polymerization to provide an initiator-polymer conjugate having the first linker with the amine group;
d. providing a second linker having at least second and third reactive groups;
e. coupling one of the second and third reactive groups of the second linker to the amine group of the first linker of the initiator-polymer conjugate to provide a linker-initiator-polymer conjugate having one or more reactive groups that were not used in the coupling step; and
f. coupling one or more functional agents to one or more of the unreacted reactive groups of the linker-initiator-polymer moiety to provide the polymer-functional agent conjugate.

Prior to the instant invention, the initiator molecule or entity had to contain a deprotectable functional group that would allow coupling of the functional agent. An example of such an initiator having a protected maleimide is shown below:

For example, if it is desired to conjugate a larger functional agent to a polymer of the instant invention such as an antibody of even a Fab fragment, a longer linker sequence can be snapped on to the polymer. In contrast, smaller functional agents may call for relatively shorter linker sequences.

In preferred embodiments of the methods, the initiator has 1, 2, 3, 4, 5, 6, 7, 8, 9, 10, 11 or 12 sites for polymer initiation. Preferably, the initiator has 3, 6 or 9 sites for polymer initiation.

In accordance with an aspect of the present invention, a second linker has second, third, fourth, fifth, and sixth reactive groups. More preferably, a second linker has just second and third reactive groups.

In accordance with an aspect of the present invention, each polymer arm has from about 20 to about 2000 monomer units. Preferably, each arm has from about 100 to 500 monomer units or from about 500 to 1000 monomer units or from about 1000 to 1500 monomer units or from about 1500 to 2000 monomer units.

In accordance with an aspect of the present invention, the peak molecular weight of the polymer-functional agent conjugate is about 100,000 to 1,500,000 Da. Preferably, the peak molecular weight of the polymer-functional agent conjugate is about 200,000 to about 300,000 Da, about 400,000 to about 600,000 Da or about 650,000 to about 850,000 Da.

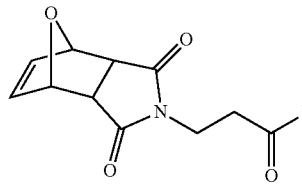

After polymer synthesis, the protected maleimide is deprotected with heat to allow for generation of maleimide which could be used to couple functional agent. If one wanted to vary the nature of the chemical entity in between the maleimide and the polymer initiation site, one would have to synthesize an entire new initiator.

Each time the initiator is changed or altered in any way, a new scaled up synthesis procedure would have to be developed. Each change in the nature of the initiator molecule can have a wide range of effects on polymer synthesis. However, in accordance with the present invention, a method is presented where the conjugation group (e.g. maleimide) is added after polymer synthesis. This is sometimes referred to as a "snap-on strategy" or "universal polymer strategy". A single initiator moiety can be used for large scale polymer and bioconjugate discovery and development. Thus, conditions can be developed for scaled up optimal polymer synthesis. Such polymer can then be adapted to various types of functional agents by "snapping-on" various types of linkers and functional conjugation chemistries.

In accordance with another aspect of the present invention, the first linker is preferably alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amino or any combination thereof. More preferably, the first linker has the formula:

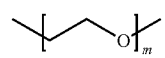

wherein m is 1 to 10. More preferably, the first linker has the above formula and m is 4.

In still other aspects of the present invention, the initiator preferably includes a structure selected from group consisting of

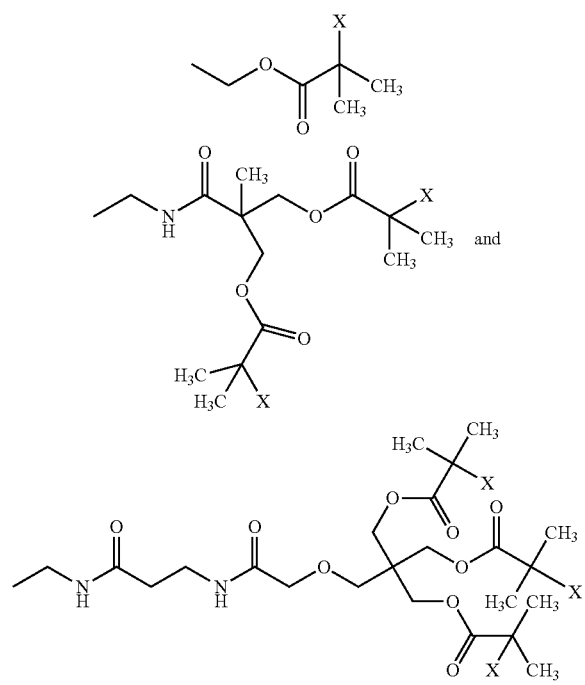

wherein X is selected from the group consisting of NCS, F, Cl, Br and I. More preferably, X is Br.

In preferred embodiments of the present invention, the monomer is selected from the group consisting of

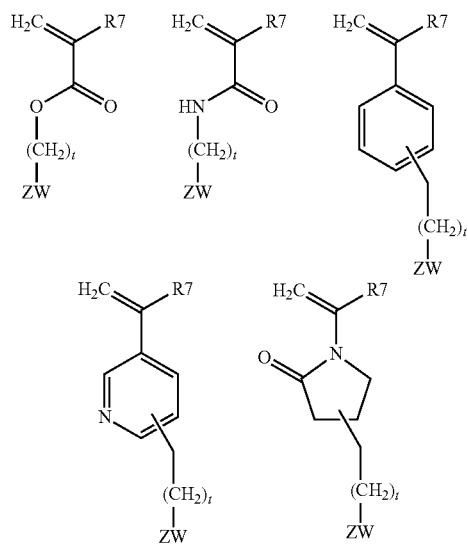

wherein R7 is H or $C_{1-6}$ alkyl and t is 1 to 6.

More preferably, the monomer is selected from the group consisting of 2-(methacryloyloxyethyl)-2'-(trimethylammoniumethyl) phosphate (HEMA-PC) and 2-(acryloyloxyethyl)-2'-(trimethylammoniumethyl) phosphate.

Most preferably, the monomer is 2-(methacryloyloxyethyl)-2'-(trimethylammoniumethyl) phosphate.

The second linker moiety preferably comprises an activated ester having the structure

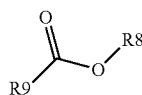

wherein R8 is selected from the group consisting of

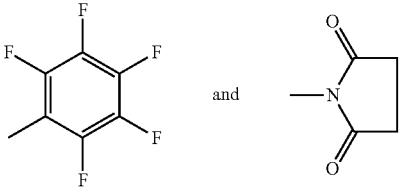

and R9 is

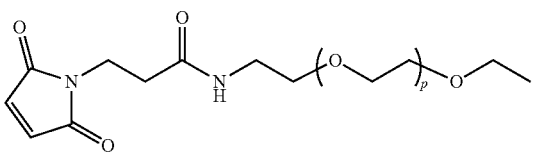

wherein p is 1 to 12.

In more preferred embodiments of the present invention, the polymer has 9 arms, m of R2 is 2-4, R9 is

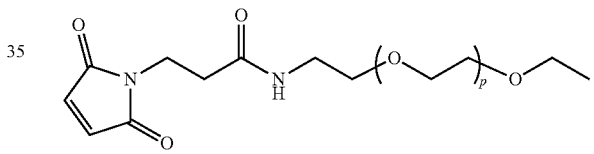

and p is 4 to 15. Still more preferably, m is 4 and p is 12.

When a polymer is to be conjugated via a cysteine (or other specified residue), the polymer can be linked directly or indirectly to the residue (e.g., with an intervening initiator, and or spacer or the like).

Dual antagonists can be incorporated into a pharmaceutical composition with a pharmaceutically acceptable excipient. Pharmaceutical compositions adapted for oral administration may be presented as discrete units such as capsules, as solutions, syrups or suspensions (in aqueous or non-aqueous liquids: or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions can be adapted for nasal administration wherein the excipient is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the excipient is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient: and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-400 mOsm/kg water.

The pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The dual antagonists and pharmaceutical compositions containing them may be administered in an effective regime for treating or prophylaxis of a patient's disease including, for instance, administration by oral, intravitreal, intravenous, subcutaneous, intramuscular, intraosseous, intranasal, topical, intraperitoneal, and intralesional administration. Parenteral infusions include intramuscular, intravenous, intraarterial, intraperitoneal, or subcutaneous administration or routes among others. In therapy or as a prophylactic, the active agent may be administered to an individual as an injectable composition, for example as a sterile aqueous dispersion, preferably isotonic or substantially isotonic.

For administration to mammals, and particularly humans, it is expected that the dosage of the active agent is from 0.011 mg/kg body weight, typically around 1 mg/kg. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited.

This dosage may be repeated as often as appropriate (e.g., weekly, fortnightly, monthly, quarterly). If side effects develop the amount and/or frequency of the dosage can be reduced, in accordance with normal clinical practice. In one embodiment, the pharmaceutical composition may be administered once every one to thirty days.

The dual antagonists and pharmaceutical compositions of the invention can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

The dual antagonists and pharmaceutical compositions disclosed herein can be used for treatment or prophylaxis of disease, particularly the ocular diseases or conditions described herein. Although both antagonist modalities within the dual antagonist are believed to contribute to efficacy as discussed above and shown in Example 40 an understanding of mechanism is not required for practice of the invention. Preferably, a dual antagonist is more effective than an equimolar concentration of each antagonist administered alone, or a 1:1 combination of the antagonists administered as separate molecules.

So used, the conjugates are typically formulated for and administered by ocular, intraocular, and/or intravitreal injection, and/or juxtascleral injection, and/or subretinal injection and/or subtenon injection, and/or superchoroidal injection and/or topical administration in the form of eye drops and/or ointment. Such dual antagonists and compositions can be delivered by a variety of methods, e.g. intravitreally as a device and/or a depot that allows for slow release of the compound into the vitreous, including those described in references such as Intraocular Drug Delivery, Jaffe, Ashton, and Pearson, editors, Taylor & Francis (March 2006). In one example, a device may be in the form of a minipump and/or a matrix and/or a passive diffusion system and/or encapsulated cells that release the compound for a prolonged period of time (Intraocular Drug Delivery, Jaffe, Ashton, and Pearson, editors, Taylor & Francis (March 2006).

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered.

Therapeutic dual agonists and related conjugates according to the present invention generally are placed into a container having a sterile access port, for example, an intravenous solution bag or vial having a stopper pierceable by a hypodermic injection needle. Such compositions may also be supplied in the form of pre-filled syringes.

A "stable" formulation is one in which the protein or protein conjugated to a polymer of other half-life extending moiety therein essentially retains its physical stability and/or chemical stability and/or biological activity upon storage. By "stable" is also meant a formulation which exhibits little or no signs of instability, including aggregation and/or deamidation. For example, in accordance with an aspect of the present invention, the formulations provided by the present invention may remain stable for at least two year, when stored as indicated at a temperature of 5-8° C.

Various analytical techniques for measuring protein stability are available in the art and are reviewed in Peptide and Protein Drug Delivery, 247-301 (Vincent Lee ed., New York, N.Y., 1991) and Jones, 1993 Adv. Drug Delivery Rev. 10: 29-90, for examples. Stability can be measured at a selected temperature for a selected time period. Storage of stable formulations is preferably for at least 6 months, more preferably 12 months, more preferably 12-18 months, and more preferably for 2 or more years.

A protein, such as an antibody or fragment thereof, "retains its physical stability" in a pharmaceutical formulation if it shows no signs of aggregation, precipitation, deamidation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

A protein-polymer conjugate "retains its chemical stability" the chemical bond between the protein and the polymer is maintained intact, e.g., it is not hydrolyzed or otherwise disrupted. The protein part of the conjugate retains its chemical stability as described above.

By "isotonic" is meant that the formulation of interest has essentially the same osmotic pressure as human blood or the vitreous for intravitreal injections. Isotonic formulations will generally have an osmotic pressure from about 250 to 400 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range of preferably from about 3.0 to about 8.0; for example from about 4.5 to 8; or about pH 6 to about 7.5; or about 6.0 to about 7.0, or about 6.5-7.0, or about pH 7.0 to about 7.5; or about 7.1 to about 7.4. A pH of any point in between the above ranges is also contemplated.

"PBS" phosphate buffered saline, Tris based buffers and histidine based buffers are particularly preferred buffers for the instantly invented dual antagonists. In the case of OG1448, PBS is particularly preferred. More preferably, in the case of OG1448, the PBS buffer has a pH of 7-8 and the concentration of OG1448 is from about 10 mg/ml to about 100 mg/ml. Still more preferably, the OG1448 is from about 25 to about 65 mg/ml and the pH is about 7.4. In the most preferred embodiments of the present invention, the concentration of OG1448 is 50 mg/ml to 60 mg/ml.

In preferred embodiments of the present invention, the PBS buffer is made up of at least $Na_2HPO_4$, $KH_2PO_4$ and NaCl adjusted so as to provide the appropriate pH. In particularly preferred embodiments of the present invention, the buffer may contain other pharmaceutical excipients such as KCl and other salts, detergents and/or preservatives so as to provide a stable storage solution.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylamrnonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In accordance with an aspect of the present invention, formulations of dual PDGF/VEGF antagonists according to the present invention to be safe for human use or for animal testing must have sufficiently low levels of endotoxin. "Endotoxin" is lipopolysaccharide (LPS) derived from the cell membrane of Gram-negative bacteria. Endotoxin is composed of a hydrophilic polysaccharide moiety covalently linked to a hydrophobic lipid moiety (lipid A). Raetz C R, Ulevitch R J, Wright S D, Sibley C H, Ding A, Nathan C F. 1991. Gram-negative endotoxin: an extraordinary lipid with profound effects on eukaryotic signal transduction. FASEB J. 5(12):2652-2660. Lipid A is responsible for most of the biological activities of endotoxin, i.e., its toxicity. Endotoxins are shed in large amount upon bacterial cell death as well as during growth and division. They are highly heat-stable and are not destroyed under regular sterilizing conditions. Extreme treatments with heat or pH, e.g., 180-250° C. and over 0.1 M of acid or base must be used (Petsch D, Anspach F. 2000. Endotoxin removal from protein solutions. J Biotechnol. 76: 97-119). Such conditions of course would be highly detrimental to biological drugs.

In the biotech and pharmaceutical industries, it is possible to find endotoxin during both production processes and in final products. As bacteria can grow in nutrient poor media, including water, saline and buffers, endotoxins are prevalent unless precautions are taken. Endotoxin injection into an animal or human causes a wide variety of pathophysiological effects, including endotoxin shock, tissue injury and even death. Ogikubo Y, Ogikubo Y, Norimatsu M, Noda K, Takahashi J, Inotsume M, Tsuchiya M, Tamura Y. 2004. Evaluation of the bacterial endotoxin test for quantifications of endotoxin contamination of porcine vaccines. Biologics 32:88-93.

Pyrogenic reactions and shock are induced in mammals upon intravenous injection of endotoxin at low concentrations (1 ng/mL) (Fiske J M, Ross A, VanDerMeid R K, McMichael J C, Arumugham. 2001. Method for reducing endotoxin in Moraxella catarrhalis UspA2 protein preparations. J Chrom B. 753:269-278). The maximum level of endotoxin for intravenous applications of pharmaceutical and biologic product is set to 5 endotoxin units (EU) per kg of body weight per hour by all pharmacopoeias (Daneshiam M, Guenther A, Wendel A, Hartung T, Von Aulock S. 2006. In vitro pyrogen test for toxic or immunomodulatory drugs. J Immunol Method 313:169-175). EU is a measurement of the biological activity of an endotoxin. For example, 100 pg of the standard endotoxin EC-5 and 120 pg of endotoxin from *Escherichia coli* O111:B4 have activity of 1 EU (Hirayama C, Sakata M. 2002. Chromatographic removal of endotoxin from protein solutions by polymer particles. J Chrom B 781:419-432). Meeting this threshold level has always been a challenge in biological research and pharmaceutical industry (Berthold W, Walter J. 1994. Protein Purification: Aspects of Processes for Pharmaceutical Products. Biologicals 22:135-150; Petsch D, Anspach F B. 2000. Endotoxin removal from protein solutions, J Biotech 76:97-119).

The presence of endotoxin in drugs to be delivered via intravitreal injection is of particular concern. Intravitreal injection of drug (penicillin) was first performed in 1945 by Rycroft. Rycroft B W. 1945. Penicillin and the control of deep intra-ocular infection. British J Ophthalmol 29 (2): 57-87. The vitreous is a chamber where high level of drug can be introduced and maintained for relatively long periods of time. The concentration of drug that can be achieved via intravitreal injection far exceeds what can be generated by topical administration or by systemic administration (e.g. intravenous).

One of the most dangerous complications potentially arising from intravitreal injections is endophthalmitis. Endophthalmitis falls into two classes: infectious and sterile. Infectious endophthalmitis is generally cause by bacteria, fungi or parasites. The symptoms of infectious endophthalmitis include severe pain, loss of vision, and redness of the conjunctiva and the underlying episclera. Infectious endophthalmitis requires urgent diagnosis and treatment. Possible treatments include intravitreal injection of antibiotics and pars plana vitrectomy in some cases. Enucleation may be called for to remove a blind and painful eye. See, e.g., Christy N E, Sommer A. 1979. Antibiotic prophylaxis of postoperative endophthalmitis. Ann Ophthalmol 11 (8): 1261-1265.

Sterile endophthalmitis in contrast does not involve an infectious agent and can be defined as the acute intraocular inflammation of the vitreous cavity that resolves without the need of intravitreal antibiotics and/or vitreoretinal surgery. If a vitreous microbiological study has been done, it needs to be negative culture proven to sustain a diagnosis of sterile endophthalmitis. Marticorena J. Romano V, Gomez-Ulla F. 2012 "Sterile Endophthalmitis after Intravitreal Injections" Med Inflam. 928123.

It has been observed that intravitreal injection of biological drugs contaminated with endotoxin can result in sterile endophthalmitis. Marticorena, et al. Bevacizumab (Avastin) is approved by the Food and Drug Administration for the treatment of glioblastoma and of metastatic colorectal cancer, advanced nonsquamous non-small-cell lung cancer and metastatic kidney cancer. Bevacizumab is also widely used off label as a treatment for wet AMD. Bevacizumab comes from the manufacturer as a 100 mg/4 ml. This solution cannot be directly used for intravitreal injection and must be compounded by a pharmacist. Clusters of sterile endophthalmitis have been observed and are theorized to be cause by inadvertent contamination of bevacizumab by endotoxin by the compounding pharmacist.

Given the dire clinical results of intravitreal injection of endotoxin, the total amount of endotoxin that can be given to a patient via intravitreal dosing is highly limited. In accordance with an aspect of the present invention, a solution having a dual VEGF/PDGF antagonist according to the present invention is provided having an endotoxin level that does not exceed 5.0 EU/ml. More preferably, the endotoxin level does not exceed 1.0 EU/ml. Still more preferably, the endotoxin level does not exceed 0.5 EU/ml. Still more preferably, the endotoxin level does not exceed 0.2 EU/ml. In still more preferred embodiments, the endotoxin level does not exceed 0.1, 0.09, 0.08, 0.07, 0.06, 0.05, 0.04, 0.03, 0.02 or 0.01 EU/ml.

Two commonly used FDA-approved tests for the presence of endotoxin are the rabbit pyrogen test and Limulus Amoebodyte Lysate (LAL) assay (Hoffman S, et al. 2005. International validation of novel pyrogen tests based on human monocytoid cells J. Immunol. Methods 298:1611-173; Ding J L, Ho B A. 2001. New era in pyrogen testing. Biotech. 19:277-281), The rabbit pyrogen test was developed in the 1920s and involves monitoring the temperature rise in a rabbit injected with a test solution. However, use of the rabbit pyrogen test has greatly diminished over the years due to expense and long turnaround time. Much more common is the LAL test. LAL is derived from the blood of a horseshoe crab and clots upon exposure to endotoxin.

One of the simplest LAL assays is the LAL gel-clot assay. Essentially, the LAL clotting assay is combined with a serial dilution of the sample in question. Formation of the gel is proportional to the amount of endotoxin in the sample. Serial dilutions are prepared from the sample and each dilution assayed for its ability to form LAL gel. At some point a negative reaction is contained. The amount of endotoxin in the original sample can be estimated from the dilution assay.

Other LAL tests have also been developed, including the turbidimetric LAL assay (Ong K G, Lelan J M, Zeng K F, Barrett G, Aourob M, Grimes C A. 2006. A rapid highly-sensitive endotoxin detection system. Biosensors and Bioelectronics 21:2270-2274) and the chromogenic LAL assay (Haishima Y, Hasegawa C, Yagarni T, Tsuchiya T, Matsuda R, Hayashi Y. 2003. Estimation of uncertainty in kinetic-colorimetric assay of bacterial endotoxins. J Pharm Biomed Analysis. 32:495-503). The turbidimetric and chromogenic assays are much more sensitive and quantitative than the simple gel-clot dilution assay.

The present invention provides a method of reducing the amount of endotoxin in a composition having a dual VEGF/PDGF antagonist, the method having the steps of contacting the composition with an affinity chromatography resin that binds to the dual VEGF/PDGF antagonist; eluting the dual VEGF/PDGF antagonist from the affinity chromatography resin to form an affinity chromatography eluent having the antagonist; contacting the affinity chromatography eluent with an ion-exchange resin that binds the dual VEGF/PDGF antagonist; and eluting the dual VEGF/PDGF antagonist from the ion-exchange resin, wherein the dual VEGF/PDGF antagonist eluted from the ion-exchange resin is substantially free from endotoxin.

The above method for reducing the amount of endotoxin, or other method or process recited herein, can be performed in the order described in the steps above or it can optionally be performed by varying the order of the steps or even repeating one or more of the steps. In one embodiment, the method of reducing the amount of endotoxin in a composition is performed in the order of the described steps. In some embodiments, the affinity chromatography resin contacting, washing and eluting steps are repeated in the same order more than one time before contacting the affinity chromatography eluent with the ion exchange resin. The method can also include a filtering step using, for example, a 0.1 micron, (122 micron, or 0.44 micron filter, that can be performed on either one or more of the eluents removed after each resin binding step.

In certain instances, the steps of contacting the composition with affinity chromatography resin, washing and eluting the antibody from the affinity chromatography resin can be repeated more than one time before contacting the first eluent with an ion-exchange resin. In one embodiment, the affinity chromatography resin comprises a recombinant Protein A ("rProteinA") resin. One example of a suitable recombinant Protein A resin is rProteinA Sepharose FF® resin (Amersham, Piscataway, N.J.). In another embodiment, a suitable affinity chromatography resin would comprise a protein G chromatography resin. In other embodiments, a suitable affinity chromatography resin comprises a mixed Protein A/Protein G resin. In other embodiments, a suitable affinity chromatography resin comprises a hydrophobic charge induction resin that comprises a 4-mercaptoethylpyridine ligand such as a MEP HyperCel® resin (Bio-Sepra, Cergy, Saint Christophe, France).

In some embodiments, it is preferred that the ion exchange resin comprises an anion-exchange resin. As will be known by the person skilled in the art, ion exchangers may be based on various materials with respect to the matrix as well as to the attached charged groups. For example, the following matrices may be used, in which the materials mentioned may be more or less cross-linked: MacroCap Q (GE Healthcare Biosciences, Piscataway, N.J.), agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange resin, the charged groups, which are covalently attached to the matrix, may, for example, be diethylaminoethyl, quaternary aminoethyl, and/or quaternary ammonium. It is preferred that the anion-exchange resin comprises a quaternary amine group. An exemplarily anion-exchange resin that has a quaternary amine group for binding the anti-M-CSF antibody is a Q Sepharose® resin (Amersham, Piscataway, N.J.).

In other aspects, if the endotoxin levels are higher than desired after subjecting the composition to the aforementioned anion-exchange chromatography step, the composition may in the alternative be subjected to a cation exchange resin. In accordance with this aspect of the present invention, any endotoxin in the composition should have a differential binding to the ion-exchange resin than the protein in question to allow purification of the protein from the endotoxin. In this regard, endotoxin is negatively charged and will generally bind to an anion exchange resin. If both the protein and the endotoxin bind to the anion exchange resin, purification of one from the other may be effectuated by using a salt gradient to elute the two into different fractions. The relative binding of the protein to a particular resin may also be effected by changing the pH of the buffer relative to the pI of the protein. In a preferred aspect of the present invention, cation-exchange chromatography is the sole ion-exchange chromatography employed.

In accordance with another aspect of the present invention, if the endotoxin levels are too high after the anion exchange resin, the composition may be further subjected to a second ion-exchange step, for example, by contacting the compositions with a cation exchange resin and followed by a wash step, then elution from the ion-exchange resin. In preferred embodiments, the cation exchange resin comprises a sulfonic group for binding. Exemplary cation exchange resins are SP Sepharose® resin FF (Amersham, Piscataway, N.J.) Pores XS (CEX) (Life Technology, Grand Island, N.Y.).

In accordance with an aspect of the invention, after the solution of dual PDGF/VEGF antagonist protein is produced having the specified level of endotoxin, there are a number of steps prior to final formulation of the protein. In some embodiments of the present invention, a half-life extending moiety is conjugated to the protein. The conjugate is then formulated into a final drug formulation which is injected into the patients. In some embodiments, the conjugate is again purified on an ion-exchange resin which can preferably be a cation-exchange resin. In other embodiments, the protein is formulated. In all cases, normal laboratory procedures must be employed to prevent the introduction of endotoxin contaminants into the protein sample or into the protein-polymer conjugate.

EXAMPLES

Example 1. Protein Sequence of PDGFRβ-GS10-anti-VEGF-A Light Chain/Anti-VEGF-A Heavy Chain (Wild Type Fc)

A PDGFR-β trap-anti-VEGF-A light chain/anti-VEGF-A heavy chain was constructed having the sequence set forth below in FIGS. 7A, B. PDGFR-GS10-anti-VEGF-A light chain amino acids 1-282 correspond to 33 to 314 of human PDGFR-β (UniProtKB/Swiss-Prot: P09619.1), followed by the linker sequence GGGGSGGGGS and the bevacizumab light chain sequence. Optionally, no linker need be used between the PDGFR-β segment and the anti-VEGF segment. Alternatively, the linker may be the GGGGS motif x1, x2 (as noted above), x3, x4, etc. such that the activity of the two proteins is optimized. Other linker motifs known to those of skill in the art may also be used in accordance with the present invention, including G, GG, GGGS and GGGES x1, x2, x3, x4, etc. The linker may be combinations of the above. The sequence of FIG. 7A is set forth in SEQ ID NO. 19. FIG. 7B shows the bevacizumab heavy chain sequence (SEQ ID NO. 2). The bevacizumab light chain optionally has an M4L mutation (Kabat numbering). The bevacizumab heavy chain optionally has one or more of the following mutations: T28D, N31H, H97Y, S100aT (Kabat numbering), L234A, L235A, G237A, Q347C and L443C EU numbering).

Example 2. Protein Sequence of PDGFRβ-GG-anti-VEGF-A Light Chain/Anti-VEGF-A Heavy Chain (Wild Type Fc)

Another PDGFR-β trap-anti-VEGF-A light chain/anti-VEGF-A heavy chain was constructed having the sequence set forth below in FIGS. 8A, B. FIG. 8A amino acids 1-282 correspond to 33 to 314 of human PDGFR-β (UniProtKB/Swiss-Prot: P096119.1), followed by the linker sequence GG and the bevacizumab light chain sequence. Alternatively, the linker may be the GGGGS motif x1, x2, x3, x4, etc. such that the activity of the two proteins is optimized. Other linker motifs may also be used in accordance with the present invention, including G, GG (as noted above), GGGS and GGGES x1, x2, x3, x4, etc. The linker may be combinations of the above. The protein sequence of FIG. 8A is set forth in SEQ ID NO. 3. FIG. 8B shows bevacizumab heavy chain sequence (SEQ ID NO. 2). The bevacizumab light chain of FIG. 8A optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 3. Protein Sequence of PDGFRβ-GS10-Anti-VEGF-A Heavy Chain (Wild Type Fc)/Anti-VEGF-A Light Chain Another PDGFR-β trap-anti-VEGF-A heavy chain (wild type Fc)/anti-VEGF-A light chain was constructed having the sequence set forth in FIGS. 9A, B. FIG. 9A amino acids 1-282 correspond to 33 to 314 of human PDGFR-β (UniProtKB/Swiss-Prot: P09619.1), followed by the linker sequence GGGGSGGGGS and the bevacizumab heavy chain sequence, optionally having Q347C or L443C (EU numbering). Alternatively, the linker may be the GGGGS motif x1, x2 (as noted above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 9A is set forth in SEQ ID NO. 4. The protein of FIG. 9B is the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 4. Protein Sequence of PDGFRβ-GG-Anti-VEGF-A Heavy Chain (Wild Type Fc)/Anti-VEGF Light Chain Another PDGFR-β trap-anti-VEGF-A heavy chain (wild type Fc)/anti-VEGF-A light chain was constructed having the sequence set forth below in FIGS. 10A, 10B. FIG. 10A amino acids 1-282 correspond to 33 to 314 of human PDGFR-β (UniProtKB/Swiss-Prot: P09619.1), followed by the linker sequence GG and the bevacizumab heavy chain sequence, optionally having Q347C or L443C. Alternatively, the linker may be the GGGGS motif x1, x2, x3, x4, etc. such that the activity of the two proteins is optimized. Other linker motifs may also be used in accordance with the present invention, including G, GG (as noted above), GGGS and GGGES x1, x2, x3, x4, etc. The linker may be combinations of the above. The protein sequence of FIG. 10A is set forth in SEQ ID NO. 6. The protein of FIG. 10B is the bevacizumab light chain sequence (SEQ ID NO. 5), The bevacizumab light chain optionally has an M4L mutation. The bevacizumab heavy chain optionally has one or more of the following mutations: T28D, N31H, H97Y, S100aT (Kabat numbering), L234A, L235 A, G237A, Q347C and L443C (EU numbering).

Example 5. Protein Sequence of Anti-VEGF-A Heavy Chain (Wild Type Fc)-GS21-PDGFRβ/Anti-VEGF-A Light Chain A PDGFR-β trap-anti-VEGF-A antibody construct was constructed with the anti-VEGF-A heavy chain being upstream or N-terminal to the PDGFR-β trap having the sequence set forth below in FIGS. 11A, B. FIG. 11A amino acids 1-451 correspond to the bevacizumab heavy chain sequence, optionally having Q347C or L443C, followed by linker sequence GGGGSGGGGSGGGGSGGGGSG. Alternatively, the linker may be the GGGGS motif x1, x2 (as noted above), x3, x4, etc. such that the activity of the two proteins is optimized. Other linker motifs also be used in accordance with the present invention, including G, GG, GGGS and GGGES x1, x2, x3, x4, etc. The linker may be combinations of the above. The linker is followed by amino acid sequences 33 to 314 of human PDGFR-β (UniProtKB/Swiss-Prot: P09619.1). The protein sequence of FIG. 11A is set forth in SEQ ID NO. 7. FIG. 11B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, S100aT (Kabat numbering), L234A, L235A, G237A, Q347C and L443C (EU numbering).

Example 6. Protein Sequence of PDGFRβ-GS10-Anti-VEGF-A Heavy Chain (Q347C)/Anti-VEGF-A Light Chain (TAF347)

Another PDGFR-β trap-anti-VEGF-A heavy chain (Q347C)/anti-VEGF-A light chain was constructed having the sequence set forth below in FIGS. 12A, B. FIG. 12A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Optionally, no linker need be used between the PDGFR-β segment and the anti-VEGF segment. The linker may be combinations of the above. Joined to the carboxyl terminus of the serine residue of the linker is the bevacizumab heavy chain with the following amino acid: T28D, N31H, H97Y, S100aT (Kabat numbering), L234A, L235A, G237A and Q347C (EU numbering). The protein sequence of FIG. 12A is set forth in SEQ ID NO. 8. The protein of FIG. 12B is ranibizumab light chain (bevacizumab w/M4L) (SEQ ID NO. 12).

Example 7. Protein Sequence of PDGFRβ-GS10-Anti-VEGF-A Heavy Chain (L443C)/Anti-VEGF-A Light Chain Another PDGFR-β trap-anti-VEGF-A heavy chain (L443C))/anti-VEGF-A light chain was constructed having the sequence set forth below in FIGS. 13A, B. FIG. 13A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Joined to the carboxyl terminus of the serine residue of the linker is the bevacizumab heavy chain with the following amino acid: T28D, N31H, H97Y, S100aT (Kabat numbering), L234A, L235A, G237A and L443C (EU numbering). The TAF443 light chain is the same as bevacizumab except for a M4L change (Kabat numbering). The protein sequence of FIG. 13A is set forth in SEQ ID NO. 9. FIG. 13B shows the ranibizumab light chain (bevacizumab w/M4L) (SEQ ID NO. 12).

Example 8. Protein Sequence of PDGFRβ-GS10-Anti-VEGF-A Light Chain/Anti-VEGF-A Fab A PDGFR-β trap-anti-VEGF-A light chain/anti-VEGF-A Fab was constructed having the sequence set forth below in FIGS. 14A, B. FIG. 14A amino acids 1-282 correspond to 33 to 314 of human PDGFR-β (UniProtKB/Swiss-Prot: P096119.1), followed by the linker sequence GGGGSGGGGS and the bevacizumab light chain sequence. Optionally, no linker need be used between the PDGFR-β segment and the anti-VEGF segment. Alternatively, the linker may be the GGGGS motif x1, x2 (as noted above), x3, x4, etc, such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 14A is set forth in SEQ ID NO. 1. The protein of FIG. 14B is the bevacizumab Fab (SEQ ID NO. 21). The bevacizumab light chain of FIG. 14A optionally has an M4L, mutation. The bevacizumab Fab of the second protein optionally has one or more of the following mutations: T28D, N31H, H97Y, and S100aT. The bevacizumab Fab of the second chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 9. Protein Sequence of PDGFRβ-GG-Anti-VEGF-A Light Chain/Anti-VEGF-A Fab A PDGFRβ trap-anti-VEGF-A light chain/anti-VEGF-A Fab was constructed having the sequence set forth below in FIGS. 15A, B. FIG. 15A amino acids 1-282 correspond to 33 to 314 of human PDGFR-β (UniProtKB/Swiss-Prot: P09619.1), followed by the linker sequence GG and the bevacizumab light chain sequence. Optionally, no linker need be used between the PDGFRβ segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG (as above), GGGS and GGGES x1, x2, x3, x4, etc. The linker may be combinations of the above. The protein sequence of FIG. 15A is set forth in SEQ ID NO. 3. FIG. 15B shows the heavy chain of bevacizumab Fab (SEQ ID NO. 21). The bevacizumab light chain of FIG. 15A optionally has an M4L mutation (Kabat numbering). The bevacizumab Fab of FIG. 15B optionally has one or more of the following mutations: T28D, N31H, H97Y, and S100aT (Kabat numbering). The bevacizumab Fab of FIG. 15B optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 10. Protein Sequence of PDGFRβ-GS10-Anti-VEGF-A Fab/Anti-VEGF-A Light Chain Another PDGFR-β trap-anti-VEGF-A Fab/anti-VEGF-A light chain was constructed having the sequence set forth below in FIGS. 16A, B. FIG. 16A amino acids 1-282 correspond to 33 to 314 of human PDGFR-β (UniProtKB/Swiss-Prot: P09619.1), followed by the linker sequence GGGGSGGGGS and the bevacizumab Fab sequence. Optionally, no linker need be used between the PDGFR-β segment and the anti-VEGF segment. Alternatively, the linker may be the GGGGS motif x1, x2 (as above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 16A is set forth in SEQ ID NO. 22. FIG. 16B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 11. Protein Sequence of PDGFR-β-GG-Anti-VEGF-A Fab/Anti-VEGF-A Light Chain Another PDGFR-β trap-anti-VEGF-A Fab/anti-VEGF-A light chain was constructed having the sequence set forth below in FIGS. 17A, B. FIG. 17A amino acids 1-282 correspond to 33 to 314 of human PDGFR-β (UniProtKB/Swiss-Prot: P09619.1), followed by the linker sequence GGGGSGGGGS and the bevacizumab Fab sequence. Optionally, no linker need be used between the PDGFR-β segment and the anti-VEGF segment. Alternatively, the linker may be the GGGGS motif x1, x2 (as above), x3, x4, etc. such that the activity of the two proteins is optimized. Other linker motifs may also be used in accordance with the present invention, including G, GG, GGGS and GGGES x1, x2, x3, x4, etc. The linker may be combinations of the above. The protein sequence of FIG. 17A is set forth in SEQ ID NO. 23. FIG. 17B shows the bevacizumab light chain sequence (SEQ ID NO. 5). The bevacizumab light chain optionally has an M41L mutation. The bevacizumab heavy chain optionally has one or more of the following mutations: T28D, N31H, H97Y, and S100aT (Kabat numbering). The bevacizumab Fab heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 12. Protein Sequence of Anti-VEGF-A Fab-GS21-PDGFRβ/Anti-VEGF-A Light Chain A PDGFR-β trap-anti-VEGF-A antibody construct was constructed with the anti-VEGF-A heavy chain being upstream or N-terminal to the PDGFR-β trap having the sequence set forth below in FIGS. 18A, B. FIG. 18A amino acids 1-231 correspond to the bevacizumab Fab followed by linker sequence GGGGSGGGGSGGGGSGGGGSG. Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The linker is followed by amino acid sequences 33 to 314 of human PDGFR-β (UniProtKB/Swiss-Prot: P09619.1). The protein sequence of FIG. 18A is set forth in SEQ ID NO. 24. FIG. 18B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT. The protein of FIG. 18A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 18B.

Example 13. Protein Sequence of PDGFRβ-GS10-Anti-VEGF-A Fab/Anti-VEGF-A Light Chain Another PDGFR-β trap-anti-VEGF-A Fab/anti-VEGF-A light chain was constructed having the sequence set forth below in FIGS. 19A, B. FIG. 19A amino acids 1-282 correspond to 33 to 314 of human PDGFR-β (UniProtKB/Swiss-Prot: P09619.1). Immediately following the PDGFR sequence is a 10 amino acid linker GGGGSGGGGS. Optionally, no linker need be used between the PDGFR-β segment and the anti-VEGF segment. Alternatively, the linker may be the GGGGS motif x1, x2 (as above), x3, x4, etc. such that the activity of the two proteins is optimized.

Other linker motifs may also be used in accordance with the present invention, including G, GG, GGGS and GGGES x1, x2, x3, x4, etc. The linker may be combinations of the above. Joined to the carboxyl terminus of the serine residue of the linker is the bevacizumab Fab having the mutations T28D, N31H, H97Y, and S100aT (Kabat numbering). The protein sequence of FIG. 19A is set forth in SEQ ID NO. 25. The protein of FIG. 19B is the ranibizumab light chain (bevacizumab w/M4L) (SEQ ID NO. 12). The protein of FIG. 19A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 19B.

Example 14. Protein Sequence of PDGFRβ-Anti-VEGF-A Fab/Anti-VEGF-A Light Chain (1a)

Another PDGFR-β trap-anti-VEGF-A Fab/anti-VEGF-A light chain was constructed having the sequence set forth in FIGS. 20A, B. FIG. 20A amino acids 1-283 correspond to 32 to 314 of human PDGFR-β (UniProtKB/Swiss-Prot: P09619.1), followed by the bevacizumab heavy chain. The protein sequence of FIG. 20A is set forth in SEQ ID NO. 26. The protein of FIG. 20B is the bevacizumab light chain sequence (SEQ ID NO. 5). As set forth in this example, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The bevacizumab light chain optionally has an M4L mutation. The bevacizumab heavy chain optionally has one or more of the following mutations: T28D, N31H, H97Y, S100aT (Kabat numbering), Q347C and L443C (EU numbering).

Example 15. Protein Sequence of PDGFR-β (D2-D3)-Anti-VEGF-A Heavy Chain/Anti-VEGF-A Light Chain (1b)

Another PDGFRβ trap (D2-D3)-anti-VEGF-A heavy chain/anti-VEGF-A light chain was constructed having the sequence set forth below in FIG. 21A, B. FIG. 21A amino acids 1-190 correspond to 125 to 314 of human PDGFR-β (UniProtKB/Swiss-Prot: P09619.1), followed by the bevacizumab heavy chain. The protein sequence of FIG. 21A is set forth in SEQ ID NO. 27. As set forth in this example, no linker need be used between the PDGFRβ segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. FIG. 21B shows the bevacizumab light chain sequence (SEQ ID NO. 5). The bevacizumab light chain optionally has an M41L mutation. The bevacizumab heavy chain optionally has one or more of the following mutations: T28D, N31H, H97Y, S100aT (Kabat numbering), Q347C and L443C (Eu numbering).

Example 16. Protein Sequence of PDGFR-β (D2-D3)-Anti-VEGF-A Fab/Anti-VEGF-A Light Chain (2b)

Another PDGFR-β trap (D2-D3)-anti-VEGF-A Fab/anti-VEGF-A light chain was constructed having the sequence set forth in FIGS. 22A, B. FIG. 22A amino acids 1-190 correspond to 125 to 314 of human PDGFR-β (UniProtKB/Swiss-Prot: P09619.1), followed by the bevacizumab Fab. As set forth in this example, no linker need be used between the PDGFR-β segment and the anti-VEGF segment. Alternatively, the linker may be the GGGGS motif x1, x2, x3, x4, etc. such that the activity of the two proteins is optimized. The GGGGSGGGGS linker is particularly preferred. Other linker motifs may also be used in accordance with the present invention, including G, GG. GGGS and GGGES x1, x2, x3, x4, etc. The linker may be combinations of the above. The sequence of FIG. 22A is set forth in SEQ ID NO. 28. FIG. 22B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The bevacizumab Fab of FIG. 22A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain of FIG. 22B.

Example 17. Protein Sequence of PDGFR-β (D2-D3)-Anti-VEGF-A Fab/Anti-VEGF-A Light Chain (2b')

Another PDGFR-β trap (D2-D3)-6×GS-anti-VEGF-A Fab/anti-VEGF-A light chain was constructed having the sequence set forth below in FIGS. 23A, B. FIG. 23A amino acids 1-190 correspond to 125 to 314 of human PDGFR-β (UniProtKB/Swiss-Prot: P09619.1), followed by the linker GGGSGGGGSGGGGSGGGGSGGGGSGGGGS and then by bevacizumab Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs known to those of skill in the art may also be used in accordance with the present invention, including G, GG, GGGS and GGGES x1, x2, x3, x4, etc. The linker may be combinations of the above. The protein sequence of FIG. 23A is set forth in SEQ ID NO. 29. FIG. 23B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The bevacizumab Fab heavy chain optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 18. Protein Sequence of PDGFR-β (D2-D3)-Anti-VEGF-A Fab/Anti-VEGF-A Light Chain (2b')

Another anti-VEGF-A Fab-6×GS-PDGFR-β trap (D2-D3)/anti-VEGF-A light chain was constructed having the sequence set forth below in FIGS. 24A, B. FIG. 24A amino acids 1-190 correspond to 125 to 314 of human PDGFR-β (UniProtKB/Swiss-Prot: P09619.1), followed by the linker GGGSGGGGSGGGGSGGGGSGGGGSGGGGS and then by bevacizumab Fab. Optionally, no linker need be used between the PDGFR-P segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The sequence of FIG. 24A is set forth in SEQ ID NO. 29. FIG. 24B shows the bevacizumab light chain sequence (SEQ ID NO. 5). The bevacizumab light chain of FIG. 24B optionally has an M4L mutation. The bevacizumab heavy chain of the first protein optionally has one or more of the following mutations: T28D, N31H, H97Y, and S100aT (Kabat numbering). The bevacizumab Fab of FIG. 24A optionally has a cysteine moiety added to the C-terminus for conjugating a half-life extending moiety. Preferably, the cysteine moiety is added via SGGGC or CAA. Alternatively, SGGGC or CAA may be added to the C-terminus of the light chain.

Example 19. Protein Sequence of Anti-VEGF-A Fab-6×GS-PDGFR-β (D2-D3)/Anti-VEGF-A Light Chain (3)

Another anti-VEGF-A Fab-6×GS-PDGFR-β (D2-D3)/anti-VEGF-A light chain was constructed having the sequence set forth below in FIGS. 25A, B. FIG. 25A amino acids 1-231 correspond to bevacizumab Fab, followed by the linker GGGSGGGGSGGGGSGGGGSGGGGSGGGGS and then 125 to 314 of human PDGFR-β (UniProtKB/Swiss-Prot: P09619.1). Optionally, no linker need be used between the PDGFR-β segment and the anti-VEGF segment. Alternatively, the linker may be the GGGGS motif x1, x2, x3, x4, etc. such that the activity of the two proteins is optimized. Other linker motifs may also be used in accordance with the present invention, including G, GG, GGGS and GGGES x1, x2, x3, x4, etc. The linker may be combinations of the above. The sequence of FIG. 25A is set forth in SEQ ID NO. 30. FIG. 25B shows the bevacizumab light chain sequence (SEQ ID NO. 5). The bevacizumab light chain optionally has an M4L mutation. The bevacizumab heavy chain optionally has one or more of the following mutations: T28D, N31H, H97Y, and S100aT (Kabat numbering). The PDGFR-β of FIG. 25A optionally has a cysteine moiety added to the C-terminus for conjugating a half-life extending moiety. Preferably, the cysteine moiety is added via SGC or CAA. Alternatively, SGGGC or CAA may be added to the C-terminus of the light chain.

Example 20. Production of Dual PDGFR/VEGF Antagonist Protein

The TAF443 heavy and light chains were cloned into expression plasmids and transfected into CHO cells. Cells were grown up in appropriate media and harvested. TAF443 was purified as follows. 10 L culture medium from CHO cells expressing SEQ ID NOS. 31 and 32 were adjusted with 5% (v/v) 1.1 M HEPES, 0.22 M EDTA, pH 6.7 or 10% 0.55 M Hepes, 0.11M EDTA, 5.5% Triton X-100, pH 6.7, and loaded onto a 167/400 ml Protein A column (2-run) packed with Mab Select Sure resin equilibrated in 50 mM Tris, 150 mM NaCl, pH 7.5 (5-CV). The column was washed with 50 mM Tris, 150 mM NaCl, pH 7.5 (2-CV), 50 mM Tris, 0.5M CaCl$_2$, pH 7.5 (5-CV), and then 10 mM Tris, 10 mM NaCl, pH 7.5 (3-CV) before the protein was eluted using 150 mM Glycine, 40 mM NaCl, pH 3.5 (4-CV). Fractions were pooled, adjusted to pH 3.5 using 2M Glycine, pH 2.7, and then neutralized to pH 7 using 2M HEPES, pH 8.0. The Protein A pool was loaded onto a 274 ml TMAE column equilibrated in 50 mM Hepes, 65 mM NaCl, pH 7.0 (5-CV). The column was washed with 50 mM Hepes, 65 mM NaCl, pH 7.0 (3-CV), and then eluted with 50 mM Tris, 200 mM NaCl, pH 7.5 (5-CV). The elution fractions were pooled and buffer exchanged in a 1150 mL Sephadex G-25 Coarse column equilibrated with PBS-CMF, pH 7.2. The pool was filtered, concentrated to >5 mg/ml via 30 k MWCO VivaFlow200. The concentrated protein was filtered through a 0.22 um filter, and then characterized by SDS-PAGE, analytical SEC, O.D.280/320, end toxin LAL, assay, Protein A ELISA, IEF, and Freeze/Thaw Analysis.

The table below summarizes the properties of an example batch of purified TAF443.

| TAF443 Purified Lot Characteristics | |
| --- | --- |
| Concentration (UV) | 5.69 mg/ml |
| Purity (SEC) | 98.6% |
| MW (SDS-PAGE) | ~200 kDa (NR) |
| pI (IEF) | 4.2-4.5 |
| Endotoxin (LAL) | 0.1 EU/mg |
| Protein A (Elisa) | <10 ng/ml |
| Final Yield | ~700 mg/L (CM) |

Example 21. TAF Bi-Functional Molecule Stability at High Concentration in Representative Formulations The TAF bi-functionals were concentrated to 50-85 mg/ml in a series of standard formulation buffers ranging from pH 4.5 to 7.5, in the presence of excipients such as sucrose. Aliquots of these samples were stored at room temperature (RT) and 4° C. over a period of 6 weeks, and sampled at time zero and after each subsequent week to measure the percentage of aggregated material by analytical SEC. The effect of pH on aggregation of TAF443 can be seen in the following table.

| % Aggregates Observed in TAF Solution at various pHs over Time | | | | |
| --- | --- | --- | --- | --- |
| | Tris pH 7.5 | His pH 6.0 | His pH 5.5 | Lac pH 4.5 |
| Time 0 | <1 | <1 | <1 | <2 |
| Day 4 | <1 | <1 | <1 | ~3 |
| Week 1 | <1 | <1 | <1 | ~4 |
| Week 2 | <1 | <1 | ~2 | ~6 |
| Week 4 | <1 | <1 | ~3 | ~10 |
| Week 6 | <1 | <1 | ~3 | ~10 |

Example 22. Transfection of Constructs into CHO Cells

DNA constructs for TAFwt, TAF443 and TAF347 were transfected into CHO-K1 SV SSI: 3 pools/construct. The normal 3 weeks of recovery was observed in most of the cell lines. However, TAFwt and TAF347 cell lines lagged approximately 1 week behind the other cell lines. Once the pools were established, day 4 for most and day 3 for TAFwt and TAF347, conditioned media samples were run on Octet. 3-day conditioned media for TAFwt and TAF347 showed about 7 mg/ml by Octet. 4-day conditioned media showed about 21 mg/ml for TAF443. Small differences were observed between pools and the pools were used to make pools of pools which were carried forward for protein generation.

Example 23. SEC-MALS of Proteins

The PDGFR segment of TAF has 7 putative glycosylation sites. The protein appears to be heavily glycosylated from SEC-MALS measurements:

| Construct | Protein (kDa) | Sugar (kDa) | Total (kDa) |
|---|---|---|---|
| TAFwt | 184 | 63 | 247 |
| TAF334 | 182 | 62 | 244 |
| TAF443 | 187 | 63 | 250 |

The samples run on SEC-MALS were all greater than 98% pure. The molecular weights measured were reasonable. Some high molecular weight material was observed, probably a tri- to pentamer (data not shown).

Example 24. Thermal Stability of TAF Proteins

Thermal stability profiles were run of TAFwt, TAF443 and TAF347 in PBS, pH 7.2. Each protein had three peaks (data not shown). The relative positions of the peaks are set forth in the table below:

| Sample | $T_m1$ (° C.) | $T_m2$ (° C.) | $T_m3$ (° C.) |
|---|---|---|---|
| TAFwt | 58.1 ± 0.1 | 71.9 ± 0.1 | 83.2 ± 0.1 |
| TAF347 | 58.2 ± 0.1 | 71.9 ± 0.1 | 81.7 ± 0.1 |
| TAF443 | 58.2 ± 0.1 | 71.9 ± 0.1 | 84.4 ± 0.1 |

The stabilities of the proteins over the temperature range are very similar. It is noted however that there are some small changes in $T_m3$. $T_m3$ likely corresponds to the CH3 domain of the antibody domain of the three TAF proteins and the changes reflect the Cys mutations. The low overall stability of the TAF proteins is likely due to unfolding of the PDGFR segment of the proteins.

Example 25. TAF Forced Aggregation

The percentage of aggregates in a solution of the three TAP proteins as a function of heat was examined (data not shown). Solutions of each of the proteins (TAFwt, TAF347 and TAF443) started to show aggregates starting around 54° C. The percentage of aggregates for each of the proteins increased sharply as the temperature was increased. At 64° C., roughly 40% of each of the TAF proteins constituted aggregates. It is noted that the aggregation starts to occur at the lowest Tm, seemingly corresponding to the unfolding of the PDGFR portion of the protein.

Example 26. TAF443 Thermal Stability as a Function of pH

The thermal stability of TAF443 was examined at various pHs as set forth in the table below. In non PBS buffers, 4 thermal denaturation peaks are seen:

| Buffer | $T_m1$ (° C.) | $T_m2$ (° C.) | $T_m3$ (° C.) | $T_m4$ (° C.) |
|---|---|---|---|---|
| Tris pH 7.5 | 57 | 67 | 74 | 85.9 |
| His pH 6.0 | 53.3 | 62.9 | 75.4 | 84.9 |
| Succinate | 55.9 | 66.7 | 74.9 | 85.8 |
| Lucentis buffer, pH 4.8 | 53.9 | 61.3 | 75.1 | 82.9 |
| PBS pH 7.2 | 58.2 | 71.9 | | 84.4 |

As can be seen, there is a weak pH dependence. Notably, the $T_m2$ and $T_m3$ domain (presumably $C_H2$, $F_{ab}$) overlap in PBS, but not in other buffers.

Example 27. Affinity of Dual PDGF/VEGF Antagonist Proteins and Conjugates to Targets Surface plasmon resonance (SPR) was used to characterize the binding kinetics of recombinant human PDGF-BB (PeproTech, 100-14B) to TAF-WT, TAF-347, TAF 443, TAF443-6A250K, and TAF443-3A250K dual PDGF/VEGF antagonist variants. Initially, an anti-human IgG antibody (GE Healthcare, BR-1008-39) was covalently amine coupled onto all four flow cells of a CM5 carboxymethylated dextran coated sensorchip to a density of about 10,000 resonance units (RUs) following the manufacturer's protocol. Each PDGF/VEGF variant was captured to a level of approximately 150 RUs. The running and sample buffer for the PDGF analysis was HBS-EP+ 300 mM NaCl (10 mM 4-(2-hydroxyethyl)-1-piperazineethanesulfonic acid (HEPES) pH 7.4, 300 mM NaCl, 3 mM ethylenediaminetetraacetic acid (EDTA), 0.05% (v/v) Tween-20). A 2-fold serial dilution series of PDGF-BB ranging in concentration from 1M to 0.125 nM was injected at a flow rate of 100 µL/minute for a 110 second association with dissociations that varied from 300 to 2700 seconds. The surface was then regenerated with a 30 second pulse of 3M $MgCl_2$, a 30 second pulse of an ionic regeneration buffer (0.46M KSCN, 1.83 M MgCl2, 0.92 M urea, and 1.83 M guanidine-HCl pH7.4, Andersson et al., Analytical Chemistry, 1999) and then equilibrated with a 30 second pulse of HBS-EP+ 300 mM NaCl running buffer.

Similarly, SPR was used to determine the binding affinities of recombinant human VEGF121 (PeproTech, 100-20A) against the TAF-WT, TAF-347, and TAF-443 dual PDGP/VEGP antagonist variants. The running and sample buffer for the VEGP analysis was HBS-EP+ with a final concentration of 150 mM NaCl. A 2-fold dilution series of VEGP121 ranging in concentration from 100 nM to 12.5 nM was injected at a flow rate of 50 uL/minute for about a 50 second association with dissociations that varied from 300 to 3600 seconds. The surface was then regenerated with a 30 second pulse of 3 M MgCh, a 30 second pulse of ionic regeneration buffer (0.46 M KSCN, 1.83 M MgCl2, 0.92 M urea, and 1.83 M guanidine-HCl pH7.4, Andersson et al., Analytical Chemistry, 1999), and then equilibrated with a 30 second pulse of HBS-EP+ 150 mM NaCl running buffer.

All SPR assays were performed at 25° C. with a data collection rate of 1 Hz using a Biacore T200 instrument (GE Healthcare). The resulting PDGP and VEGP sensorgrams were double referenced using both a control surface and buffer injections. The rate constants were determined by fitting the data to a 1:1 Langmuir model with Biacore T200 evaluation software v2.0 and the equation $K_D = k_a/k_d$.

| Biacore Affinity to PDGF-BB | | | | | | | |
|---|---|---|---|---|---|---|---|
| Analyte | Ligand | ka (1/Ms) | kd (1/s) | t½ (min) | Rmax (RU) | Chi2/Rmax | KD (pM)* |
| PDGF-A* | TAF-WT | 7.97E+07 | 8.01E−05 | 144.28 | 15.16 | 0.16% | 1.01 |
| PDGF-B* | TAF-WT | 8.01E+07 | 9.19E−05 | 125.68 | 15.15 | 0.20% | 1.15 |
| PDGF-C* | TAF-WT | 8.65E+07 | 1.03E−04 | 111.94 | 15.32 | 0.15% | 1.19 |
| | | | | | | AVG +/− STDEV | 1.1 ± 0.1 |
| PDGF-A* | TAF-347C | 4.15E+07 | 8.41E−05 | 137.33 | 13.99 | 0.86% | 2.03 |
| PDGF-B* | TAF-347C | 5.82E+07 | 7.87E−05 | 146.79 | 13.08 | 1.05% | 1.35 |
| | | | | | | AVG +/− STDEV | 1.7 ± 0.3 |
| PDGF-A* | TAF-443C | 3.22E+07 | 4.96E−05 | 233.15 | 13.15 | 0.81% | 1.54 |
| PDGF-B* | TAF-443C | 5.62E+07 | 8.76E−05 | 131.89 | 12.19 | 0.96% | 1.56 |
| | | | | | | AVG +/− STDEV | 1.55 ± 0.01 |
| PDGF-A* | R3643-6A (TAF443-6A250K) | 7.60E+07 | 9.46E−05 | 122.09 | 8.11 | 0.41% | 1.25 |
| PDGF-B* | R3643-6A (TAF443-6A250K) | 5.62E+07 | 5.85E−05 | 197.55 | 8.33 | 0.30% | 1.04 |
| PDGF-C* | R3643-6A (TAF443-6A250K) | 3.48E+07 | 5.13E−05 | 225.41 | 8.45 | 0.80% | 1.47 |
| | | | | | | AVG +/− STDEV | 1.3 ± 0.2 |
| PDGF-A* | R3644-3A (TAF443-3A250K) | 5.76E+07 | 5.92E−05 | 195.04 | 8.15 | 0.31% | 1.03 |
| PDGF-B* | R3644-3A (TAF443-3A250K) | 2.86E+07 | 4.96E−05 | 233.05 | 8.52 | 0.60% | 1.73 |
| PDGF-C* | R3644-3A (TAF443-3A250K) | 4.71E+07 | 7.52E−05 | 153.56 | 8.15 | 0.49% | 1.60 |
| | | | | | | AVG +/− | 1.5 ± 0.4 |

*A B and C refer to separate runs or measurements concerning the same analyte PDGF-BB

| Biacore Affinity to VEGF121 | | | | | | | |
|---|---|---|---|---|---|---|---|
| Analyte* | Ligand | ka (1/Ms) | kd (1/s) | T½ (min) | Rmax (RU) | Chi2/Rmax | KD (pM) |
| VEGF-A | TAF-WT | 1.14E+05 | 2.01E−05 | 573.89 | 29.4 | 0.17% | 176.60 |
| VEGF-B | TAF-WT | 6.85E+05 | 5.89E−05 | 196.00 | 13.90 | 0.16% | 86.03 |
| VEGF-C | TAF-WT | 1.40E+05 | 2.96E−05 | 390.68 | 27.36 | 0.17% | 212.00 |
| VEGF-D | TAF-WT | 1.55E+05 | 2.69E−05 | 429.78 | 24.92 | 0.23% | 173.00 |
| | | | | | | AVG/STD DEV | 161.96 ± 53.46 |
| VEGF-A | TAF347 | 1.37E+05 | 3.83E−05 | 301.55 | 26.57 | 0.87% | 280.30 |
| VEGF-B | TAF347 | 1.42E+05 | 2.59E−05 | 446.21 | 24.56 | 0.35% | 182.40 |
| | | | | | | AVG | 231.35 ± 48.95 |
| VEGF-A | TAF443 | 1.46E+05 | 3.20E−05 | 361.01 | 25.87 | 0.75% | 219.30 |
| VEGF-B | TAF443 | 1.35E+05 | 3.10E−05 | 372.18 | 25.47 | 0.31% | 229.70 |
| | | | | | | AVG | 224.5 ± 5.2 |

*A, B C, D, refer to different runs of the same analyte (VEGF121).

Example 28. Decapping of TAF443 Prior to Maleimide Conjugation

The TAF443 Cysteine residue is typically "capped" or oxidized by chemicals in the cell culture media and is not available for conjugation. In this regard, purified TAF443 (OG1321) is subjected to a decapping (i.e. reducing) procedure to remove the cap and enable the free (i.e. those not involved in Cys-Cys disulfide bonds) cysteine residue to be conjugated to the maleimide functionality of a polymer. Decapping is done by mixing TAF protein with a 30× molar excess for 1 hour at 25° C. of the reducing agent TCEP (3,3',3"-Phosphanetriyltripropanoic acid). The reduction reaction with TCEP is monitored by SDS-PAGE. Undenatured TAF runs as a single band at about 250 kDa (about 40 kDa of this weight is carbohydrate). When fully denatured the single 250 kDa band is converted into bands corresponding to the light and heavy chains. Following denaturation, the TAF protein was washed by UFdF using a Pellion XL Ultrafiltration Cassette with 20 mM Tris pH17.5, 150 mM NaCl, 0.5 m/M TCEP buffer to remove the cap. The TCEP reagent was then removed in the same UFdF setup with 20 mM Tris pH7.5, 150 mM NaCl. Reduced TAF was allowed to refold using air (ambient Oxygen) which was again followed by SDS-PAGE as an assay.

A detailed procedure for decapping is as follows:
500 mg of OG1321 was thawed from −80° C. at 4° C. overnight, and warmed up in the 25° C. water bath before mixing with TCEP at 30× molar excess. The reaction was incubated in the 25° C. water bath for 1 hour. Samples were taken out at 15, 30, and 60 minutes to run on SDS-PAGE in order to evaluate the reduction completeness. A UFdF cassette with 10 kD MWCO was used to carry out buffer exchange. First buffer exchange step was done with 20 mM Tris ph7.5, 100 m/M NaCl, 0.5 mM TCEP for ~100× to thoroughly remove the cap. A second buffer exchange step was done with 20 mM Tris pH7.5, 100 mM NaCl for ~1000× for TCEP remove prior to air refolding. The final TCEP concentration in the sample was ~0.5 µM. Samples were taken out from both buffer exchange steps for both SDS-PAGE and SEC analyses to evaluate the protein reoxidation status and protein aggregation. After the second buffer exchange step, the OG1321 was concentrated to ~2 mg/ml, 0.22 µm filtered, and allowed to re-oxidize with air at 4° C. Samples were taken out for SDS-PAGE and SEC analyses at different time points to evaluate the re-oxidation status. Re-oxidized OG1321 was 0.22 µm filtered and further concentrated. Continued to concentrate the sample with VIVACELL 100 30 k MWCO spin concentrators to 4-6 mg/ml and sterile filtered the sample. Quantified by OD280.

Example 29. Conjugation of TAF443 to Biopolymer

TAF443 which is also called OG1321 was conjugated to polymer OG1802 (see below) after decapping using a 15× excess of polymer in pH 7.5 Tris buffer to produce OG1448, shown in FIG. 26, showing the chemical structure of OG1448 which is TAF443 conjugated to biopolymer OG1802. TAF443 is on the extreme right hand of the molecule shown in the figure, conjugated via the cysteine 443 residue to the 5 member ring. Conjugation was monitored by SDS-PAGE and driven to near completion. Conjugate was purified via anion exchange chromatography and buffer exchanged into the formulation buffer by UF/DF.

In general, there are three steps involved in the synthesis of OG1448 from components OG1802 and OG1321. Step A: OG1321 much be reduced or decapped to free up the sulfhydryl groups at cysteine position 443. Although the cysteine position at 443 of the heavy chain of TAF is not believed to be involved in cysteine-cysteine disulfide pairing, this cysteine is typically capped by components of the media and absent reduction is not available to react with maleimide. Step B: reduced TAF is then conjugated to OG1802. Step C: conjugated TAF (OG1448) is then separated from unconjugated TAF and polymer via chromatography. These three general steps are broken down into seven smaller steps in the following table:

| General Step | Description | IPC Assays | Target Range |
|---|---|---|---|
| A | Step 1: To reduce OG1321 using tris (2-carboxyethyl) phosphine (TCEP). 30x molar of TCEP at 25° C. for 1 hour. | Non-reducing SDS-PAGE | >95% reduction |
| | Step 2: To remove TCEP reducing agent and cap groups using UF/DF. First, wash with 0.5 mM TCEP in Tris pH 7.5 for a 100-fold volume exchange factor; followed by a 2$^{nd}$ wash with Tris buffer pH 7.5 for 1,000 fold volume exchange factor to remove the TCEP, targeting final TCEP level lower than 0.5 µM. | Non-reducing SDS-PAGE. | Band shift upon removal of the reducing agent. |
| | Step 3: To refold protein to ensure the native disulfide pairs are fully oxidized while the internal cysteine residues remain reduced. | Non-reducing SDS-PAGE | Band upshift upon oxidation of the native disulfide pairs. |
| | | UV/Vis for protein | Final protein concentration at 6-8 mg/ml. |
| B | Step 4: To conjugate OG1321 protein to OG1802 biopolymer. Conjugate by mixing the oxidized OG1321 with OG1802. The process requires 15x molar of biopolymer to decapped protein and constant mixing. Low temperature at 2-8° C. for 20 hours and overlay the reaction with nitrogen gas to minimize oxidation. | Non-reducing SDS-PAGE | <20% full length band remains. |
| | | Analytical AE-HPLC | <20% unreacted protein at OD 280 nm. |
| C | Step 5: To separate OG1448 conjugate from the unreacted OG1321 protein, unreacted OG1802 biopolymer, protein aggregates and other process contaminants. Purify OG1448 using MacroCap Q (AEX). The chromatography is performed at pH 7.5 in 20 mM Tris buffer and eluted using a NaCl gradient. A pool is made by combining fractions. | Analytical AE-HPLC for unreacted polymer and unreacted protein | <5% unreacted protein at OD 180 nm: <15% unreacted polymer at OD 220 nm. |
| | | Non-reducing SDS PAGE | <5% unreacted protein |
| | Step 6: To concentrate the OG1448 and to exchange the chromatography buffers for the formulation buffers. The pooled fractions from the previous step are diafiltered and then concentrated by UF/DF to achieve the target OG1448. | UV/Vis for protein concentration | OG1448 at 50 mg/ml |
| | Step 7: To remove bioburden from the final product and to dispense into storage containers. The UF/DF final pool is 0.2 µm filtered into sterile containers, and pH | UV/Vis for protein concentration | OG1448 at 50 mg/ml |

Example 30. Purification of OG1448 Via Anion Exchange (Macrocap Q)

After conjugation of TAF443 to OG1802 as described above, OG1448 was purified as follows: After conjugation of TAF443 to OG1802 as described above, OG1448 was purified as follows: 2×400 ml of Macrocap Q columns were packed according to ~3:1 ratio of resin:conjugate. The columns were flushed with 5 M of NaCl and equilibrated with 20 mM Tris pH7.5, 20 mM NaCl (equilibration buffer) by syphoning. The conjugation reaction mixture was diluted with 20 mM Tris pH7.5 and loaded on the columns. The columns were then chased with the equilibration buffer, and washed with 20 mM Tris pH7.5, 50 mM NaCl (Wash 1) and then 20 mM Tris pH7.5, 100 mM NaCl (Wash 2). Elution was done with 20 mM Tris pH7.5, with step gradient of 150 mM, 200 mM, 220 mM, 250 mM, 300 mM, and 500 mM NaCl. All the column flow-through, washes, and elution were collected in clean bottles for SDS-PAGE and AEX analyses. Elution fractions containing the conjugate were pooled and concentrated using Pellicon XL TFF cassette with 30 kD MWCO and PES membrane. The concentrated pool was then buffer exchanged against 1×PBS pH7.4 buffer for ~100× using the same TFF cassette and transferred to the VIVACELL 100 spin concentrators to further concentrate until the targeted concentration (~30 mg/ml) was achieved. The final conjugate was filtered through a 0.2 µm PES syringe filter for lot release.

Example 31. Reduction of Bacterial Endotoxin

To reduce levels of endotoxin in the final protein (OG132) or conjugate (OG1448), purification procedures may be employed for either protein or conjugate which utilize cation exchanges in place of anion exchanges. For example, in the above procedure for purifying OG1321, the anion exchange TMAE resin is employed. In place of TMAE resin, the cation exchange resin CEX may be used. However, in order to use CEX residue the pH of the solution containing the protein in question must be reduced to below the protein's pI. For OG1321, the pH of the protein solution after the protein A column, is reduced to pH 3.5. The OG1321 is bound to the Poros XS column at pH5. Then, Porox XS (CEX) can be used to bind and elute the OG1321.

Example 32. Route 1 Synthesis of OG1802

Figure 27:
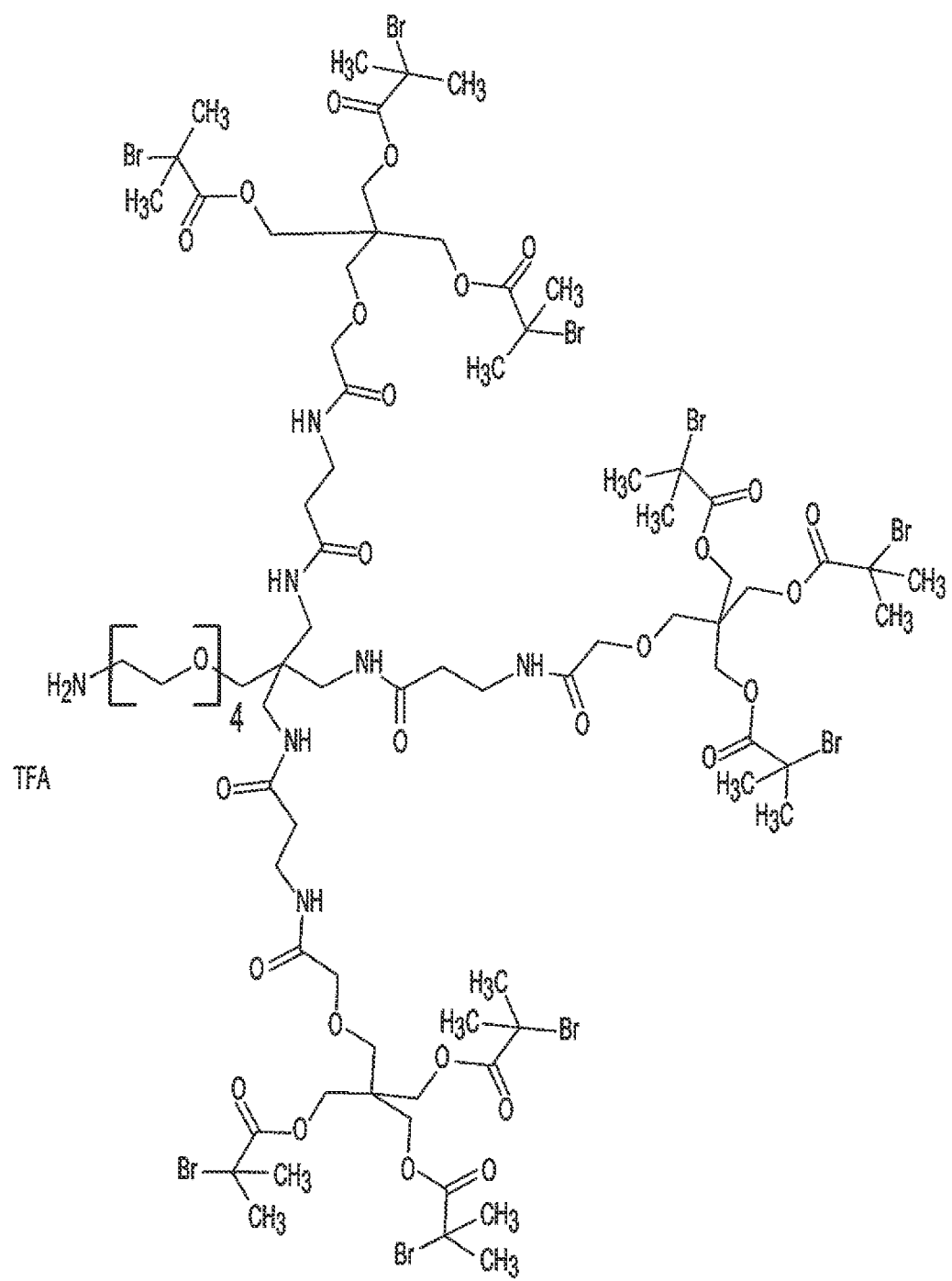
FIG. 27 shows Compound L.

A first route for the synthesis of OG1802 is as follows. First, TFA/amine salt initiator (Compound L) having the structure shown in FIG. 27 was synthesized as follows.

Figure 28:
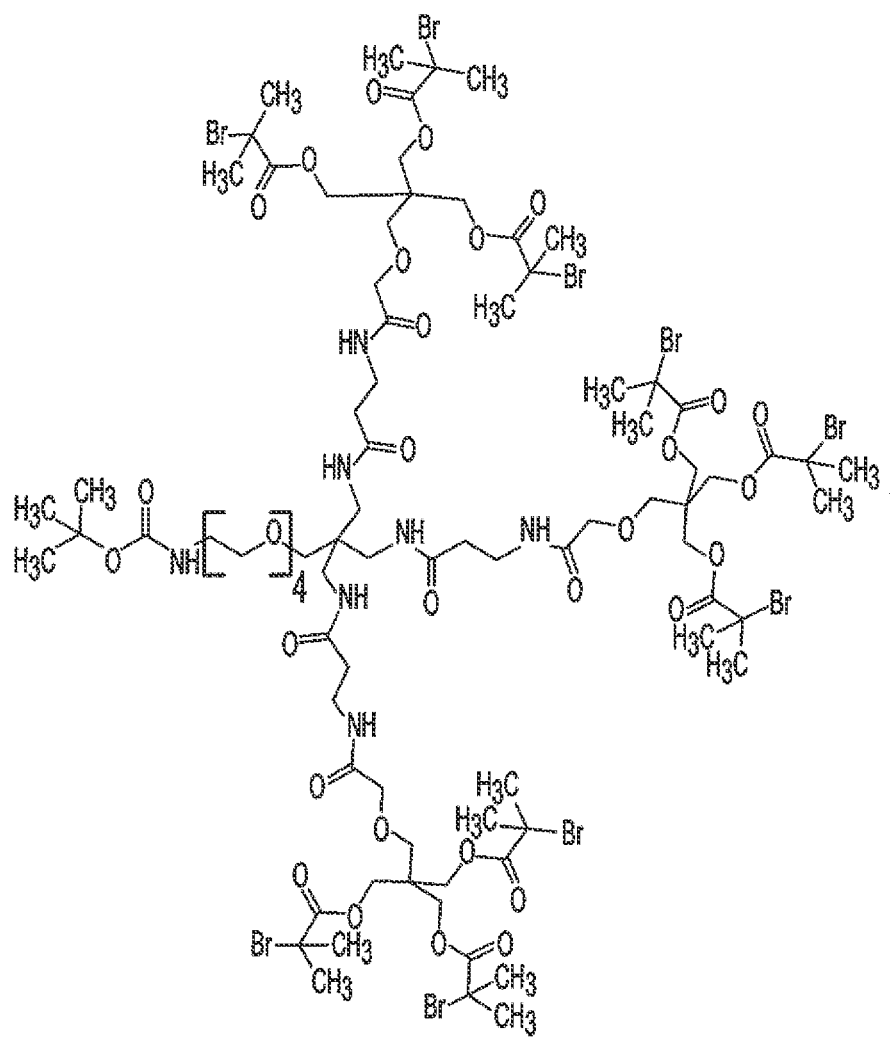
FIG. 28 shows Compound K.

First, Compound K, having the structure shown in FIG. 28 was synthesized as follows. Into a 200 mL round bottom flask under nitrogen was placed Compound J (OG1563) (1.9 g, 2.67 mmol, 3.3 equiv)

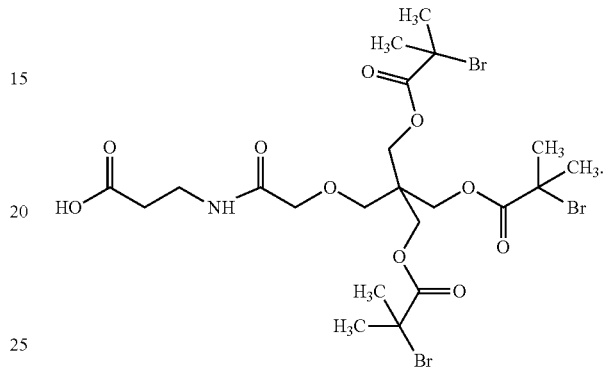

Figure 38:
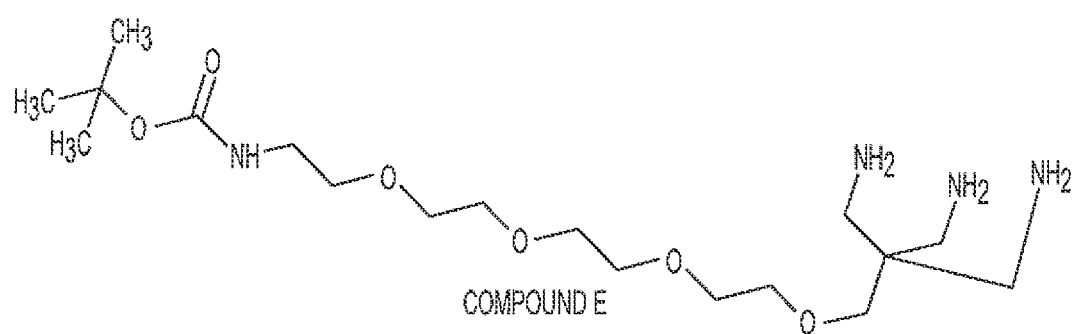
FIG. 38 shows Compound E.
Figure 39:
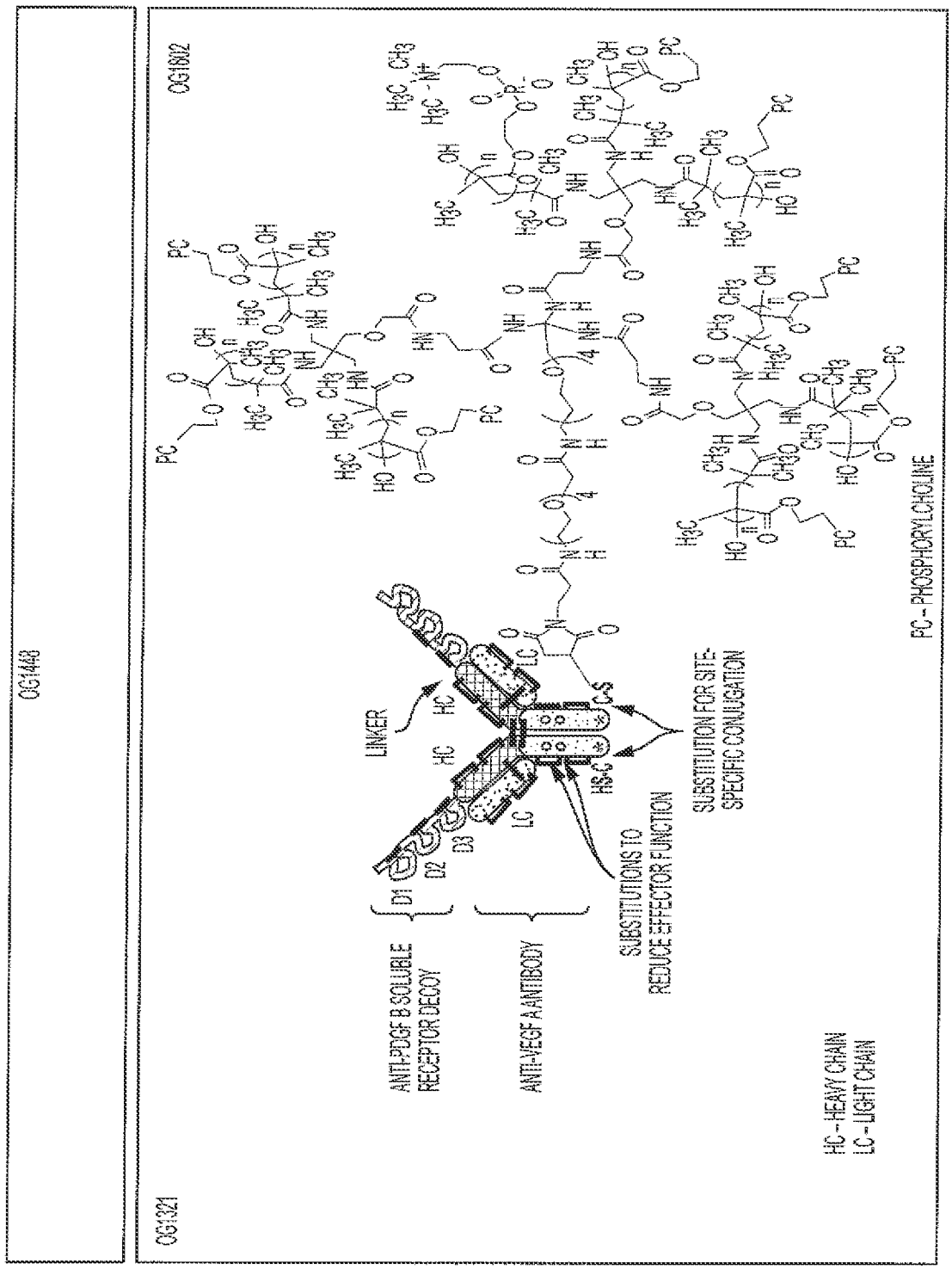
FIG. 39 depicts OG1448.

Compound J and Compound E (0.525 g, 0.81 mmol, 1.0 equiv) (see FIG. 38) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv.) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): □□=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, O═CCH2), 4.27 (s, 18H, CCH2OC═O), 6.74 (br t, 1H, CH2NHC═O), 7.69 (t, J=6.8 Hz, 3H, CH2NHC═O), 7.84 (t, J=6.0 Hz, 3H, CH2NHC═O). LC-MS (ES, m/z): [(M+2H-boc)/2]+ Calcd for (C84H136Br9N7O33+2H−Boc)/2=1196.6; Found 1196.6.

Next Compound L (FIG. 27) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizes. This resulted in 990 mgs (0.4 mmol, 50% over 2 steps) Compound L as a white powder.

1H NMR (400 MHz DMSO-d6): ☐☐=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s. 2H, OCH2C), 3.3 (q, 6H, CH2CH2NHC=O), 3.4-3.59 (m, 20H, CH2x), 3.87 (s, 6H, O=CCH2), 4.27 (s, 18H, CCH2OC=O), 7.69-7.84 (m, 9H, both CH2NHC=O and NH3+).

LC-MS (ES, m/z): [(M+2H)/2]+ Calcd for (C84H136Br9N7O33+2H)/2=1196.6; Found 1197.4.

Next, compound L was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stifling). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. The table below sets forth polymer data for polymer employing compound L as an initiator.

| Theor. MW (kDa) | Polymer ID No. | Initiator | Mn (kDa) | Mp (kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 29) to the 750 kDa polymer referred to above to provide OG1802. Into a 20 mL vial was placed Polymer R3707 (750 kDa polymer made using Las initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 485 mgs as a white powder.

Example 33. Biacore Binding Studies of TAF (OG1448 and OG1321)

The binding affinity of OG1448 (and OG1321) to its intended targets was evaluated via Biacore assay. Binding studies were performed at 25° C. and 37° C. using BioRad Proteon XPR36 and Biacore 2000 optical biosensors equipped with GLM (Proteon) and CM4 (Biacore) sensor chips and equilibrated with running buffer (10 m/M HEPES, 150 mM NaCl, 0.005% Teen-20, 0.2 mg/ml BSA). OG1448, OG1321, bevacizumab, aflibercept and anti-PDGF were immobilized to the sensor surface via amine-coupling.

Binding of the coupled proteins to the ligands was determined by standard methodology. For example, rhVEGFA-165 was tested for binding in a three-fold dilution series starting at 52 nM. rhVEGFA-165 was injected across the surface for five minutes and then the dissociation phase was monitored for >1000 seconds as the surfaces were washed with buffer. The rhVEGFA-165/OG1448 complex appeared quite stable, as indicated by the apparently flat response during the wash phase (>300 seconds) (data not shown). The dissociation phase for the 52 nM rhVEGFA-165 was monitored for more than 2 hours. No decrease in the binding response over time was observed.

Similarly, rhPDGF-BB was tested for binding in a three-fold series starting at 11.4 nM. For the rhPDGF-BB/OG1448 interactions, the rate constants were too fast to be reported with confidence because of mass transport effects. The following $K_D$ constants were observed:

| | $K_D$ (pM) | | | |
|---|---|---|---|---|
| | OG1321 | OG1448 | Bevacizumab | Aflibercept | Anti-PDGF |
| rhVEGFA-165 (25° C.) | 9.8 ± 0.1 | 5.1 ± 0.1 | 9.6 ± 0.8 | 1.56 ± 0.2 | |
| rhPDGF-BB (25° C.) | 14 ± 3 | 17 ± 2 | | | 107 ± 3 |

Example 34. TAF—a Competitive Inhibitor of rhVEGFA-165 Binding to rhVEGFR

As a measure of its potential potency on anti-VEGF activity, binding activity of TAF (OG1448 and OG1321) to VEGFA-1165 was evaluated in a competitive binding assay where TAF, at different concentrations, was competing with immobilized rhVEGFR for binding of rhVEGF. rhVEGFA-165 bound by the immobilized VEGFR was determined by ELISA (data not shown).

Human VEGFR1/Fc was coated onto the bottom of 96-well ELISA plates at 1.0 μg/mL. Various concentrations of TAF (OG1448 and OG1321), ranging from 0.39 to 200 nM, were incubated with 0.1 nM of biotinylated VEGFA-165 for 30 min before adding to the ELISA plates. Biotinylated-rhVEGFA-165 bound to VEGFR1 was detected by streptavidin-HRP and followed by development with HRP substrates. Ranibizumab (Lucentis) and bevacizumab (Avastin) were similarly tested for competitive binding inhibition of VEGFA-165 to VEGFR1.

OG1321, OG1448, ranibizumab and bevacizumab showed similar $IC_{50}$s in inhibiting the binding of VEGF-165 to rhVEGFR suggesting similar potential potency in anti-VEGF activity. These results suggest that TAF (both OG1448 and OG1321) can be as potent as the approved agents ranibizumab and bevacizumab, hence, suitable for treating neovascular (i.e., wet) AMD.

| | $IC_{50}$ (nM) | | | |
|---|---|---|---|---|
| | OG1321 | OG1448 | Ranibizumab | Bevacizumab |
| Competitive binding to rhVEGEA-165 (vs VEGFR) | 12.5 ± 1.2* | 8.5 ± 1.1* | 12.5 ± 1.2* | 10.7 ± 0.9* |

*Mean and SD of at least three trials.

Example 35. OG1448—a Competitive Inhibitor of rhVEGFA-165 Binding to rhVEGFR in the Presence of rhPDGF-BB To evaluate whether OG1448 can bind rhVEGFA-165 in the presence of rhPDGF-BB, i.e., whether rhPDGF-BB binding to the receptor decoy of TAF inhibits the ability of TAF to bind to rhVEGFA-165, a similar binding study to Example 27 was conducted but in the presence of various concentrations of rhPDGF-BB.

Human VEGFR1/Fc was coated onto the bottom of 96 well ELISA plates at 1.0 μg/mL. Various concentrations of OG1448 were incubated with 0.1 nM of rhVEGFA-165 plus rhPDGF-BB at 0.4, 1.2 and 2.0 nM, respectively, for 30 minutes before adding to the ELISA plates. rhVEGFA-165 binding to rhVEGFR1 was detected by biotinylated anti-VEGFA antibody, 0.4 μg/mL, followed with streptavidin HRP and HRP substrate. OG1448 was found to have an IC50 (nM) of 10.1. This is quite comparable to the IC50 observed without rhPDGF-BB from example 28. The value for OG1321 was not determined in this assay but is expected to be similar to OG1448.

Example 36. TAF-A Competitive Inhibitor of rhPDGF-BB Binding to rhPDGFR

As a measure of its potential potency of anti-PDGF activity, the binding activity of TAF (OG1448 and OG1321) to rhPDGF-BB was evaluated in a competitive binding assay where TAP, at different concentrations, was competing with immobilized PDGFR for binding of rhPDGFBB. rhPDGF-BB bound to immobilized PDGFR was determined by ELISA assay.

Human PDGFR/Fc was coated onto the bottom of 96-well ELISA plates at 0.4 μg/mL. Various concentrations of OG1448 and OG1321, ranging from 1 pM to 20 nM, were incubated with 0.2 nM of rhPDGF-BB for 30 minutes before adding to the ELISA plates. rhPDGF-BB bound to rhPDGFR was detected by biotinylated anti-PDGFBB antibody, 0.4 μg/mL, followed with streptavidin-HRP and HRP substrate.

OG1448, OG1321 and a reference anti-PDGF antibody showed similar IC50s in inhibiting rhPDGFBB binding to PDGFR, as shown in the following table, suggesting highly potent anti-PDGF activity.

| | IC50 (pM) | | |
|---|---|---|---|
| | OG1321 | OG1448 | Anti-PDGFBB |
| Competitive Binding to rhPDGFBB (vs rhPDGFR) | 46 ± 21* | 54 ± 21 | 66 |

*Mean and SD of at least 3 trials.

Example 37. OG1448—a Competitive Inhibitor of rhPDGF-BB Binding to rhPDGFR in the Presence of rhVEGFA-165

To evaluate whether OG1448 can bind rhPDGF-BB in the presence of rhVEGFA-165, a similar competitive inhibition of binding study towards PDGF (as Example 29) was performed in the presence and absence of rhVEGFA-165.

Human PDGFRb/Fc was coated onto the bottom of 96-well ELISA plates at 0.4 μg/mL. Various concentrations of OG1448 were incubated with 0.2 nM of PDGFBB and with 0.2 nM of PDGFRb plus rhVEGFA-165 at 0.2 nM, 0.6 nM and 1.0 nM, respectively, for 30 minutes before adding to the ELISA plates. PDGF-BB bind to PDGFRh was detected by biotinylated anti-PEGFBB antibody, 0.4 μg/mL, followed by streptavidin HRP and HRP substrate. The IC50 (pM) in the presence of rhVEGFA-165 (25) was comparable to the figure derived in Example 29. The figure for OG1321 in the presence of rhVEGFA-165 was not determined but is expected to be similar.

Example 38. Inhibition of VEGF-Induced Proliferation of Primary Human Retinal Microvascular Endothelial Cells (HRMVEC)

Endothelial cell proliferation is a crucial step in angiogenesis and hence in the pathogenesis of neovascular AMD. The ability of OG1448 to antagonize the proliferating action of VEGF on primary human retinal microvascular endothelial cells can be a measure of its bioactivity in treating neovascular AMD.

HRMVECs were stimulated with 1.3 nM of rhVEGH65-A for 3 days in the presence of various concentrations of TAF (OG1448 and OG1321) and reference drugs. Cell proliferation was measured by WST-1 cell proliferation detection reagent. Results are shown in the table below:

| IC50 (nM) | | | | | |
|---|---|---|---|---|---|
| | OG1321 | OG1448 | Ranibizumab | Bevacizumab | Aflibercept |
| Inhibition of VEGF induced proliferation of HRMVECs | 0.43 ± 0.05* | 0.49 ± 0.05* | 0.98 ± 1.21* | 0.81 ± 0.32* | 0.55 ± 0.08* |

*Mean and SD of at least 3 trials.

OG1448 and OG1321 demonstrated an IC50 in this assay comparable to other approved anti-VEGF therapies. These data show that TAF (both OG1448 and OG1321) has at least comparable potency to inhibit VEGF-mediated retinal microvascular endothelial cell proliferation activity as ranibizumab, bevacizumab and aflibercept.

Example 39. Inhibition of PDGF-Induced Proliferation of Primary Human Brain Vascular Pericytes (HBVP)

Pericyte migration and proliferation are crucial events in angiogenesis and hence play important roles in the pathogenesis of neovascular AMD. The ability of TAF (OG1448 and OG1321) to antagonize the proliferating action of PDGF on human brain pericytes can be a measure of its effectiveness in treating neovascular AMD.

HBVPs were stimulated with 2.0 nM of PDGFBB for 3 days in the presence of various concentrations of TAF (OG1449 and OG1321) and a reference anti-PDGF-BB antibody (R&D Systems, Catalog # AB-220-NA). Cell proliferation was measured by WST-1 cell proliferation detection reagent.

| IC50 (nM) | | | |
|---|---|---|---|
| | OG1321 | OG1448 | Anti-PDGF |
| Inhibition of PDGF induced proliferation of HPVPs | 5.0 ± 2.0* | 2.9 ± 1.4 | 5.4 |

*Mean and SD of at least 3 trials.

From the various experiments above comparing OG1321 (TAF443) to OG1448 (TAF443 polymer conjugate), it can be seen that conjugation to the HEMA-PC biopolymer does not negatively impact protein activity.

OG1448 and OG1321 show a comparable IC50 to the anti-PDGF antibody.

Example 40. Inhibition of Sprouting in Co-Culture of Human Retinal Microvascular Endothelial Cells (HRMVEC) and Human Mesenchymal Pericytes (HMPs)

To mimic in vivo conditions where endothelial cells and pericytes coexist in blood vessels and proliferate and migrate together during angiogenesis, events crucial in neovascular AMD, a three dimensional co-culture of HRMVECs and HMPs was established with the goal of evaluating the ability of OG1448 to inhibit angiogenesis in this complex model.

Vehicle, Avastin, an anti-PDGF-BB antibody (same as above), Avastin in combination with the anti-PDGF-BB antibody and OG1448 were added to the co-cultures on day 7. On day 14, immunohistochemical staining of CD31 (endothelial cells) and aSMA (pericytes) was used to quantify the lengths of sprouts emanating from established endothelial cell spheroids as compared across the experimental groups.

Figure 40:
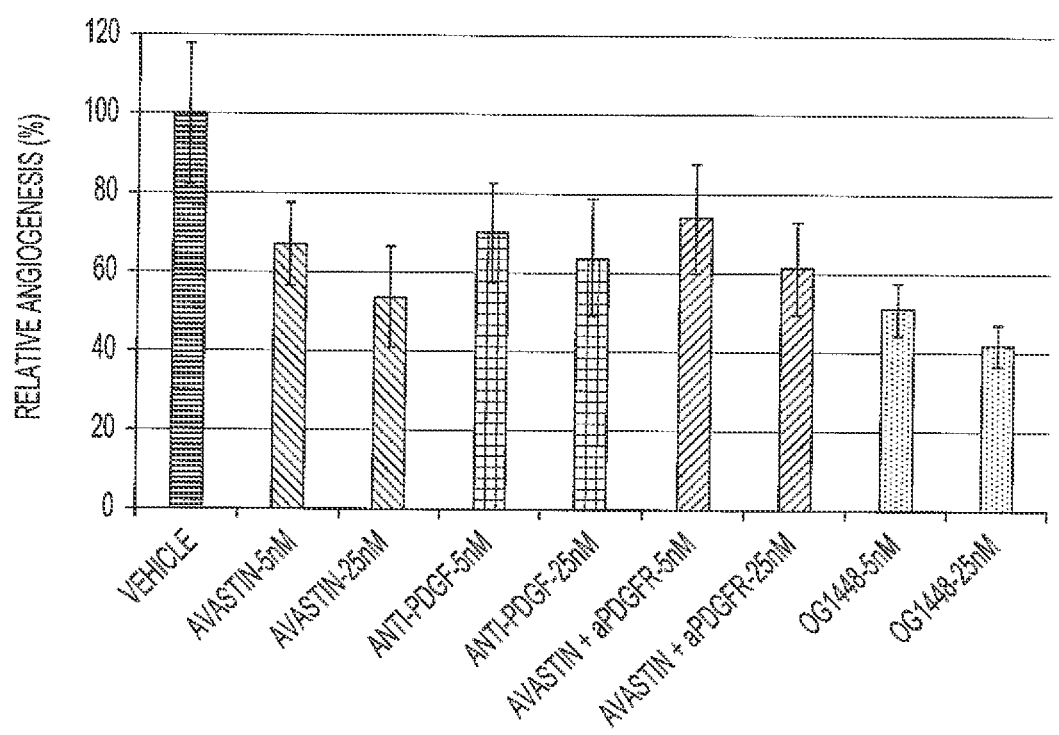
FIG. 40 shows relative angiogenesis using OG1448, Avastin, and an anti-PDGF-BB antibody and various combinations thereof.

OG1448 was more effective in inhibiting endothelial/pericyte sprouting in HRMVEC-HMP co-culture than Avastin alone or anti-PDGF alone at two different concentrations. Moreover, OG1448 was also more effective in inhibiting sprouting then a combination of Avastin and the anti-PDGF-BB antibody. This demonstrates that OG1448 is synergistic relative to Avastin and an anti-PDGF-BB antibody. The results are shown in the table below and in FIG. 40.

| Drug | Mean Total Sprout Length (pix) | S.D. (pix) | Relative Angiogenesis % | S.D. % |
|---|---|---|---|---|
| Vehicle | 6999 | 1766 | 100 | 18 |
| Avastin-5 nM | 4700 | 722 | 67 | 10 |
| Avastin-25 nM | 3763 | 909 | 54 | 13 |
| Anti-PDGF-5 nM | 4924 | 884 | 70 | 13 |
| Anti-PDGF-25 nM | 4461 | 1051 | 64 | 15 |
| Avastin + anti-PDGF-5 nM | 5197 | 948 | 74 | 14 |
| Avastin + anti-PDGF-25 nM | 4287 | 822 | 61 | 12 |
| OG1448-5 nM | 3584 | 478 | 51 | 7 |
| OG1448-25 nM | 2933 | 360 | 42 | 5 |

Example 41. Efficacy of OG1448 on Inhibition of Laser-Induced Choroidal Neovascularization in Cynomolgus Monkeys The in vivo efficacy of OG1448 was evaluated using the laser-induced choroidal neovascularization (CNV) model in cynomolgus monkeys, a well-recognized primate model of CNV. See, e.g., Nork Dubielzig R R, Christian B J, et al. 2011. Prevention of experimental choroidal neovascularization and resolution of active lesions by VEGF trap in nonhuman primates. Arch Ophthalmol. 129: 1042-1052; Lloyd R L, Harris J, Wadhwa S, Chambers W. 2008. Food and Drug Administration approval process for ophthalmic drugs in the U.S. Curr Opin Ophthalmol. 19:190-194, both of which are hereby incorporated by reference. In this model, laser lesions are placed in the chorioretinal complex in the macula of the monkey eye with evidence of Bruch's membrane breakage. Choroidal neovascularization is developed in two to three weeks. At various time points, fluorescein angiography is used to evaluate the clinically relevant lesions (Grade IV) which show fluorescein leakage beyond the primary lesion. This CNV model has been used extensively for the study of CNV lesions and used as a benchmark for all currently approved treatment for neovascular AMD. In this model, all approved anti-VEGF agents for neovascular AMD are effective in inhibiting the leakage from the clinically relevant Grade IV lesions. The study was conducted at Covance, Madison, Wis.

In summary, a dose-related response to a single intravitreal injection of OG1448 at 0.5 or 2.4 mg/eye (calculated based on protein content) was observed in the animals in which CNV lesions were allowed to develop for 14 days before treatment and evaluated at subsequent time points using fluorescein angiography focusing on the clinically relevant Grade IV lesions on the retina/choroid. At 0.5 mg/eye, the beneficial effect on the Grade IV lesions was noticeable (p=0.019; generalized estimating equation [GEE] model; 0.5 mg treatment Group 7 vs PBS injected placebo Group 5). At 2.4 mg/eye OG1448, a dose (in molar equivalence) within the therapeutic dose of bevacizumab or aflibercept, was highly effective (75% reduction in Grade IV-CNV like lesions on Day 43 from Day 15 versus 27% reduction in the PBS-treated group) (p=0.0007; GEE model; 2.4 mg treatment Group 9 vs PBS injected placebo Group 5) in ameliorating the leakage of Grade IV-CNV lesions.

OG1448 shows effectiveness in inhibiting the leakage from the clinically relevant Grade IV lesion in this benchmark CNV model.

The groups and study design are shown in the following table. The study included groups for tolerability (Groups 1 thorough 4) however for purposes of this patent application only the groups for pharmacological activity and a control group treated with phosphate buffered saline (PBS) injection are shown.

|  |  |  | Dose Level | | | Dose |
|---|---|---|---|---|---|---|
| Group | No. of Females | Dose Route | mg/left eye/dose | mg/right eye/dose | mg/kg/dose | Concentration (mg/ml) |
| 5 | 6 | Intravitreous[a] | 0 | 0 | NA | 0 |
| 6 | 6 | Intravitreous[a] | 0.24 | 0.24 | NA | 5.9 |
| 7 | 6 | Intravitreous[b] | 0.51 | 0.51 | NA | 10.2 |
| 9 | 6 | Intravitreous[b] | 2.40 | 2.40 | NA | 26.6 |

NA = not applicable
[a] = at days 1, 15, and 29 (a total of 3 doses); laser on day 8 of the dosing phase.
[b] = once; laser treatment on 15 days prior to injection Two treatment regimens were evaluated. In the prevention regimen, OG1448 was given intravitreally three times bilaterally at 0.24 mg/eye/dose (dose content was based on protein content; Group 6) or PBS (Group 5) on days 1, 15 and 29 with laser treatment on day 8 of the dosing phase. Fluorescein angiograms on days 115, 21, 30, 37 and 43 of laser treatment (days 22, 28, 37, 44 and 50 of the dosing phase) were used for evaluation of the clinically relevant Grade IV lesions.

In the treatment regimen (Groups 7 [0.5 mg], 8 [0.5 mg] and 9 [2.4 mg], OG1448 was administered intravitreally to both eyes of 6 animals at doses of 0.5 mg (Groups 7 and 9) or 2.4 mg/eye (Group 9) 15 days after laser induction when CNV lesions were established. Fluorescein angiograms obtained at Days 15, 21, 30, 37 and 43 of laser treatment were used for evaluation of the clinically relevant Grade IV lesions.

Figure 41:
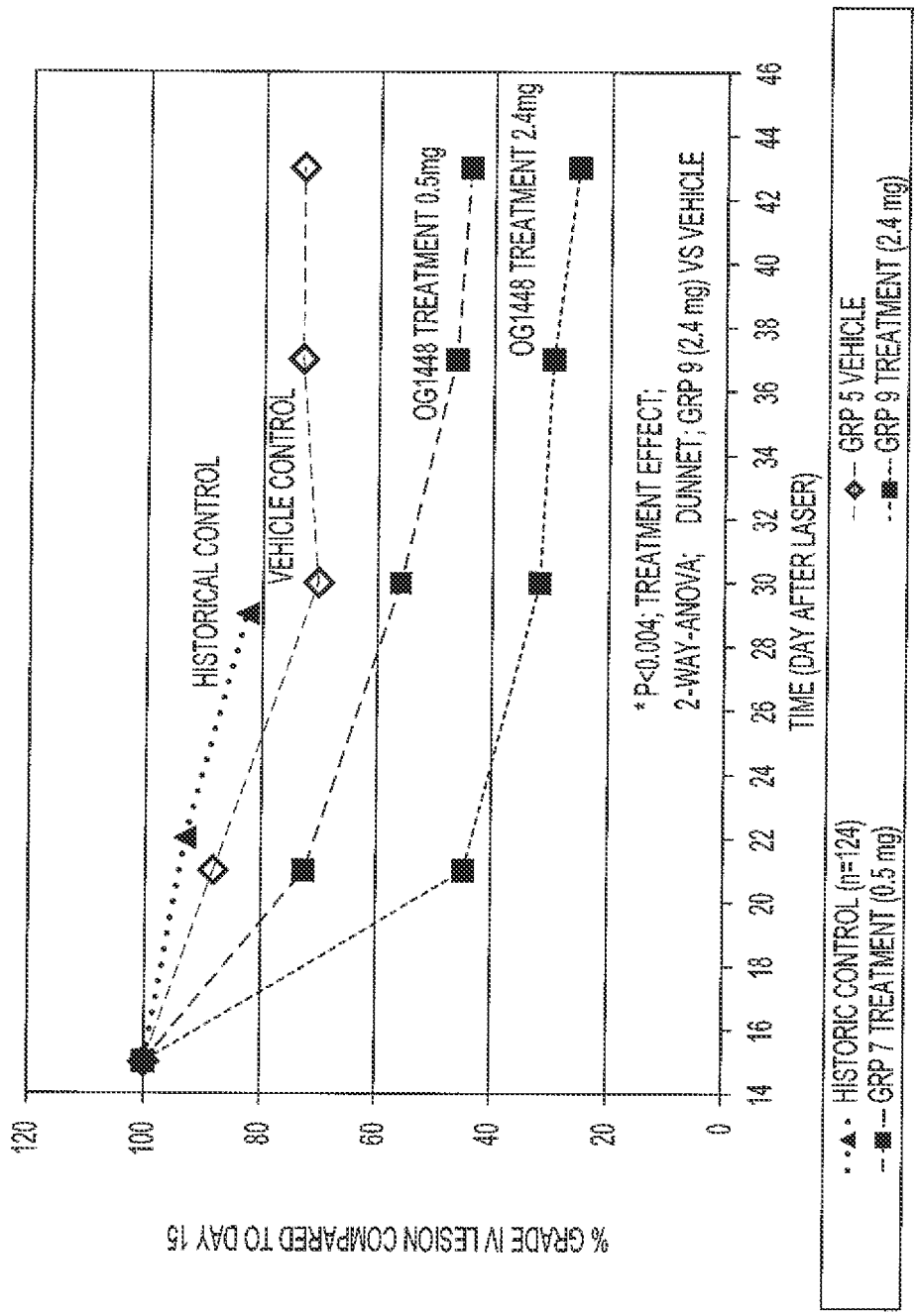
FIG. 41 shows the % grade IV lesions compared to day in the CNV monkey model for the compounds indicated.

Using generalized estimating equation (Gee) models (Halekoh, U & Yan J (2006) The R Package geepack for Generalized Estimating Equations Journal of Statistical Software 15, 2, pp 1-11), a dose-related response to OG1448 was observed in the intervention regimen. At 0.5 mg/eye, the effect was notable as shown by the difference in the percent change in Grade IV lesions as compared to the vehicle control (0.5 mg treatment Group 7 vs PBS injected placebo Group 5; p=0.019, GEE). With 2.4 mg/eye OG1448 (a dose in molar equivalence within the therapeutic dose of bevacizumab or aflibercept) a 75% reduction in percent change in Grade IV lesions (2.4 mg treatment Group 9 vs PBS injected placebo Group 5; p=0.0007, GEE) was observed on day 43 as compared to a 27% reduction in CNV in the PBS control group. The data from the various experiments in the monkey CNV model are shown in FIG. 41.

OG1448 shows dose dependent effectiveness in inhibiting the leakage from the clinically relevant Grade IV lesion in this CNV model. These results are consistent with the studies described above showing activity of OG1448 against VEGF-mediated angiogenic activities.

Example 42. Tissue Distribution and Pharmacokinetics

A tissue distribution and pharmacokinetic study using $^{125}$I-OG1448 was conducted using male New Zealand Red White E1 Cross pigmented rabbits. In summary, this study showed a vitreal half-life of 16.1 days for OG1448 in rabbits, approximately three times that reported for aflibercept (4.5 days) and 5 times that of ranibizumab (2.9 days) (Bakri S J, Snyder M R, Reid J M et al. 2007. Pharmacokinetics of Intravitreal Ranibizumab [Lucentis]. Ophthalmology 114:2179-2182) with little plasma exposure (approximately 0.2% of that of vitreous exposure) and a plasma half-life of 6.5 days (aflibercept reported 6.5 days) (Struble C, Koehler-Stec E, Zimmer E, and Tu W. 2008. Pharmacokinetics and ocular tissue penetration of VEGF Trap after intravitreal injections in rabbits. EVER; Portorz, Slovenia).

The purpose of this study was to assess the ocular distribution and pharmacokinetics of non-radiolabeled test articles and radiolabeled test articles following an intravitreal or intravenous dose administration to male New Zealand Red White F1 rabbits. Treatment groups and the study design are shown in the table below:

| Groups and Study Design (Covance study) | | | | | |
|---|---|---|---|---|---|
| Group | # of males | Dose Route | Test Article | Dose (mg) | Sample Collected |
| 1 | 14 | IVT | $^{125}$I-OG1448 | 0.25/eye (OU) | Blood, ocular tissues |
| 2 | 2 | IV | $^{125}$I-OG1448 | 0.25/animal | Blood |
| 3 | 6 | IVT | OG1448 | 0.25 (OD) | Blood, whole eyes for histology |

-continued

Groups and Study Design (Covance study)

| Group | # of males | Dose Route | Test Article | Dose (mg) | Sample Collected |
|---|---|---|---|---|---|
| 4 | 6 | IVT | OG1448 | 0.25 (OD) | Blood, vitreous humor |

IVT: intravitreal;
IV: intravenous;
OU: Both eyes;
OD: right eye

PK parameters were obtained based on radioanalysis. Clearance profiles from vitreous, retina and choroid were similar to one another. This pattern is consistent with other established CNV treatments such as ranibizumab or allibercept. Set forth in the table below are pharmacokinetic parameters in different ocular tissues after single bilateral intravitreal injection of 0.25 mg $^{125}$I-OG1448.

| Matrix | $C_{MAX}$ (NG Eq./G) | $T_{1/2}$ (day) | $AUC_{0-\infty}$ (Day*NG EQ./G) | Exposure as % of vitreous exposure |
|---|---|---|---|---|
| Plasma | 494 | 6.48 | 3,790 | 0.189 |
| Aqueous humor | 5,250 | 11.6 | 68,800 | 3.423 |
| Choroid-RPE | 4,170 | 32.8 | 134,000 | 6.667 |
| Iris-ciliary body | 12,100 | 42.6 | 235,000 | 11.692 |
| Retina | 13,500 | 30.4 | 309,000 | 15.373 |
| Vitreous humor | 112,000 | 16.1 | 2,010,000 | 100.00 |

Figure 42:
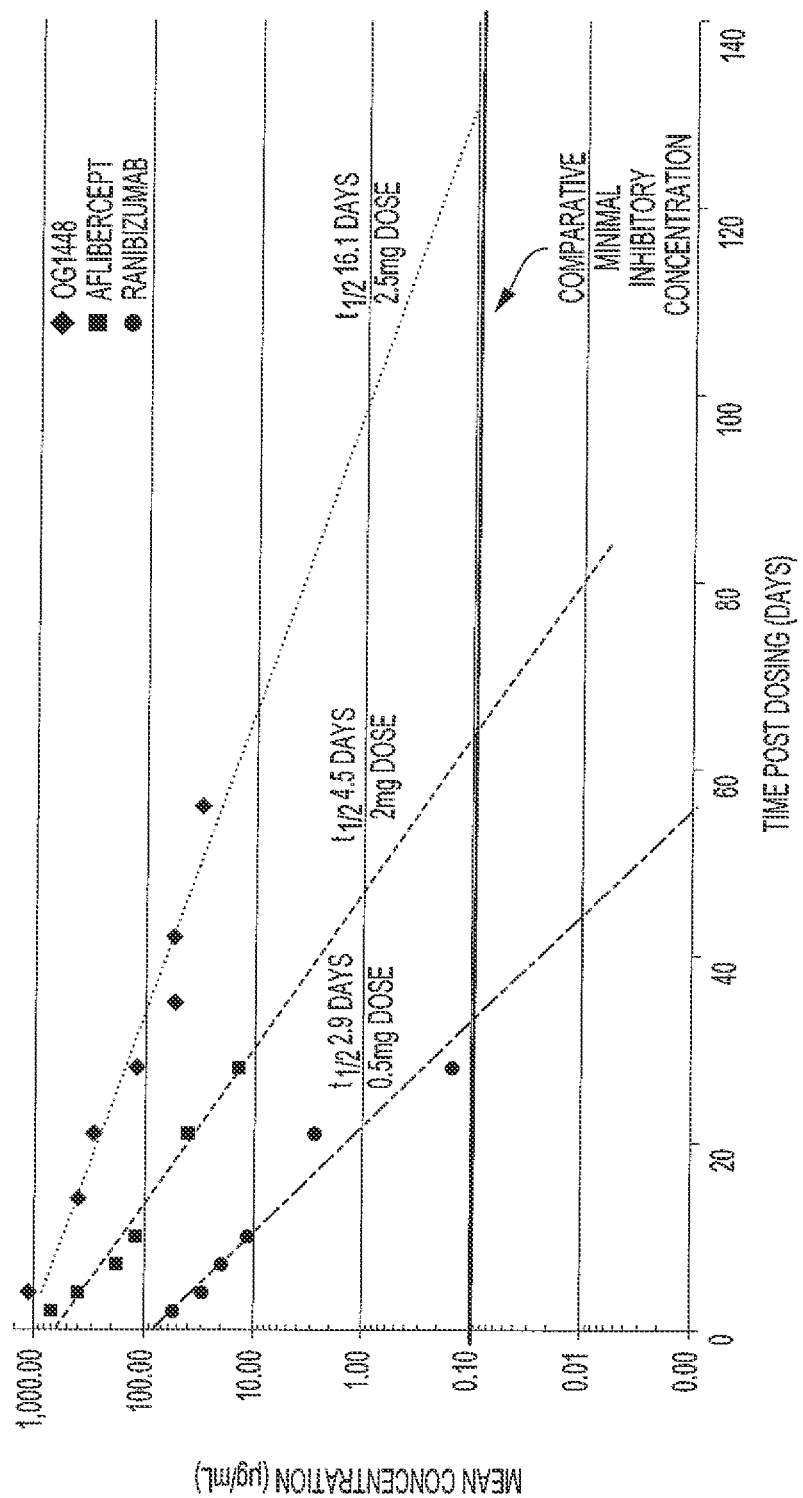
FIG. 42 shows OG1448 ocular pharmacokinetics versus aflibercept and ranibizumab in the rabbit vitreous.

The ocular tissue half-life of various VEGF inhibitors is compared with OG1448 in the table below and in FIG. 42, which suggests that OG1448 can stay above a pharmaceutically active minimal inhibitory concentration of 0.1 µg/ml for greater than 90 days, as opposed to 30 days for Lucentis and 50 days for Eylea:

Ocular Tissue Elimination Half Life (Days)

|  | Vitreous | Retina | Choroid |
|---|---|---|---|
| Pegaptinib[1] | 3.5 | — | — |
| Ranibizumab[1] | 2.9 | 2.9 | — |
| Aflibercept[1] | 4.5 | 5.5 | 4.8 |
| OG1448[2] | 16.1 | 30.5 | 32.9 |

[1]Based on publicly available data from 28-day rabbit studies: Drolet D W, Nelson J, Tucker C E, et al. 2000. Pharmacokinetics and safety of an anti-vascular endothelial growth factor Aptamer (NX 1828) following injection into the vitreous humor of rhesus monkeys. Pharm Res. 17: 1503-1510; Gaudreault J, Fei D, Beyer J C et al. 2007. Pharmacokinetics and retinal distribution of ranibizumab, a humanized antibody fragment directed against VEGF-A, following intravitreal administration in rabbits. Retina 27: 859-870; Bakri (2007), supra; Struble 2008, supra.
[2]Based on intravitreal injection of 250 µg in the rabbit eye.

The study showed a vitreal half-life of 16.1 days for OG1448 in rabbits, approximately three times the 4.5 day vitreal half-life reported for aflibercept and five times the vitreal half-life of ranibizumab (2.9 days) (Bakri 2007, supra) with low plasma exposure (approximately 0.2% of that of vitreous exposure); the plasma exposure is consistent to that of aflibercept (Sinapis C I, Routsias Sinapis A I, et al. 2011. Pharmacokinetics of intravitreal bevacizumab [Avastin®] in rabbits. Clinical Ophthalmology 5:697-704). Similar to the reported data for ranibizumab and aflibercept, the vitreal, retinal and choroidal clearance profiles are similar to one another.

Example 43. Toxicology

Two pilot non-GLP single dose ocular and systemic tolerability studies on OG1448 were conducted at Covance: (i) a single dose 57-day intravitreal or intravenous tolerability study in pigmented rabbits and (ii) a single dose tolerability study after intravitreal (58-day study) or intravenous (28-day study) administration in cynomolgus monkeys.

In brief, single dose intravitreal injection of 0.25 mg OG1448/dose/eye in rabbits was initially well tolerated but was associated with persistent anterior (mild to moderate conjunctival hyperemia, mild to moderate aqueous flare and cells) and posterior segment (mild to severe white vitreous cells, mild to moderate vitreous haze and presence of vitreous floaters, and multifocal grey-white subretinal inflammatory foci) inflammation which developed approximately two weeks postdose (or later). This inflammatory response improved with immune-suppressive and anti-inflammatory therapy. The time of onset post-dose and response to treatment are consistent with an immune-mediated response typical for intraocularly administered humanized biopharmaceuticals in animals.

In contrast, a single intravitreal dose at 0.24 or 1.4 mg OG1448/dose/eye was well tolerated in cynomolgus monkeys with no adverse finding or evidence of immune reactions ophthalmologically, clinically, and histopathologically.

In the efficacy study (discussed above), intravitreal injections of 0.24 mg/eye/dose for three times at 14 days apart or a single injection of 0.5 mg/eye/dose were well tolerated with at least 40 days of follow-up as shown on ocular examinations. No immune-related reactions were noted in the eyes of treated animals.

These studies demonstrate that OG1448 is well tolerated when administered intravitreally or intravenously at the doses evaluated.

Example 44. Single-Dose Tolerance in Cynomolgus Monkeys

The purpose of this part of the study was to evaluate tolerability of OG1448 after intravitreous or intravenous administration in cynomolgus monkeys.

Ocular and systemic tolerability groups and study design are shown in the table below:

Group and Study Design

| Group | No. of females | Dose Route | Dose Level[a,b] µg/left eye/dose | Dose Level[a,b] mg/right eye/dose | Dose Level[a,b] mg/Kg/ (mg/ml) | Dose Concentration dose |
|---|---|---|---|---|---|---|
| 1 | 3 | IVT | 0 | 0.236 | NA | 5.9 |
| 2 | 3 | IVT | 0 | 1.36 | NA | 27.2 |
| 3 | 2 | IV | NA | NA | 0.235 | 9.4 |
| 4 | 2 | IV | NA | NA | 1.41 | 9.4 |

IVT = intravitreal;
IV = intravenous;
NA = not applicable
[a]The right eye of animals in Groups 1 and 2 received the test article via intravitreous injection. Animals in Groups 3 and 4 received the test article via colus intravenous injection.
[b]The left eye of animals in Groups 1 and 2 animals received vehicle control only (phosphate buffered saline, pH 74).

Ocular examinations by board certified veterinary ophthalmologists were performed across all four groups predose and (i) for intravitreal groups: on days 3, 8, 15, 29, 43 and 57, and (ii) for intravenous groups: on days 3, 8, 15, and 29. Animals were followed with clinical observations and clinical pathology on days 3, 8, 15, 29, 43 and 57 when applicable. Anatomic pathology was also performed macroscopic observation during necropsy for all animals, and microscopic evaluations for ocular tissues for groups 1 and 2 (day 57) and for a standard list of systemic organs for groups 3 and 4 (day 29).

There were no adverse or toxicologically meaningful findings in any group. There were no findings in clinical observations and body weight in any group. There were no OG1448-related macroscopic or microscopic findings from anatomic pathology for any group (ocular tissues for intravitreally injected groups and standard list of organs/tissues for intravenously injected groups).

Ophthalmic findings for intravitreal administration groups were limited to injection-related events such as mild to moderate and transient presence of aqueous and/or vitreous cells and scars at the site of aqueous humor sampling.

Example 45. Synthesis of Polymer OG1786

Figure 30:
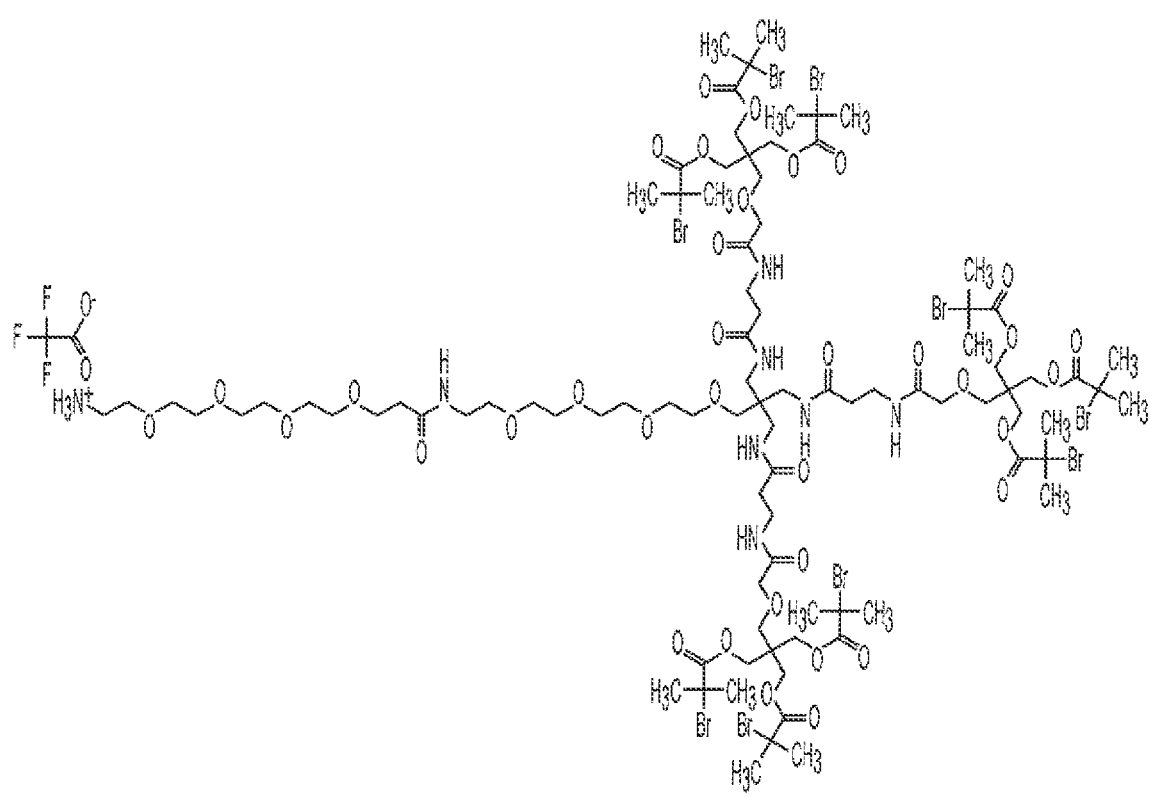
FIG. 30 shows OG1786.
Figure 31:
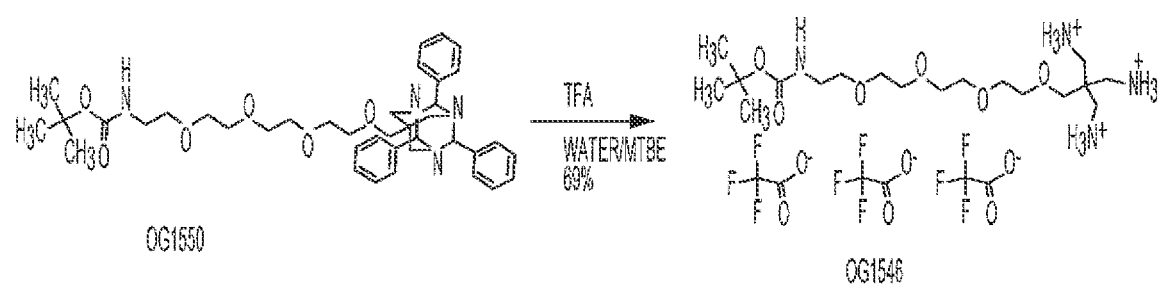
FIG. 31 shows the synthesis of OG1546 from OG1550.

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TEA) as shown in FIG. 30. OG1786 is prepared as follows. First, OG1550 is reacted with TEA (trifluoro acetic acid) to produce OG1546 as depicted in FIG. 31.

In a 1 L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH ~4, by pH paper).

The product was collected by lyophilization. 11.5 g white solid was obtained. This material is extremely hygroscopic, so best handled under nitrogen. The product was confirmed by LCMS.

Figure 32:
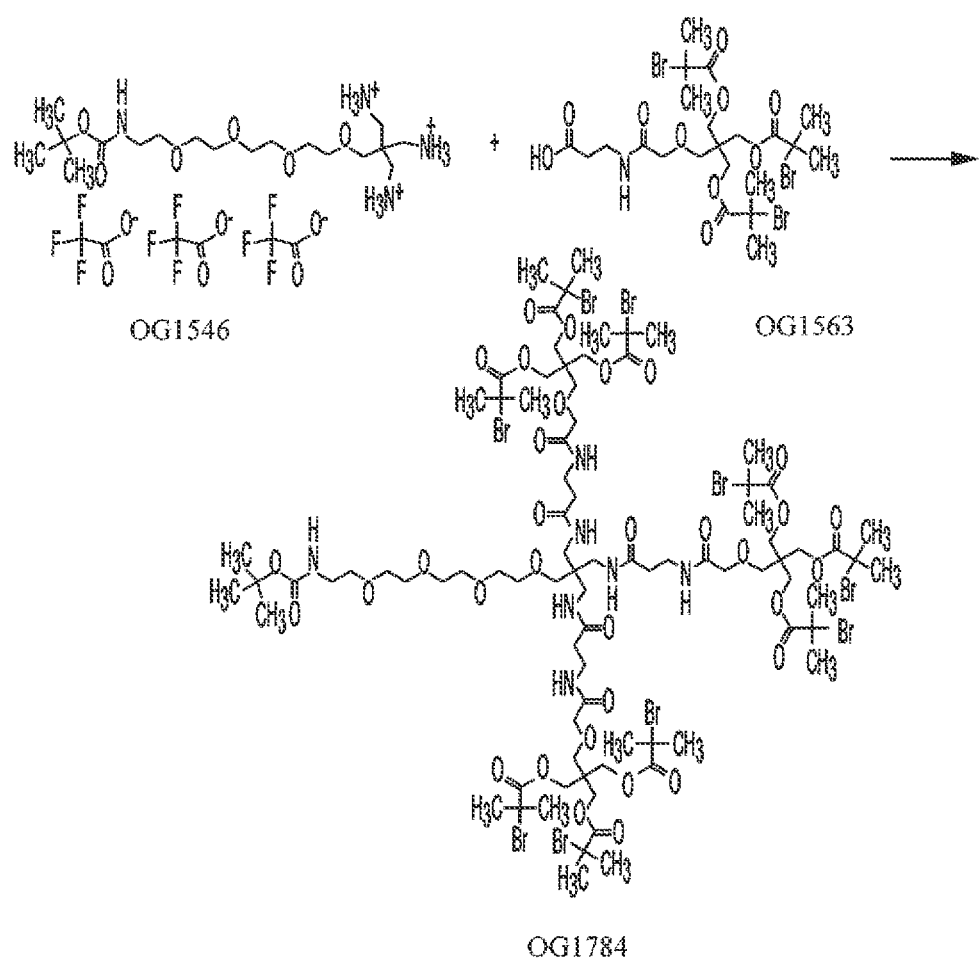
FIG. 32 shows the synthesis of OG1784 from OG1546 and OG1563.

The prepared OG1546 was then reacted with OG1563 to yield OG1784 (as depicted in FIG. 32).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH~3). The organic phase was washed with water/saturated sodium chloride (100 ml/25 ml), and the aqueous phase was AQ3 (pH~3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 µm, product number 02915-20). The filtrate was split into three equal portions and purified in three runs.

Loaded onto a RediSep Rf Gold C18 column (275 g, SN 69-2203-339, Lot #24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods.

| OG1784 lot | R5172 | R5228 |
|---|---|---|
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Figure 33:
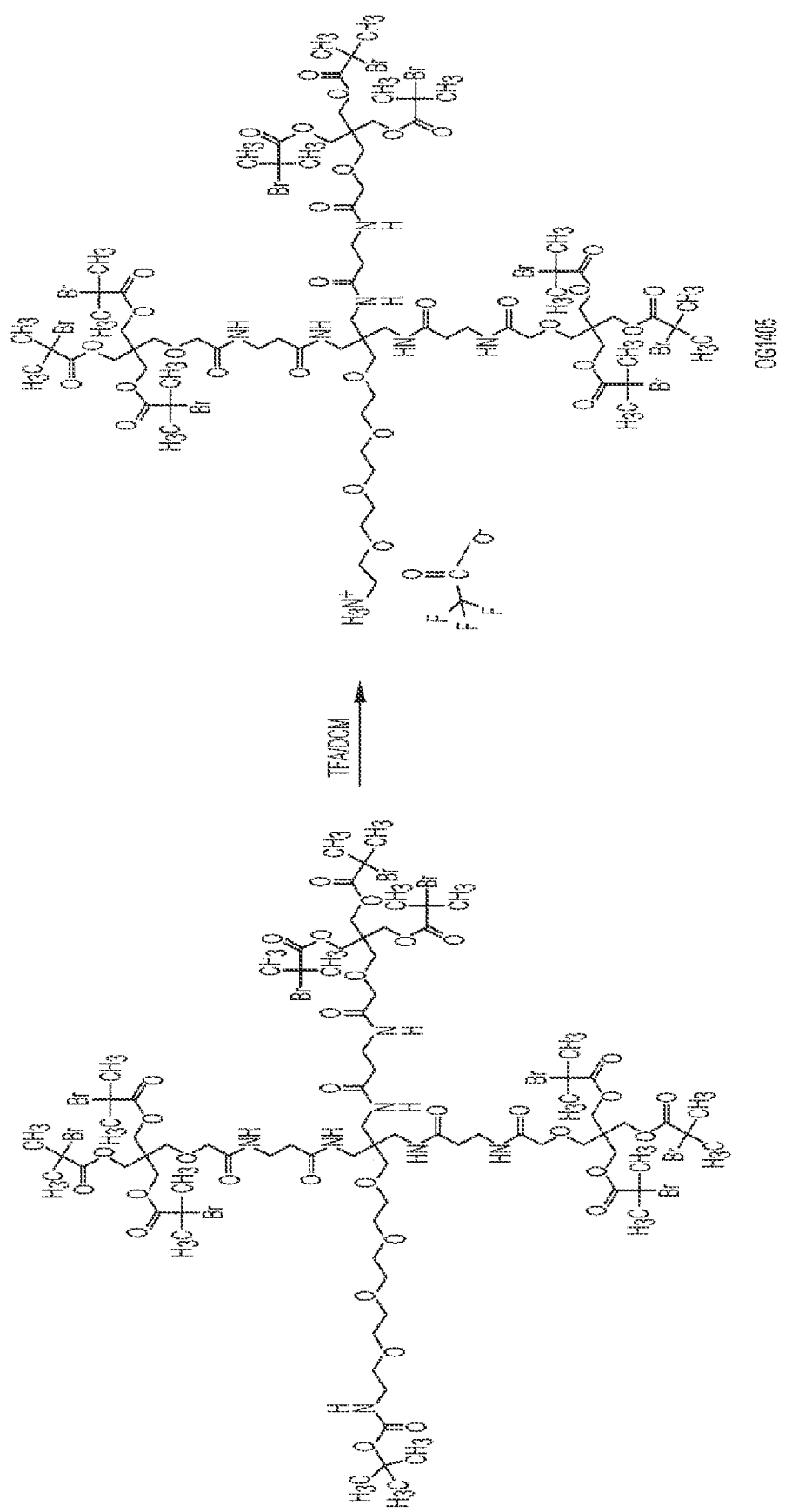
FIG. 33 shows the synthesis of OG1405 from OG1784.

Next OG1405 was prepared from OG1784 as depicted in FIG. 33. In a 500 ml round bottom flask equipped with a magnetic stir bar was added OG1784 (20.9 g), followed by dichloromethane (50 ml) then trifluoroacetic acid (20 ml), The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed. Next, OG1405 was reacted with OG1402 to prepare OG1785 as set forth in FIG. 34. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml) and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 μm, product number 02915-20) and split into three equal portions, each of which were individually purified as follows.

Portions were loaded onto Redi-Sep Gold C18 column (275 g, SN-69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS: OG1785 was isolated as a foamy solid (R5329, 19.0 g, 83% yield, 95.1% purity (a/a 210 nm), stored under nitrogen at 4° C.

Next, the test-butyloxycarbonyl protecting group on OG1785 was removed using trifluoroacetic acid (TFA) to produce OG1786 as depicted in FIG. 35.

Example 46. Synthesis of Polymer 1801

Compound OG1802 is conjugated to a sulfhydryl group of TAF443 to produce OG1448. Polymer OG1801 is made first from the initiator OG1786. OG1801 has an amine functionality, which is more stable (than maleimide) during polymer synthesis. To synthesize polymer OG1801, a modified version of MRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL, of DMF under room temperature to make 100 mg/mL stock solution; Sampled for initiator concentration and purity test; Added the initiator solution to the flask under Argon. The reaction solution became dark brown and started thickening over time; Sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, transferred all the fractions to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 47. Synthesis of Polymer OG1802

Starting materials and reagents needed in the reaction is calculated based on batch input of OG1801. The linker is 3-maleimidopropionic acid, NHS ester. Added 30 ml of 0.5 M sodium phosphate (in WFI, pH8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln; Added linker solution dropwise 815 uL per minute to the polymer sln with strong stirring. Took 5 min to added 4095 uL of linker solution. Reacted at room temperature for 30 min. Quenched reaction with 20 mL of 5% acetic acid to achieve a final pH of 5. Filtered the solution using 1 L vacuum filter (0.2 um).

OG1802 is then purified as follows: Milipore cross flow cassettes was used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 μM 1 L filter bottle. The polymer solution could be stored at 2-8° C. for up to 3 month before conjugation.

Example 48. Formulations of OG1448; Injectability 27.2 mg/ml and 44.5 mg/ml solutions of OG1448 were prepared using 1.7 mM $KH_2PO_4$; 5 mM $Na_2HPO_4$; 150 mM NaCl in sterile water for injection. The OG1448 conjugate was concentrated by a Millipore Pellicon XL TEE cartridge (catalog # PXB030A50, EMI) Millipore), 30 kD MWCO or VIVACELL 100 spin concentrator (catalog # VC1022, Sartorius), 30 kD MWCO, depending on the volume. The 27.2 mg/ml solution of TAF was injected intravitreally into the monkeys for the efficacy experiments described above through a 30 gauge (G) ½ inch needle. Excessive pressure was not required to push the OG1448 through the needle. The 44.5 mg/ml solution was tested for injectability in the laboratory and was also capable of being pushed through the needle without excessive pressure by a female operator.

Example 49. Storage Stability

An ongoing stability study was conducted using OG1448 reference lot R5606 at 44.5 mg/ml in PBS at pH 7.4 (as described above). Three temperatures were chosen for the study: room temperature (RT), 4° C. and −20° C. Sampling frequency is at 0, 14, 28, 91, 181 and 362 days. Samples were evaluated by SDS-PAGE and analytical AE-HPLC for unreacted and sequestered protein, and potential aggregates. It was observed (data not shown) that OG1448 demonstrates less than 5% protein impurity by AE-HPLC at all three temperatures up to six months, which is similar to the level at time 0. This study is ongoing.

Example 50. Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

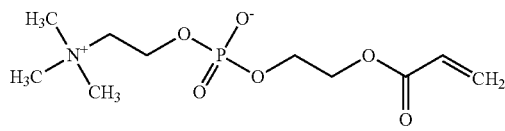 [SMILES: C=CC(=O)OCCOP(=O)([O-])OCC[N+](C)(C)C]

HEA-PC

HEA-PC was polymerized to the initiator shown in Example 23 as compound L.

| Reactant | Name | Amount | MW |
| --- | --- | --- | --- |
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-Oimethylamino)ethyl]amine (Me6TREN) | 2.73 mg | 230.39 |
| Solvent A | N,N-Dimethylformamide (DMF) | 21.85 µl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 µl of dry DMF and a 200 mg/ml solution of ligand by dissolving 4.6 mg of Me6TREN in 23 µL of dry DMF. Dispense 8.25 µl of the stock solution of initiator and 13.6 µl of the ligand into a tube. Degas at −78° C. for 5 min then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at −78° C. Rinse the vial with 200 µl of methanol and add it inside the reactor at −78° C. and then 0.5 mL of distilled water then another 200 µl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 µL) was added. Another 2-3 ml of methanol was added and the catalyst was allowed to oxidize overnight at 4° C. Conversion determined by NMR was estimated to be 94%.

The next day the polymer was dialyzed and subjected SEC/MALS analysis using Shodex SB806M_HQ column (7.8×300 mm) in 1×PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein, including TAF443.

Next, the maleimide Mal-PEG4-PFP (see Example 23 above) ester was snapped on to the HEA-PC polymer as shown in Example 23. The resulting maleimide functionalized HEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am-PC), having the following structure:

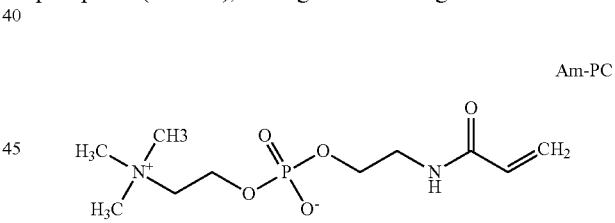

Am-PC

The Am-PC was used for polymerization employing a 3 am initiator (a TFA salt) having the structure:

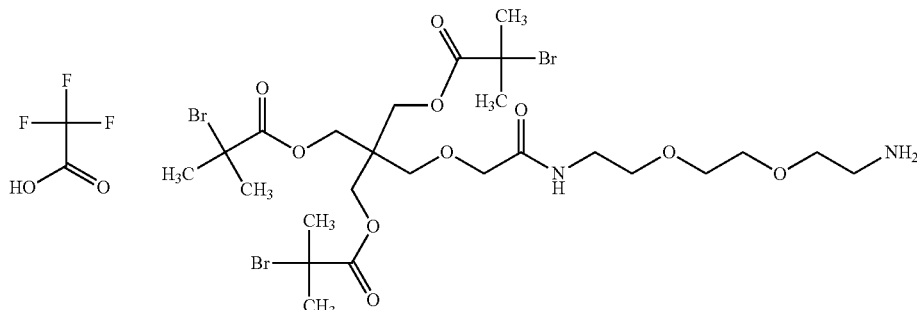

The synthesis of the Am-PC polymer was conducted as follows:

| Reactant | Name/Identity | Amount | MW |
|---|---|---|---|
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 730.39 |
| Solvent A | N,N-Dimethylformamide (DMF) | 31.7 | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 µL of dry DMF. Add 19.7 µL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 mn. Add 1 mg of CuBr. Prepared a stock solution of CuBr$_2$ at 200 mg/mL by dissolving 4 mg CuBr$_2$ in 20 µL of DMF. Add 0.5 g of monomer (AmPC) to 1 mL of methanol (slow dissolution/viscous solution), followed by 1 uL of the stock solution of CuBr$_2$. Add the monomer solution dropwise to the reaction mixture above. Rinse with 1 mL of water. Degas the reaction mixture thoroughly (freeze-thaw). Let the reaction proceed for 24 hours.

Afterwards the Am-PC polymer may be dialyzed. The molecular weight of the above polymer was determined by SEC/MALS: Mn is 21.5 kDa, Mp: 250 kDa, PDI is 1.17. Conversion was estimated by 1H NMR to be 94%. A maleimide functionality can be added to the Am-PC polymer as discussed above for HEMA-PC and HEA-PC. Maleimide functionalized Am-PC polymer can be conjugated to a protein, such as TAF443, as described above.

Example 51. Reverse Ellman's Assay for Calculating Free Maleimide in a Compound

After addition of the maleimide functionality to polymer OG1801 to form OG1802 (see above), an Ellman's assay is used to determine the amount of functional maleimide (i.e. conjugatable) in a sample. Thiol converts Ellman's reagent (DTNB) to TNB- then to TNB2- in water at neutral and alkaline pH, which gives off a yellow color (measured at 412 nm). A standard curve is established with cysteine. Since the maleimide reacts with thiol, this assay actually measures the thiol (cysteine) left. The inhibition is calculated as the (original thiol-thiol left after maleimide polymer addition)/(original thiol) and is expressed as a percentage.

Reagents Employed in Assay: A standard curve was prepared using the cysteine from 62.5 µM to 2 µM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 µM of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

SEQUENCES

SEQ ID NO. 1
```
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIELTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGSGGG GSDIQMTQSP SSLSASVGDR VTITCSASQD

321 ISNYLNWYQQ KPGKAPKVLI TFTSSLHSGV PSRFSGSGSG TDFTLTISSL QPEDFATYYC QQYSTVPWTF GQGTKVEIKR

401 TVAAPSVFIF PPSDEQLKSG TASVVCLLNN FYPREAKVQW KVDNALQSGN SQESVTEQDS KDSTYSLSST LTLSKADYEK

481 HKVYACEVTH QGLSSPVTKS FNRGEC
```

SEQ ID NO. 2
```
  1 EVLQVESGGG LVQPGGSLRL SCAASGYTFT NYGMNWVRQA PGKGLEWVGW INTYTGEPTY AADFKRRFTF SLDTSKSTAY

81 LQMNSLRAED TAVYYCAKYP HYYGSSHWYF DVWGQGTLVT VSSASTKGPS VFPLAPSSKS TSGGTAALGC LVKDYFPEPV

161 TVSWNSGALT SGVHTFPAVL QSSGLYSLSS VVTVPSSSLG TQTYICNVNH KPSNTKVDKK VEPKSCDKTH TCPPCPAPEL

241 LGGPSVFLFP PKPKDTLMIS RTPEVTCVVV DVSHEDPEVK FNWYVDGVEV HNAKTKPREE QYNSTYRVVS VLTVLHQDWL
```

```
321 NGKEYKCKVS NKALPAPIEK TISKAKGQPR EPQVYTLPPS REEMTKNQVS LTCLVKGFYP SDIAVEWESN GQPENNYKTT

401 PPVLDSDGSF FLYSKLTVDK SRWQQGNVFS CSVMHEALHN HYTQKSLSLS PGK
                                                                         SEQ ID NO. 3
  1 LVVTPPGPEL VLNVSSTFVL TCSGSAPVVW ERMSQEPPQE MAKAQDGTFS SVLTLTNLTG LDTGYEGCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNANQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGDIQMTQ SPSSLSASVG DRVTITCSAS QDISNYLNWY

321 QQKPGKAPKV LIYFTSSLHS GVPSRFSGSG SGTDFTLTIS SLQPEDFATY YCQQYSTVPW TFGQGTKVEI KRTVAAPSVF

401 IFPPSDEQLK SGTASVVCLL NNFYPREAKV QWKVDNALQS GNSQESVTEQ DSKDSTYSLS STLTLSKADY EKHKVYACEV

481 THQGLSSPVT KSFNRGEC
                                                                         SEQ ID NO. 4
  1 LVVTPPGPEL VLNVSSTFVL TCSGSAPVVW ERMSQEPPQE MAKAQDGTFS SVLTLTNLTG LDTGYEGCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNANQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGGGSGGG GSEVQLVESG GGLVQPGGSL RLSCAASGYT

321 FTNYGMNWVR QAPGKGLEWV GWINTYTGEP TYADDFKRRF TFSLDTSKST AYLQMNSLRA EDTAVYYCAK YPHYYGSSHW

401 YFDVWGQGTL VTVSSASTKG PSVFPLAPSS KSTSGGTAAL GCLVKDYFPE PVTVSWNSGA LTSGVHTFPA VLQSSGLYSL

481 SSVVTVPSSS LGTQTYICNV NHKPSNTKVD KKVEPKSCDK THTCPPCPAP ELLGGPSVFL FPPKPKDTLM ISRTPEVTCV

561 VVDVSHEDPE VKFNWYVDGV EVHNAKTKPR EEQYNSTYRV VSVLTVLHQD WLNGKEYKCK VSNKALPAPI EKTISKAKGQ

641 PREPQVYTLP PSREEMTKNQ VSLTCLVKGF YPSDIAVEWE SNGQPENNYK TTPPVLDSDG SFFLYSKLTV DKSRWQQGNV

721 FSCSVMHEAL HNHYTQKSLS LSPGK
                                                                         SEQ ID NO. 5
  1 DIQMTQSPSS LSASVGDRVT ITCSASQDIS NYLNWYQQKP GKAPKVLIYF TSSLHSGVPS RFSGSGSGTD FTLTISSLQP

81 EDFATYYCQQ YSTVPWTFGQ GTKVEIKRTV AAPSVFIFPP SDEQLKSGTA SVVCLLNNFY PREAKVQWKV DNALQSGNSQ

161 ESVTEQDSKD STYSLSSTLT LSKADYEKHK VYACEVTHQG LSSPVTKSFN RGEC
                                                                         SEQ ID NO. 6
  1 LVVTPPGPEL VLNVSSTFVL TCSGSAPVVW ERMSQEPPQE MAKAQDGTFS SVLTLTNLTG LDTGEYFCTH NDSRGLETDE

81 RKRLYIFVPD PTVGFLPNDA EELFIFLTEI TEITIPCRVT DPQLVVTLHE KKGDVALPVP YDHQRGFSGI FEDRSYICKT

161 TIGDREVDSD AYYVYRLQVS SINVSVNAVQ TVVRQGENIT LMCIVIGNEV VNFEWTYPRK ESGRLVEPVT DFLLDMPYHI

241 RSILHIPSAE LEDSGTYTCN VTESVNDHQD EKAINITVVE SGGGEVQLVE SGGGLVQPGG SLRLSCAASG YTFTNYGMNW

321 VRQAPGKGLE WVGWINTYTG EPTYAADFKR RFTFSLDTSK STAYLQMNSL RAEDTAVYYC AKYPHYYGSS HWYFDVWGQG

401 TLVTVSSAST KGPSVFPLAP SSKSTSGGTA ALGCLVKDYF PEPVTVSWNS GALTSGVHTF PAVLQSSGLY SLSSVVTVPS

481 SSLGTQTYIC NVNHKPSNTK VDKKVEPKSC DKTHTCPPCP APELLGGPSV FLFPPKPKDT LMISRTPEVT CVVVDVSHED

561 PEVKFNWYVD GVEVHNAKTK PREEQYNSTY TVVSVLTVLH QDWLNGKEYK CKVNSKALPA PIEKTISKAK GQPREPQVYT

641 LPPSREEMTK NQVSLTCLVK GFYPSDIAVE WESNGQPENN YKTTPPVLDS DGSFFLYSKL TVDKSRWQQG VNFSCSVMHE

721 ALHNHYTQKS LSLSPGK
                                                                         SEQ ID NO. 7
  1 EVQLVESGGG LVQPGGSLRL SCAASGYTFT NYGMNWVRQA PGKGLEWVGW INTYTGEPTY AADFKRRFTF SLDTSKSTAY

81 LQMNSLRAED TAVYYCAKYP HYYGSSHWYF DVWGQGTLVT VSSASTKGPS VFPLAPSSKS TSGGTAALGC KVKDYFPEPV

161 TVSWNSGALT SGVHTFPAVL QSSGLYSLSS VVTVPSSSLG TQTYICNVNH KPSNTKVDKK VEPKSCDKTH TCPPCPAPEL

241 LGGPSVFLFP PKPKDTLMIS RTPEVTCVVV DVSHEDPEVK FNWYVDGVEV HANKTKPREE QYNSTYRVVS VLTVLHQDWL

321 NGKEYKCKVS NKALPAPIEK TISKAKGQPR EPQVYTLPPS REEMTKNQVS LTCLVKGFYP SDIAVEWESN GQPENNYKTT

401 PPVLDSDGSF FLYSKLTVDK SRWQQGNVFS CSVMHEALHN HYTQKSLSLS PGGGGGSGGG GSGGGGSGGG GSGLVVTPPG
```

```
481 PELVLNVSST FVLTCSGSAP VVWERMSQEP PQEMAKAQDG TFSSVLVLTN LTGLDTGEYF CTHNDSRGLE TDERKRLYIF
561 VPDPTVGFLP NDAEELFIFL TEITEITIPC RVTDPQLVVT LHEKKGDVAL PVPYDHQRGF SGIFEDRSYI CKTTIGDREV
641 DSDAYYVYRL QVSSINVSVN AVQTVVRQGE NITLMCIVIG NEVVNFEWTY PRKESGRLVE PVTDFLLDMP YHIRSILHIP
721 SAELEDSGTY TCNVTESVND HQDEKAINIT VVESG
```

SEQ ID NO. 8

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNANQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTYTYICNV NHKPSNTKVD KKVEPKSCDK THTCPPCPAP EAAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTIAKAKGQ
641 PRPECVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS LSPGK
```

SEQ ID NO. 9

```
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI IEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THTCPPCPAP EAAGAPSVFL FPPKPKDTLM ISRTPEVTCV
561 VVDVSHEDPE VKFNWYVDGV EVHNAKTKPR EEQYNSTYRV VSVLTVLHQD WLNGKEYKCK VSNKALPAPI EKTISKAKGQ
641 PREPQVYTLP PSREEMTKNQ VSLTCLVKGF YPSDIAVEWE SNGQPENNYK TTPPVLDSDG SFFLYSKLTV DKSRWQQGNV
721 FSCSVMHEAL HNHYTQKSLS CSPGK
```

SEQ ID NO. 10

```
  1 EVQLVESGGG LVQPGGSLRL SCAASGYDFT HYGMNWVRQA PGKGLEWVGW INTYTGEPTY AADFKRRFTF SLDTSKSTAY
 81 EDFATYYCQQ YSTVPWTFGQ GTKVEIKRTV AAPSVFIFPP SEEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC
```

SEQ ID NO. 11

```
  1 MRLPGAMPAL ALKGELLLLS LLLLLEPQIS QGLVVTPPGP ELVLNVSSTF VLTCSGSAPV VWERMSQEPP QEMAKAQDGT
 81 FSSVLTLTNL TGLDTGEYFC THNDSRGLET DERKRLYIFV PDPTVGFLPN DAEELFIFLT EITEITIPCR VTDPQLVVTL
161 HEKKGDVALP VPYDHQRGFS GIFEDRSYIC KTTIGDREVD SDAYYVYRLQ VSSINVSVNA VQTVVRQGEN ITLMCIVIGN
241 EVVNFEWTYP RKESGRLVEP VTDFLLDMPY HIRSILHIPS AELEDSGTYT CNVTESVNDH QDEKAINITV VESGYVRLLG
321 EVGTLQFAEL HRSRTLQVVF EAYPPPTVLW FKDNRTLGDS SAGEIALSTR NVSETRYVSE LTLVRVKVAE AGHYTMRAFH
401 EDAEVQLSFQ LQINVPVRVL ELSESHPDSG EQTVRCRGRG MPQPNIIWSA CRDLKRCPRE LPPTLLGNSS EEESQLETNV
481 TYWEEEQEFE VVSTLRLQHV DRPLSVRCTL RNAVGQDTQE VIVVPHSLPF KVVVISAILA LVVLTIISLI ILIMLWQKKP
561 RYEIRWKVIE SVSSDGHEYI YVDPMQLPYD STWELPRDQL VLGRTLGSGA FGQVVEATAH GLSHSQATMK VAVKMLKSTA
641 RSSEKQALMS ELKIMSHLGP HLNVVNLLGA CTKGGPIYII TEYCRYGDLV DYLHRNKHTF LQHHSDKRRP PSAELYSNAL
721 PVGLPLPSHV SLTGESDGGY MDMSKDESVD YVPMLDMKGD VKYADIESSN YMAPYDNYVP SAPERTCRAT LINESPVLSY
801 MDLVGFSYQV ANGMEFLASK NCVHRDLAAR NVLICEGKLV KICDFGLARD IMRDSNYISK GSTFLPLKWM APESIFNSLY
881 TTLSDVWSFG ILLWEIFTLG GTPYPELPMN EQFYNAIKRG YRMAQPAHAS DEIYEIMQKC WEEKFEIRPP FSQLVLLLER
```

```
                                                                       -continued
 961 LLGEGYKKKY QQVDEEFLRS DHPAILRSQA RLPGFHGLRS PLDTSSVLYT AVQPNEGDND YIIPLPDPKP EVADEGPLEG

1041 SPSLASSTLN EVNTSSTISC DSPLEPQDEP EPEPQLELQV EPEPELEQLP DSGCPAPRAE AEDSFL

SEQ ID NO. 12
   1 DIQLTQSPSS LSASVGDRVT ITCSASQDIS NYLNWYQQKP GKAPKVLIYF TSSLHSGVPS RFSGSGSGTD TTLTISSLQP

81 EDFATYYCQQ YSTVPWTFGQ GTKVEIKRTV AAPSVFIFPP SDEQLKSGTA SVVCLLNNFY PREAKVQWKV DNALQSGNSQ

161 ESVTEQDSKS STYSLSSTLT LSKADYEKHK VYACEVTHQG LSSPVTKSFN RGEC

SEQ ID NO. 13
   1 EVQLVESGGG LVQPGGSLRL SCAASGYDFT HYGMNWVRQA PGKGLEWVGW INTYTGEPTY AADFKRRFTF SLDTSKSTAY

81 LQMNSLRAED TAVYYCAKYP YYYGTSHWYF DVWGQGTLVT VSSASTKGPS VFPLAPSSKS TSGGTAALGC LVKDYFPEPV

161 TVSWNSGALT SGVHTFPAVL QSSGLYSLSS VVTVPSSSLG TQTYICNVNH KPSNTKVDKK VEPKSCDKTH L

SEQ ID NO. 14
   1 MVSYWDTGVL LCALLSCLLL TGSSSGSKLK DPELSLKGTQ HIMQAGQTLH LQCRGEAAHK WSLPEMVSKE SERLSITKSA

81 CGRNGKQFCS TLTLNTAQAN HTGFYSCKYL AVPTSKKKET ESAIYIFISD TGRPFVEMYS EIPEIIHMTE GRELVIPCRV

161 TSPNITVTLK KFPLDTLIPD GKRIIWDSRK GFIISNATYK EIGLLTCEAT VNGHLYKTNY LTHRQTNTII DVQISTPRPV

241 KLLRGHTLVL NCTATTPLNT EVQMTWSYPD EKNKRASVRR RIDQSNSHAN IFYSVLTIDK MQNKDKGLYT CRVRSGPSFK

321 SVNTSVHIYD KAFITVKHRK QQVLETVAGK RSYRLSMKVK APFSEVWL KDGLAPTEKS ARYLTRGYSL IIKDVTEEDA

401 GNYTILLSIK QSNVFKNLTA TLIVNVKPQI YEAAVDDFPD PALYPLGSRQ ILTCTAYGIP QPTIKWFWHP CNHNHSEARC

481 DFCSNNEESF ILDADSNMGN RIESITQRMA IIEGKNKMAS TLVVADSRIS GIYICIASNK VGTVGRNISF YITDVPNGFH

561 VNLEKMPTEG EDLKLSCTVN KFLYRDVTWI LLRTVNNRTM HYSISKQKMA ITKEHSITLN LTTMNVSLQD SGTYACRARN

641 VYTGEEILQK KEITIRDQEA PYLLRNLSDH TVAISSSTTL DCHANGVPEP QITWFKNNHK IQQPEGIILG PGSSTLFIER

721 VTEEDEGVYH CKATNQKGSV ESSAYLTVQG TSDKSNLELI TLTCTCVAAT LFWLLLTLFI RKMKRSSSEI KTDYLSIIMD

801 PDEVPLDEQC ERLPYDASKW EFARERLKLG KSLGRGAFGK VVQASAFGIK KSPTCRTVAV KMLKEGATAS EYKALMTELK

881 ILTHIGHHLN VVNLLGACTK QGGPLMVIVE YCKYGNLSNY LKSKRDLFFL NKDAALHMEP KKEKMEPGLE QGKKPRLDSV

961 TSSESFASSG FQEDKSLSDV EEEEDSDGFY KEPITMEDLI SYSFQVARGM EFLSSRKCIH RDLAARNILL SENNVVKICD

1041 FGLARDIYKN PDYVRKGDTR LPLKWMAPES IFDKIYSTKS DVWSYGVLLW EIFSLGGSPY PGVQMDEDFC SRLREGMRMR

1121 APEYSTPEIY QIMLDCWHRD PKERPRFAEL VEKLGDLLQA NVQQDGKDYI PINAILTGNS GFTYSTPAFS EDFFKESISA

1201 PKFNSGSSDD VRYVNAFKFM SLERIKTFEE LLPNATSMFD DYQGDSSTLL ASPMLKRFTW TDSKPKASLK IDLRVTSKSK

1281 ESGLSDVSRP SFCHSSCGHV SEGKRRFTYD HAELERKIAC CSPPPDYNSV CLYSTPPI

SEQ ID NO. 15
   1 MQSKVLLAVA LWLCVETRAA SVGLPSVSLD LPRLSIQKDI LTIKANTTLQ ITCRGQRDLD WLWPNNQSGS EQRVEVTECS

81 DGLFCKTLTI PKVIGNDTGA YKCFYRETDL ASVIYVYVQD YRSPFIASVS DQHGVVYITE NKNKTVVIPC LGSISNLNVS

161 LCARYPEKRF VPDGNRISWD SKKGFTIPSY MISYAGMVFC EAKINDESYQ SIMYIVVVG YRIYDVVLSP SHGIELSVGE

241 KLVLNCTART ELNVGIDFNW EYPSSKHQHK KLVNRDLKTQ SGSEMKKFLS TLTIDGVTRS DQGLYTCAAS SGLMTKKNST

321 FVRVHEKPFV AFGSGMESLV EATVGERVRI PAKYLGYPPP EIKWYKNGIP LESNHTIKAG HVLTIMEVSE RDTGNYTVIL

401 TNPISKEKQS HVVSLVVYVP PQIGEKSLIS PVDSYQYGTT QTLTCTVYAI PPPHHIHWYW QLEEECANEP SQAVSVTNPY

481 PCEEWRSVED FQGGNKIEVN KNQFALIEGK NKTVSTLVIQ AANVSALYKC EAVNKVGRGE RVISFHVTRG PEITLQPDMQ

561 PTQEESVSLW CTADRSTFEN LTWYKLGPQP LPIHVGELPT PVCKNLDTLW KLNATMFSNS TNDILIMELK NASLQDQGDY

641 VLCAQDRKTK KRHCVVRQLT VLERVAPTIT GNLENQTTSI GESIEVSCTA SGNPPPQIMW FKDNETLVED SGIVLKDGNR

721 NLTIRRVRKE DEGLYTCQAC SVLGCAKVEA FFIIEGAQEK TNLEIIILVG TAVIAMFFWL LLVIILRTVK RANGGELKTG

801 YLSIVMDPDE LPLDEHCERL PYDADKWEFP RDRLKLGKPL GRGAFGQVIE ADAFGIDKTA TCRTVAVKML KEGATHSEHR

881 ALMSELKILI HIGHHLNVVN LLGACTKPGG PLMVIVEFCK FGNLSTYLRS KRNEFVPYKT KGARGRQGKD YVGAIPVDLK

961 RRLDSITSSQ SSASSGFVEE KSLSDVEEEE APEDLYKDFL TLEHLICYSF QVAKGMEFLA SRKCIHRDLA ARNILLSEKN
```

```
1041  VVKICDFGLA RDIYKDPDYV RKGDARLPLK WMAPETIFDR VYTIQSDVWS FGVLLWRIFS LGASPYPGVK IDEEFCRRLK

1121  EGTRMRAPDY TTPEMYQTML DCWHGEPSQR PTFSELVEHL GNLLQANAQQ DGKDYIVLPI SETLSMEEDS GLSLPTSPVS

1201  CMEEEEVCDP KFHYDNTAGI SQYLQNSKRK SRPVSVKTFE DIPLEEPEVK VIPDDNQTDS GMVLASEELK TLEDRTKLSP

1281  SFGGMVPSKS RESVASEGSN QTSGYQSGYH SDDTDTTVYS SEEAELLKLI EIGVQTGSTA QILQPDSGTT LSSPPV

SEQ ID NO. 16
   1  MQRGAALCLR LWLCLGLLDG LVSGYSMTPP TLNITEESHV IDTGDSLSIS CRGQHPLEWA WPGAQEAPAT GDKDSEDTGV

81  VRDCEGTDAR PYCKVLLLHE VHANDTGSYV CYYKYIKARI EGTTAASSYV FVRDFEQPFI NKPDTLLVNR KDAMWVPCLV

161  SIPGLNVTLR SQSSVLWPDG QEVVWDDRRG MLVSTPLLHD ALYLQCETTW GDQDFLSNPF LVHITGNELY DIQLLPRKSL

241  ELLVGEKLVL NCTVWAEFNS GVTFDWFYPG KQAERGKWVP ERRSQQTHTE LSSILTIHVN SQHDLGSYVC KANNGIQRFR

321  ESTEVIVHEN PFISVEWLKG PILEATAGDE LVKLPVKLAA YPPPEFQWYK DGKALSGRHS PHALVLKEVT EASTYTYTLA

401  LWNSAAGLRR NISLELVVNV PPQIHEKEAS SPSIYSRHSR QALTCTAYGV PLPLSIQWHW RPWTPCKMFA QRSLRRRQQQ

481  DLMPQCRDWR AVTTQDAVNP IESLDTWTEF VEGKNKTVSK LVIQNANVSA MYKCVVSNKV GQDERLIYFY VTTIPDGFTI

561  ESKPSEELLE GQPVLLSCQA DSYKYEHLRW YRLNLSTLHD AHGNPLLLDC KNVHLFATPL AASLEEVAPG ARHATLSLSI

641  PRVAPEHEGH YVCEVQDRRS HDKHCHKKYL SVQALEAPRL TQNLTDLLVN VSDSLEMQCL VAGAHAPSIV WYKDERLLEE

721  KSGVDLADSN QKLSIQRVRE EDAGRYLCSV CNAKGCVNSS ASVAVEGSED KGSMEIVILV GTGVIAVFFW VLLLLIFCNM

801  RRPAHADIKT GYLSIIMDPG EVPLEEQCEY LSYDASQWEF PRERLHGRV LGYGAFGKVV EASAFGIHKG SSCDTVAVKM

881  LKEGATASEH RALMSELKIL IHIGNHLNVV NLLGACTKPQ GPLMVIVEFC KYGLNSNFLR AKRDAFSPCA EKSPEQRGRF

961  RAMVELARLD RRRPGSSDRV LFARFSKTEG GARRASPDQE AEDLWLSPLT MEDLVCYSFQ VARGMEFLAS RKCIHRDLAA

1041  RNILLSESDV VKICDFGLAR DIYKDPDYVR KGSARLPLKW MAPESIFDKV YTTQSDVWSF GVLLWEIFSL GASPYPGVQI

1121  NEEFCQRLRD GTRMRAPELA TPAIRRIMLN CWSGDPKARP AFSELVEILG DLLQGRGLQE EEEVCMAPRS SQSSEEGSFS

1201  QVSTMALHIA QADAEDSPPS LQRHSLAARY YNWVSFPGCL ARGAETRGSS RMKTFEEFPM TPTTYKGSVD NQTDSGMVLA

1281  SEEFEQIESR HRQESGFSCK GPGQNVAVTR AHPDSQGRRR RPERGARGGQ VFYNSEYGEL SEPSEEDHCS PSARVTFFTD

1361  NSY

SEQ ID NO. 17
   1  ASTKGPSVFP LAPSSKSTSG GTAALGCLVK DYFPEPVTVS WNSGALTSGV HTFPAVLQSS GLYSLSSVVT VPSSSLGTQT

81  YICNVNHKPS NTKVDKKVEP KSCDKTHTCP PCPAPELLGG PSVFLFPPKP KDTLMISRTP EVTCVVVDVS HEDPEVKFNW

161  YVDGVEVHAN AKTKPREEQYN STYRVVSVLT VLHQDWLNGK EYKCKVSNKA LPAPIEKTIS KAKGQPREPQ VYTLPPSRDE

241  LTKNQVSLTC LVKGFYPSDI AVEWESNGQP ENNYKTTPPV LDSDGSFFLY SKLTVDKSRS QQGNVFSCSV MHEALHNHYT

321  QKSLSLSPGK

SEQ ID NO. 18
   1  TVAAPSVFIF PPSDEQLKSG TASVVCLLNN FYPREAKVQW KVDNALQSGN SQESVTEQDS KDSTYSLSST LTLSKADYEK

81  HKVYACEVTH QGLSSPVTKS FNRGEC

SEQ ID NO. 19
   1  LVVTPPGPEL VLNVSSTFVL TCSGSAPVVW ERMSQEPPQE MAKAQDGTFS SVLTLTNLTG LDTGEYFCTH NDSRGLETDE

81  RKRLYIFVPD PTVGFLPNDA EELFIFLTEI TEITIPCRVT DPQLVVTLHE KKGDVALPVP YDRQRGFSGI FEDRSYICKT

161  TIGDREVDSD AYYVYRLQVS SINVSVNAVQ TVVRQGENIT LMCIVIGNEV VNFEWTYPRK ESGRLVEPVT DFLLDMPYHI

241  RSILHIPSAE LEDSGTYTCN VTESVNDHQD EKAINITVVE SGGGGSGGGG GSDIQMTQSP SSLSASVGDR VTITCSASQD

321  ISNYLNWYQQ KPGKAPKVLI YFTSSLHSGV PSRFSGSGSG TDFTLTISSL QPEDFATYYC QQYSTVPWTF GQGTKVEIKR

401  TVAAPSVFIF PPSDEQLKSG TASVVCLLNN FYPREAKVQW KVDNALQSGN SQESVTEQDS KDSTYSLSST LTLSKADYEK

481  HKVYACEVTH QGLSSPVTKS FNRGEC
```

```
                                                              SEQ ID NO. 21
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH T
                                                              SEQ ID NO. 22
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYT
321 FTNYGMNWVR QAPGKGLEWV GWINTYTGEP TYAADFKRRF TFSLDTSKST AYLQMNSLRA EDTAVYYCAK YPHYYGSSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THT
                                                              SEQ ID NO. 23
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGEVQLVE SGGGLVQPGG SLRLSCAASG TYFTNYGMNW
321 VRQAPGKELW WVGWINTYTG EPTYAADFKR RFTFSLDTSK STAYLQMNSL RAEDTAVYYC AKYPHYYGSS HWYFDVWGQG
401 TLVTVSSAST KGPSVFPLAP SSKSTSGGTA ALGCLVKDYF PEPVTVSWNS GALTSGVHTF PAVLQSSGLY SLSSVVTVPS
481 SSLGTQTYIC NVNHKPSNTK VDKKVEPKSC DKTHT
                                                              SEQ ID NO. 24
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGGGSGGG
241 GSGGGGSGGG GSGLVVTPPG PELVLNVSST FVLTCSGSAP VVWERMSQEP PQEMAKAQDG TFSSVLTLTN LTGLDTGEYF
321 CTHNDSRGLE TDERKRLYIF VPDPTVGFLP NDAEELFIFL TEITEITIPC RVTDPQLVVT LHEKKGDVAL PVPYDHQRGF
401 SGIFEDRSYI CKTTIGDREV DSDAYYVYRL QVSSINVSVN AVQTVVRQGE NITLMCIVIG NEVVVFEWTY PRKESGRLVE
481 PVTDFLLDMP YHIRSILHIP SAELEDSGTY TCNVTESVND NQDEKAINIT VVESG
                                                              SEQ ID NO. 25
  1 LVVTPPGPEL VLNVSSTFVL TCSGSAPVVW ERMSQEPPQE MAKAQDGTFS SVLTLTNLTG LDTGEYFCTH NDSRGLETDE
 81 RKRLYIFVPD PTVGFLPNDA EELFIFLTEI TEITIPCRVT DPQLVVTLHE KKGDVALPVP YDHQRGFSGI FEDRSYICKT
161 TIGDREVDSD AYYVYRLQVS SINVSVNAVQ TVVRQGENIT LMCIVIGNEV VNFEWTYPRK ESGRLVEPVT DFLLDMPYHI
241 RSILHIPSAE LEDSGTYTCN VTESVNDHQD EKAINITVVE SGGGGSGGGG GSEVQLVESG GGLVQPGGSL RLSCAASGYD
321 FTHYGMNWVR QAPGKGLEWV GWINTYTGEP TYAADFKRRF TFSLDTSKST AYLQMNSLRA EDTAVYYCAK YPYYGTSHW
401 YFDVWGQGTL VTVSSASTKG PSVFPLAPSS KSTSGGTAAL GCLVKDYFPE PVTVSWNSGA LTSGVHTFPA VLQSSGLYSL
481 SSVVTVPSSS LGTQTYICNV NHKPSNTKVD KKVEPKSCDK THL
                                                              SEQ ID NO. 26
  1 LVVTPPGPE LVLNVSSTFV LTCSGSAPVV WERMSQEPPQ EMAKAQDGTF SSVLTLTNLT GLDTGEYFCT HNDSRGLETD
 80 ERKRLYIFVP DPTVGFLPND AEELFIFLTE ITEITIPCRV TDPQLVVTLH EKKGDVAPPV PYDHQRGFSG IFEDRSYICK
160 TTIGDREVDS DAYYVYRLQV SSINVSVNAV QTVVRQGENI TLMCIVIGNE VVNFEWTYPR KESGRLVEPV TDFLLDMPYH
240 IRSILHIPSA ELEDSGTYTC NVTESVNDHQ DEKAINITVV ESGEVQLVES GGGLVQPGGS LRLSCAASGY TFTNYGMNWV
320 RQAPGKGLEW VGWINTYTGE PYTAADRKRR FTFSLDTSKS TAYLQMNSLR AEDTAVYYCA KYPHYYGSSH WYFDVWGQGT
400 LVTVSSASTK GPSVFPLAPS SKSTSGGTAA LGCLVKDYFP EPVTVSWNSG ALTSGVHTFP AVLQSSGLYS LSSVVTVPSS
```

```
480 LSGTQTYICN VNHKPSNTKV DKKVEPKSCD KTHTCPPCPA PELLGGPSVF LFPPKPKDTL MISRTPEVTC VVVDVSHEDP
560 EVKFNWYVDG VEVHNAKTKP REEQYNSTYR VVSVLTVLHQ DWLNGKEYKC KVSNKALPAP IEKTISKAKG QPREPQVYTL
640 PPSREEMTKN QVSLTCLVKG FYPSDIAVEW ESNGQPENNY KTTPPVLDSD GSGGLYSKLT VDKSRWQQGN VFSCSVMHEA
720 LHNHYTQKSL SLSPGK
```

SEQ ID NO. 27
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVNH
401 KPSNTKVDKK VEPKSCDKTH TCPPCPAPEL LGGPSVFLFP PKPKDTLMIS RTPEVTCVVV DVSHEDPEVK FNWYVDGVEV
481 HNAKTKPREE QYNSTYRVVS VLTVLHQDWL NGKEYKCKVS NKALPAPIEK TIAKAKGQPR EPAVYTLPPS REEMTKNQVS
561 LTCLVKGFYP SDIAVEWESN GQPENNYKTT PPVLDSDGSF FLYSKLTVDK SRWQQGNVFS CSVMHEALHN HYTQKSLSLS
641 PGK
```

SEQ ID NO. 28
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV VRQGENITLM CIVIGNEVVN FEWTYPRKES GRLVEPVTDF LLDMPYHIRS ILHIPSAELE
161 DSGTYTCNVT ESVNDHQDEK AINITVVESG EVQLVESGGG LVQPGGSLRL SCAASGYTFT NYGMNWVRQA PGKGLEWVGW
241 INTYTGEPTY AADFKRRFTF SLDTSKSTAY LQMNSLRAED TAVYYCAKYP HYYGSSHWYF DVWGQGTLVT VSSASTKGPS
321 VFPLAPSSKS TSGGTAALGC LVKDYFPEPV TVSWNSGALT SGVHTFPAVL QSSGLYSLSS VVTVPSSSLG TQTYICNVVH
401 KPSNTKVDKK VEPKSCDKTH T
```

SEQ ID NO. 29
```
  1 VGFLPNDAEE LFIFLTEITE ITIPCRVTDP QLVVTLHEKK GDVALPVPYD HQRGFSGIFE DRSYICKTTI GDREVDSDAY
 81 YVYRLQVSSI NVSVNAVQTV NRQGENITLM CIVIGNEVVN FEWTYPRKES GRLVEPVTDF LLDMPYHIRS ILHIPSAELE
161 DSGTYTCNVT ESVNDHQDEK AINITVVESG GGGSGGGGSG GGGSGGGGSG GGGSGGGGSE VQLVESGGGL VQPGGSLRLS
241 CAASGYTFTN YGMNWVRQAP GKGLEWVGWI NTYTGEPTYA ADFKRRFTFS LDTSKSTAYL QMNSLRAEDT AVYYCAKYPH
321 YYGSSHWYFD VWGQGTLVTV SSASTKGPSV FPLAPSSKST SGGTAALGCL VKDYFPEPVT VSWNSGLATS GVHTFPAVLQ
401 SSGLYSLSSV VTVPSSSLGT QTYICNVNHK PSNTKVDKKV EPKSCDKTHT
```

SEQ ID NO. 30
```
  1 EVQLVESGGG LVQPGGSLRL SCAASGYTFT NYGMNWVRQA PGKGLEWVGW INTYTGEPTY AADFKRRFTF SLDTSKSTAY
 81 LQMNSLRAED TAVYYCAKYP HYYGSSHWYF DVWGQGTLVT VSSASTKGPS VFPLAPSSKS TSGGTAALGC LVKDYFPEPV
161 TVSWNSGALT SGVHTFPAVL QSSGLYSLSS VVTVPSSSLG TQTYICNVNH KPSNTKVDKK VEPKSCDKTH TGGGSGGGGS
241 GGGGSGGGGS GGGGSGGGGS VGFLPNDAEE LFIFLTEITE ITIPCRVTDP QLVVTLHEKK GDVALPVPYD HQRGFSGIFE
321 DRSYICKTTI GDFEVDSDAY YVYRLQVSSI NVSVNAVQTV VRQGENITLM CIVIGNEVVN FEWTYPRKES GRLVEPVTDF
401 LLDMPYHIRS ILHIPSAELE DSGTYTCNVT ESVNDHQDES AINITVVESG
```

SEQ ID NO: 31 Nucleic acid encoding heavy chain anti-VEGF-PDGFR fusion
```
GACGGATCGGGAGATCTCCCGATCCCCTATGGTGCACTCTCAGTACAATCTGCTCTGATGCCGCATAGTTAAGCCAGTATCTGCTCCCTGC
TTGTGTGTTGGAGGTCGCTGAGTAGTGCGCGAGCAAAATTTAAGCTACAACAAGGCAAGGCTTGACCGACAATTGCATGAAGAATCTGCTT
AGGGTTAGGCGTTTTGCGCTGCTTCGCGATGTACGGGCCAGATATACGCGTTGACATTGATTATTGACTAGTTATTAATAGTAATCAATTA
CGGGGTCATTAGTTCATAGCCCATATATGGAGTTCCGCGTTACATAACTTACGGTAAATGGCCCGCCTGGCTGACCGCCCAACGACCCCCG
CCCATTGACGTCAATAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCCGCCTGGCATTATGCCC
AGTACATGACCTTATGGGACTTTCCTACTTGGCAGTACATCTACGTATTAGTCATCGCTATTACCATGGTGATGCGGTTTTGGCAGTACAT
```

```
CAATGGGCGTGGATAGCGGTTTGACTCACGGGGATTTCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTAGGCGTGTACGGTGGGAGGTCTATATAAGCAGAGCTC
TCTGGCTAACTAGAGAACCCACTGCTTACTGGCTTATCGAAATTAATACGACTCACTATAGGGAGACCCAAGCTGGCTAGCGTTTAAACTT
AAGCTTGGTACCGAGCTCGGATCCACTAGTCCAGTGTGGTGGAATTCTGCAGATATCCAGCACAGTGCGGCCGCCatgaaagctgtggtg
ctggccgtggctctggtcttcctgacagggagccaggctctggtcgtcacaccccggggccagagcttgtcctcaatgtctccagcacct
tcgttctgacctgctcgggttcagctccggtggtgtgggaacggatgtcccaggagcccccacaggaaatggccaaggcccaggatggcac
cttctccagcgtgctcacactgaccaacctcactgggctagacacgggagaatacttttgcacccacaatgactcccgtggactggagacc
gatgagcggaaacggctctacatctttgtgccagatcccaccgtgggcttcctccctaatgatgccgaggaactattcatctttctcacgg
aaataactgagatcaccattccatgccgagtaacagacccacagctggtggtgacactgcacgagaagaaaggggacgttgcactgcctgt
ccctatgatcaccaacgtggcttttctggtatctttgaggacagaagctacatctgcaaaaccaccattggggacaggaggtggattct
gatgcctactatgtctacagactccaggtgtcatccatcaacgtctctgtgaacgcagtgcagactgtggtccgccagggtgagaacatca
ccctcatgtgcattgtgatcgggaatgaggtggtcaacttcgagtggacataccccgcaaagaaagtgggcggctggtggagccggtgac
tgacttcctcttggatatgccttaccacatccgctccatcctgcacatcccagtgccgagttagaagactcggggacctacacctgcaat
gtgacggagagtgtgaatgaccatcaggatgaaaaggccatcaacatcaccgtggttgagagcggcggtggtggcggctccggtggaggcg
gaagcgaggtgcagctggtggaatccggcggaggcctggtccagcctggcggatccctgagactgtcctgtgccgcctccggctacgactt
cacccattacggcatgaactgggtccgacaggcccctggcaagggcctggaatgggtcggatggatcaacacctacaccggcgagcccacc
tacgccgccgacttcaagcggcggttcaccttctccctggacacctccaagtccaccgcctacctgcagatgaactccctgcgggccgagg
acaccgccgtgtactactgcgccaagtaccctactactacggcacctcccactggtacttcgacgtgtggggccagggcaccctggtcac
cgtgtcctccgcctctaccaagggccctcgtgttccctctggccccctccagcaagtccacctctggcggcaccgccgctctgggctgc
ctggtcaaggactacttccccgagccgtgaccgtgtcctggaactctggcgccctgacctccggcgtgcacacctttccagccgtgctgc
agtcctccggcctgtactccctgtcctccgtcgtgaccgtgccctccagctctctgggcacccagacctacatctgcaacgtgaaccacaa
gccctccaacaccaaggtggacaagaaggtggaacccaagtcctgcgacaagacccacacctgtcccccctgccctgccctgaagcagcc
ggtgcacccagcgtgttcctgttccccccaaagcccaaggacaccctgatgatctcccggacccccgaagtgacctgcgtggtggtggacg
tgtcccacgaggaccctgaagtgaagttcaattggtacgtggacggcgtggaagtgcacaatgccaagaccaagcccagagaggaacagta
caactccacctacggggtggtgtccgtgctgaccgtgctgcatcaggactggctgaacggcaaagagtacaagtgcaaggtctccaacaag
gccctgcctgcccccatcgaaaagaccatctccaaggccaagggccagccccgcgagcctcaggtgtacacactgccacccagccgggaag
agatgaccaagaaccaggtctccctgacctgtctggtcaagggcttctacccctccgatatcgccgtcgaatgggagtccaacggccagcc
cgagaacaactacaagaccacccccctgtgctggactccgacggctcattcttcctgtactccaagctgaccgtggacaagtcccggtgg
cagcagggcaacgtgttctcctgctccgtgatgcacgaggccctgcacaaccactacacccagaagtccctgtcctgcagccccggcaagt
gataaTCTAGAGGGCCCGTTTAAACCCGCTGATCAGCCTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCATCGCATTGTCTGAGTAGGTGTCATTCTATT
CTGGGGGGTGGGGTGGGCAGGACAGCAAGGGGGAGGATTGGGAAGACAATAGCAGGCATGCTGGGGATGCGGTGGGCTCTATGGCTTCTG
AGGCGGAAAGAACCAGCTGGGGCTCTAGGGGGTATCCCCACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTTCTCGCCACGTTCGCCGGCTTTCCCCGTCAA
GCTCTAAATCGGGGGCTCCCTTTAGGGTTCCGATTTAGTGCTTTACGGCACCTCGACCCCAAAAAACTTGATTAGGGTGATGGTTCACGTA
GTGGGCCATCGCCCTGATAGACGGTTTTTCGCCCTTTGACGTTGGAGTCCACGTTCTTTAATAGTGGACTCTTGTTCCAAACTGGAACAAC
ACTCAACCCTATCTCGGTCTATTCTTTTGATTTATAAGGGATTTTGCCGATTTCGGCCTATTGGTTAAAAAATGAGCTGATTTAACAAAAA
TTTAACGCGAATTAATTCTGTGGAATGTGTGTCAGTTAGGGTGTGGAAAGTCCCCAGGCTCCCCAGCAGGCAGAAGTATGCAAAGCATGCA
TCTCAATTAGTCAGCAACCAGGTGTGGAAAGTCCCCAGGCTCCCCAGCAGGCAGAAGTATGCAAAGCATGCATCTCAATTAGTCAGCAACC
ATAGTCCCGCCCCTAACTCCGCCCATCCCGCCCCTAACTCCGCCCAGTTCCGCCCATTCTCCGCCCCATGGCTGACTAATTTTTTTTATTT
ATGCAGAGGCCGAGGCCGCCTCTGCCTCTGAGCTATTCCAGAAGTAGTGAGGAGGCTTTTTTGGAGGCCTAGGCTTTTGCAAAAAGCTCCC
```

```
GGGAGCTTGTATATCCATTTTCGGATCTGATCAAGAGACAGGATGAGGATCGTTTCGCATGATTGAACAAGATGGATTGCACGCAGGTTCT
CCGGCCGCTTGGGTGGAGAGGCTATTCGGCTATGACTGGGCACAACAGACAATCGGCTGCTCTGATGCCGCCGTGTTCCGGCTGTCAGCGC
AGGGGCGCCCGGTTCTTTTTGTCAAGACCGACCTGTCCGGTGCCCTGAATGAACTGCAGGACGAGGCAGCGCGGCTATCGTGGCTGGCCAC
GACGGGCGTTCCTTGCGCAGCTGTGCTCGACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCTGCATACGCTTGATCCGGCTACCTGCCCAT
TCGACCACCAAGCGAAACATCGCATCGAGCGAGCACGTACTCGGATGGAAGCCGGTCTTGTCGATCAGGATGATCTGGACGAAGAGCATCA
GGGGCTCGCGCCAGCCGAACTGTTCGCCAGGCTCAAGGCGCGCATGCCCGACGGCGAGGATCTCGTCGTGACCCATGGCGATGCCTGCTTG
CCGAATATCATGGTGGAAAATGGCCGCTTTTCTGGATTCATCGACTGTGGCCGGCTGGGTGTGGCGGACCGCTATCAGGACATAGCGTTGG
CTACCCGTGATATTGCTGAAGAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGACGCCCAACCTGCCATCACGAG
ATTTCGATTCCACCGCCGCCTTCTATGAAAGGTTGGGCTTCGGAATCGTTTTCCGGGACGCCGGCTGGATGATCCTCCAGCGCGGGATCT
CATGCTGGAGTTCTTCGCCCACCCCAACTTGTTTATTGCAGCTTATAATGGTTACAAATAAAGCAATAGCATCACAAATTTCACAAATAAA
GCATTTTTTTCACTGCATTCTAGTTGTGGTTTGTCCAAACTCATCAATGTATCTTATCATGTCTGTATACCGTCGACCTCTAGCTAGAGCT
TGGCGTAATCATGGTCATAGCTGTTTCCTGTGTGAAATTGTTATCCGCTCACAATTCCACACAACATACGAGCCGGAAGCATAAAGTGTAA
AGCCTGGGGTGCCTAATGAGTGAGCTAACTCACATTAATTGCGTTGCGCTCACTGCCCGCTTTCCAGTCGGGAAACCTGTCGTGCCAGCTG
CATTAATGAATCGGCCAACGCGCGGGGAGAGGCGGTTTGCGTATTGGGCGCTCTTCCGCTTCCTCGCTCACTGACTCGCTGCGCTCGGTCG
TTCGGCTGCGGCGAGCGGTATCAGCTCACTCAAAGGCGGTAATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCTGAAGCCAGTTACCTTCGGAAAAAGAGT
TGGTAGCTCTTGATCCGGCAAACAAACCACCGCTGGTAGCGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGGGATTTTGGTCATGAGATTATCAAAAAGGA
TCTTCACCTAGATCCTTTTAAATTAAAAATGAAGTTTTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTTTGGTATGGCTTCATTCAGCTCCGGTTCCCAA
CGATCAAGGCGAGTTACATGATCCCCCATGTTGTGCAAAAAAGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTCATGCCATCCGTAAGATGCTTTTCTGTGACTGGTGAGTACTC
AACCAAGTCATTCTGAGAATAGTGTATGCGGCGACCGAGTTGCTCTTGCCCGGCGTCAATACGGGATAATACCGCGCCACATAGCAGAACT
TTAAAAGTGCTCATCATTGGAAAACGTTCTTCGGGGCGAAAACTCTCAAGGATCTTACCGCTGTTGAGATCCAGTTCGATGTAACCCACTC
GTGCACCCAACTGATCTTCAGCATCTTTTACTTTCACCAGCGTTTCTGGGTGAGCAAAAACAGGAAGGCAAAATGCCGCAAAAAAGGGAAT
AAGGGCGACACGGAAATGTTGAATACTCATACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGTGCCACCTGACGTC
SEQ ID NO: 32: Light chain encoding anti-VEGF light chain
GACGGATCGGGAGATCTCCCGATCCCCTATGGTGCACTCTCAGTACAATCTGCTCTGATGCCGCATAGTTAAGCCAGTATCTGCTCCCTGC
TTGTGTGTTGGAGGTCGCTGAGTAGTGCGCGAGCAAAATTTAAGCTACAACAAGGCAAGGCTTGACCGACAATTGCATGAAGAATCTGCTT
AGGGTTAGGCGTTTTGCGCTGCTTCGCGATGTACGGGCCAGATATACGCGTTGACATTGATTATTGACTAGTTATTAATAGTAATCAATTA
```

CGGGGTCATTAGTTCATAGCCCATATATGGAGTTCCGCGTTACATAACTTACGGTAAATGGCCCGCCTGGCTGACCGCCCAACGACCCCCG

CCCATTGACGTCAATAATGACGTATGTTCCCATAGTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTCAATGACGGTAAATGGCCCGCCTGGCATTATGCCC

AGTACATGACCTTATGGGACTTTCCTACTTGGCAGTACATCTACGTATTAGTCATCGCTATTACCATGGTGATGCGGTTTTGGCAGTACAT

CAATGGGCGTGGATAGCGGTTTGACTCACGGGGATTTCCAAGTCTCCACCCCATTGACGTCAATGGGAGTTTGTTTTGGCACCAAAATCAA

CGGGACTTTCCAAAATGTCGTAACAACTCCGCCCCATTGACGCAAATGGGCGGTAGGCGTGTACGGTGGGAGGTCTATATAAGCAGAGCTC

TCTGGCTAACTAGAGAACCCACTGCTTACTGGCTTATCGAAATTAATACGACTCACTATAGGGAGACCCAAGCTGGCTAGCGTTTAAACTT

AAGCTTGGTACCGAGCTCGGATCCACTAGTCCAGTGTGGTGGAATTCTGCAGATATCCAGCACAGTGGCGGCCGCCatgggatggagctgt atcatcctcttcttggtggcaacagctacaggcgtgcactccgacatccagctgacccagtcccctccagcctgtccgcctctgtgggcg acagagtgaccatcacctgttccgccagccaggacatctccaactacctgaactggtatcagcagaagcccggcaaggcccccaaggtgct gatctacttcacctcctccctgcactccggcgtgccctccagattctccggctctggctccggcaccgactttaccctgaccatctccagc ctgcagcccgaggacttcgccacctactactgccagcagtactccaccgtgccctggaccttcggccagggcaccaaggtggaaatcaagc ggaccgtggccgctcccctccgtgttcatcttcccacccctccgacgagcagctgaagtccggaaccgcctccgtcgtgtgcctgctgaacaa cttctaccccgcgaggccaaggtgcagtggaaggtggacaacgccctgcagagcggcaactcccaggaatccgtcaccgagcaggactcc aaggacagcacctactccctgtccagcaccctgaccctgtccaaggccgactacgagaagcacaaggtgtacgcctgcgaagtgacccacc agggcctcagctccccagtgaccaagtccttcaaccggggcgagtgctagtaTCTAGAGGGCCCGTTTAAACCCGCTGATCAGCCTCGAC TGTGCCTTCTAGTTGCCAGCCATCTGTTGTTTGCCCCTCCCCCGTGCCTTCCTTGACCCTGGAAGGTGCCACTCCCACTGTCCTTTCCTAA TAAAATGAGGAAATTGCATCGCATTGTCTGAGTAGGTGTCATTCTATTCTGGGGGGTGGGGTGGGGCAGGACAGCAAGGGGGAGGATTGGG AAGACAATAGCAGGCATGCTGGGGATGCGGTGGGCTCTATGGCTTCTGAGGCGGAAAGAACCAGCTGGGGCTCTAGGGGGTATCCCCACGC GCCCTGTAGCGGCGCATTAAGCGCGGCGGGTGTGGTGGTTACGCGCAGCGTGACCGCTACACTTGCCAGCGCCCTAGCGCCCGCTCCTTTC GCTTTCTTCCCTTCCTTTCTCGCCACGTTCGCCGGCTTTCCCCGTCAAGCTCTAAATCGGGGGCTCCCTTTAGGGTTCCGATTTAGTGCTT TACGGCACCTCGACCCCAAAAAACTTGATTAGGGTGATGGTTCACGTAGTGGGCCATCGCCCTGATAGACGGTTTTTCGCCCTTTGACGTT GGAGTCCACGTTCTTTAATAGTGGACTCTTGTTCCAAACTGGAACAACACTCAACCCTATCTCGGTCTATTCTTTTGATTTATAAGGGATT TTGCCGATTTCGGCCTATTGGTTAAAAAATGAGCTGATTTAACAAAAATTTAACGCGAATTAATTCTGTGGAATGTGTGTCAGTTAGGGTG TGGAAAGTCCCCAGGCTCCCCAGCAGGCAGAAGTATGCAAAGCATGCATCTCAATTAGTCAGCAACCAGGTGTGGAAAGTCCCCAGGCTCC CCAGCAGGCAGAAGTATGCAAAGCATGCATCTCAATTAGTCAGCAACCATAGTCCCGCCCCTAACTCCGCCCATCCCGCCCCTAACTCCGC CCAGTTCCGCCCATTCTCCGCCCCATGGCTGACTAATTTTTTTTATTTATGCAGAGGCCGAGGCCGCCTCTGCCTCTGAGCTATTCCAGAA GTAGTGAGGAGGCTTTTTTGGAGGCCTAGGCTTTTGCAAAAAGCTCCCGGGAGCTTGTATATCCATTTTCGGATCTGATCAAGAGACAGGA TGAGGATCGTTTCGCATGATTGAACAAGATGGATTGCACCTGCTCTGATGCCGCCGTGTTCCGGCTGTCAGCGCAGGGGCGCCCGGTTCTT TTTGTCAAGACCGACCTGTCCGGTGCCCTGAATGAACTGCAGGACGAGGCAGCGCGGCTATCGTGGCTGGCCACGACGGGCGTTCCTTGCG CAGCTGTGCTCGACGTTGTCACTGAAGCGGGAAGGGACTGGCTGCTATTGGGCGAAGTGCCGGGGCAGGATCTCCTGTCATCTCACCTTGC TCCTGCCGAGAAAGTATCCATCATGGCTGATGCAATGCGGCGGCTGCATACGCTTGATCCGGCTACCTGCCCATTCGACCACCAAGCGAAA CATCGCATCGAGCGAGCACGTACTCGGATGGAAGCCGGTCTTGTCGATCAGGATGATCTGGACGAAGAGCATCAGGGGCTCGCGCCAGCCG AACTGTTCGCCAGGCTCAAGGCGCGCATGCCCGACGGCGAGGATCTCGTCGTGACCCATGGCGATGCCTGCTTGCCGAATATCATGGTGGA AAATGGCCGCTTTTCTGGATTCATCGACTGTGGCCGGCTGGGTGTGGCGGACCGCTATCAGGACATAGCGTTGGCTACCCGTGATATTGCT GAAGAGCTTGGCGGCGAATGGGCTGACCGCTTCCTCGTGCTTTACGGTATCGCCGCTCCCGATTCGCAGCGCATCGCCTTCTATCGCCTTC TTGACGAGTTCTTCTGAGCGGGACTCTGGGGTTCGAAATGACCGACCAAGCGACGCCCAACCTGCCATCACGAGATTTCGATTCCACCGCC GCCTTCTATGAAAGGTTGGGCTTCGGAATCGTTTTCCGGGACGCCGGCTGGATGATCCTCCAGCGCGGGGATCTCATGCTGGAGTTCTTCG CCCACCCCAACTTGTTTATTGCAGCTTATAATGGTTACAAATAAAGCAATAGCATCACAAATTTCACAAATAAAGCATTTTTTTCACTGCA TTCTAGTTGTGGTTTGTCCAAACTCATCAATGTATCTTATCATGTCTGTATACCGTCGACCTCTAGCTAGAGCTTGGCGTAATCATGGTCA -continued

```
TAGCTGTTTCCTGTGTGAAATTGTTATCCGCTCACAATTCCACACAACATACGAGCCGGAAGCATAAAGTGTAAAGCCTGGGGTGCCTAAT
GAGTGAGCTAACTCACATTAATTGCGTTGCGCTCACTGCCCGCTTTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCGGTGCTACAGAGTTCTTGAAGTGGTGGCCT
AACTACGGCTACACTAGAAGAACAGTATTTGGTATCTGCGCTCTGCTGAAGCCAGTTACCTTCGGAAAAAGAGTTGGTAGCTCTTGATCCG
GCAAACAAACCACCGCTGGTAGCGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAAAAGGATCTTCACCTAGATCCTT
TTAAATTAAAAATGAAGTTTTAAATCAATCTAAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGATCGTTGTCAGAAGTAAGTTGGCCGCAGTGTTATCACTCATG
GTTATGGCAGCACTGCATAATTCTCTTACTGTCATGCCATCCGTAAGATGCTTTTCTGTGACTGGTGAGTACTCAACCAAGTCATTCTGAG
AATAGTGTATGCGGCGACCGAGTTGCTCTTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGTC
```

---

SEQUENCE LISTING

<160> NUMBER OF SEQ ID NOS: 56

<210> SEQ ID NO 1
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

```
Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
            130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
            210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
            275                 280                 285

Gly Gly Gly Ser Asp Ile Gln Met Thr Gln Ser Pro Ser Ser Leu Ser
290                 295                 300

Ala Ser Val Gly Asp Arg Val Thr Ile Thr Cys Ser Ala Ser Gln Asp
305                 310                 315                 320

Ile Ser Asn Tyr Leu Asn Trp Tyr Gln Gln Lys Pro Gly Lys Ala Pro
                325                 330                 335

Lys Val Leu Ile Tyr Phe Thr Ser Ser Leu His Ser Gly Val Pro Ser
            340                 345                 350

Arg Phe Ser Gly Ser Gly Ser Gly Thr Asp Phe Thr Leu Thr Ile Ser
            355                 360                 365

Ser Leu Gln Pro Glu Asp Phe Ala Thr Tyr Tyr Cys Gln Gln Tyr Ser
            370                 375                 380

Thr Val Pro Trp Thr Phe Gly Gln Gly Thr Lys Val Glu Ile Lys Arg
385                 390                 395                 400

Thr Val Ala Ala Pro Ser Val Phe Ile Phe Pro Pro Ser Asp Glu Gln
                405                 410                 415

Leu Lys Ser Gly Thr Ala Ser Val Val Cys Leu Leu Asn Asn Phe Tyr
            420                 425                 430

Pro Arg Glu Ala Lys Val Gln Trp Lys Val Asp Asn Ala Leu Gln Ser
            435                 440                 445

Gly Asn Ser Gln Glu Ser Val Thr Glu Gln Asp Ser Lys Asp Ser Thr
450                 455                 460

Tyr Ser Leu Ser Ser Thr Leu Thr Leu Ser Lys Ala Asp Tyr Glu Lys
465                 470                 475                 480

His Lys Val Tyr Ala Cys Glu Val Thr His Gln Gly Leu Ser Ser Pro
                485                 490                 495

Val Thr Lys Ser Phe Asn Arg Gly Glu Cys
```

-continued

```
                500               505

<210> SEQ ID NO 2
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 3
<211> LENGTH: 498
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255
```

```
Tyr Thr Cys Asn Val Thr Glu Ser Val Asn Asp His Gln Asp Glu Lys
            260                 265                 270

Ala Ile Asn Ile Thr Val Val Glu Ser Gly Gly Asp Ile Gln Met
        275                 280                 285

Thr Gln Ser Pro Ser Ser Leu Ser Ala Ser Val Gly Asp Arg Val Thr
    290                 295                 300

Ile Thr Cys Ser Ala Ser Gln Asp Ile Ser Asn Tyr Leu Asn Trp Tyr
305                 310                 315                 320

Gln Gln Lys Pro Gly Lys Ala Pro Lys Val Leu Ile Tyr Phe Thr Ser
                325                 330                 335

Ser Leu His Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Gln Gln Tyr Ser Thr Val Pro Trp Thr Phe Gly Gln
    370                 375                 380

Gly Thr Lys Val Glu Ile Lys Arg Thr Val Ala Ala Pro Ser Val Phe
385                 390                 395                 400

Ile Phe Pro Pro Ser Asp Glu Gln Leu Lys Ser Gly Thr Ala Ser Val
                405                 410                 415

Val Cys Leu Leu Asn Asn Phe Tyr Pro Arg Glu Ala Lys Val Gln Trp
            420                 425                 430

Lys Val Asp Asn Ala Leu Gln Ser Gly Asn Ser Gln Glu Ser Val Thr
        435                 440                 445

Glu Gln Asp Ser Lys Asp Ser Thr Tyr Ser Leu Ser Ser Thr Leu Thr
    450                 455                 460

Leu Ser Lys Ala Asp Tyr Glu Lys His Lys Val Tyr Ala Cys Glu Val
465                 470                 475                 480

Thr His Gln Gly Leu Ser Ser Pro Val Thr Lys Ser Phe Asn Arg Gly
                485                 490                 495

Glu Cys

<210> SEQ ID NO 4
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
                100                 105                 110
```

-continued

```
Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
            275                 280                 285

Gly Gly Gly Ser Glu Val Gln Leu Val Glu Ser Gly Gly Gly Leu Val
    290                 295                 300

Gln Pro Gly Gly Ser Leu Arg Leu Ser Cys Ala Ala Ser Gly Tyr Thr
305                 310                 315                 320

Phe Thr Asn Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
    355                 360                 365

Ser Thr Ala Tyr Leu Gln Met Asn Ser Leu Arg Ala Glu Asp Thr Ala
    370                 375                 380

Val Tyr Tyr Cys Ala Lys Tyr Pro His Tyr Tyr Gly Ser Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
    450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Thr Cys Pro Pro Cys Pro
            515                 520                 525
```

```
Ala Pro Glu Leu Leu Gly Gly Pro Ser Val Phe Leu Phe Pro Pro Lys
        530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 737
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Glu Val Gln Leu

-continued

```
                275                 280                 285
Val Glu Ser Gly Gly Gly Leu Val Gln Pro Gly Gly Ser Leu Arg Leu
        290                 295                 300

Ser Cys Ala Ala Ser Gly Tyr Thr Phe Thr Asn Tyr Gly Met Asn Trp
305                 310                 315                 320

Val Arg Gln Ala Pro Gly Lys Gly Leu Glu Trp Val Gly Trp Ile Asn
                325                 330                 335

Thr Tyr Thr Gly Glu Pro Thr Tyr Ala Ala Asp Phe Lys Arg Arg Phe
                340                 345                 350

Thr Phe Ser Leu Asp Thr Ser Lys Ser Thr Ala Tyr Leu Gln Met Asn
        355                 360                 365

Ser Leu Arg Ala Glu Asp Thr Ala Val Tyr Tyr Cys Ala Lys Tyr Pro
        370                 375                 380

His Tyr Tyr Gly Ser Ser His Trp Tyr Phe Asp Val Trp Gly Gln Gly
385                 390                 395                 400

Thr Leu Val Thr Val Ser Ser Ala Ser Thr Lys Gly Pro Ser Val Phe
                405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
        435                 440                 445

Asn Ser Gly Ala Leu Thr Ser Gly Val His Thr Phe Pro Ala Val Leu
450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Asn His Lys Pro
                485                 490                 495

Ser Asn Thr Lys Val Asp Lys Lys Val Glu Pro Lys Ser Cys Asp Lys
                500                 505                 510

Thr His Thr Cys Pro Pro Cys Pro Ala Pro Glu Leu Leu Gly Gly Pro
        515                 520                 525

Ser Val Phe Leu Phe Pro Pro Lys Pro Lys Asp Thr Leu Met Ile Ser
530                 535                 540

Arg Thr Pro Glu Val Thr Cys Val Val Val Asp Val Ser His Glu Asp
545                 550                 555                 560

Pro Glu Val Lys Phe Asn Trp Tyr Val Asp Gly Val Glu Val His Asn
                565                 570                 575

Ala Lys Thr Lys Pro Arg Glu Glu Gln Tyr Asn Ser Thr Tyr Arg Val
                580                 585                 590

Val Ser Val Leu Thr Val Leu His Gln Asp Trp Leu Asn Gly Lys Glu
        595                 600                 605

Tyr Lys Cys Lys Val Ser Asn Lys Ala Leu Pro Ala Pro Ile Glu Lys
        610                 615                 620

Thr Ile Ser Lys Ala Lys Gly Gln Pro Arg Glu Pro Gln Val Tyr Thr
625                 630                 635                 640

Leu Pro Pro Ser Arg Glu Glu Met Thr Lys Asn Gln Val Ser Leu Thr
                645                 650                 655

Cys Leu Val Lys Gly Phe Tyr Pro Ser Asp Ile Ala Val Glu Trp Glu
                660                 665                 670

Ser Asn Gly Gln Pro Glu Asn Asn Tyr Lys Thr Thr Pro Pro Val Leu
        675                 680                 685

Asp Ser Asp Gly Ser Phe Phe Leu Tyr Ser Lys Leu Thr Val Asp Lys
690                 695                 700
```

-continued

```
Ser Arg Trp Gln Gln Gly Asn Val Phe Ser Cys Ser Val Met His Glu
705                 710                 715                 720

Ala Leu His Asn His Tyr Thr Gln Lys Ser Leu Ser Leu Ser Pro Gly
                725                 730                 735

Lys

<210> SEQ ID NO 7
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

```
Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Gly Gly Gly Ser Gly Gly Gly Ser Gly Gly
            450                 455                 460

Gly Gly Ser Gly Gly Gly Ser Gly Leu Val Val Thr Pro Gly
465                 470                 475                 480

Pro Glu Leu Val Leu Asn Val Ser Ser Thr Phe Val Leu Thr Cys Ser
            485                 490                 495

Gly Ser Ala Pro Val Val Trp Glu Arg Met Ser Gln Glu Pro Pro Gln
            500                 505                 510

Glu Met Ala Lys Ala Gln Asp Gly Thr Phe Ser Ser Val Leu Thr Leu
            515                 520                 525

Thr Asn Leu Thr Gly Leu Asp Thr Gly Glu Tyr Phe Cys Thr His Asn
            530                 535                 540

Asp Ser Arg Gly Leu Glu Thr Asp Glu Arg Lys Arg Leu Tyr Ile Phe
545                 550                 555                 560

Val Pro Asp Pro Thr Val Gly Phe Leu Pro Asn Asp Ala Glu Glu Leu
            565                 570                 575

Phe Ile Phe Leu Thr Glu Ile Thr Glu Ile Thr Ile Pro Cys Arg Val
            580                 585                 590

Thr Asp Pro Gln Leu Val Val Thr Leu His Glu Lys Lys Gly Asp Val
            595                 600                 605

Ala Leu Pro Val Pro Tyr Asp His Gln Arg Gly Phe Ser Gly Ile Phe
            610                 615                 620

Glu Asp Arg Ser Tyr Ile Cys Lys Thr Thr Ile Gly Asp Arg Glu Val
625                 630                 635                 640

Asp Ser Asp Ala Tyr Tyr Val Tyr Arg Leu Gln Val Ser Ser Ile Asn
            645                 650                 655

Val Ser Val Asn Ala Val Gln Thr Val Val Arg Gln Gly Glu Asn Ile
            660                 665                 670

Thr Leu Met Cys Ile Val Ile Gly Asn Glu Val Val Asn Phe Glu Trp
            675                 680                 685

Thr Tyr Pro Arg Lys Glu Ser Gly Arg Leu Val Glu Pro Val Thr Asp
            690                 695                 700

Phe Leu Leu Asp Met Pro Tyr His Ile Arg Ser Ile Leu His Ile Pro
705                 710                 715                 720

Ser Ala Glu Leu Glu Asp Ser Gly Thr Tyr Thr Cys Asn Val Thr Glu
            725                 730                 735
```

-continued

Ser Val Asn Asp His Gln Asp Glu Lys Ala Ile Asn Ile Thr Val Val
            740                 745                 750

Glu Ser Gly
    755

<210> SEQ ID NO 8
<211> LENGTH: 745
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Gly Leu Val
    290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

```
Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
            355                 360                 365

Ser Thr Ala Tyr Leu Gln Met Asn Ser Leu Arg Ala Glu Asp Thr Ala
370                 375                 380

Val Tyr Tyr Cys Ala Lys Tyr Pro Tyr Tyr Gly Thr Ser His Trp
385                 390                 395             400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
            450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Thr Cys Pro Pro Cys Pro
            515                 520                 525

Ala Pro Glu Ala Ala Gly Ala Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
            610                 615                 620

Ala Leu Pro Ala Pro Ile Glu Lys Thr Ile Ser Lys Ala Lys Gly Gln
625                 630                 635                 640

Pro Arg Glu Pro Cys Val Tyr Thr Leu Pro Pro Ser Arg Glu Glu Met
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Phe Leu
            690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745
```

<210> SEQ ID NO 9
<211> LENGTH: 745
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
    50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Gly Leu Val
    290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
        355                 360                 365
```

-continued

```
Ser Thr Ala Tyr Leu Gln Met Asn Ser Leu Arg Ala Glu Asp Thr Ala
    370                 375                 380
Val Tyr Tyr Cys Ala Lys Tyr Pro Tyr Tyr Gly Thr Ser His Trp
385                 390                 395                 400
Tyr Phe Asp Val Trp Gly Gln Gly Thr Leu Val Thr Val Ser Ser Ala
                405                 410                 415
Ser Thr Lys Gly Pro Ser Val Phe Pro Leu Ala Pro Ser Ser Lys Ser
                420                 425                 430
Thr Ser Gly Gly Thr Ala Ala Leu Gly Cys Leu Val Lys Asp Tyr Phe
                435                 440                 445
Pro Glu Pro Val Thr Val Ser Trp Asn Ser Gly Ala Leu Thr Ser Gly
    450                 455                 460
Val His Thr Phe Pro Ala Val Leu Gln Ser Ser Gly Leu Tyr Ser Leu
465                 470                 475                 480
Ser Ser Val Val Thr Val Pro Ser Ser Ser Leu Gly Thr Gln Thr Tyr
                485                 490                 495
Ile Cys Asn Val Asn His Lys Pro Ser Asn Thr Lys Val Asp Lys Lys
                500                 505                 510
Val Glu Pro Lys Ser Cys Asp Lys Thr His Thr Cys Pro Pro Cys Pro
    515                 520                 525
Ala Pro Glu Ala Ala Gly Ala Pro Ser Val Phe Leu Phe Pro Pro Lys
530                 535                 540
Pro Lys Asp Thr Leu Met Ile Ser Arg Thr Pro Glu Val Thr Cys Val
545                 550                 555                 560
Val Val Asp Val Ser His Glu Asp Pro Glu Val Lys Phe Asn Trp Tyr
                565                 570                 575
Val Asp Gly Val Glu Val His Asn Ala Lys Thr Lys Pro Arg Glu Glu
                580                 585                 590
Gln Tyr Asn Ser Thr Tyr Arg Val Val Ser Val Leu Thr Val Leu His
    595                 600                 605
Gln Asp Trp Leu Asn Gly Lys Glu Tyr Lys Cys Lys Val Ser Asn Lys
610                 615                 620
Ala Leu Pro Ala Pro Ile Glu Lys Thr Ile Ser Lys Ala Lys Gly Gln
625                 630                 635                 640
Pro Arg Glu Pro Gln Val Tyr Thr Leu Pro Pro Ser Arg Glu Glu Met
                645                 650                 655
Thr Lys Asn Gln Val Ser Leu Thr Cys Leu Val Lys Gly Phe Tyr Pro
                660                 665                 670
Ser Asp Ile Ala Val Glu Trp Glu Ser Asn Gly Gln Pro Glu Asn Asn
    675                 680                 685
Tyr Lys Thr Thr Pro Pro Val Leu Asp Ser Asp Gly Ser Phe Phe Leu
690                 695                 700
Tyr Ser Lys Leu Thr Val Asp Lys Ser Arg Trp Gln Gln Gly Asn Val
705                 710                 715                 720
Phe Ser Cys Ser Val Met His Glu Ala Leu His Asn His Tyr Thr Gln
                725                 730                 735
Lys Ser Leu Ser Cys Ser Pro Gly Lys
                740                 745

<210> SEQ ID NO 10
<211> LENGTH: 214
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 10

```
Asp Ile Gln Leu Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
            20                  25                  30
Leu Asn Trp Tyr Gln Gln Lys Pro Gly Lys Ala Pro Lys Val Leu Ile
        35                  40                  45
Tyr Phe Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 11
<211> LENGTH: 1106
<212> TYPE: PRT
<213> ORGANISM: Homo sapiens

<400> SEQUENCE: 11

```
Met Arg Leu Pro Gly Ala Met Pro Ala Leu Ala Leu Lys Gly Glu Leu
1               5                   10                  15
Leu Leu Leu Ser Leu Leu Leu Leu Glu Pro Gln Ile Ser Gln Gly
            20                  25                  30
Leu Val Val Thr Pro Pro Gly Pro Glu Leu Val Leu Asn Val Ser Ser
        35                  40                  45
Thr Phe Val Leu Thr Cys Ser Gly Ser Ala Pro Val Val Trp Glu Arg
    50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
            100                 105                 110
Arg Lys Arg Leu Tyr Ile Phe Val Pro Asp Pro Thr Val Gly Phe Leu
        115                 120                 125
```

```
Pro Asn Asp Ala Glu Glu Leu Phe Ile Phe Leu Thr Glu Ile Thr Glu
    130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
            195                 200                 205
Leu Gln Val Ser Ser Ile Asn Val Ser Val Asn Ala Val Gln Thr Val
210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
    275                 280                 285
Tyr Thr Cys Asn Val Thr Glu Ser Val Asn Asp His Gln Asp Glu Lys
            290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
            340                 345                 350
Asp Asn Arg Thr Leu Gly Asp Ser Ser Ala Gly Glu Ile Ala Leu Ser
        355                 360                 365
Thr Arg Asn Val Ser Glu Thr Arg Tyr Val Ser Glu Leu Thr Leu Val
370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Val Pro His Ser Leu
        515                 520                 525
Pro Phe Lys Val Val Val Ile Ser Ala Ile Leu Ala Leu Val Val Leu
530                 535                 540
Thr Ile Ile Ser Leu Ile Ile Leu Ile Met Leu Trp Gln Lys Lys Pro
```

```
                545                 550                 555                 560
            Arg Tyr Glu Ile Arg Trp Lys Val Ile Glu Ser Val Ser Ser Asp Gly
                            565                 570                 575

His Glu Tyr Ile Tyr Val Asp Pro Met Gln Leu Pro Tyr Asp Ser Thr
                            580                 585                 590

Trp Glu Leu Pro Arg Asp Gln Leu Val Leu Gly Arg Thr Leu Gly Ser
                            595                 600                 605

Gly Ala Phe Gly Gln Val Val Glu Ala Thr Ala His Gly Leu Ser His
                610                 615                 620

Ser Gln Ala Thr Met Lys Val Ala Val Lys Met Leu Lys Ser Thr Ala
            625                 630                 635                 640

Arg Ser Ser Glu Lys Gln Ala Leu Met Ser Glu Leu Lys Ile Met Ser
                            645                 650                 655

His Leu Gly Pro His Leu Asn Val Val Asn Leu Leu Gly Ala Cys Thr
                            660                 665                 670

Lys Gly Gly Pro Ile Tyr Ile Ile Thr Glu Tyr Cys Arg Tyr Gly Asp
                            675                 680                 685

Leu Val Asp Tyr Leu His Arg Asn Lys His Thr Phe Leu Gln His His
                690                 695                 700

Ser Asp Lys Arg Arg Pro Pro Ser Ala Glu Leu Tyr Ser Asn Ala Leu
            705                 710                 715                 720

Pro Val Gly Leu Pro Leu Pro Ser His Val Ser Leu Thr Gly Glu Ser
                            725                 730                 735

Asp Gly Gly Tyr Met Asp Met Ser Lys Asp Glu Ser Val Asp Tyr Val
                            740                 745                 750

Pro Met Leu Asp Met Lys Gly Asp Val Lys Tyr Ala Asp Ile Glu Ser
                            755                 760                 765

Ser Asn Tyr Met Ala Pro Tyr Asp Asn Tyr Val Pro Ser Ala Pro Glu
                770                 775                 780

Arg Thr Cys Arg Ala Thr Leu Ile Asn Glu Ser Pro Val Leu Ser Tyr
            785                 790                 795                 800

Met Asp Leu Val Gly Phe Ser Tyr Gln Val Ala Asn Gly Met Glu Phe
                            805                 810                 815

Leu Ala Ser Lys Asn Cys Val His Arg Asp Leu Ala Ala Arg Asn Val
                            820                 825                 830

Leu Ile Cys Glu Gly Lys Leu Val Lys Ile Cys Asp Phe Gly Leu Ala
                            835                 840                 845

Arg Asp Ile Met Arg Asp Ser Asn Tyr Ile Ser Lys Gly Ser Thr Phe
                850                 855                 860

Leu Pro Leu Lys Trp Met Ala Pro Glu Ser Ile Phe Asn Ser Leu Tyr
            865                 870                 875                 880

Thr Thr Leu Ser Asp Val Trp Ser Phe Gly Ile Leu Leu Trp Glu Ile
                            885                 890                 895

Phe Thr Leu Gly Gly Thr Pro Tyr Pro Glu Leu Pro Met Asn Glu Gln
                            900                 905                 910

Phe Tyr Asn Ala Ile Lys Arg Gly Tyr Arg Met Ala Gln Pro Ala His
                            915                 920                 925

Ala Ser Asp Glu Ile Tyr Glu Ile Met Gln Lys Cys Trp Glu Glu Lys
                930                 935                 940

Phe Glu Ile Arg Pro Pro Phe Ser Gln Leu Val Leu Leu Leu Glu Arg
            945                 950                 955                 960

Leu Leu Gly Glu Gly Tyr Lys Lys Lys Tyr Gln Gln Val Asp Glu Glu
                            965                 970                 975
```

```
Phe Leu Arg Ser Asp His Pro Ala Ile Leu Arg Ser Gln Ala Arg Leu
                980                 985                 990

Pro Gly Phe His Gly Leu Arg Ser  Pro Leu Asp Thr Ser  Ser Val Leu
            995                 1000                1005

Tyr Thr  Ala Val Gln Pro Asn  Glu Gly Asp Asn Asp  Tyr Ile Ile
    1010                 1015                1020

Pro Leu  Pro Asp Pro Lys Pro  Glu Val Ala Asp Glu  Gly Pro Leu
    1025                 1030                1035

Glu Gly  Ser Pro Ser Leu Ala  Ser Ser Thr Leu Asn  Glu Val Asn
    1040                 1045                1050

Thr Ser  Ser Thr Ile Ser Cys  Asp Ser Pro Leu Glu  Pro Gln Asp
    1055                 1060                1065

Glu Pro  Glu Pro Glu Pro Gln  Leu Glu Leu Gln Val  Glu Pro Glu
    1070                 1075                1080

Pro Glu  Leu Glu Gln Leu Pro  Asp Ser Gly Cys Pro  Ala Pro Arg
    1085                 1090                1095

Ala Glu  Ala Glu Asp Ser Phe  Leu
    1100                 1105

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

<210> SEQ ID NO 13
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230
```

<210> SEQ ID NO 14
<211> LENGTH: 1338
<212> TYPE: PRT
<213> ORGANISM: Homo sapiens

<400> SEQUENCE: 14

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
```

-continued

```
                65                  70                  75                  80
Cys Gly Arg Asn Gly Lys Gln Phe Cys Ser Thr Leu Thr Leu Asn Thr
                    85                  90                  95

Ala Gln Ala Asn His Thr Gly Phe Tyr Ser Cys Lys Tyr Leu Ala Val
                    100                 105                 110

Pro Thr Ser Lys Lys Lys Glu Thr Glu Ser Ala Ile Tyr Ile Phe Ile
                    115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                    165                 170                 175

Leu Ile Pro Asp Gly Lys Arg Ile Ile Trp Asp Ser Arg Lys Gly Phe
                    180                 185                 190

Ile Ile Ser Asn Ala Thr Tyr Lys Glu Ile Gly Leu Leu Thr Cys Glu
                    195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                    245                 250                 255

Pro Leu Asn Thr Arg Val Gln Met Thr Trp Ser Tyr Pro Asp Glu Lys
                    260                 265                 270

Asn Lys Arg Ala Ser Val Arg Arg Arg Ile Asp Gln Ser Asn Ser His
                    275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                    325                 330                 335

Lys His Arg Lys Gln Gln Val Leu Glu Thr Val Ala Gly Lys Arg Ser
                    340                 345                 350

Tyr Arg Leu Ser Met Lys Val Lys Ala Phe Pro Ser Pro Glu Val Val
                    355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                    405                 410                 415

Asn Leu Thr Ala Thr Leu Ile Val Asn Val Lys Pro Gln Ile Tyr Glu
                    420                 425                 430

Lys Ala Val Ser Ser Phe Pro Asp Pro Ala Leu Tyr Pro Leu Gly Ser
                    435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                    485                 490                 495
```

-continued

Asn Met Gly Asn Arg Ile Glu Ser Ile Thr Gln Arg Met Ala Ile Ile
          500                 505                 510

Glu Gly Lys Asn Lys Met Ala Ser Thr Leu Val Val Ala Asp Ser Arg
          515                 520                 525

Ile Ser Gly Ile Tyr Ile Cys Ile Ala Ser Asn Lys Val Gly Thr Val
          530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
              565                 570                 575

Cys Thr Val Asn Lys Phe Leu Tyr Arg Asp Val Thr Trp Ile Leu Leu
          580                 585                 590

Arg Thr Val Asn Asn Arg Thr Met His Tyr Ser Ile Ser Lys Gln Lys
          595                 600                 605

Met Ala Ile Thr Lys Glu His Ser Ile Thr Leu Asn Leu Thr Ile Met
          610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
              645                 650                 655

Asp Gln Glu Ala Pro Tyr Leu Leu Arg Asn Leu Ser Asp His Thr Val
          660                 665                 670

Ala Ile Ser Ser Ser Thr Thr Leu Asp Cys His Ala Asn Gly Val Pro
          675                 680                 685

Glu Pro Gln Ile Thr Trp Phe Lys Asn Asn His Lys Ile Gln Gln Glu
          690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
              725                 730                 735

Lys Gly Ser Val Glu Ser Ser Ala Tyr Leu Thr Val Gln Gly Thr Ser
          740                 745                 750

Asp Lys Ser Asn Leu Glu Leu Ile Thr Leu Thr Cys Thr Cys Val Ala
          755                 760                 765

Ala Thr Leu Phe Trp Leu Leu Leu Thr Leu Phe Ile Arg Lys Met Lys
          770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                  805                 810                 815

Ala Ser Lys Trp Glu Phe Ala Arg Glu Arg Leu Lys Leu Gly Lys Ser
              820                 825                 830

Leu Gly Arg Gly Ala Phe Gly Lys Val Val Gln Ala Ser Ala Phe Gly
              835                 840                 845

Ile Lys Lys Ser Pro Thr Cys Arg Thr Val Ala Val Lys Met Leu Lys
              850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
              885                 890                 895

Ala Cys Thr Lys Gln Gly Gly Pro Leu Met Val Ile Val Glu Tyr Cys
              900                 905                 910

```
Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
        930                 935                 940

Met Glu Pro Gly Leu Glu Gln Gly Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
```

-continued

```
            1310                1315                1320
Pro Pro Asp Tyr Asn Ser Val Val Leu Tyr Ser Thr Pro Pro Ile
    1325                1330                1335

<210> SEQ ID NO 15
<211> LENGTH: 1356
<212> TYPE: PRT
<213> ORGANISM: Homo sapiens

<400> SEQUENCE: 15

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350
```

-continued

```
Lys Tyr Leu Gly Tyr Pro Pro Glu Ile Lys Trp Tyr Lys Asn Gly
            355                 360                 365
Ile Pro Leu Glu Ser Asn His Thr Ile Lys Ala Gly His Val Leu Thr
370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
        595                 600                 605
Leu Trp Lys Leu Asn Ala Thr Met Phe Ser Asn Ser Thr Asn Asp Ile
    610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Arg His Cys Val Val
                645                 650                 655
Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Gln Ile Met Trp Phe Lys Asp Asn
    690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu Ile Ile Leu
        755                 760                 765
Val Gly Thr Ala Val Ile Ala Met Phe Phe Trp Leu Leu Leu Val Ile
```

-continued

```
                770             775             780
Ile Leu Arg Thr Val Lys Arg Ala Asn Gly Gly Glu Leu Lys Thr Gly
785             790             795             800

Tyr Leu Ser Ile Val Met Asp Pro Asp Glu Leu Pro Leu Asp Glu His
                805             810             815

Cys Glu Arg Leu Pro Tyr Asp Ala Ser Lys Trp Glu Phe Pro Arg Asp
                820             825             830

Arg Leu Lys Leu Gly Lys Pro Leu Gly Arg Gly Ala Phe Gly Gln Val
                835             840             845

Ile Glu Ala Asp Ala Phe Gly Ile Asp Lys Thr Ala Thr Cys Arg Thr
850             855             860

Val Ala Val Lys Met Leu Lys Glu Gly Ala Thr His Ser Glu His Arg
865             870             875             880

Ala Leu Met Ser Glu Leu Lys Ile Leu Ile His Ile Gly His His Leu
                885             890             895

Asn Val Val Asn Leu Leu Gly Ala Cys Thr Lys Pro Gly Gly Pro Leu
                900             905             910

Met Val Ile Val Glu Phe Cys Lys Phe Gly Asn Leu Ser Thr Tyr Leu
                915             920             925

Arg Ser Lys Arg Asn Glu Phe Val Pro Tyr Lys Thr Lys Gly Ala Arg
930             935             940

Phe Arg Gln Gly Lys Asp Tyr Val Gly Ala Ile Pro Val Asp Leu Lys
945             950             955             960

Arg Arg Leu Asp Ser Ile Thr Ser Ser Gln Ser Ser Ala Ser Ser Gly
                965             970             975

Phe Val Glu Glu Lys Ser Leu Ser Asp Val Glu Glu Glu Glu Ala Pro
                980             985             990

Glu Asp Leu Tyr Lys Asp Phe Leu Thr Leu Glu His Leu Ile Cys Tyr
                995             1000            1005

Ser Phe Gln Val Ala Lys Gly Met Glu Phe Leu Ala Ser Arg Lys
    1010            1015            1020

Cys Ile His Arg Asp Leu Ala Ala Arg Asn Ile Leu Leu Ser Glu
    1025            1030            1035

Lys Asn Val Val Lys Ile Cys Asp Phe Gly Leu Ala Arg Asp Ile
    1040            1045            1050

Tyr Lys Asp Pro Asp Tyr Val Arg Lys Gly Asp Ala Arg Leu Pro
    1055            1060            1065

Leu Lys Trp Met Ala Pro Glu Thr Ile Phe Asp Arg Val Tyr Thr
    1070            1075            1080

Ile Gln Ser Asp Val Trp Ser Phe Gly Val Leu Leu Trp Glu Ile
    1085            1090            1095

Phe Ser Leu Gly Ala Ser Pro Tyr Pro Gly Val Lys Ile Asp Glu
    1100            1105            1110

Glu Phe Cys Arg Arg Leu Lys Glu Gly Thr Arg Met Arg Ala Pro
    1115            1120            1125

Asp Tyr Thr Thr Pro Glu Met Tyr Gln Thr Met Leu Asp Cys Trp
    1130            1135            1140

His Gly Glu Pro Ser Gln Arg Pro Thr Phe Ser Glu Leu Val Glu
    1145            1150            1155

His Leu Gly Asn Leu Leu Gln Ala Asn Ala Gln Gln Asp Gly Lys
    1160            1165            1170

Asp Tyr Ile Val Leu Pro Ile Ser Glu Thr Leu Ser Met Glu Glu
    1175            1180            1185
```

-continued

```
Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 16
<211> LENGTH: 1363
<212> TYPE: PRT
<213> ORGANISM: Homo sapiens

<400> SEQUENCE: 16

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
        50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
```

```
            180              185              190
Val Ser Thr Pro Leu Leu His Asp Ala Leu Tyr Leu Gln Cys Glu Thr
        195              200              205
Thr Trp Gly Asp Gln Asp Phe Leu Ser Asn Pro Phe Leu Val His Ile
        210              215              220
Thr Gly Asn Glu Leu Tyr Asp Ile Gln Leu Leu Pro Arg Lys Ser Leu
225              230              235              240
Glu Leu Leu Val Gly Glu Lys Leu Val Leu Asn Cys Thr Val Trp Ala
                245              250              255
Glu Phe Asn Ser Gly Val Thr Phe Asp Trp Asp Tyr Pro Gly Lys Gln
            260              265              270
Ala Glu Arg Gly Lys Trp Val Pro Glu Arg Arg Ser Gln Gln Thr His
        275              280              285
Thr Glu Leu Ser Ser Ile Leu Thr Ile His Asn Val Ser Gln His Asp
        290              295              300
Leu Gly Ser Tyr Val Cys Lys Ala Asn Asn Gly Ile Gln Arg Phe Arg
305              310              315              320
Glu Ser Thr Glu Val Ile Val His Glu Asn Pro Phe Ile Ser Val Glu
                325              330              335
Trp Leu Lys Gly Pro Ile Leu Glu Ala Thr Ala Gly Asp Glu Leu Val
            340              345              350
Lys Leu Pro Val Lys Leu Ala Ala Tyr Pro Pro Pro Glu Phe Gln Trp
        355              360              365
Tyr Lys Asp Gly Lys Ala Leu Ser Gly Arg His Ser Pro His Ala Leu
        370              375              380
Val Leu Lys Glu Val Thr Glu Ala Ser Thr Gly Thr Tyr Thr Leu Ala
385              390              395              400
Leu Trp Asn Ser Ala Ala Gly Leu Arg Arg Asn Ile Ser Leu Glu Leu
                405              410              415
Val Val Asn Val Pro Pro Gln Ile His Glu Lys Glu Ala Ser Ser Pro
            420              425              430
Ser Ile Tyr Ser Arg His Ser Arg Gln Ala Leu Thr Cys Thr Ala Tyr
        435              440              445
Gly Val Pro Leu Pro Leu Ser Ile Gln Trp His Trp Arg Pro Trp Thr
        450              455              460
Pro Cys Lys Met Phe Ala Gln Arg Ser Leu Arg Arg Arg Gln Gln Gln
465              470              475              480
Asp Leu Met Pro Gln Cys Arg Asp Trp Arg Ala Val Thr Thr Gln Asp
                485              490              495
Ala Val Asn Pro Ile Glu Ser Leu Asp Thr Trp Thr Glu Phe Val Glu
            500              505              510
Gly Lys Asn Lys Thr Val Ser Lys Leu Val Ile Gln Asn Ala Asn Val
        515              520              525
Ser Ala Met Tyr Lys Cys Val Val Ser Asn Lys Val Gly Gln Asp Glu
        530              535              540
Arg Leu Ile Tyr Phe Tyr Val Thr Thr Ile Pro Asp Gly Phe Thr Ile
545              550              555              560
Glu Ser Lys Pro Ser Glu Glu Leu Leu Glu Gly Gln Pro Val Leu Leu
                565              570              575
Ser Cys Gln Ala Asp Ser Tyr Lys Tyr Glu His Leu Arg Trp Tyr Arg
            580              585              590
Leu Asn Leu Ser Thr Leu His Asp Ala His Gly Asn Pro Leu Leu Leu
        595              600              605
```

```
Asp Cys Lys Asn Val His Leu Phe Ala Thr Pro Leu Ala Ala Ser Leu
610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Val Ala Gly Ala
            690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
            755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu  Ala Glu Asp Leu Trp  Leu Ser Pro
            995             1000                1005

Leu Thr Met Glu Asp Leu Val  Cys Tyr Ser Phe Gln  Val Ala Arg
    1010                1015                1020
```

```
Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Glu Asp His Cys Ser Pro Ser Ala
    1340                1345                1350

Arg Val Thr Phe Phe Thr Asp Asn Ser Tyr
    1355                1360

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15
```

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 106
<212> TYPE: PRT
<213> ORGANISM: Homo sapiens

<400> SEQUENCE: 18

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr

```
                 50                  55                  60
Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
                100                 105
```

<210> SEQ ID NO 19
<211> LENGTH: 506
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 19

```
Leu Val Val Thr Pro Pro Gly Pro Glu Leu Val Leu Asn Val Ser Ser
 1               5                  10                  15

Thr Phe Val Leu Thr Cys Ser Gly Ser Ala Pro Val Val Trp Glu Arg
                 20                  25                  30

Met Ser Gln Glu Pro Pro Gln Glu Met Ala Lys Ala Gln Asp Gly Thr
                 35                  40                  45

Phe Ser Ser Val Leu Thr Leu Thr Asn Leu Thr Gly Leu Asp Thr Gly
                 50                  55                  60

Glu Tyr Phe Cys Thr His Asn Asp Ser Arg Gly Leu Glu Thr Asp Glu
 65                  70                  75                  80

Arg Lys Arg Leu Tyr Ile Phe Val Pro Asp Pro Thr Val Gly Phe Leu
                 85                  90                  95

Pro Asn Asp Ala Glu Glu Leu Phe Ile Phe Leu Thr Glu Ile Thr Glu
                100                 105                 110

Ile Thr Ile Pro Cys Arg Val Thr Asp Pro Gln Leu Val Val Thr Leu
                115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
                195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Gly Gly Gly Ser Gly
                275                 280                 285

Gly Gly Gly Ser Asp Ile Gln Met Thr Gln Ser Pro Ser Ser Leu Ser
    290                 295                 300
```

Ala Ser Val Gly Asp Arg Val Thr Ile Thr Cys Ser Ala Ser Gln Asp
305                 310                 315                 320

Ile Ser Asn Tyr Leu Asn Trp Tyr Gln Gln Lys Pro Gly Lys Ala Pro
            325                 330                 335

Lys Val Leu Ile Tyr Phe Thr Ser Ser Leu His Ser Gly Val Pro Ser
            340                 345                 350

Arg Phe Ser Gly Ser Gly Ser Gly Thr Asp Phe Thr Leu Thr Ile Ser
        355                 360                 365

Ser Leu Gln Pro Glu Asp Phe Ala Thr Tyr Tyr Cys Gln Gln Tyr Ser
370                 375                 380

Thr Val Pro Trp Thr Phe Gly Gln Gly Thr Lys Val Glu Ile Lys Arg
385                 390                 395                 400

Thr Val Ala Ala Pro Ser Val Phe Ile Phe Pro Pro Ser Asp Glu Gln
            405                 410                 415

Leu Lys Ser Gly Thr Ala Ser Val Val Cys Leu Leu Asn Asn Phe Tyr
            420                 425                 430

Pro Arg Glu Ala Lys Val Gln Trp Lys Val Asp Asn Ala Leu Gln Ser
        435                 440                 445

Gly Asn Ser Gln Glu Ser Val Thr Glu Gln Asp Ser Lys Asp Ser Thr
450                 455                 460

Tyr Ser Leu Ser Ser Thr Leu Thr Leu Ser Lys Ala Asp Tyr Glu Lys
465                 470                 475                 480

His Lys Val Tyr Ala Cys Glu Val Thr His Gln Gly Leu Ser Ser Pro
            485                 490                 495

Val Thr Lys Ser Phe Asn Arg Gly Glu Cys
            500                 505

<210> SEQ ID NO 20
<211> LENGTH: 498
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
            85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
    130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
    210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Asp Ile Gln Met
        275                 280                 285

Thr Gln Ser Pro Ser Ser Leu Ser Ala Ser Val Gly Asp Arg Val Thr
    290                 295                 300

Ile Thr Cys Ser Ala Ser Gln Asp Ile Ser Asn Tyr Leu Asn Trp Tyr
305                 310                 315                 320

Gln Gln Lys Pro Gly Lys Ala Pro Lys Val Leu Ile Tyr Phe Thr Ser
                325                 330                 335

Ser Leu His Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
        355                 360                 365

Thr Tyr Tyr Cys Gln Gln Tyr Ser Thr Val Pro Trp Thr Phe Gly Gln
    370                 375                 380

Gly Thr Lys Val Glu Ile Lys Arg Thr Val Ala Ala Pro Ser Val Phe
385                 390                 395                 400

Ile Phe Pro Pro Ser Asp Glu Gln Leu Lys Ser Gly Thr Ala Ser Val
                405                 410                 415

Val Cys Leu Leu Asn Asn Phe Tyr Pro Arg Glu Ala Lys Val Gln Trp
            420                 425                 430

Lys Val Asp Asn Ala Leu Gln Ser Gly Asn Ser Gln Glu Ser Val Thr
        435                 440                 445

Glu Gln Asp Ser Lys Asp Ser Thr Tyr Ser Leu Ser Ser Thr Leu Thr
    450                 455                 460

Leu Ser Lys Ala Asp Tyr Glu Lys His Lys Val Tyr Ala Cys Glu Val
465                 470                 475                 480

Thr His Gln Gly Leu Ser Ser Pro Val Thr Lys Ser Phe Asn Arg Gly
                485                 490                 495

Glu Cys

<210> SEQ ID NO 21
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
 130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr
225                 230

<210> SEQ ID NO 22
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
 50                  55                  60

Glu Tyr Phe Cys Thr His Asn Asp Ser Arg Gly Leu Glu Thr Asp Glu
 65                  70                  75                  80

Arg Lys Arg Leu Tyr Ile Phe Val Pro Asp Pro Thr Val Gly Phe Leu
            85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln

```
            130                 135                 140
Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
                180                 185                 190

Val Arg Gln Gly Glu Asn Ile Thr Leu Met Cys Ile Val Ile Gly Asn
            195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
                260                 265                 270

Ala Ile Asn Ile Thr Val Val Glu Ser Gly Gly Gly Gly Ser Gly
                275                 280                 285

Gly Gly Gly Ser Glu Val Gln Leu Val Glu Ser Gly Gly Gly Leu Val
            290                 295                 300

Gln Pro Gly Gly Ser Leu Arg Leu Ser Cys Ala Ala Ser Gly Tyr Thr
305                 310                 315                 320

Phe Thr Asn Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
                340                 345                 350

Ala Ala Asp Phe Lys Arg Arg Phe Thr Phe Ser Leu Asp Thr Ser Lys
                355                 360                 365

Ser Thr Ala Tyr Leu Gln Met Asn Ser Leu Arg Ala Glu Asp Thr Ala
            370                 375                 380

Val Tyr Tyr Cys Ala Lys Tyr Pro His Tyr Tyr Gly Ser Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
                420                 425                 430

Thr Ser Gly Gly Thr Ala Ala Leu Gly Cys Leu Val Lys Asp Tyr Phe
            435                 440                 445

Pro Glu Pro Val Thr Val Ser Trp Asn Ser Gly Ala Leu Thr Ser Gly
450                 455                 460

Val His Thr Phe Pro Ala Val Leu Gln Ser Ser Gly Leu Tyr Ser Leu
465                 470                 475                 480

Ser Ser Val Val Thr Val Pro Ser Ser Ser Leu Gly Thr Gln Thr Tyr
                485                 490                 495

Ile Cys Asn Val Asn His Lys Pro Ser Asn Thr Lys Val Asp Lys Lys
                500                 505                 510

Val Glu Pro Lys Ser Cys Asp Lys Thr His Thr
            515                 520

<210> SEQ ID NO 23
<211> LENGTH: 515
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 23

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

Phe Ser Ser Val Leu Thr Leu Thr Asn Leu Thr Gly Leu Asp Thr Gly
50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
        115                 120                 125

His Glu Lys Lys Gly Asp Val Ala Leu Pro Val Pro Tyr Asp His Gln
130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Glu Val Gln Leu
        275                 280                 285

Val Glu Ser Gly Gly Gly Leu Val Gln Pro Gly Gly Ser Leu Arg Leu
290                 295                 300

Ser Cys Ala Ala Ser Gly Tyr Thr Phe Thr Asn Tyr Gly Met Asn Trp
305                 310                 315                 320

Val Arg Gln Ala Pro Gly Lys Gly Leu Glu Trp Val Gly Trp Ile Asn
                325                 330                 335

Thr Tyr Thr Gly Glu Pro Thr Tyr Ala Ala Asp Phe Lys Arg Arg Phe
            340                 345                 350

Thr Phe Ser Leu Asp Thr Ser Lys Ser Thr Ala Tyr Leu Gln Met Asn
        355                 360                 365

Ser Leu Arg Ala Glu Asp Thr Ala Val Tyr Tyr Cys Ala Lys Tyr Pro
370                 375                 380

His Tyr Tyr Gly Ser Ser His Trp Tyr Phe Asp Val Trp Gly Gln Gly
```

```
              385                 390                 395                 400
     Thr Leu Val Thr Val Ser Ser Ala Ser Thr Lys Gly Pro Ser Val Phe
                     405                 410                 415

Pro Leu Ala Pro Ser Ser Lys Ser Thr Ser Gly Gly Thr Ala Ala Leu
                     420                 425                 430

Gly Cys Leu Val Lys Asp Tyr Phe Pro Glu Pro Val Thr Val Ser Trp
                     435                 440                 445

Asn Ser Gly Ala Leu Thr Ser Gly Val His Thr Phe Pro Ala Val Leu
                     450                 455                 460

Gln Ser Ser Gly Leu Tyr Ser Leu Ser Val Val Thr Val Pro Ser
     465                 470                 475                 480

Ser Ser Leu Gly Thr Gln Thr Tyr Ile Cys Asn Val Asn His Lys Pro
                     485                 490                 495

Ser Asn Thr Lys Val Asp Lys Lys Val Glu Pro Lys Ser Cys Asp Lys
                     500                 505                 510

Thr His Thr
                     515

<210> SEQ ID NO 24
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220
```

Ser Cys Asp Lys Thr His Thr Gly Gly Gly Gly Ser Gly Gly Gly
225                 230                 235                 240

Gly Ser Gly Gly Gly Ser Gly Gly Gly Ser Gly Leu Val Val
            245                 250                 255

Thr Pro Pro Gly Pro Glu Leu Val Leu Asn Val Ser Ser Thr Phe Val
            260                 265                 270

Leu Thr Cys Ser Gly Ser Ala Pro Val Val Trp Glu Arg Met Ser Gln
        275                 280                 285

Glu Pro Pro Gln Glu Met Ala Lys Ala Gln Asp Gly Thr Phe Ser Ser
    290                 295                 300

Val Leu Thr Leu Thr Asn Leu Thr Gly Leu Asp Thr Gly Glu Tyr Phe
305                 310                 315                 320

Cys Thr His Asn Asp Ser Arg Gly Leu Glu Thr Asp Glu Arg Lys Arg
                325                 330                 335

Leu Tyr Ile Phe Val Pro Asp Pro Thr Val Gly Phe Leu Pro Asn Asp
            340                 345                 350

Ala Glu Glu Leu Phe Ile Phe Leu Thr Glu Ile Thr Glu Ile Thr Ile
                355                 360                 365

Pro Cys Arg Val Thr Asp Pro Gln Leu Val Val Thr Leu His Glu Lys
370                 375                 380

Lys Gly Asp Val Ala Leu Pro Val Pro Tyr Asp His Gln Arg Gly Phe
385                 390                 395                 400

Ser Gly Ile Phe Glu Asp Arg Ser Tyr Ile Cys Lys Thr Thr Ile Gly
                405                 410                 415

Asp Arg Glu Val Asp Ser Asp Ala Tyr Tyr Val Tyr Arg Leu Gln Val
            420                 425                 430

Ser Ser Ile Asn Val Ser Val Asn Ala Val Gln Thr Val Val Arg Gln
        435                 440                 445

Gly Glu Asn Ile Thr Leu Met Cys Ile Val Ile Gly Asn Glu Val Val
    450                 455                 460

Asn Phe Glu Trp Thr Tyr Pro Arg Lys Glu Ser Gly Arg Leu Val Glu
465                 470                 475                 480

Pro Val Thr Asp Phe Leu Leu Asp Met Pro Tyr His Ile Arg Ser Ile
                485                 490                 495

Leu His Ile Pro Ser Ala Glu Leu Glu Asp Ser Gly Thr Tyr Thr Cys
            500                 505                 510

Asn Val Thr Glu Ser Val Asn Asp His Gln Asp Glu Lys Ala Ile Asn
        515                 520                 525

Ile Thr Val Val Glu Ser Gly
    530                 535

<210> SEQ ID NO 25
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Val Val Thr Pro Pro Gly Pro Glu Leu Val Leu Asn Val Ser Ser
1               5                   10                  15

Thr Phe Val Leu Thr Cys Ser Gly Ser Ala Pro Val Val Trp Glu Arg
            20                  25                  30

Met Ser Gln Glu Pro Pro Gln Glu Met Ala Lys Ala Gln Asp Gly Thr
        35                  40                  45

-continued

Phe Ser Ser Val Leu Thr Leu Thr Asn Leu Thr Gly Leu Asp Thr Gly
        50                  55                  60

Glu Tyr Phe Cys Thr His Asn Asp Ser Arg Gly Leu Glu Thr Asp Glu
65                      70                  75                  80

Arg Lys Arg Leu Tyr Ile Phe Val Pro Asp Pro Thr Val Gly Phe Leu
                    85                  90                  95

Pro Asn Asp Ala Glu Glu Leu Phe Ile Phe Leu Thr Glu Ile Thr Glu
                100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
        130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Gly Gly Gly Ser Gly
        275                 280                 285

Gly Gly Gly Ser Glu Val Gln Leu Val Glu Ser Gly Gly Gly Leu Val
        290                 295                 300

Gln Pro Gly Gly Ser Leu Arg Leu Ser Cys Ala Ala Ser Gly Tyr Asp
305                 310                 315                 320

Phe Thr His Tyr Gly Met Asn Trp Val Arg Gln Ala Pro Gly Lys Gly
                325                 330                 335

Leu Glu Trp Val Gly Trp Ile Asn Thr Tyr Thr Gly Glu Pro Thr Tyr
            340                 345                 350

Ala Ala Asp Phe Lys Arg Arg Phe Thr Phe Ser Leu Asp Thr Ser Lys
        355                 360                 365

Ser Thr Ala Tyr Leu Gln Met Asn Ser Leu Arg Ala Glu Asp Thr Ala
370                 375                 380

Val Tyr Tyr Cys Ala Lys Tyr Pro Tyr Tyr Gly Thr Ser His Trp
385                 390                 395                 400

Tyr Phe Asp Val Trp Gly Gln Gly Thr Leu Val Thr Val Ser Ser Ala
                405                 410                 415

Ser Thr Lys Gly Pro Ser Val Phe Pro Leu Ala Pro Ser Ser Lys Ser
            420                 425                 430

Thr Ser Gly Gly Thr Ala Ala Leu Gly Cys Leu Val Lys Asp Tyr Phe
        435                 440                 445

Pro Glu Pro Val Thr Val Ser Trp Asn Ser Gly Ala Leu Thr Ser Gly
    450                 455                 460

```
Val His Thr Phe Pro Ala Val Leu Gln Ser Ser Gly Leu Tyr Ser Leu
465                 470                 475                 480

Ser Ser Val Val Thr Val Pro Ser Ser Leu Gly Thr Gln Thr Tyr
                485                 490                 495

Ile Cys Asn Val Asn His Lys Pro Ser Asn Thr Lys Val Asp Lys Lys
            500                 505                 510

Val Glu Pro Lys Ser Cys Asp Lys Thr His Leu
            515                 520

<210> SEQ ID NO 26
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Val Val Thr Pro Gly Pro Glu Leu Val Leu Asn Val Ser Ser
1               5                   10                  15

Thr Phe Val Leu Thr Cys Ser Gly Ser Ala Pro Val Val Trp Glu Arg
                20                  25                  30

Met Ser Gln Glu Pro Pro Gln Glu Met Ala Lys Ala Gln Asp Gly Thr
            35                  40                  45

Phe Ser Ser Val Leu Thr Leu Thr Asn Leu Thr Gly Leu Asp Thr Gly
50                  55                  60

Glu Tyr Phe Cys Thr His Asn Asp Ser Arg Gly Leu Glu Thr Asp Glu
65                  70                  75                  80

Arg Lys Arg Leu Tyr Ile Phe Val Pro Asp Pro Thr Val Gly Phe Leu
                85                  90                  95

Pro Asn Asp Ala Glu Glu Leu Phe Ile Phe Leu Thr Glu Ile Thr Glu
            100                 105                 110

Ile Thr Ile Pro Cys Arg Val Thr Asp Pro Gln Leu Val Val Thr Leu
            115                 120                 125

His Glu Lys Lys Gly Asp Val Ala Leu Pro Val Pro Tyr Asp His Gln
130                 135                 140

Arg Gly Phe Ser Gly Ile Phe Glu Asp Arg Ser Tyr Ile Cys Lys Thr
145                 150                 155                 160

Thr Ile Gly Asp Arg Glu Val Asp Ser Asp Ala Tyr Tyr Val Tyr Arg
                165                 170                 175

Leu Gln Val Ser Ser Ile Asn Val Ser Val Asn Ala Val Gln Thr Val
            180                 185                 190

Val Arg Gln Gly Glu Asn Ile Thr Leu Met Cys Ile Val Ile Gly Asn
        195                 200                 205

Glu Val Val Asn Phe Glu Trp Thr Tyr Pro Arg Lys Glu Ser Gly Arg
210                 215                 220

Leu Val Glu Pro Val Thr Asp Phe Leu Leu Asp Met Pro Tyr His Ile
225                 230                 235                 240

Arg Ser Ile Leu His Ile Pro Ser Ala Glu Leu Glu Asp Ser Gly Thr
                245                 250                 255

Tyr Thr Cys Asn Val Thr Glu Ser Val Asn Asp His Gln Asp Glu Lys
            260                 265                 270

Ala Ile Asn Ile Thr Val Val Glu Ser Gly Glu Val Gln Leu Val Glu
        275                 280                 285

Ser Gly Gly Gly Leu Val Gln Pro Gly Gly Ser Leu Arg Leu Ser Cys
290                 295                 300
```

```
Ala Ala Ser Gly Tyr Thr Phe Thr Asn Tyr Gly Met Asn Trp Val Arg
305                 310                 315                 320

Gln Ala Pro Gly Lys Gly Leu Glu Trp Val Gly Trp Ile Asn Thr Tyr
            325                 330                 335

Thr Gly Glu Pro Thr Tyr Ala Ala Asp Phe Lys Arg Arg Phe Thr Phe
            340                 345                 350

Ser Leu Asp Thr Ser Lys Ser Thr Ala Tyr Leu Gln Met Asn Ser Leu
            355                 360                 365

Arg Ala Glu Asp Thr Ala Val Tyr Tyr Cys Ala Lys Tyr Pro His Tyr
            370                 375                 380

Tyr Gly Ser Ser His Trp Tyr Phe Asp Val Trp Gly Gln Gly Thr Leu
385                 390                 395                 400

Val Thr Val Ser Ser Ala Ser Thr Lys Gly Pro Ser Val Phe Pro Leu
            405                 410                 415

Ala Pro Ser Ser Lys Ser Thr Ser Gly Gly Thr Ala Ala Leu Gly Cys
            420                 425                 430

Leu Val Lys Asp Tyr Phe Pro Glu Pro Val Thr Val Ser Trp Asn Ser
            435                 440                 445

Gly Ala Leu Thr Ser Gly Val His Thr Phe Pro Ala Val Leu Gln Ser
450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Asn His Lys Pro Ser Asn
            485                 490                 495

Thr Lys Val Asp Lys Lys Val Glu Pro Lys Ser Cys Asp Lys Thr His
            500                 505                 510

Thr Cys Pro Pro Cys Pro Ala Pro Glu Leu Leu Gly Gly Pro Ser Val
            515                 520                 525

Phe Leu Phe Pro Pro Lys Pro Lys Asp Thr Leu Met Ile Ser Arg Thr
            530                 535                 540

Pro Glu Val Thr Cys Val Val Val Asp Val Ser His Glu Asp Pro Glu
545                 550                 555                 560

Val Lys Phe Asn Trp Tyr Val Asp Gly Val Glu Val His Asn Ala Lys
            565                 570                 575

Thr Lys Pro Arg Glu Glu Gln Tyr Asn Ser Thr Tyr Arg Val Val Ser
            580                 585                 590

Val Leu Thr Val Leu His Gln Asp Trp Leu Asn Gly Lys Glu Tyr Lys
            595                 600                 605

Cys Lys Val Ser Asn Lys Ala Leu Pro Ala Pro Ile Glu Lys Thr Ile
            610                 615                 620

Ser Lys Ala Lys Gly Gln Pro Arg Glu Pro Gln Val Tyr Thr Leu Pro
625                 630                 635                 640

Pro Ser Arg Glu Glu Met Thr Lys Asn Gln Val Ser Leu Thr Cys Leu
            645                 650                 655

Val Lys Gly Phe Tyr Pro Ser Asp Ile Ala Val Glu Trp Glu Ser Asn
            660                 665                 670

Gly Gln Pro Glu Asn Asn Tyr Lys Thr Thr Pro Pro Val Leu Asp Ser
            675                 680                 685

Asp Gly Ser Phe Phe Leu Tyr Ser Lys Leu Thr Val Asp Lys Ser Arg
            690                 695                 700

Trp Gln Gln Gly Asn Val Phe Ser Cys Ser Val Met His Glu Ala Leu
705                 710                 715                 720
```

```
His Asn His Tyr Thr Gln Lys Ser Leu Ser Leu Ser Pro Gly Lys
                725                 730                 735

<210> SEQ ID NO 27
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Gly Phe Leu Pro Asn Asp Ala Glu Glu Leu Phe Ile Phe Leu Thr
  1               5                  10                  15

Glu Ile Thr Glu Ile Thr Ile Pro Cys Arg Val Thr Asp Pro Gln Leu
             20                  25                  30

Val Val Thr Leu His Glu Lys Lys Gly Asp Val Ala Leu Pro Val Pro
         35                  40                  45

Tyr Asp His Gln Arg Gly Phe Ser Gly Ile Phe Glu Asp Arg Ser Tyr
     50                  55                  60

Ile Cys Lys Thr Thr Ile Gly Asp Arg Glu Val Asp Ser Asp Ala Tyr
 65                  70                  75                  80

Tyr Val Tyr Arg Leu Gln Val Ser Ser Ile Asn Val Ser Val Asn Ala
                 85                  90                  95

Val Gln Thr Val Val Arg Gln Gly Glu Asn Ile Thr Leu Met Cys Ile
            100                 105                 110

Val Ile Gly Asn Glu Val Val Asn Phe Glu Trp Thr Tyr Pro Arg Lys
        115                 120                 125

Glu Ser Gly Arg Leu Val Glu Pro Val Thr Asp Phe Leu Leu Asp Met
    130                 135                 140

Pro Tyr His Ile Arg Ser Ile Leu His Ile Pro Ser Ala Glu Leu Glu
145                 150                 155                 160

Asp Ser Gly Thr Tyr Thr Cys Asn Val Thr Glu Ser Val Asn Asp His
                165                 170                 175

Gln Asp Glu Lys Ala Ile Asn Ile Thr Val Val Glu Ser Gly Glu Val
            180                 185                 190

Gln Leu Val Glu Ser Gly Gly Leu Val Gln Pro Gly Gly Ser Leu
        195                 200                 205

Arg Leu Ser Cys Ala Ala Ser Gly Tyr Thr Phe Thr Asn Tyr Gly Met
    210                 215                 220

Asn Trp Val Arg Gln Ala Pro Gly Lys Gly Leu Glu Trp Val Gly Trp
225                 230                 235                 240

Ile Asn Thr Tyr Thr Gly Glu Pro Thr Tyr Ala Ala Asp Phe Lys Arg
                245                 250                 255

Arg Phe Thr Phe Ser Leu Asp Thr Ser Lys Ser Thr Ala Tyr Leu Gln
            260                 265                 270

Met Asn Ser Leu Arg Ala Glu Asp Thr Ala Val Tyr Tyr Cys Ala Lys
        275                 280                 285

Tyr Pro His Tyr Tyr Gly Ser Ser His Trp Tyr Phe Asp Val Trp Gly
    290                 295                 300

Gln Gly Thr Leu Val Thr Val Ser Ser Ala Ser Thr Lys Gly Pro Ser
305                 310                 315                 320

Val Phe Pro Leu Ala Pro Ser Ser Lys Ser Thr Ser Gly Gly Thr Ala
                325                 330                 335

Ala Leu Gly Cys Leu Val Lys Asp Tyr Phe Pro Glu Pro Val Thr Val
            340                 345                 350
```

```
Ser Trp Asn Ser Gly Ala Leu Thr Ser Gly Val His Thr Phe Pro Ala
        355                 360                 365

Val Leu Gln Ser Ser Gly Leu Tyr Ser Leu Ser Ser Val Val Thr Val
    370                 375                 380

Pro Ser Ser Ser Leu Gly Thr Gln Thr Tyr Ile Cys Asn Val Asn His
385                 390                 395                 400

Lys Pro Ser Asn Thr Lys Val Asp Lys Lys Val Glu Pro Lys Ser Cys
                405                 410                 415

Asp Lys Thr His Thr Cys Pro Pro Cys Pro Ala Pro Glu Leu Leu Gly
            420                 425                 430

Gly Pro Ser Val Phe Leu Phe Pro Pro Lys Pro Lys Asp Thr Leu Met
        435                 440                 445

Ile Ser Arg Thr Pro Glu Val Thr Cys Val Val Val Asp Val Ser His
    450                 455                 460

Glu Asp Pro Glu Val Lys Phe Asn Trp Tyr Val Asp Gly Val Glu Val
465                 470                 475                 480

His Asn Ala Lys Thr Lys Pro Arg Glu Glu Gln Tyr Asn Ser Thr Tyr
                485                 490                 495

Arg Val Val Ser Val Leu Thr Val Leu His Gln Asp Trp Leu Asn Gly
            500                 505                 510

Lys Glu Tyr Lys Cys Lys Val Ser Asn Lys Ala Leu Pro Ala Pro Ile
        515                 520                 525

Glu Lys Thr Ile Ser Lys Ala Lys Gly Gln Pro Arg Glu Pro Gln Val
    530                 535                 540

Tyr Thr Leu Pro Pro Ser Arg Glu Glu Met Thr Lys Asn Gln Val Ser
545                 550                 555                 560

Leu Thr Cys Leu Val Lys Gly Phe Tyr Pro Ser Asp Ile Ala Val Glu
                565                 570                 575

Trp Glu Ser Asn Gly Gln Pro Glu Asn Asn Tyr Lys Thr Thr Pro Pro
            580                 585                 590

Val Leu Asp Ser Asp Gly Ser Phe Phe Leu Tyr Ser Lys Leu Thr Val
        595                 600                 605

Asp Lys Ser Arg Trp Gln Gln Gly Asn Val Phe Ser Cys Ser Val Met
    610                 615                 620

His Glu Ala Leu His Asn His Tyr Thr Gln Lys Ser Leu Ser Leu Ser
625                 630                 635                 640

Pro Gly Lys

<210> SEQ ID NO 28
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Gly Phe Leu Pro Asn Asp Ala Glu Glu Leu Phe Ile Phe Leu Thr
1               5                   10                  15

Glu Ile Thr Glu Ile Thr Ile Pro Cys Arg Val Thr Asp Pro Gln Leu
                20                  25                  30

Val Val Thr Leu His Glu Lys Lys Gly Asp Val Ala Leu Pro Val Pro
            35                  40                  45

Tyr Asp His Gln Arg Gly Phe Ser Gly Ile Phe Glu Asp Arg Ser Tyr
        50                  55                  60
```

Ile Cys Lys Thr Thr Ile Gly Asp Arg Glu Val Asp Ser Asp Ala Tyr
65                  70                  75                  80

Tyr Val Tyr Arg Leu Gln Val Ser Ser Ile Asn Val Ser Val Asn Ala
                85                  90                  95

Val Gln Thr Val Val Arg Gln Gly Glu Asn Ile Thr Leu Met Cys Ile
            100                 105                 110

Val Ile Gly Asn Glu Val Val Asn Phe Glu Trp Thr Tyr Pro Arg Lys
        115                 120                 125

Glu Ser Gly Arg Leu Val Glu Pro Val Thr Asp Phe Leu Leu Asp Met
    130                 135                 140

Pro Tyr His Ile Arg Ser Ile Leu His Ile Pro Ser Ala Glu Leu Glu
145                 150                 155                 160

Asp Ser Gly Thr Tyr Thr Cys Asn Val Thr Glu Ser Val Asn Asp His
                165                 170                 175

Gln Asp Glu Lys Ala Ile Asn Ile Thr Val Val Glu Ser Gly Glu Val
            180                 185                 190

Gln Leu Val Glu Ser Gly Gly Gly Leu Val Gln Pro Gly Gly Ser Leu
        195                 200                 205

Arg Leu Ser Cys Ala Ala Ser Gly Tyr Thr Phe Thr Asn Tyr Gly Met
    210                 215                 220

Asn Trp Val Arg Gln Ala Pro Gly Lys Gly Leu Glu Trp Val Gly Trp
225                 230                 235                 240

Ile Asn Thr Tyr Thr Gly Glu Pro Thr Tyr Ala Ala Asp Phe Lys Arg
                245                 250                 255

Arg Phe Thr Phe Ser Leu Asp Thr Ser Lys Ser Thr Ala Tyr Leu Gln
            260                 265                 270

Met Asn Ser Leu Arg Ala Glu Asp Thr Ala Val Tyr Tyr Cys Ala Lys
        275                 280                 285

Tyr Pro His Tyr Tyr Gly Ser Ser His Trp Tyr Phe Asp Val Trp Gly
    290                 295                 300

Gln Gly Thr Leu Val Thr Val Ser Ser Ala Ser Thr Lys Gly Pro Ser
305                 310                 315                 320

Val Phe Pro Leu Ala Pro Ser Ser Lys Ser Thr Ser Gly Gly Thr Ala
                325                 330                 335

Ala Leu Gly Cys Leu Val Lys Asp Tyr Phe Pro Glu Pro Val Thr Val
            340                 345                 350

Ser Trp Asn Ser Gly Ala Leu Thr Ser Gly Val His Thr Phe Pro Ala
        355                 360                 365

Val Leu Gln Ser Ser Gly Leu Tyr Ser Leu Ser Ser Val Val Thr Val
    370                 375                 380

Pro Ser Ser Ser Leu Gly Thr Gln Thr Tyr Ile Cys Asn Val Asn His
385                 390                 395                 400

Lys Pro Ser Asn Thr Lys Val Asp Lys Lys Val Glu Pro Lys Ser Cys
                405                 410                 415

Asp Lys Thr His Thr
            420

<210> SEQ ID NO 29
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Val Gly Phe Leu Pro Asn Asp Ala Glu Glu Leu Phe Ile Phe Leu Thr
1               5                   10                  15

Glu Ile Thr Glu Ile Thr Ile Pro Cys Arg Val Thr Asp Pro Gln Leu
            20                  25                  30

Val Val Thr Leu His Glu Lys Lys Gly Asp Val Ala Leu Pro Val Pro
        35                  40                  45

Tyr Asp His Gln Arg Gly Phe Ser Gly Ile Phe Glu Asp Arg Ser Tyr
    50                  55                  60

Ile Cys Lys Thr Thr Ile Gly Asp Arg Glu Val Asp Ser Asp Ala Tyr
65                  70                  75                  80

Tyr Val Tyr Arg Leu Gln Val Ser Ser Ile Asn Val Ser Val Asn Ala
                85                  90                  95

Val Gln Thr Val Val Arg Gln Gly Glu Asn Ile Thr Leu Met Cys Ile
            100                 105                 110

Val Ile Gly Asn Glu Val Val Asn Phe Glu Trp Thr Tyr Pro Arg Lys
        115                 120                 125

Glu Ser Gly Arg Leu Val Glu Pro Val Thr Asp Phe Leu Leu Asp Met
    130                 135                 140

Pro Tyr His Ile Arg Ser Ile Leu His Ile Pro Ser Ala Glu Leu Glu
145                 150                 155                 160

Asp Ser Gly Thr Tyr Thr Cys Asn Val Thr Glu Ser Val Asn Asp His
                165                 170                 175

Gln Asp Glu Lys Ala Ile Asn Ile Thr Val Val Glu Ser Gly Gly Gly
            180                 185                 190

Gly Ser Gly Gly Gly Ser Gly Gly Gly Ser Gly Gly Gly Gly
    195                 200                 205

Ser Gly Gly Gly Ser Gly Gly Gly Ser Glu Val Gln Leu Val
    210                 215                 220

Glu Ser Gly Gly Gly Leu Val Gln Pro Gly Gly Ser Leu Arg Leu Ser
225                 230                 235                 240

Cys Ala Ala Ser Gly Tyr Thr Phe Thr Asn Tyr Gly Met Asn Trp Val
                245                 250                 255

Arg Gln Ala Pro Gly Lys Gly Leu Glu Trp Val Gly Trp Ile Asn Thr
            260                 265                 270

Tyr Thr Gly Glu Pro Thr Tyr Ala Ala Asp Phe Lys Arg Arg Phe Thr
        275                 280                 285

Phe Ser Leu Asp Thr Ser Lys Ser Thr Ala Tyr Leu Gln Met Asn Ser
    290                 295                 300

Leu Arg Ala Glu Asp Thr Ala Val Tyr Tyr Cys Ala Lys Tyr Pro His
305                 310                 315                 320

Tyr Tyr Gly Ser Ser His Trp Tyr Phe Asp Val Trp Gly Gln Gly Thr
                325                 330                 335

Leu Val Thr Val Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

-continued

```
Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
            435                 440                 445

His Thr
    450

<210> SEQ ID NO 30
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Gly Gly Gly Ser Gly Gly Gly Gly Ser
225                 230                 235                 240

Gly Gly Gly Gly Ser Gly Gly Gly Ser Gly Gly Gly Gly Ser Gly
                245                 250                 255

Gly Gly Gly Ser Val Gly Phe Leu Pro Asn Asp Ala Glu Glu Leu Phe
            260                 265                 270

Ile Phe Leu Thr Glu Ile Thr Glu Ile Thr Ile Pro Cys Arg Val Thr
            275                 280                 285

Asp Pro Gln Leu Val Val Thr Leu His Glu Lys Lys Gly Asp Val Ala
            290                 295                 300

Leu Pro Val Pro Tyr Asp His Gln Arg Gly Phe Ser Gly Ile Phe Glu
```

```
                    305                 310                 315                 320
Asp Arg Ser Tyr Ile Cys Lys Thr Thr Ile Gly Asp Arg Glu Val Asp
                325                 330                 335

Ser Asp Ala Tyr Tyr Val Tyr Arg Leu Gln Val Ser Ser Ile Asn Val
                340                 345                 350

Ser Val Asn Ala Val Gln Thr Val Arg Gln Gly Glu Asn Ile Thr
                355                 360                 365

Leu Met Cys Ile Val Ile Gly Asn Glu Val Val Asn Phe Glu Trp Thr
        370                 375                 380

Tyr Pro Arg Lys Glu Ser Gly Arg Leu Val Glu Pro Val Thr Asp Phe
385                 390                 395                 400

Leu Leu Asp Met Pro Tyr His Ile Arg Ser Ile Leu His Ile Pro Ser
                405                 410                 415

Ala Glu Leu Glu Asp Ser Gly Thr Tyr Thr Cys Asn Val Thr Glu Ser
                420                 425                 430

Val Asn Asp His Gln Asp Glu Lys Ala Ile Asn Ile Thr Val Val Glu
            435                 440                 445

Ser Gly
    450

<210> SEQ ID NO 31
<211> LENGTH: 7719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacgc aaatgggcg      780 gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattctgc     960
agatatccag cacagtggcg gccgccatga agctgtggt gctggccgtg gctctggtct    1020
tcctgacagg gagccaggct ctggtcgtca caccccgggg gccagagctt gtcctcaatg    1080
tctccagcac cttcgttctg acctgctcgg gttcagctcc ggtggtgtgg gaacggatgt    1140
cccaggagcc cccacaggaa atggccaagg cccaggatgg caccttctcc agcgtgctca    1200
```

```
cactgaccaa cctcactggg ctagacacgg gagaatactt ttgcacccac aatgactccc   1260
gtggactgga gaccgatgag cggaaacggc tctacatctt tgtgccagat cccaccgtgg   1320
gcttcctccc taatgatgcc gaggaactat tcatctttct cacggaaata actgagatca   1380
ccattccatg ccgagtaaca gacccacagc tggtggtgac actgcacgag aagaaagggg   1440
acgttgcact gcctgtcccc tatgatcacc aacgtggctt ttctggtatc tttgaggaca   1500
gaagctacat ctgcaaaacc accattgggg acagggaggt ggattctgat gcctactatg   1560
tctacagact ccaggtgtca tccatcaacg tctctgtgaa cgcagtgcag actgtggtcc   1620
gccagggtga acatcacc ctcatgtgca ttgtgatcgg aatgaggtg gtcaacttcg     1680
agtggacata cccccgcaaa gaaagtgggc ggctggtgga gccggtgact gacttcctct   1740
tggatatgcc ttaccacatc cgctccatcc tgcacatccc cagtgccgag ttagaagact   1800
cggggaccta cacctgcaat gtgacggaga gtgtgaatga ccatcaggat gaaaaggcca   1860
tcaacatcac cgtggttgag agcggcggtg gtggcggctc cggtggaggc ggaagcgagg   1920
tgcagctggt ggaatccggc ggaggcctgg tccagcctgg cggatccctg agactgtcct   1980
gtgccgcctc cggctacgac ttcacccatt acggcatgaa ctgggtccga caggcccctg   2040
gcaagggcct ggaatgggtc ggatggatca cacctacac cggcgagccc acctacgccg   2100
ccgacttcaa gcggcggttc accttctccc tggacacctc caagtccacc gcctacctgc   2160
agatgaactc cctgcgggcc gaggacaccg ccgtgtacta ctgcgccaag taccccact   2220
actacggcac ctcccactgg tacttcgacg tgtggggcca gggcaccctg gtcaccgtgt   2280
cctccgcctc taccaagggc ccctccgtgt tccctctggc cccctccagc aagtccacct   2340
ctgggggcac cgccgctctg ggctgcctgg tcaaggacta cttccccgag cccgtgaccg   2400
tgtcctggaa ctctggcgcc ctgaccctcg gcgtgcacac cttccagcc gtgctgcagt   2460
cctccggcct gtactccctg tcctccgtcg tgaccgtgcc ctccagctct ctgggcaccc   2520
agacctacat ctgcaacgtg aaccacaagc cctccaacac caaggtggac aagaaggtgg   2580
aacccaagtc ctgcgacaag acccacacct gtccccctg ccctgcccct gaagcagccg   2640
gtgcacccag cgtgttcctg ttcccccaa gcccaaggga caccctgatg atctccgga   2700
cccccgaagt gacctgcgtg gtggtggacg tgtcccacga ggaccctgaa gtgaagttca   2760
attggtacgt ggacggcgtg gaagtgcaca atgccaagac caagcccaga gaggaacagt   2820
acaactccac ctaccgggtg gtgtccgtgc tgaccgtgct gcatcaggac tggctgaacg   2880
gcaaagagta caagtgcaag gtctccaaca aggccctgcc tgcccccatc gaaaagacca   2940
tctccaaggc caagggccag ccccgcgagc ctcaggtgta cacactgcca cccagccggg   3000
aagagatgac caagaaccag gtctccctga cctgtctggt caagggcttc taccctcccg   3060
atatcgccgt cgaatgggag tccaacggcc agcccgagaa caactacaag accacccccc   3120
ctgtgctgga ctccgacggc tcattcttcc tgtactccaa gctgaccgtg gacaagtccc   3180
ggtggcagca gggcaacgtg ttctcctgct ccgtgatgca cgaggccctg cacaaccact   3240
acacccagaa gtccctgtcc tgcagccccg gcaagtgata atctagaggg cccgtttaaa   3300
cccgctgatc agcctcgact gtgccttcta gttgccagcc atctgttgtt tgcccctccc   3360
ccgtgccttc cttgaccctg gaaggtgcca ctcccactgt cctttcctaa taaaatgagg   3420
aaattgcatc gcattgtctg agtaggtgtc attctattct ggggggtggg gtggggcagg   3480
acagcaaggg ggaggattgg gaagacaata gcaggcatgc tggggatgcg gtgggctcta   3540
```

```
tggcttctga ggcggaaaga accagctggg gctctagggg gtatccccac gcgccctgta    3600
gcggcgcatt aagcgcggcg ggtgtggtgg ttacgcgcag cgtgaccgct acacttgcca    3660
gcgccctagc gcccgctcct ttcgctttct tcccttcctt tctcgccacg ttcgccggct    3720
ttccccgtca agctctaaat cggggctcc ctttagggtt ccgatttagt gctttacggc    3780
acctcgaccc caaaaaactt gattaggtgt atggttcacg tagtgggcca tcgccctgat    3840
agacggtttt tcgccctttg acgttggagt ccacgttctt taatagtgga ctcttgttcc    3900
aaactggaac aacactcaac cctatctcgg tctattcttt tgatttataa gggattttgc    3960
cgatttcggc ctattggtta aaaatgagc tgatttaaca aaaatttaac gcgaattaat    4020
tctgtggaat gtgtgtcagt tagggtgtgg aaagtcccca ggctcccag caggcagaag    4080 tatgcaaagc atgcatctca attagtcagc aaccaggtgt ggaaagtccc caggctcccc    4140
agcaggcaga agtatgcaaa gcatgcatct caattagtca gcaaccatag tcccgcccct    4200
aactccgccc atcccgcccc taactccgcc cagttccgcc cattctccgc cccatggctg    4260
actaattttt tttatttatg cagaggccga ggccgcctct gcctctgagc tattccagaa    4320
gtagtgagga ggcttttttg gaggcctagg cttttgcaaa aagctcccgg gagcttgtat    4380 atccatttc ggatctgatc aagagacagg atgaggatcc tttcgcatga ttgaacaaga    4440
tggattgcac gcaggttctc cggccgcttg ggtggagagg ctattcggct atgactgggc    4500
acaacagaca atcggctgct ctgatgccgc cgtgttccgg ctgtcagcgc aggggcgccc    4560
ggttcttttt gtcaagaccg acctgtccgg tgccctgaat gaactgcagg acgaggcagc    4620
gcggctatcg tggctggcca cgacgggcgt tccttgcgca gctgtgctcg acgttgtcac    4680
tgaagcggga agggactggc tgctattggg cgaagtgccg gggcaggatc tcctgtcatc    4740
tcaccttgct cctgccgaga aagtatccat catggctgat gcaatgcggc ggctgcatac    4800
gcttgatccg gctacctgcc cattcgacca ccaagcgaaa catcgcatcg agcgagcacg    4860
tactcggatg gaagccggtc ttgtcgatca ggatgatctg gacgaagagc atcaggggct    4920
cgcgccagcc gaactgttcg ccaggctcaa ggcgcgcatg cccgacggcg aggatctcgt    4980
cgtgacccat ggcgatgcct gcttgccgaa tatcatggtg gaaaatggcc gcttttctgg    5040
attcatcgac tgtggccggc tgggtgtggc ggaccgctat caggacatag cgttggctac    5100
ccgtgatatt gctgaagagc ttggcggcga atgggctgac cgcttcctcg tgctttacgg    5160
tatcgccgct cccgattcgc agcgcatcgc cttctatcgc cttcttgacg agttcttctg    5220
agcgggactc tggggttcga aatgaccgac caagcgacgc ccaacctgcc atcacgagat    5280
ttcgattcca ccgccgcctt ctatgaaagg ttgggcttcg gaatcgtttt ccgggacgcc    5340
ggctggatga tcctccagcg cggggatctc atgctggagt tcttcgccca ccccaacttg    5400
tttattgcag cttataatgg ttacaaataa agcaatagca tcacaaattt cacaaataaa    5460 gcatttttt cactgcattc tagttgtggt ttgtccaaac tcatcaatgt atcttatcat    5520
gtctgtatac cgtcgacctc tagctagagc ttggcgtaat catggtcata gctgtttcct    5580
gtgtgaaatt gttatccgct cacaattcca cacaacatac gagccggaag cataaagtgt    5640
aaagcctggg gtgcctaatg agtgagctaa ctcacattaa ttgcgttgcg ctcactgccc    5700
gctttccagt cgggaaacct gtcgtgccag ctgcattaat gaatcggcca acgcgcgggg    5760
agaggcggtt tgcgtattgg gcgctcttcc gcttcctcgc tcactgactc gctgcgctcg    5820
gtcgttcggc tgcggcgagc ggtatcagct cactcaaagg cggtaatacg gttatccaca    5880
gaatcagggg ataacgcagg aaagaacatg tgagcaaaag gccagcaaaa ggccaggaac    5940
```

```
cgtaaaaagg ccgcgttgct ggcgtttttc cataggctcc gcccccctga cgagcatcac      6000
aaaaatcgac gctcaagtca gaggtggcga aacccgacag gactataaag ataccaggcg      6060
tttccccctg gaagctccct cgtgcgctct cctgttccga ccctgccgct taccggatac      6120
ctgtccgcct ttctcccttc gggaagcgtg gcgctttctc atagctcacg ctgtaggtat      6180
ctcagttcgg tgtaggtcgt tcgctccaag ctgggctgtg tgcacgaacc ccccgttcag      6240
cccgaccgct gcgccttatc cggtaactat cgtcttgagt ccaacccggt aagacacgac      6300
ttatcgccac tggcagcagc cactggtaac aggattagca gagcgaggta tgtaggcggt      6360
gctacagagt tcttgaagtg gtggcctaac tacggctaca ctagaagaac agtatttggt      6420
atctgcgctc tgctgaagcc agttaccttc ggaaaaagag ttggtagctc ttgatccggc      6480
aaacaaacca ccgctggtag cggtttttttt gtttgcaagc agcagattac gcgcagaaaa      6540
aaaggatctc aagaagatcc tttgatcttt tctacggggt ctgacgctca gtggaacgaa      6600
aactcacgtt aagggatttt ggtcatgaga ttatcaaaaa ggatcttcac ctagatcctt      6660
ttaaattaaa aatgaagttt taaatcaatc taaagtatat atgagtaaac ttggtctgac      6720
agttaccaat gcttaatcag tgaggcacct atctcagcga tctgtctatt tcgttcatcc      6780
atagttgcct gactccccgt cgtgtagata actacgatac gggagggctt accatctggc      6840
cccagtgctg caatgatacc gcgagaccca cgctcaccgg ctccagattt atcagcaata      6900
aaccagccag ccggaagggc cgagcgcaga agtggtcctg caactttatc cgcctccatc      6960
cagtctatta attgttgccg ggaagctaga gtaagtagtt cgccagttaa tagtttgcgc      7020
aacgttgttg ccattgctac aggcatcgtg gtgtcacgct cgtcgtttgg tatggcttca      7080
ttcagctccg gttcccaacg atcaaggcga gttacatgat cccccatgtt gtgcaaaaaa      7140
gcggttagct ccttcggtcc tccgatcgtt gtcagaagta agttggccgc agtgttatca      7200
ctcatggtta tggcagcact gcataattct cttactgtca tgccatccgt aagatgcttt      7260
tctgtgactg gtgagtactc aaccaagtca ttctgagaat agtgtatgcg gcgaccgagt      7320
tgctcttgcc cggcgtcaat acgggataat accgcgccac atagcagaac tttaaaagtg      7380
ctcatcattg gaaaacgttc ttcggggcga aaactctcaa ggatcttacc gctgttgaga      7440
tccagttcga tgtaacccac tcgtgcaccc aactgatctt cagcatcttt tactttcacc      7500
agcgtttctg ggtgagcaaa aacaggaagg caaaatgccg caaaaaaggg aataagggcg      7560
acacggaaat gttgaatact catactcttc ctttttcaat attattgaag catttatcag      7620
ggttattgtc tcatgagcgg atacatattt gaatgtattt agaaaaataa acaaataggg      7680
gttccgcgca catttccccg aaaagtgcca cctgacgtc                              7719
```

<210> SEQ ID NO 32
<211> LENGTH: 6129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gacggatcgg gagatctccc gatcccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
```

-continued

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgccatgg gatggagctg tatcatcctc ttcttggtgg   1020
caacagctac aggcgtgcac tccgacatcc agctgaccca gtccccctcc agcctgtccg   1080
cctctgtggg cgacagagtg accatcacct gttccgccag ccaggacatc tccaactacc   1140
tgaactggta tcagcagaag cccggcaagg cccccaaggt gctgatctac ttcacctcct   1200
ccctgcactc cggcgtgccc tccagattct ccggctctgg ctccggcacc gactttaccc   1260
tgaccatctc cagcctgcag cccgaggact tcgccaccta ctactgccag cagtactcca   1320
ccgtgccctg gaccttcggc cagggcacca aggtggaaat caagcggacc gtggccgctc   1380
cctccgtgtt catcttccca ccctccgacg agcagctgaa gtccggaacc gcctccgtcg   1440
tgtgcctgct gaacaacttc taccccgcg aggccaaggt gcagtggaag gtggacaacg   1500
ccctgcagag cggcaactcc caggaatccg tcaccgagca ggactccaag gacagcacct   1560
actccctgtc cagcaccctg accctgtcca aggccgacta cgagaagcac aaggtgtacg   1620
cctgcgaagt gacccaccag ggcctcagct ccccagtgac caagtccttc aaccggggcg   1680
agtgctagta atctagaggg cccgtttaaa cccgctgatc agcctcgact gtgccttcta   1740
gttgccagcc atctgttgtt tgcccctccc ccgtgccttc cttgaccctg gaaggtgcca   1800
ctcccactgt cctttcctaa taaaatgagg aaattgcatc gcattgtctg agtaggtgtc   1860
attctattct ggggggtggg gtggggcagg acagcaaggg ggaggattgg gaagacaata   1920
gcaggcatgc tggggatgcg gtgggctcta tggcttctga ggcggaaaga accagctggg   1980
gctctagggg gtatccccac gcgccctgta gcggcgcatt aagcgcggcg ggtgtggtgg   2040
ttacgcgcag cgtgaccgct acacttgcca gcgccctagc gcccgctcct ttcgctttct   2100
tcccttcctt tctcgccacg ttcgccggct ttccccgtca agctctaaat cgggggctcc   2160
ctttagggtt ccgatttagt gctttacggc acctcgaccc caaaaaactt gattagggtg   2220
atggttcacg tagtgggcca tcgccctgat agacggtttt tcgccctttg acgttggagt   2280
ccacgttctt taatagtgga ctcttgttcc aaactggaac aacactcaac cctatctcgg   2340
tctattcttt tgatttataa gggattttgc cgatttcggc ctattggtta aaaaatgagc   2400
tgatttaaca aaaatttaac gcgaattaat tctgtggaat gtgtgtcagt tagggtgtgg   2460
aaagtcccca ggctcccag caggcagaag tatgcaaagc atgcatctca attagtcagc   2520
aaccaggtgt ggaaagtccc caggctcccc agcaggcaga agtatgcaaa gcatgcatct   2580
```

```
caattagtca gcaaccatag tcccgcccct aactccgccc atcccgcccc taactccgcc    2640
cagttccgcc cattctccgc cccatggctg actaattttt tttatttatg cagaggccga    2700
ggccgcctct gcctctgagc tattccagaa gtagtgagga ggcttttttg gaggcctagg    2760
cttttgcaaa aagctcccgg gagcttgtat atccattttc ggatctgatc aagagacagg    2820
atgaggatcg tttcgcatga ttgaacaaga tggattgcac gcaggttctc cggccgcttg    2880
ggtggagagg ctattcggct atgactgggc acaacagaca atcggctgct ctgatgccgc    2940
cgtgttccgg ctgtcagcgc aggggcgccc ggttcttttt gtcaagaccg acctgtccgg    3000
tgccctgaat gaactgcagg acgaggcagc gcggctatcg tggctggcca cgacgggcgt    3060
tccttgcgca gctgtgctcg acgttgtcac tgaagcggga agggactggc tgctattggg    3120
cgaagtgccg gggcaggatc tcctgtcatc tcaccttgct cctgccgaga agtatccat     3180 catggctgat gcaatgcggc ggctgcatac gcttgatccg gctacctgcc cattcgacca    3240
ccaagcgaaa catcgcatcg agcgagcacg tactcggatg aagccggtc ttgtcgatca     3300 ggatgatctg gacgaagagc atcaggggct cgcgccagcc gaactgttcg ccaggctcaa    3360
ggcgcgcatg cccgacggcg aggatctcgt cgtgacccat ggcgatgcct gcttgccgaa    3420
tatcatggtg gaaaatggcc gcttttctgg attcatcgac tgtggccggc tgggtgtggc    3480
ggaccgctat caggacatag cgttggctac ccgtgatatt gctgaagagc ttggcggcga    3540
atgggctgac cgcttcctcg tgctttacgg tatcgccgct cccgattcgc agcgcatcgc    3600
cttctatcgc cttcttgacg agttcttctg agcgggactc tggggttcga atgaccgac    3660 caagcgacgc ccaacctgcc atcacgagat ttcgattcca ccgccgcctt ctatgaaagg    3720
ttgggcttcg gaatcgtttt ccgggacgcc ggctggatga tcctccagcg cggggatctc    3780
atgctggagt tcttcgccca ccccaacttg tttattgcag cttataatgg ttacaaataa    3840
agcaatagca tcacaaattt cacaaataaa gcattttttt cactgcattc tagttgtggt    3900
ttgtccaaac tcatcaatgt atcttatcat gtctgtatac cgtcgacctc tagctagagc    3960
ttggcgtaat catggtcata gctgtttcct gtgtgaaatt gttatccgct cacaattcca    4020
cacaacatac gagccggaag cataaagtgt aaagcctggg gtgcctaatg agtgagctaa    4080
ctcacattaa ttgcgttgcg ctcactgccc gctttccagt cgggaaacct gtcgtgccag    4140
ctgcattaat gaatcggcca acgcgcgggg agaggcggtt tgcgtattgg gcgctcttcc    4200
gcttcctcgc tcactgactc gctgcgctcg gtcgttcggc tgcggcgagc ggtatcagct    4260
cactcaaagg cggtaatacg gttatccaca gaatcagggg ataacgcagg aaagaacatg    4320
tgagcaaaag gccagcaaaa ggccaggaac cgtaaaaagg ccgcgttgct ggcgtttttc    4380
cataggctcc gccccctga cgagcatcac aaaaatcgac gctcaagtca gaggtggcga    4440
aacccgacag gactataaag ataccaggcg tttccccctg gaagctccct cgtgcgctct    4500
cctgttccga ccctgccgct taccggatac ctgtccgcct ttctcccttc gggaagcgtg    4560
gcgctttctc atagctcacg ctgtaggtat ctcagttcgg tgtaggtcgt tcgctccaag    4620
ctgggctgtg tgcacgaacc ccccgttcag cccgaccgct gcgccttatc cggtaactat    4680
cgtcttgagt ccaacccggt aagacacgac ttatcgccac tggcagcagc cactggtaac    4740
aggattagca gagcgaggta tgtaggcggt gctacagagt tcttgaagtg gtggcctaac    4800
tacggctaca ctagaagaac agtatttggt atctgcgctc tgctgaagcc agttaccttc    4860
ggaaaaagag ttggtagctc ttgatccggc aaacaaacca ccgctggtag cggttttttt    4920
gtttgcaagc agcagattac gcgcagaaaa aaaggatctc aagaagatcc tttgatcttt    4980
```

-continued

```
tctacggggt ctgacgctca gtggaacgaa aactcacgtt aagggatttt ggtcatgaga   5040
ttatcaaaaa ggatcttcac ctagatcctt ttaaattaaa aatgaagttt taaatcaatc   5100
taaagtatat atgagtaaac ttggtctgac agttaccaat gcttaatcag tgaggcacct   5160
atctcagcga tctgtctatt tcgttcatcc atagttgcct gactcccgt cgtgtagata    5220 actacgatac gggagggctt accatctggc cccagtgctg caatgatacc gcgagaccca   5280
cgctcaccgg ctccagattt atcagcaata accagccag ccggaagggc cgagcgcaga    5340
agtggtcctg caactttatc cgcctccatc cagtctatta attgttgccg ggaagctaga   5400
gtaagtagtt cgccagttaa tagtttgcgc aacgttgttg ccattgctac aggcatcgtg   5460
gtgtcacgct cgtcgtttgg tatggcttca ttcagctccg gttcccaacg atcaaggcga   5520
gttacatgat cccccatgtt gtgcaaaaaa gcggttagct ccttcggtcc tcgatcgtt    5580 gtcagaagta agttggccgc agtgttatca ctcatggtta tggcagcact gcataattct   5640
cttactgtca tgccatccgt aagatgcttt tctgtgactg gtgagtactc aaccaagtca   5700
ttctgagaat agtgtatgcg gcgaccgagt tgctcttgcc cggcgtcaat acgggataat   5760
accgcgccac atagcagaac tttaaaagtg ctcatcattg gaaaacgttc ttcggggcga   5820
aaactctcaa ggatcttacc gctgttgaga tccagttcga tgtaacccac tcgtgcaccc   5880
aactgatctt cagcatcttt tactttcacc agcgtttctg ggtgagcaaa acaggaagg    5940 caaaatgccg caaaaaaggg aataagggcg acacggaaat gttgaatact catactcttc   6000 cttttcaat attattgaag catttatcag ggttattgtc tcatgagcgg atacatattt    6060
gaatgtattt agaaaaataa acaaataggg gttccgcgca catttccccg aaaagtgcca   6120
cctgacgtc                                                          6129
```

<210> SEQ ID NO 33
<211> LENGTH: 1106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Met Arg Leu Pro Gly Ala Met Pro Ala Leu Ala Leu Lys Gly Glu Leu
 1               5                  10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140
```

```
Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
                195                 200                 205

Leu Gln Val Ser Ser Ile Asn Val Ser Val Asn Ala Val Gln Thr Val
                210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
                275                 280                 285

Tyr Thr Cys Asn Val Thr Glu Ser Val Asn Asp His Gln Asp Glu Lys
                290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
                355                 360                 365

Thr Arg Asn Val Ser Glu Thr Arg Tyr Val Ser Glu Leu Thr Leu Val
                370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
                435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
                500                 505                 510

Ala Val Gly Gln Asp Thr Gln Glu Val Ile Val Val Pro His Ser Leu
                515                 520                 525

Pro Phe Lys Val Val Val Ile Ser Ala Ile Leu Ala Leu Val Val Leu
                530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
```

```
                565                 570                 575
His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990
```

```
Pro Gly Phe His Gly Leu Arg Ser Pro Leu Asp Thr Ser Ser Val Leu
        995                 1000                1005

Tyr Thr Ala Val Gln Pro Asn Glu Gly Asp Asn Asp Tyr Ile Ile
    1010                1015                1020

Pro Leu Pro Asp Pro Lys Pro Glu Val Ala Asp Glu Gly Pro Leu
    1025                1030                1035

Glu Gly Ser Pro Ser Leu Ala Ser Ser Thr Leu Asn Glu Val Asn
    1040                1045                1050

Thr Ser Ser Thr Ile Ser Cys Asp Ser Pro Leu Glu Pro Gln Asp
    1055                1060                1065

Glu Pro Glu Pro Glu Pro Gln Leu Glu Leu Gln Val Glu Pro Glu
    1070                1075                1080

Pro Glu Leu Glu Gln Leu Pro Asp Ser Gly Cys Pro Ala Pro Arg
    1085                1090                1095

Ala Glu Ala Glu Asp Ser Phe Leu
    1100                1105

<210> SEQ ID NO 34
<211> LENGTH: 1338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
```

```
            225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
                260                 265                 270
Asn Lys Arg Ala Ser Val Arg Arg Ile Asp Gln Ser Asn Ser His
                275                 280                 285
Ala Asn Ile Phe Tyr Ser Val Leu Thr Ile Asp Lys Met Gln Asn Lys
                290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
                355                 360                 365
Trp Leu Lys Asp Gly Leu Pro Ala Thr Glu Lys Ser Ala Arg Tyr Leu
                370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
                435                 440                 445
Arg Gln Ile Leu Thr Cys Thr Ala Tyr Gly Ile Pro Gln Pro Thr Ile
                450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
                515                 520                 525
Ile Ser Gly Ile Tyr Ile Cys Ile Ala Ser Asn Lys Val Gly Thr Val
                530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
                580                 585                 590
Arg Thr Val Asn Asn Arg Thr Met His Tyr Ser Ile Ser Lys Gln Lys
                595                 600                 605
Met Ala Ile Thr Lys Glu His Ser Ile Thr Leu Asn Leu Thr Ile Met
                610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
```

```
Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                 1005

Gly Met  Glu Phe Leu Ser Ser  Arg Lys Cys Ile His  Arg Asp Leu
    1010                 1015                 1020

Ala Ala  Arg Asn Ile Leu Leu  Ser Glu Asn Asn Val  Val Lys Ile
    1025                 1030                 1035

Cys Asp  Phe Gly Leu Ala Arg  Asp Ile Tyr Lys Asn  Pro Asp Tyr
    1040                 1045                 1050

Val Arg  Lys Gly Asp Thr Arg  Leu Pro Leu Lys Trp  Met Ala Pro
    1055                 1060                 1065
```

```
Glu  Ser  Ile  Phe  Asp  Lys  Ile  Tyr  Ser  Thr  Lys  Ser  Asp  Val  Trp
1070                1075                1080

Ser  Tyr  Gly  Val  Leu  Leu  Trp  Glu  Ile  Phe  Ser  Leu  Gly  Gly  Ser
     1085                1090                1095

Pro  Tyr  Pro  Gly  Val  Gln  Met  Asp  Glu  Asp  Phe  Cys  Ser  Arg  Leu
1100                1105                1110

Arg  Glu  Gly  Met  Arg  Met  Arg  Ala  Pro  Glu  Tyr  Ser  Thr  Pro  Glu
1115                1120                1125

Ile  Tyr  Gln  Ile  Met  Leu  Asp  Cys  Trp  His  Arg  Asp  Pro  Lys  Glu
1130                1135                1140

Arg  Pro  Arg  Phe  Ala  Glu  Leu  Val  Glu  Lys  Leu  Gly  Asp  Leu  Leu
1145                1150                1155

Gln  Ala  Asn  Val  Gln  Asp  Gly  Lys  Asp  Tyr  Ile  Pro  Ile  Asn
1160                1165                1170

Ala  Ile  Leu  Thr  Gly  Asn  Ser  Gly  Phe  Thr  Tyr  Ser  Thr  Pro  Ala
1175                1180                1185

Phe  Ser  Glu  Asp  Phe  Phe  Lys  Glu  Ser  Ile  Ser  Ala  Pro  Lys  Phe
1190                1195                1200

Asn  Ser  Gly  Ser  Ser  Asp  Asp  Val  Arg  Tyr  Val  Asn  Ala  Phe  Lys
1205                1210                1215

Phe  Met  Ser  Leu  Glu  Arg  Ile  Lys  Thr  Phe  Glu  Glu  Leu  Leu  Pro
1220                1225                1230

Asn  Ala  Thr  Ser  Met  Phe  Asp  Asp  Tyr  Gln  Gly  Asp  Ser  Ser  Thr
1235                1240                1245

Leu  Leu  Ala  Ser  Pro  Met  Leu  Lys  Arg  Phe  Thr  Trp  Thr  Asp  Ser
1250                1255                1260

Lys  Pro  Lys  Ala  Ser  Leu  Lys  Ile  Asp  Leu  Arg  Val  Thr  Ser  Lys
1265                1270                1275

Ser  Lys  Glu  Ser  Gly  Leu  Ser  Asp  Val  Ser  Arg  Pro  Ser  Phe  Cys
1280                1285                1290

His  Ser  Ser  Cys  Gly  His  Val  Ser  Glu  Gly  Lys  Arg  Arg  Phe  Thr
1295                1300                1305

Tyr  Asp  His  Ala  Glu  Leu  Glu  Arg  Lys  Ile  Ala  Cys  Cys  Ser  Pro
1310                1315                1320

Pro  Pro  Asp  Tyr  Asn  Ser  Val  Val  Leu  Tyr  Ser  Thr  Pro  Pro  Ile
1325                1330                1335

<210> SEQ ID NO 35
<211> LENGTH: 1356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met  Gln  Ser  Lys  Val  Leu  Leu  Ala  Val  Ala  Leu  Trp  Leu  Cys  Val  Glu
1                  5                   10                  15

Thr  Arg  Ala  Ala  Ser  Val  Gly  Leu  Pro  Ser  Val  Ser  Leu  Asp  Leu  Pro
                20                  25                  30

Arg  Leu  Ser  Ile  Gln  Lys  Asp  Ile  Leu  Thr  Ile  Lys  Ala  Asn  Thr  Thr
            35                  40                  45

Leu  Gln  Ile  Thr  Cys  Arg  Gly  Gln  Arg  Asp  Leu  Asp  Trp  Leu  Trp  Pro
        50                  55                  60

Asn  Asn  Gln  Ser  Gly  Ser  Glu  Gln  Arg  Val  Glu  Val  Thr  Glu  Cys  Ser
65                  70                  75                  80
```

-continued

```
Asp Gly Leu Phe Cys Lys Thr Leu Thr Ile Pro Lys Val Ile Gly Asn
                85                  90                  95
Asp Thr Gly Ala Tyr Lys Cys Phe Tyr Arg Glu Thr Asp Leu Ala Ser
            100                 105                 110
Val Ile Tyr Val Tyr Val Gln Asp Tyr Arg Ser Pro Phe Ile Ala Ser
        115                 120                 125
Val Ser Asp Gln His Gly Val Val Tyr Ile Thr Glu Asn Lys Asn Lys
    130                 135                 140
Thr Val Val Ile Pro Cys Leu Gly Ser Ile Ser Asn Leu Asn Val Ser
145                 150                 155                 160
Leu Cys Ala Arg Tyr Pro Glu Lys Arg Phe Val Pro Asp Gly Asn Arg
                165                 170                 175
Ile Ser Trp Asp Ser Lys Lys Gly Phe Thr Ile Pro Ser Tyr Met Ile
            180                 185                 190
Ser Tyr Ala Gly Met Val Phe Cys Glu Ala Lys Ile Asn Asp Glu Ser
        195                 200                 205
Tyr Gln Ser Ile Met Tyr Ile Val Val Val Gly Tyr Arg Ile Tyr
    210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
            260                 265                 270
Val Asn Arg Asp Leu Lys Thr Gln Ser Gly Ser Glu Met Lys Lys Phe
        275                 280                 285
Leu Ser Thr Leu Thr Ile Asp Gly Val Thr Arg Ser Asp Gln Gly Leu
    290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
        355                 360                 365
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
```

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
    850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu

-continued

```
            915                 920                 925
Arg Ser Lys Arg Asn Glu Phe Val Pro Tyr Lys Thr Lys Gly Ala Arg
            930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                965                 970                 975
Phe Val Glu Glu Lys Ser Leu Ser Asp Val Glu Glu Glu Ala Pro
            980                 985                 990
Glu Asp Leu Tyr Lys Asp Phe Leu Thr Leu Glu His Leu Ile Cys Tyr
                995                 1000                1005
Ser Phe Gln Val Ala Lys Gly Met Glu Phe Leu Ala Ser Arg Lys
            1010                1015                1020
Cys Ile His Arg Asp Leu Ala Ala Arg Asn Ile Leu Leu Ser Glu
            1025                1030                1035
Lys Asn Val Val Lys Ile Cys Asp Phe Gly Leu Ala Arg Asp Ile
            1040                1045                1050
Tyr Lys Asp Pro Asp Tyr Val Arg Lys Gly Asp Ala Arg Leu Pro
            1055                1060                1065
Leu Lys Trp Met Ala Pro Glu Thr Ile Phe Asp Arg Val Tyr Thr
            1070                1075                1080
Ile Gln Ser Asp Val Trp Ser Phe Gly Val Leu Leu Trp Glu Ile
            1085                1090                1095
Phe Ser Leu Gly Ala Ser Pro Tyr Pro Gly Val Lys Ile Asp Glu
            1100                1105                1110
Glu Phe Cys Arg Arg Leu Lys Glu Gly Thr Arg Met Arg Ala Pro
            1115                1120                1125
Asp Tyr Thr Thr Pro Glu Met Tyr Gln Thr Met Leu Asp Cys Trp
            1130                1135                1140
His Gly Glu Pro Ser Gln Arg Pro Thr Phe Ser Glu Leu Val Glu
            1145                1150                1155
His Leu Gly Asn Leu Leu Gln Ala Asn Ala Gln Gln Asp Gly Lys
            1160                1165                1170
Asp Tyr Ile Val Leu Pro Ile Ser Glu Thr Leu Ser Met Glu Glu
            1175                1180                1185
Asp Ser Gly Leu Ser Leu Pro Thr Ser Pro Val Ser Cys Met Glu
            1190                1195                1200
Glu Glu Glu Val Cys Asp Pro Lys Phe His Tyr Asp Asn Thr Ala
            1205                1210                1215
Gly Ile Ser Gln Tyr Leu Gln Asn Ser Lys Arg Lys Ser Arg Pro
            1220                1225                1230
Val Ser Val Lys Thr Phe Glu Asp Ile Pro Leu Glu Glu Pro Glu
            1235                1240                1245
Val Lys Val Ile Pro Asp Asp Asn Gln Thr Asp Ser Gly Met Val
            1250                1255                1260
Leu Ala Ser Glu Glu Leu Lys Thr Leu Glu Asp Arg Thr Lys Leu
            1265                1270                1275
Ser Pro Ser Phe Gly Gly Met Val Pro Ser Lys Ser Arg Glu Ser
            1280                1285                1290
Val Ala Ser Glu Gly Ser Asn Gln Thr Ser Gly Tyr Gln Ser Gly
            1295                1300                1305
Tyr His Ser Asp Asp Thr Asp Thr Thr Val Tyr Ser Ser Glu Glu
            1310                1315                1320
```

```
Ala Glu  Leu Leu Lys Leu Ile  Glu Ile Gly Val Gln  Thr Gly Ser
    1325             1330                 1335

Thr Ala  Gln Ile Leu Gln Pro  Asp Ser Gly Thr Thr  Leu Ser Ser
1340                 1345                 1350

Pro Pro  Val
    1355

<210> SEQ ID NO 36
<211> LENGTH: 1363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
```

```
            305                 310                 315                 320
        Glu Ser Thr Glu Val Ile Val His Glu Asn Pro Phe Ile Ser Val Glu
                        325                 330                 335
        Trp Leu Lys Gly Pro Ile Leu Glu Ala Thr Ala Gly Asp Glu Leu Val
                        340                 345                 350
        Lys Leu Pro Val Lys Leu Ala Ala Tyr Pro Pro Glu Phe Gln Trp
                        355                 360                 365
        Tyr Lys Asp Gly Lys Ala Leu Ser Gly Arg His Ser Pro His Ala Leu
                        370                 375                 380
        Val Leu Lys Glu Val Thr Glu Ala Ser Thr Gly Thr Tyr Thr Leu Ala
        385                 390                 395                 400
        Leu Trp Asn Ser Ala Ala Gly Leu Arg Arg Asn Ile Ser Leu Glu Leu
                        405                 410                 415
        Val Val Asn Val Pro Pro Gln Ile His Glu Lys Glu Ala Ser Ser Pro
                        420                 425                 430
        Ser Ile Tyr Ser Arg His Ser Arg Gln Ala Leu Thr Cys Thr Ala Tyr
                        435                 440                 445
        Gly Val Pro Leu Pro Leu Ser Ile Gln Trp His Trp Arg Pro Trp Thr
                        450                 455                 460
        Pro Cys Lys Met Phe Ala Gln Arg Ser Leu Arg Arg Gln Gln Gln
        465                 470                 475                 480
        Asp Leu Met Pro Gln Cys Arg Asp Trp Arg Ala Val Thr Thr Gln Asp
                        485                 490                 495
        Ala Val Asn Pro Ile Glu Ser Leu Asp Thr Trp Thr Glu Phe Val Glu
                        500                 505                 510
        Gly Lys Asn Lys Thr Val Ser Lys Leu Val Ile Gln Asn Ala Asn Val
                        515                 520                 525
        Ser Ala Met Tyr Lys Cys Val Val Ser Asn Lys Val Gly Gln Asp Glu
                        530                 535                 540
        Arg Leu Ile Tyr Phe Tyr Val Thr Thr Ile Pro Asp Gly Phe Thr Ile
        545                 550                 555                 560
        Glu Ser Lys Pro Ser Glu Glu Leu Leu Glu Gly Gln Pro Val Leu Leu
                        565                 570                 575
        Ser Cys Gln Ala Asp Ser Tyr Lys Tyr Glu His Leu Arg Trp Tyr Arg
                        580                 585                 590
        Leu Asn Leu Ser Thr Leu His Asp Ala His Gly Asn Pro Leu Leu Leu
                        595                 600                 605
        Asp Cys Lys Asn Val His Leu Phe Ala Thr Pro Leu Ala Ala Ser Leu
                        610                 615                 620
        Glu Glu Val Ala Pro Gly Ala Arg His Ala Thr Leu Ser Leu Ser Ile
        625                 630                 635                 640
        Pro Arg Val Ala Pro Glu His Glu Gly His Tyr Val Cys Glu Val Gln
                        645                 650                 655
        Asp Arg Arg Ser His Asp Lys His Cys His Lys Lys Tyr Leu Ser Val
                        660                 665                 670
        Gln Ala Leu Glu Ala Pro Arg Leu Thr Gln Asn Leu Thr Asp Leu Leu
                        675                 680                 685
        Val Asn Val Ser Asp Ser Leu Glu Met Gln Cys Leu Val Ala Gly Ala
                        690                 695                 700
        His Ala Pro Ser Ile Val Trp Tyr Lys Asp Glu Arg Leu Leu Glu Glu
        705                 710                 715                 720
        Lys Ser Gly Val Asp Leu Ala Asp Ser Asn Gln Lys Leu Ser Ile Gln
                        725                 730                 735
```

-continued

```
Arg Val Arg Glu Glu Asp Ala Gly Arg Tyr Leu Cys Ser Val Cys Asn
        740                 745                 750

Ala Lys Gly Cys Val Asn Ser Ala Ser Val Ala Val Glu Gly Ser
        755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
                820                 825                 830

Tyr Asp Ala Ser Gln Trp Glu Phe Pro Arg Glu Arg Leu His Leu Gly
                835                 840                 845

Arg Val Leu Gly Tyr Gly Ala Phe Gly Lys Val Val Glu Ala Ser Ala
        850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
        915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
                965                 970                 975

Ser Asp Arg Val Leu Phe Ala Arg Phe Ser Lys Thr Glu Gly Gly Ala
                980                 985                 990

Arg Arg Ala Ser Pro Asp Gln Glu Ala Glu Asp Leu Trp Leu Ser Pro
        995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140
```

```
Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Ser Cys Lys Gly Pro Gly Gln Asn Val Ala Val
    1295                1300                1305

Thr Arg Ala His Pro Asp Ser Gln Gly Arg Arg Arg Pro Glu
    1310                1315                1320

Arg Gly Ala Arg Gly Gly Gln Val Phe Tyr Asn Ser Glu Tyr Gly
    1325                1330                1335

Glu Leu Ser Glu Pro Ser Glu Asp His Cys Ser Pro Ser Ala
    1340                1345                1350

Arg Val Thr Phe Phe Thr Asp Asn Ser Tyr
    1355                1360

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser
1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Ser
1

<210> SEQ ID NO 39
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 39

Gly Gly Gly Glu Ser
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser Gly Gly Gly Gly Ser
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Gly Ser Gly Gly Gly Gly Ser Gly Gly Gly Gly Ser Gly
1               5                   10                  15

Gly Gly Gly Ser Gly
            20

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Asp Phe Thr His Tyr Gly Met Asn
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ile Asn Thr Tyr Thr Gly Glu Pro Thr Tyr Ala Ala Asp Phe Lys
1               5                   10                  15

Arg

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Tyr Pro Tyr Tyr Tyr Gly Thr Ser His Trp Tyr Phe Asp Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Ala Ser Gln Asp Ile Ser Asn Tyr Leu Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Thr Ser Ser Leu His Ser
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Ser Thr Val Pro Trp Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Tyr Thr Phe Thr Asn Tyr Gly Met Asn
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Pro His Tyr Tyr Gly Ser Ser His Trp Tyr Phe Asp Val
1               5                   10

<210> SEQ ID NO 50
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1-4 'Gly-Gly-Gly-
      Gly-Ser' repeating units

<400> SEQUENCE: 50

Gly Gly Gly Gly Ser Gly Gly Gly Gly Ser Gly Gly Gly Gly Ser Gly
1               5                   10                  15

Gly Gly Gly Ser
            20

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: This sequence may encompass 1-4 'Gly'
      residues

<400> SEQUENCE: 51

Gly Gly Gly Gly
1

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This sequence may encompass 1-4 'Gly-Gly'
      repeating units

<400> SEQUENCE: 52

Gly Gly Gly Gly Gly Gly Gly Gly
1               5

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This sequence may encompass 1-4 'Gly-Gly-Gly-
      Ser' repeating units

<400> SEQUENCE: 53

Gly Gly Gly Ser Gly Gly Gly Ser Gly Gly Gly Ser Gly Gly Gly Ser
1               5                   10                  15

<210> SEQ ID NO 54
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1-4 'Gly-Gly-Gly-
      Glu-Ser' repeating units

<400> SEQUENCE: 54

Gly Gly Gly Glu Ser Gly Gly Gly Glu Ser Gly Gly Gly Glu Ser Gly
1               5                   10                  15

Gly Gly Glu Ser
            20

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Gly Gly Cys
1               5

<210> SEQ ID NO 56
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Gly Ser Gly Gly Gly Ser Gly Gly Gly Ser Gly Gly
1               5                   10                  15

Gly Gly Ser Gly Gly Gly Gly Ser Gly Gly Gly Gly Ser
            20                  25
```

What is claimed is:

1. A fusion protein comprising a vascular endothelial growth factor (hereinafter "VEGF") antagonist linked to a platelet-derived growth factor (hereinafter "PDGF") antagonist, wherein the VEGF antagonist is an anti-VEGF antibody, and the PDGF antagonist is a PDGF receptor (hereinafter "PDGFR") extracellular trap segment, wherein the PDGFR extracellular trap segment comprises domains D1-D3 of PDGFR-β.

2. The fusion protein of claim 1, wherein the anti-VEGF antibody comprises a heavy chain and a light chain, and the heavy chain is fused via a linker to the C-terminus of the PDGFR extracellular trap segment.

3. The fusion protein of claim 2, wherein the linker has the amino acid sequence GG, or has the amino acid sequence as set forth in SEQ ID NO: 40 or SEQ ID NO: 41.

4. The fusion protein of claim 3, wherein the linker has the amino acid sequence as set forth in SEQ ID NO: 40.

5. The fusion protein of claim 4, wherein the heavy chain of the anti-VEGF antibody comprises three complementarity determining regions (CDRs) having the amino acid sequences as set forth in SEQ ID NO: 42, SEQ ID NO: 43, and SEQ ID NO: 44, respectively, and wherein the light chain of the anti-VEGF comprises three CDRs having the amino acid sequences as set forth in SEQ ID NO: 45, SEQ ID NO: 46 and SEQ ID NO: 47, respectively.

6. The fusion protein of claim 5, wherein the isotype of the heavy chain is IgG1, and the isotype of the light chain is kappa.

7. The fusion protein of claim 6, wherein the heavy chain constant domain has the amino acid sequence as set forth in SEQ ID NO: 17, and the light chain constant domain has the amino acid sequence as set forth in SEQ ID NO: 18.

8. The fusion protein of claim 6, wherein the heavy chain constant domain has the amino acid sequence as set forth in SEQ ID NO: 17 except for the presence of one or more mutations to reduce effector function.

9. The fusion protein of claim 8, wherein the mutations are to one or more of the following amino acid positions with reference to SEQ ID NO: 17: E116, L117, L118, G119, G120, A210, A213 and P214.

10. The fusion protein of claim 9, wherein the mutations are selected from the group consisting of E116P, L117V, L117A, L118A, G120A, A210G, A213S and P214S.

11. The fusion protein of claim 10, wherein the mutations are: L117A, L118A and G120A.

12. The fusion protein of claim 6, wherein the heavy chain constant domain has the amino acid sequence as set forth in SEQ ID NO: 17 except for the presence of mutations L117A, L118A and G120A and a cysteine residue added at another position of the heavy chain constant domain by recombinant DNA technology.

13. The fusion protein of claim 12, wherein the cysteine residue added is selected from the group consisting of Q230C and L326C.

14. The fusion protein of claim 1, wherein the anti-VEGF antibody is an IgG.

15. The fusion protein of claim 1, wherein the PDGFR extracellular trap segment comprises the amino acid sequence as set forth in amino acids 33-314 of SEQ ID NO: 11.

16. The fusion protein of claim 1, wherein the anti-VEGF antibody is an anti-VEGF-A antibody.

17. A method for the treatment of an ocular disease in a patient in need thereof, said method comprising administering to the patient the fusion protein of claim 1.

18. The method of claim 17, wherein the ocular disease is a disease with a neovascular component, said method comprising administering to the patient the fusion protein of claim 1.

19. A method of inhibiting VEGF-induced proliferation of primary human retinal microvascular endothelial cells (HRMVEC), said method comprising administering to the patient the fusion protein of claim 1.

20. A method of inhibiting PDGF-induced proliferation of primary human brain vascular pericytes (HBVP), said method comprising administering to the patient the fusion protein of claim 1.

21. A method of inhibiting sprouting in a co-culture of human retinal microvascular endothelial cells (HRMVEC) and human mesenchymal pericytes (HMPs), said method comprising administering to the patient the fusion protein of claim 1.

22. A method of inhibiting laser-induced chloroidal neovascularization, said method comprising administering to the patient the fusion protein of claim 1.

* * * * *